(12) United States Patent
Li et al.

(10) Patent No.: US 12,359,200 B2
(45) Date of Patent: Jul. 15, 2025

(54) METHODS AND COMPOSITIONS FOR EXPANSION OF CELL POPULATION

(71) Applicants: STOWERS INSTITUTE FOR MEDICAL RESEARCH, Kansas City, MO (US); UNIVERSITY OF CHICAGO, Chicago, IL (US)

(72) Inventors: Zhenrui Li, Kansas City, KS (US); Pengxu Qian, Kansas City, MO (US); Linheng Li, Kansas City, MO (US); Chuan He, Chicago, IL (US)

(73) Assignees: STOWERS INSTITUTE FOR MEDICAL RESEARCH, Kansas City, MO (US); UNIVERSITY OF CHICAGO, Chicago, IL (US)

(*) Notice: Subject to any disclaimer, the term of this patent is extended or adjusted under 35 U.S.C. 154(b) by 1496 days.

(21) Appl. No.: 16/754,714

(22) PCT Filed: Oct. 9, 2018

(86) PCT No.: PCT/US2018/055092
§ 371 (c)(1),
(2) Date: Aug. 11, 2020

(87) PCT Pub. No.: WO2019/074980
PCT Pub. Date: Apr. 18, 2019

(65) Prior Publication Data
US 2020/0370044 A1    Nov. 26, 2020

Related U.S. Application Data

(60) Provisional application No. 62/695,820, filed on Jul. 9, 2018, provisional application No. 62/570,076, filed on Oct. 9, 2017.

(51) Int. Cl.
*C12N 15/113* (2010.01)
*A61K 35/28* (2015.01)
*C12N 5/0789* (2010.01)

(52) U.S. Cl.
CPC ............ *C12N 15/113* (2013.01); *A61K 35/28* (2013.01); *C12N 5/0647* (2013.01); *C12N 2310/14* (2013.01); *C12N 2310/531* (2013.01)

(58) Field of Classification Search
CPC .......................... C12N 15/113; C12N 5/0647; C12N 2310/14; C12N 2310/531; C12N 2330/50;
(Continued)

(56) References Cited

U.S. PATENT DOCUMENTS 9,439,928 B2    9/2016  Kasahara et al.
10,787,643 B2 * 9/2020  Perry ..................... A61P 3/00
(Continued)

FOREIGN PATENT DOCUMENTS

JP    2023171952    12/2023
WO    2012027376     3/2012

OTHER PUBLICATIONS

Ma (et al. 2009. Adult neural stem cells in the mammalian central nervous system. Cell Res. 19:672-682) (Year: 2009).*
(Continued)

*Primary Examiner* — Nancy J Leith
*Assistant Examiner* — Ruth Sophia Arieti
(74) *Attorney, Agent, or Firm* — Bryan Cave Leighton Paisner LLP

(57) ABSTRACT

The present invention relates to methods for expanding a stem cell population, as well as other cell populations. More particularly, the invention relates, inter alia, to methods and compositions for expanding a stem cell and/or other cell
(Continued)

population, particularly a hematopoietic stem cell population.

12 Claims, 78 Drawing Sheets

Specification includes a Sequence Listing.

(58) Field of Classification Search
CPC ...... C12N 15/10; C12N 15/09; C12N 15/102; A61K 35/28
See application file for complete search history.

(56) References Cited

U.S. PATENT DOCUMENTS

| | | |
|---|---|---|
| 2016/0264934 A1 | 9/2016 | Giallourakis et al. |
| 2017/0037396 A1* | 2/2017 | Lee ...................... C12N 15/113 |

OTHER PUBLICATIONS

Lo (and Parham. 2009. Ethical Issues in Stem Cell Research. Endocrine Re. 30[3]:204-213) (Year: 2009).*
Selem (et al. 2011. Cardiac Stem Cells: Biology and Therapeutic Applications. Chapter 19 in Principles of Regenerative Medicine. Elsevier) (Year: 2011).*
Wang (et al. 2014. N6-methyladenosine modification destabilizes developmental regulators in embryonic stem cells. Nature Cell Biol. 16[2]:191-198) (Year: 2014).*
Caplan (2015. Are All Adult Stem Cells the Same. Regen. Eng. Transl. Med. 1:4-10) (Year: 2015).*
Mayani (2016. The regulation of hematopoietic stem cell populations. F1000Research 5:1524) (Year: 2016).*
Velasco (-Hernandez et al. 2016. Potential Pitfalls of the Mx1-Cre System: Implications for Experimental Modeling of Normal and Malignant Hematopoiesis. Stem Cell Rep. 7[1]:11-18) (Year: 2016).*
Faulds (2016. Regulation of m6A mRNA Methylation and Stem Cell Pluripotency Through GSK-3. MS Thesis. Retrieved from ProQuest.com on Aug. 20, 2024) (Year: 2016).*
Wu (et al. 2019. m6A methylation controls pluripotency of porcine induced pluripotent stem cells by targeting SOCS3/JAK2/STAT3 pathway in a YTHDF1/YTHDF2-orchestrated manner. Cell Death Dis. 10:1071) (Year: 2019).*
Huang (et al. 2021. N6-methyladenosine methyltransferases: functions, regulation, and clinical potential. J. Hematol. Oncol. 14:117) (Year: 2021).*
Wendler (2022. Autologous stem cell transplants: What to expect. Available online at mdanderson.org. Accessed Aug. 21, 2024) (Year: 2022).*
Kwok (et al. 2017. Genetic alterations of m6A regulators predict poorer survival in acute myeloid leukemia. J. Hematol. Oncol. 10:39) (Year: 2017).*
Zhang, et al. "m6A Demethylase ALKBH5 Maintains Tumorigenicity of Glioblastoma Stem-like Cells by Sustaining FOXM1 Expression and Cell Proliferation Program," Cancer Cell 31, 591-606 e596 (2017).
Lence, et al. "m6A modulates neuronal functions and sex determination in *Drosophila*," Nature 540, 242-247 (2016).
Haussmann, et al. "m6A potentiates Sxl alternative pre-mRNA splicing for robust *Drosophila* sex determination," Nature 540, 301-304 (2016).
Chen, et al. "m(6)A RNA methylation is regulated by microRNAs and promotes reprogramming to pluripotency," Cell Stem Cell 16, 289-301 (2015).
Alarcon, et al. "N6-methyladenosine marks primary microRNAs for processing," Nature 519, 482-485 (2015).
Xiao, et al. "Nuclear m(6)A Reader YTHDC1 Regulates mRNA Splicing," Molecular Cell 61, 507-519 (2016).
Wojtas, et al. "Regulation of m6A Transcripts by the 3'->5' RNA Helicase YTHDC2 Is Essential for a Successful Meiotic Program in the Mammalian Germline," Molecular Cell 68, 374-387 e312 (2017).
Ivanova, et al. "The RNA m6A Reader YTHDF2 Is Essential for the Post-transcriptional Regulation of the Maternal Transcriptome and Oocyte Competence," Molecular Cell 67, 1059-1067 e1054 (2017).
Fustin, et al. "RNA-methylation-dependent RNA processing controls the speed of the circadian clock," Cell 155, 793-806 (2013).
Slobodin, et al. "Transcription Impacts the Efficiency of mRNA Translation via Co-transcriptional N6-adenosine Methylation," Cell 169, 326-337 e312 (2017).
Schwartz, et al. "Transcriptome-wide mapping reveals widespread dynamic-regulated pseudouridylation of ncRNA and mRNA," Cell 159, 148-162 (2014).
Pendleton, et al. "The U6 snRNA m6A Methyltransferase METTL16 Regulates SAM Synthetase Intron Retention," Cell 169, 824-835 e814 (2017).
Shi, et al. "YTHDF3 facilitates translation and decay of N6-methyladenosine-modified RNA," Cell Research 27, 315-328 (2017).
Huang, et al. "Recognition of RNA N(6)-methyladenosine by IGF2BP proteins enhances mRNA stability and translation," Nature Cell Biology 20, 285-295 (2018).
Bertero, et al. "The SMAD2/3 interactome reveals that TGFbeta controls m(6)A mRNA methylation in pluripotency," Nature (2018).
Liu, et al. "N(6)-methyladenosine-dependent RNA structural switches regulate RNA-protein interactions," Nature 518, 560-564 (2015).
Joseph, et al. "Deciphering hematopoietic stem cells in their niches: a critical appraisal of genetic models, lineage tracing, and imaging strategies," Cell Stem Cell 13, 520-533 (2013).
Zhou, et al. "Tracing haematopoietic stem cell formation at single-cell resolution," Nature 533, 487-492 (2016).
He, et al. "Mechanisms of stem cell self-renewal," Annual Review of Cell and Developmental Biology 25, 377-406 (2009).
Qian, et al. "The Dlk1-Gtl2 Locus Preserves LT-HSC Function by Inhibiting the PI3K-mTOR Pathway to Restrict Mitochondrial Metabolism," Cell Stem Cell 18, 214-228 (2016).
He, et al. "Homing and migration assays of hematopoietic stem/progenitor cells," Methods in Molecular Biology 1185, 279-284 (2014).
Hu & Smyth "ELDA: extreme limiting dilution analysis for comparing depleted and enriched populations in stem cell and other assays," Journal of Immunological Methods 347, 70-78 (2009).
Purton & Scadden, "Limiting factors in murine hematopoietic stem cell assays," Cell Stem Cell 1, 263-270 (2007).
Perry, et al. Cooperation between both Wnt/{beta}-catenin and PTEN/PI3K/Akt signaling promotes primitive hematopoietic stem cell self-renewal and expansion, Genes & Development 25, 1928-1942 (2011).
Simsek, et al. "The Mammalian Ribo-interactome Reveals Ribosome Functional Diversity and Heterogeneity," Cell 169, 1051-1065 e1018 (2017).
Acar, et al. "Deep imaging of bone marrow shows non-dividing stem cells are mainly perisinusoidal," Nature 526, 126-130 (2015).
Arai, et al. "Tie2/angiopoietin-1 signaling regulates hematopoietic stem cell quiescence in the bone marrow niche," Cell 118, 149-161 (2004).
Beerman, et al. "Quiescent hematopoietic stem cells accumulate DNA damage during aging that is repaired upon entry into cell cycle," Cell Stem Cell 15, 37-50 (2014).
Benveniste, et al. "Intermediate-term hematopoietic stem cells with extended but time-limited reconstitution potential," Cell stem cell 6, 48-58 (2010).
Benz, et al. "Hematopoietic stem cell subtypes expand differentially during development and display distinct lymphopoietic programs," Cell Stem Cell 10, 273-283 (2012).
Bowers, et al. "Osteoblast ablation reduces normal long-term hematopoietic stem cell self-renewal but accelerates leukemia development," Blood 125, 2678-2688 (2015).
Bruns, et al. "Megakaryocytes regulate hematopoietic stem cell quiescence through CXCL4 secretion," Nat Med 20(11), 1315-1320 (2014).

(56) References Cited

OTHER PUBLICATIONS

Calvi, et al. "Osteoblastic cells regulate the haematopoietic stem cell niche," Nature 425, 841-846 (2003).
Chen, et al. "Hoxb5 marks long-term haematopoietic stem cells and reveals a homogenous perivascular niche," Nature 530, 223-227 (2016).
Dacic, et al. "Col1a1-driven transgenic markers of osteoblast lineage progression," J Bone Miner Res 16, 1228-1236 (2001).
Ding & Morrison "Haematopoietic stem cells and early lymphoid progenitors occupy distinct bone marrow niches," Nature 495, 231-235 (2013).
Ding, et al. "Endothelial and perivascular cells maintain haematopoietic stem cells," Nature 481, 457-462 (2012).
Dominici, et al. "Restoration and reversible expansion of the osteoblastic hematopoietic stem cell niche after marrow radioablation," Blood 114, 2333-2343 (2009).
Fleming, et al. "Functional heterogeneity is associated with the cell cycle status of murine hematopoietic stem cells," The Journal of cell biology 122, 897-902 (1993).
Foudi, et al. "Analysis of histone 2B-GFP retention reveals slowly cycling hematopoietic stem cells," Nature biotechnology (2008).
Gazit, et al. "Fgd5 identifies hematopoietic stem cells in the murine bone marrow," The Journal of experimental medicine 211, 1315-1331 (2014).
Greenbaum, et al. "CXCL12 in early mesenchymal progenitors is required for haematopoietic stem-cell maintenance," Nature 495, 227-230 (2013).
Haug, et al. "N-cadherin expression level distinguishes reserved versus primed states of hematopoietic stem cells," Cell stem cell 2, 367-379 (2008).
Hooper, et al. "Engraftment and reconstitution of hematopoiesis is dependent on VEGFR2-mediated regeneration of sinusoidal endothelial cells," Cell Stem Cell 4, 263-274 (2009).
Itkin, et al. "Corrigendum: Distinct bone marrow blood vessels differentially regulate haematopoiesis," Nature 538, 274 (2016).
Kiel, et al. "SLAM family receptors distinguish hematopoietic stem and progenitor cells and reveal endothelial niches for stem cells," Cell 121, 1109-1121 (2005).
Kunisaki, et al. "Arteriolar niches maintain haematopoietic stem cell quiescence," Nature (2013).
Lerner and Harrison, "5-Fluorouracil spares hemopoietic stem cells responsible for longterm repopulation," Experimental hematology 18, 114-118 (1990).
Longley, et al. "5-fluorouracil: mechanisms of action and clinical strategies," Nature reviews Cancer 3, 330-338 (2003).
Walter, et al. "Exit from dormancy provokes DNA-damage-induced attrition in haematopoietic stem cells," Nature 520, 549-552 (2015).
Mendelson and Frenette, "Hematopoietic stem cell niche maintenance during homeostasis and regeneration," Nat Med 20, 833-846 (2014).
Mendez-Ferrer, et al. "Mesenchymal and haematopoietic stem cells form a unique bone marrow niche," Nature 466, 829-834 (2010).
Morita, et al. "Heterogeneity and hierarchy within the most primitive hematopoietic stem cell compartment," The Journal of experimental medicine 207, 1173-1182.
Nilsson, et al. "Spatial localization of transplanted hemopoietic stem cells: inferences for the localization of stem cell niches," Blood 97, 2293-2299 (2001).
Park, et al. "Association of Lbc Rho guanine nucleotide exchange factor with alpha-catenin-related protein, alpha-catulin/CTNNAL1, supports serum response factor activation," The Journal of biological chemistry 277, 45361-45370 (2002).
Qian, et al. "The Dlk1-Gtl2 Locus Preserves LT-HSC Function by Inhibiting the PI3K-mTOR Pathway to Restrict Mitochondrial Metabolism," Cell stem cell (2015).
Raghunath, et al. "Advancing cartilage tissue engineering: the application of stem cell technology," Current opinion in biotechnology 16, 503509 (2005).
Rodina, et al. "The epichaperome is an integrated chaperome network that facilitates tumour survival," Nature 538, 397-401 (2016).
Sanjuan-Pla, et al. "Platelet-biased stem cells reside at the apex of the haematopoietic stem-cell hierarchy," Nature (2013).
Scadden, "Nice Neighborhood: Emerging Concepts of the Stem Cell Niche. Cell /57, 41-50. Schofield, R. (1978). The relationship between the spleen colony-forming cell and the haemopoietic stem cell," Blood Cells 4, 7-25 (2014).
Sophia Fox, et al. "The basic science of articular cartilage: structure, composition, and function.," Sports Health 1(6), 461-468 (2009).
Sugimura, et al. "Noncanonical Wnt signaling maintains hematopoietic stem cells in the niche," Cell 150, 351-365 (2012).
Sugiyama, et al. "Maintenance of the hematopoietic stem cell pool by CXCL12-CXCR4 chemokine signaling in bone marrow stromal cell niches," Immunity 25, 977988 (2006).
Takubo, et al. "Regulation of glycolysis by pdk functions as a metabolic checkpoint for cell cycle quiescence in hematopoietic stem cells," Cell stem cell 3;12, 49-61 (2013).
Venkatraman, et al. "Maternal-imprinting at H19-Igf2 locus maintains adult hematopoietic stem cell quiescence," Nature 500, 345-349 (2013).
Wagers and Weissman Differential expression of {alpha}2 integrin separates long-term and short-term reconstituting Lin-/loThy1.1loc-kit+Sca-1+ hematopoietic stem cells. Stem cells (Dayton, Ohio) 24(4):1087-94.
Tirumuru, et al. "N6-methyladenosine of HIV-1 RNA regulates viral infection and HIV-1 Gag protein expression," eLife Microbilogy and Infectious Disease Jul. 2, 2016 vol. 5, No. e15528.
Wilson, et al. "Hematopoietic Stem Cells Reversibly Switch from Dormancy to Self-Renewal during Homeostasis and Repair," Cell 135, 1118-1129 (2008).
Xie, et al. "Detection of functional haematopoietic stem cell niche using real-time imaging," Nature 457, 97-101 (2009).
Yamazaki, et al. "Nonmyelinating schwann cells maintain hematopoietic stem cell hibernation in the bone marrow niche," Cell 147, 1146-1158 (2011).
Yang, et al. "Osteogenic fate of hypertrophic chondrocytes," Cell research 24, 1266-1269 (2014).
Yang, et al. "Identification of Lin(-)Sca1(+)kit(+)CD34(+)Flt3-short-term hematopoietic stem cells capable of rapidly reconstituting and rescuing myeloablated transplant recipients," Blood 105, 2717-2723 (2005).
Zhang, et al. "Identification of the haematopoietic stem cell niche and control of the niche size," Nature 425, 836-841 (2003).
Zhao, et al. "Megakaryocytes maintain homeostatic quiescence and promote post-injury regeneration of hematopoietic stem cells," Nat Med 20, 1321-1326 (2014).
Zhou, et al. "Bone marrow adipocytes promote the regeneration of stem cells and haematopoiesis by secreting SCF," Nature cell biology 19(8), 891-903 (2017).
Morrison and Scadden, "The bone marrow niche for haematopoietic stem cells," Nature 505, 327-334 (2014).
PCT/US2018/055092 Search Report and Written Opinion dated Mar. 22, 2019.
Li, et al. "Suppression of m6A reader Ythdf2 promotes hematopoietic stem cell expansion," Cell Research vol. 28, No. 9, Jul. 3, 2018 pp. 904-914.
Extended European Search Report for Application No. 18866285.2 dated Jun. 16, 2021.
Hsieh, et al. "miR-146a-5p circuitry uncouples cell proliferation and migration, but not differentiation, in human mesenchymal stem cells," Nucleic Acids Research, 2013, vol. 41, No. 21, p. 9753-9763.
Li & Clevers "Coexistence of quiescent and active adult stem cells in mammals," Science 327, 542-545 (2010).
Weissman, I. L. "Stem cells: units of development, units of regeneration, and units in evolution," Cell 100, 157-168 (2000).
Walasek, et al. "Hematopoietic stem cell expansion: challenges and opportunities," Annals of the New York Academy of Sciences 1266, 138-150 (2012).
Sung & Chao, "Concise review: acute graft-versus-host disease: immunobiology, prevention, and treatment," Stem cells translational medicine 2, 25-32 (2013).

(56) References Cited

OTHER PUBLICATIONS

Shlomchik, W. D. "Graft-versus-host disease," Nature reviews. Immunology 7, 340-352 (2007).
Huang, et al. "Activation of OCT4 enhances ex vivo expansion of human cord blood hematopoietic stem and progenitor cells by regulating HOXB4 expression," Leukemia 30, 144-153 (2016).
Boitano, et al. "Aryl hydrocarbon receptor antagonists promote the expansion of human hematopoietic stem cells," Science 329, 1345-1348 (2010).
Fares, et al. "Pyrimidoindole derivatives are agonists of human hematopoietic stem cell self-renewal," Science (New York, N. Y 345, 1509-1512 (2014).
Amsellem, et al. "Ex vivo expansion of human hematopoietic stem cells by direct delivery of the HOXB4 homeoprotein," Nature medicine 9, 1423-1427 (2003).
Antonchuk, et al. "HOXB4-induced expansion of adult hematopoietic stem cells ex vivo," Cell 109, 39-45 (2002).
Rentas, et al. "Musashi-2 attenuates AHR signalling to expand human haematopoietic stem cells," Nature 532, 508-511 (2016).
Himburg, et al. "Pleiotrophin regulates the expansion and regeneration of hematopoietic stem cells," Nature medicine 16, 475-482 (2010).
North, et al. "Prostaglandin E2 regulates vertebrate haematopoietic stem cell homeostasis," Nature 447, 1007-1011 (2007).
Varnum-Finney, et al. "Pluripotent, cytokine-dependent, hematopoietic stem cells are immortalized by constitutive Notch1 signaling," Nature medicine 6, 1278-1281 (2000).
Chou, et al. "Fetal hepatic progenitors support long-term expansion of hematopoietic stem cells," Experimental hematology 41, 479-490 e474 (2013).
Guo, et al. "Antagonism of PPAR-gamma signaling expands human hematopoietic stem and progenitor cells by enhancing glycolysis," Nature medicine 24, 360-367 (2018).
Zhao, et al. "Post-transcriptional gene regulation by mRNA modifications," Nature reviews. Molecular cell biology 18, 31-42 (2017).
Roundtree, et al. "Dynamic RNA Modifications in Gene Expression Regulation," Cell 169, 1187-1200 (2017).
Li & Mason "The pivotal regulatory landscape of RNA modifications," Annual review of genomics and human genetics 15, 127-150 (2014).
Batista, et al. "m(6)A RNA modification controls cell fate transition in mammalian embryonic stem cells," Cell stem cell 15, 707-719 (2014).
Geula, et al. "Stem cells. m6A mRNA methylation facilitates resolution of naive pluripotency toward differentiation," Science 347, 1002-1006 (2015).
Yoon, et al. "Temporal Control of Mammalian Cortical Neurogenesis by m6A Methylation," Cell 171, 877-889 (2017).
Zhang, et at. "m6A modulates haematopoietic stem and progenitor cell specification," Nature 549, 273-276 (2017).
Zhao, et al. "m6A-dependent maternal mRNA clearance facilitates zebrafish maternal-to-zygotic transition," Nature 542, 475-478 (2017).
Li, et at. "FTO Plays an Oncogenic Role in Acute Myeloid Leukemia as a N6-Methyladenosine RNA Demethylase," Cancer cell 31, 127-141 (2017).
Vu, et al. "The N6-methyladenosine (m6A)-forming enzyme METTL3 controls myeloid differentiation of normal hematopoietic and leukemia cells," Nature medicine 23, 1369-1376 (2017).
Weng, et al. "METTL14 Inhibits Hematopoietic Stem/Progenitor Differentiation and Promotes Leukemogenesis via mRNA m(6)A Modification," Cell stem cell 22, 191-205 e199 (2018).

Barbieri, et al. "Promoter-bound METTL3 maintains myeloid leukaemia by m(6)A-dependent translation control," Nature 552, 126-131 (2017).
Wang, et al. "N6-methyladenosine-dependent regulation of messenger RNA stability," Nature 505, 117-120 (2014).
Meyer, et al. "Comprehensive analysis of mRNA methylation reveals enrichment in 3' UTRs and near stop codons," Cell 149, 1635-1646 (2012).
Schwartz, et al. "High-resolution mapping reveals a conserved, widespread, dynamic mRNA methylation program in yeast meiosis," Cell 155, 1409-1421 (2013).
Dominissini, et al. "Topology of the human and mouse m6A RNA methylomes revealed by m6A-seq," Nature 485, 201-206 (2012).
Wang, et al. "Conditional deletion of STAT5 in adult mouse hematopoietic stem cells causes loss of quiescence and permits efficient nonablative stem cell replacement," Blood 113, 4856-4865 (2009).
Ebina, et al. "Transcription factor-mediated reprogramming toward hematopoietic stem cells," The EMBO journal 34, 694-709 (2015).
Orkin & Zon, "Hematopoiesis: an evolving paradigm for stem cell biology," Cell 132, 631-644 (2008).
De Pater, et al., "Gata2 is required for HSC generation and survival," The Journal of experimental medicine 210, 2843-2850 (2013).
Hock, et al. "Tel/Etv6 is an essential and selective regulator of adult hematopoietic stem cell survival," Genes & development 18, 2336-2341 (2004).
Lim, et at. "Conditional Gata2 inactivation results in HSC loss and lymphatic mispatterning," The Journal of clinical investigation 122, 3705-3717 (2012).
Reynaud, et al. "SCL/TAL1 expression level regulates human hematopoietic stem cell self-renewal and engraftment," Blood 106, 2318-2328 (2005).
Kato, et al. "Selective activation of STAT5 unveils its role in stem cell self-renewal in normal and leukemic hematopoiesis," The Journal of experimental medicine 202, 169-179 (2005).
Li, et al. "m6A mRNA methylation controls T cell homeostasis by targeting the IL-7/STAT5/SOCS pathways," Nature 548, 338-342 (2017).
Pinto do O, et al. "Expression of the LIM-homeobox gene LH2 generates immortalized steel factor-dependent multipotent hematopoietic precursors," The EMBO journal 17, 5744-5756 (1998).
Zarnegar, et al. "irCLIP platform for efficient characterization of protein-RNA interactions," Nature methods 13, 489-492 (2016).
Sheth & Parker, et al. "Decapping and decay of messenger RNA occur in cytoplasmic processing bodies," Science 300, 805-808 (2003).
Kedersha & Anderson, "Mammalian stress granules and processing bodies," Methods in enzymology 431, 61-81 (2007).
Lacombe, et al. "Scl regulates the quiescence and the long-term competence of hematopoietic stem cells," Blood 115, 792-803 (2010).
Galan-Caridad, J. M. et al. Zfx controls the self-renewal of embryonic and hematopoietic stem cells. Cell 129, 345-357 (2007).
Zheng, et al. "ALKBH5 is a mammalian RNA demethylase that impacts RNA metabolism and mouse fertility," Molecular cell 49, 18-29 (2013).
Zhou, et al. "Dynamic m(6)A mRNA methylation directs translational control of heat shock response," Nature 526, 591-594 (2015).
Alarcon, et al. "HNRNPA2B1 Is a Mediator of m(6)A-Dependent Nuclear RNA Processing Events," Cell 162, 1299-1308 (2015).
Zhang, et al. "RNA epigenetic modification: N6-methyladenosine," Hereditas, 38(4):275-288, Apr. 2016.

* cited by examiner

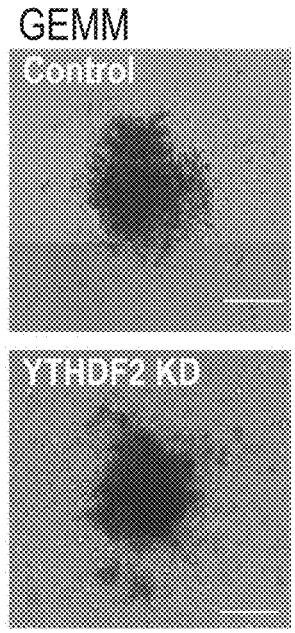
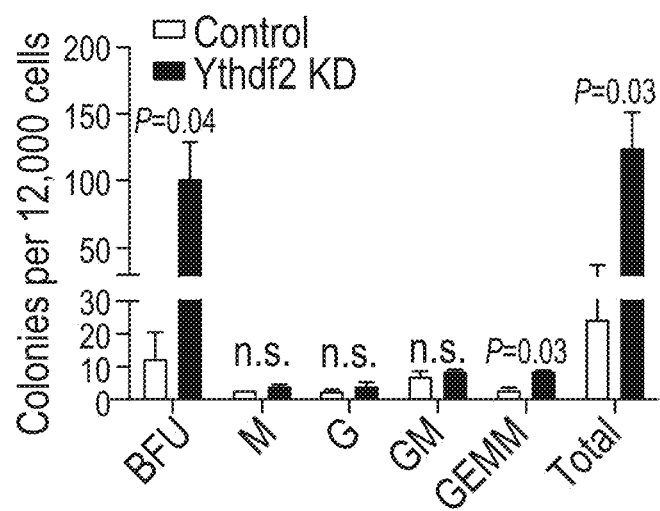
FIG. 5C
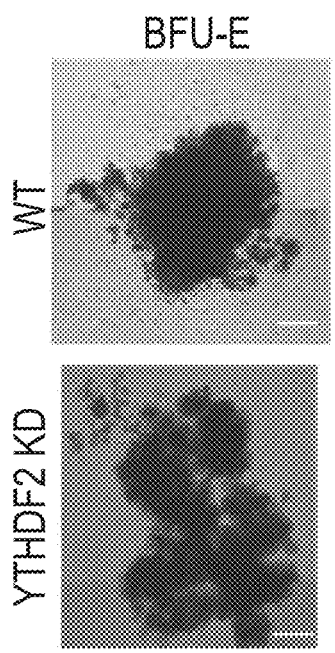
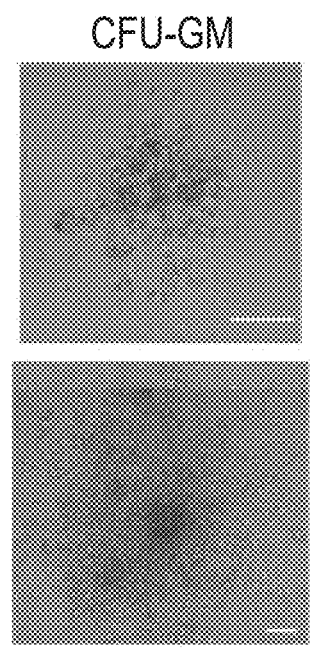
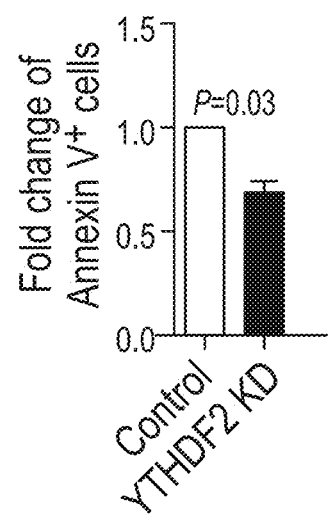
FIG. 5D
FIG. 5E

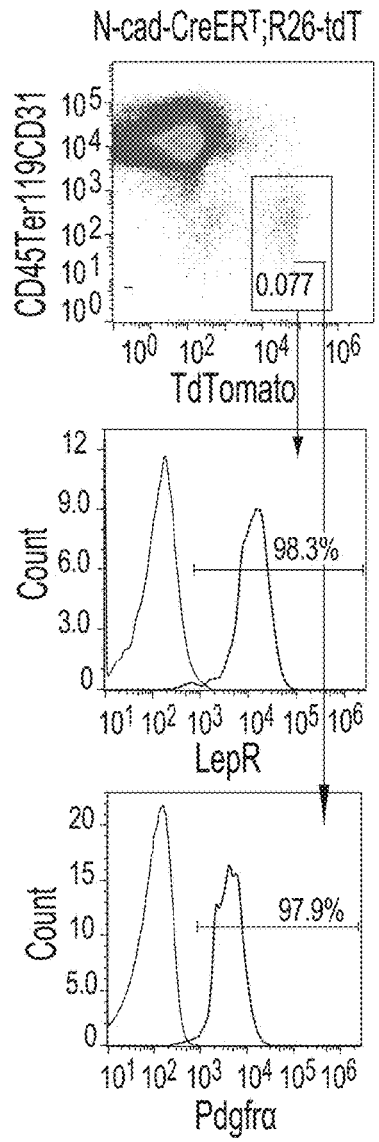
FIG. 20J
| Stromal cell population | Cell dose | CFU-F colony per well | CFU-F frequency |
|---|---|---|---|
| N-cad-TdT(B) | 1<br>5<br>10 | 4/32<br>12/32<br>12/16 | 1 in 8.79 |
| LepR | 1<br>5<br>10 | 1/8<br>17/40<br>25/40 | 1 in 9.7 |
| NG2-RFP | 1<br>5<br>10 | 1/2<br>4/5<br>4/7 | 1 in 6.72 |
| Nestin-GFP | 1<br>5<br>10 | 0/8<br>8/40<br>19/40 | 1 in 17.6 |
| N-cad-CreERT(B) | 1<br>5<br>10 | 2/32<br>12/32<br>20/32 | 1 in 10.7 |
| N-cad-CreERT(M) | 1<br>5<br>10 | 1/8<br>18/40<br>31/40 | 1 in 7.37 |
FIG. 20K
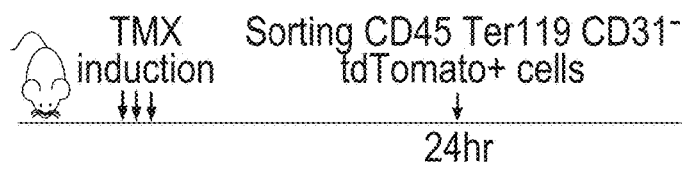
FIG. 21A

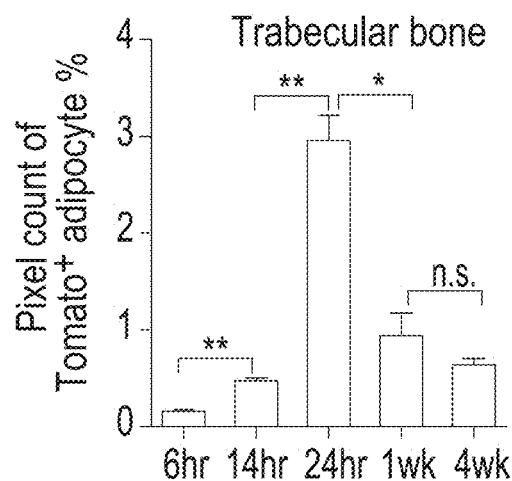 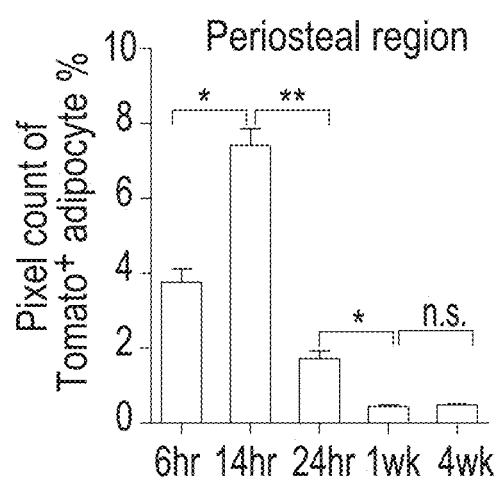
FIG. 22J     FIG. 22K
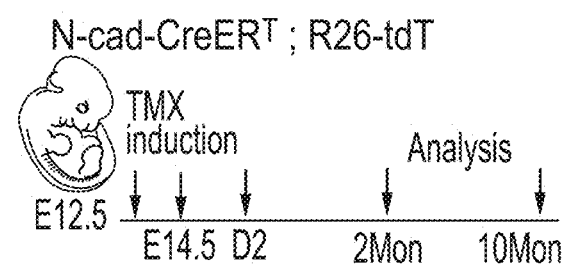
FIG. 23A

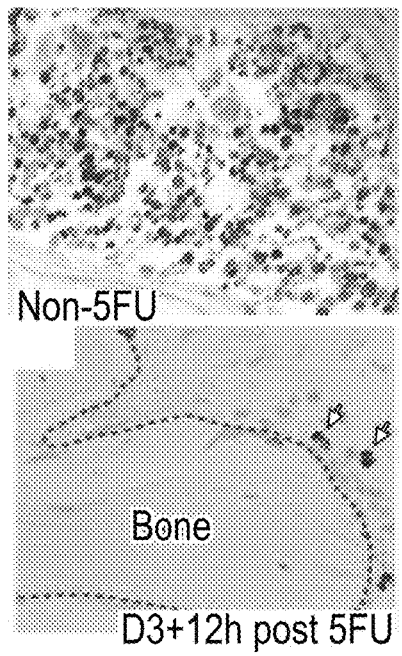
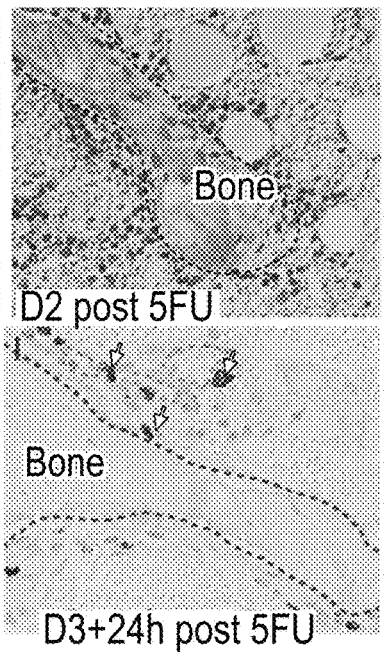
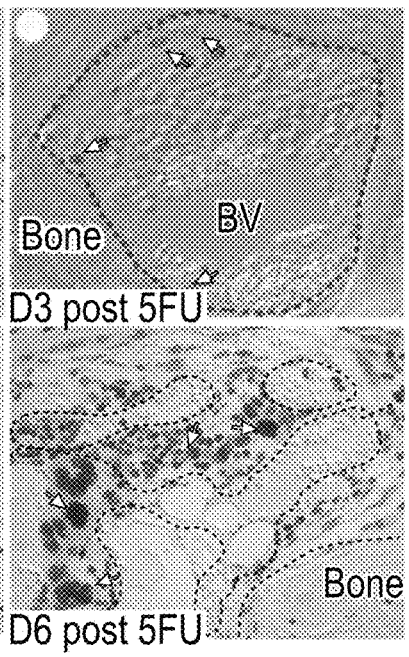
FIG. 24A     FIG. 24B     FIG. 24C
FIG. 24D     FIG. 24E     FIG. 24F

SEQUENCE LISTING

<160> NUMBER OF SEQ ID NOS: 19

<210> SEQ ID NO 1
<211> LENGTH: 10
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t

<400> SEQUENCE: 1 vahmmcaaan                                                          10

<210> SEQ ID NO 2
<211> LENGTH: 29
<212> TYPE: DNA
<213> ORGANISM: Artificial Sequence
<220> FEATURE:

<223> OTHER INFORMATION: synthetic construct

<400> SEQUENCE: 2
cgcggatcct cggccagcag cctcttgga                                  29

<210> SEQ ID NO 3
<211> LENGTH: 38
<212> TYPE: DNA
<213> ORGANISM: Artificial Sequence
<220> FEATURE:
<223> OTHER INFORMATION: synthetic construct

<400> SEQUENCE: 3
ataagaatgc ggccgcctat ttcccacgac cttgacgt                        38

<210> SEQ ID NO 4
<211> LENGTH: 42
<212> TYPE: DNA
<213> ORGANISM: Artificial Sequence
<220> FEATURE:
<223> OTHER INFORMATION: synthetic construct

<400> SEQUENCE: 4
gtcgacggta ccgcgggccc atggattaca aggatgacga cg                   42

<210> SEQ ID NO 5
<211> LENGTH: 42
<212> TYPE: DNA
<213> ORGANISM: Artificial Sequence
<220> FEATURE:
<223> OTHER INFORMATION: synthetic construct

<400> SEQUENCE: 5
gagggagagg ggcggatccc ctatttccca cgaccttgac gt                   42

<210> SEQ ID NO 6
<211> LENGTH: 27
<212> TYPE: DNA
<213> ORGANISM: Artificial Sequence
<220> FEATURE:
<223> OTHER INFORMATION: synthetic construct

<400> SEQUENCE: 6
cgttcgaaat gtcggccagc agcctct                                    27

<210> SEQ ID NO 7
<211> LENGTH: 26
<212> TYPE: DNA
<213> ORGANISM: Artificial Sequence
<220> FEATURE:
<223> OTHER INFORMATION: synthetic construct

<400> SEQUENCE: 7
tcccccgggt tatttcccac gacctt                                     26

<210> SEQ ID NO 8
<211> LENGTH: 21
<212> TYPE: DNA
<213> ORGANISM: Artificial Sequence
<220> FEATURE:
<223> OTHER INFORMATION: synthetic construct

<400> SEQUENCE: 8
aaggacgttc ccaatagcca a                                          21

```
<210> SEQ ID NO 9
<211> LENGTH: 19
<212> TYPE: DNA
<213> ORGANISM: Artificial Sequence
<220> FEATURE:
<223> OTHER INFORMATION: synthetic construct

<400> SEQUENCE: 9
gcgcgatagc gctaataat                                            19

<210> SEQ ID NO 10
<211> LENGTH: 21
<212> TYPE: DNA
<213> ORGANISM: Artificial Sequence
<220> FEATURE:
<223> OTHER INFORMATION: synthetic construct

<400> SEQUENCE: 10
cgctgctcta tagccttagc c                                         21

<210> SEQ ID NO 11
<211> LENGTH: 20
<212> TYPE: DNA
<213> ORGANISM: Artificial Sequence
<220> FEATURE:
<223> OTHER INFORMATION: synthetic construct

<400> SEQUENCE: 11
ctcttcaccc ggttgttgtt                                           20

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
caacccttac tacgccaacc                                           20

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13
gctgtgcaac aagtgtggtc                                           20

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
ccagcctctc tgcagaactt                                           20

<210> SEQ ID NO 15
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 15
ggagatggac ggcagagtag                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic construct

<400> SEQUENCE: 16
agaagcaagt gtccctggag                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
gtcgtccagg atgatggtct                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
tgtcaccaac tgggacgata                                               20

<210> SEQ ID NO 19
<211> LENGTH: 20
<212> TYPE: DNA
<213> ORGANISM: Artificial Sequence
<220> FEATURE:
<223> OTHER INFORMATION: synthetic construct

<400> SEQUENCE: 19
accctcatag atgggcacag                                               20
```

METHODS AND COMPOSITIONS FOR EXPANSION OF CELL POPULATION

CROSS REFERENCE TO RELATED APPLICATIONS

The present application is the National Stage of International Application No. PCT/US2018/055092, filed on Oct. 9, 2018, which claims benefit to U.S. Provisional Patent Application No. 62/570,076, filed Oct. 9, 2017, and U.S. Provisional Patent Application No. 62/695,820, filed Jul. 9, 2018. The entire contents of the above applications are incorporated by reference as if recited in full herein.

FIELD OF THE INVENTION

The present invention relates to methods and compositions for expanding a cell population, and particularly stem cell populations such as a hematopoietic stem cell population.

INCORPORATION BY REFERENCE OF SEQUENCE LISTING

This application contains references to amino acids and/or nucleic acid sequences that have been filed concurrently herewith as sequence listing text file "1065334.000151-seq.txt", file size of 4,097 bytes, created on Nov. 25, 2024. The aforementioned sequence listing is hereby incorporated by reference in its entirety pursuant to 37 C.F.R. § 1.52(e)(5).

BACKGROUND

Hematopoietic stem cells (HSCs) are clonogenic cells, which possess the properties of both self-renewal (expansion) and multilineage potential giving rise to all types of mature blood cells. HSCs are responsible for hematopoiesis and undergo proliferation and differentiation to produce mature blood cells of various lineages while still maintaining their capacity for self-renewal. The ability to self-renew maintains the HSC population for the lifespan of an animal and also allows HSCs to repopulate the bone marrow of lethally irradiated congenic hosts.

Early HSC development displays a hierarchical arrangement, starting from long-term (LT-) HSCs, which have extensive self-renewal capability, followed by the expansion state, which corresponds to short-term (ST-) HSCs (having limited self-renewal ability) and proliferative multipotent progenitors (MPPs) (having multipotent potential but no self-renewal capability). MPP is also a stage of priming or preparation for differentiation. An MPP differentiates and commits to become either a common lymphoid progenitor (CLP), which gives rise to all the lymphoid lineages, or a common myeloid progenitor (CMP), which produces all the myeloid lineages. During this process, the more primitive population gives rise to a less primitive population of cells, which is unable to give rise to a more primitive population of cells. The intrinsic genetic programs that control these processes including the multipotential, self-renewal, and activation (or transient amplification) of HSCs, and lineage commitment from MPP to CLP or CMP, remain largely unknown.

To sustain constant generation of blood cells for the lifetime of an individual, HSCs located in bone marrow niches (Zhang, J. et al. *Nature* 425, 836-841, 2003; Calvi, L. M. et al. *Nature* 425, 841-846, 2003; Kiel, M. J., et al. *Cell* 121, 1109-1121, 2005; Arai, F. et al. *Cell* 118, 149-161, 2004) must achieve a balance between quiescence and activation so that immediate demands for hematopoiesis are fulfilled, while long-term stem cell maintenance is also assured. In adults, homeostasis between the quiescent and activated states of stem cells is important to protect HSCs from losing their potential for self-renewal and, at the same time, support ongoing tissue regeneration (Li, L. and Xie, T. *Annu. Rev. Cell. Dev. Biol.* 21, 605-631, 2005). Over-activation and expansion of stem cells risks both eventual depletion of the stem cell population and a predisposition to tumorigenesis. Although some factors important for stem cell activation have been identified (Heissig, B. et al. *Cell* 109, 625-637, 2002), the molecular events governing the transition between quiescence and activation are poorly understood.

HSCs are responsible for life-long hematopoiesis under homeostatic and stress conditions, which relies on an exquisite balance between stem cell self-renewal and differentiation (Li et al. *Science*, 327: 542-545, 2010; Weissman et al. *Cell*, 100: 157-168, 2000). Thus, HSC transplantation is a life-saving therapy for a broad spectrum of disorders, including hematologic, immune, and genetic diseases, as well as cancers (Walasek et al. *Annals of the New York Academy of Sciences* 1266: 138-150, 2012). However, HSC-based treatment can be limited primarily by the lack of HLA-matched donor bone marrow (BM). Allogeneic transplantation offers an alternative approach, but graft vs host disease (GvHD) remains a life-time challenge, since taking immune suppression medicine has numerous side effects, such as delayed immunological recovery, thrombotic microangiopathy (Sung et al. *Stem Cells Translational Medicine*, 2: 25-32 (2013); Shlomchik et al. *Nature Reviews. Immunology*, 7: 340-352, 2007). Transplantation of HSCs from hUCB reduces the risk of GvHD; however, the lower number of HSCs in hUCB than in BM or mobilized peripheral blood limits its application (Walasek et al. *Annals of the New York Academy of Sciences*, 1266: 138-150, 2012). Targeting single molecules or pathways has been studied for hUCB HSC expansion (Huang et al. *Leukemia*, 30: 144-153, 2016; Boitano et al. *Science*, 329: 1345-1348, 2010; Fares et al. *Science*, 345; 1509-1512, 2014; Ansellem et al. *Nature Medicine*, 9: 1423-1427, 2003; Antonchuk et al. *Cell*, 109: 39-45, 2002; Rentas et al. *Nature*, 532: 508-511, 2016; Himburg et al. *Nature Medicine*, 16: 475-482, 2010; North et al. *Nature*, 447: 1007-1011, 2007; Guo et al. *Nature Medicine*, 2018); Varnum-Finney et al. *Nature Medicine*, 6: 1278-1281, 2000; and Chou et al. *Experimental Hematology*, 41: 479-490 e474, 2013). However, other approaches are sought in order to relatively favor stem cell self-renewal versus differentiation (Zhao et al. *Molecular Cell Biology*, 18: 31-42, 2017).

$m^6A$ is a prevalent internal modification in mRNAs that regulates the outcome of gene expression by modulating RNA processing, localization, translation, and eventual decay, which is modulated by "writers," "erasers" and "readers" of the mark (Roundtree et al. *Cell*, 169: 1187-1200, 2017; Li et al. *Annual Review of Genomics and Human Genetics*, 15: 127-150, 2014). Recent studies have elucidated the roles of $m^6A$ modification in stem cell fate determination and endothelial-to-hematopoietic transition during embryogenesis (Batista et al. *Cell Stem Cell*, 15: 707-719, 2014; Geula et al. *Science*, 347: 1002-1006, 2015; Yoon et al. *Cell*, 2017; Zhang et al. *Nature*, 549: 273-276, 2017; Zhao et al. *Nature*, 542: 475-478, 2017) as well as in leukemia development (Li et al. *Cancer Cell*, 31: 127-141, 2017; Vu et al. *Nature Medicine*, 2017; Barbieri et al.

Nature, 2017; Weng et al. *Cell Stem Cell*, 22: 191-205 e199, 2018). Interestingly, deficiency in m⁶A writer complex, Mettl3 and Mettl14, leads to distinct outcomes in different types of stem cells. For example, Mettl3 or Mettl14 KO promoted differentiation in HSCs (Vu et al. *Nature Medicine*, 2017; Weng et al. *Cell Stem Cell*, 22: 191-205 e199, 2018; Barbieri et al. *Nature*, 2017) while resulting in enhanced stem cell self-renewal and maintenance in mouse embryonic stem cells (mESCs) and embryonic neuronal stem cells (NSCs) (Batista et al. *Cell Stem Cell*, 15: 707-719, 2014; Yoon et al. *Cell*, 2017). Besides, the physiological function of m⁶A in stem cells and leukemia are mediated through different mechanisms. In stem cells, m⁶A modifications regulate stem cell fate determination by m⁶A-mediated decay of mRNAs encoding stem cell fate determinant (Batista et al. *Cell Stem Cell*, 15: 707-719, 2014; Yoon et al. *Cell*, 2017) while in acute myeloid leukemia (AML), Mettl3 and Mettl14 promote leukemogenesis as m⁶A modifications stabilize the mRNAs of oncogenes and/or increase their translation (Vu et al. *Nature Medicine*, 2017; Barbieri et al. *Nature*, 2017; Weng et al. *Cell Stem Cell*, 22: 191-205 e199, 2018). Furthermore, previous studies have reported that the leukemogenic functions of FTO and Mettl14 are independent of YTHDF reader proteins (Li et al. *Cancer Cell*, 31: 127-141, 2017; Weng et al. *Cell Stem Cell*, 22: 191-205 e199, 2018).

As the m⁶A RNA modification is modulated by "writers," "erasers" and "readers" of the mark (Wang et al. *Nature*, 505(7481): 117-120, 2014), processes that install, recognize and remove this and other marks may have various implications for cellular, developmental, and disease processes. For example, studies have shown that the m⁶A mark may act as a key post-transcriptional modification to promote initiation of microRNA (miRNA) biogenesis (Alarcon et al. *Nature*, 519(7544): 482-485, 2015). Evidence also points to m⁶A RNA modifications possibly being involved in the differentiation of stem cells to specific lineages (Batista, *Cell stem Cell*, 15(6): 707-719, 2014; Zhang et al. *Nature*, 549(7671): 273-276, 2017), and in regulating gene expression (Dominissini et al., *Nature* 485(7397):201-206, 2012; Haussmann et al, *Nature* 540(7632): 301-304, 2016). A m⁶A transferase METTL3 has been identified as a regulator for terminating murine naïve pluripotency (Geula et al. *Science*, 347(6225): 1002-1006, 2015). The m⁶A "writer" protein METTL3 has also been demonstrated in mouse T cells to disrupt T cell homeostasis and differentiation (Li et al. *Nature*, 548(7667): 338-342, 2017), and m⁶A RNA methylation has been found to promote XIST-mediated transcriptional repression (Patil et al. *Nature*, 537(7620): 369-373, 2016). M⁶A RNA modifications have also been shown to regulate the ultraviolet-induced DNA damage response (Xiang et al. *Nature*, 543(7646): 573-576, 2017). Study of the maternal-to-zygotic transition (MZT) as in zebrafish also indicated a role for m⁶A mRNA methylation in transcriptome switching and animal development (Zhao et al. *Nature*, 542(7642): 475-478, 2017). Accordingly, while accumulative evidence has brought insights into the biological functions of m⁶A (Lence et al. *Nature*, 540 (7632); 242-247, 2016), the function of m⁶A in adult stems cells are largely unknown.

Hematopoietic stem cells (HSCs) in bone marrow (BM) maintain homeostasis hematopoiesis throughout life and also support regeneration after myeloablation (Weissman, 2000). Quiescent HSCs perform superiorly to proliferative HSCs in lethally irradiated mice, which largely attributes to the quiescent state that protects HSCs from DNA damage (Arai et al., 2004; Fleming et al., 1993; Wilson et al., 2008) (Walter et al., 2015). However, a recent study showed that DNA damage accumulation in HSCs was associated with broad attenuation of DNA repair and response pathways that were dependent upon HSC quiescence (Beerman et al., 2014). In fact, the majority of HSCs, despite their quiescence, are sensitive to DNA damage from chemotherapeutic drugs, such as 5-Fluorouracil (5FU) (Lerner and Harrison, 1990). The unresolved issue is how the hematopoietic system overcomes the consequence of myeloablation. In respect to the remarkable heterogeneity of HSCs during development and in adult (Benveniste et al., 2010; Benz et al., 2012; Fleming et al., 1993; Morita et al., 2010; Zhou et al., 2016), the existence of a reserve HSC (rHSC) subpopulation was proposed, with the features of drug-resistance and capacity to regenerate the bulk of HSCs to overcome stress-caused myeloablation (Haug et al., 2008; Li and Clevers, 2010; Wilson et al., 2008). Thus far, however, no functional evidence has been provided in supporting existence of rHSCs in the blood system.

HSCs are preserved in complex BM niches for their maintenance and regeneration (Li and Clevers, 2010; Mendelson and Frenette, 2014; Morrison and Scadden, 2014; Scadden, 2014; Schofield, 1978). In the past decades, multiple studies have uncovered the complexity of HSC bone marrow niche components, including: endosteal (inner bone surface) cells (Calvi et al., 2003; Zhang et al., 2003), sinusoidal endothelial cells (Hooper et al., 2009; Kiel et al., 2005), Cxcl12 abundant reticular (CAR) cells (Sugiyama et al., 2006), Nestin⁺ and NG2⁺ perivascular cells (Kunisaki et al., 2013; Mendez-Ferrer et al., 2010), LepR⁺ and Prx-1⁺ mesenchymal stem and progenitor cells (Ding and Morrison, 2013; Ding et al., 2012; Greenbaum et al., 2013), non-myelinating Schwann cells (Yamazaki et al., 2011), and megakaryocytes (Bruns et al., 2014; Zhao et al., 2014). However, whether and how the BM niche complexity contributes to HSC heterogeneity regulation remain largely unclear (Itkin et al., 2016). Furthermore, the first HSC niche was initially identified as the spindle shaped N-Cadherin⁺ (N-cad⁺) pre-osteoblastic cells in the endosteum of the trabecular bone region (Calvi et al., 2003; Xie et al., 2009; Zhang et al., 2003), but the nature and function of N-cad⁺ niche cells in BM remain unclear.

Accordingly, there remains a need for elucidation and understanding of the role of m⁶A and m⁶A mRNA pathways to provide insight into molecular regulation of stem cell proliferation and differentiation. There remains a further need for methods of expanding populations of stem cells, both in vivo and ex vivo, and methods of providing treatment with such expanded stem cell populations, such as via transplant into a suitable subject.

SUMMARY

In one embodiment of the present disclosure, a method for expanding a population of stem cells is provided, the population of stem cells being obtained from a tissue selected from the group consisting of peripheral blood, cord blood and bone marrow. The method includes modulating a N-Methyladenosine (m⁶A) mRNA modification pathway in the population of stem cells, to expand the number of stem cells.

In yet another embodiment, a method for ex vivo expansion of a substantially undifferentiated stem cell population is provided, comprising modulating a N⁶-Methyladenosine (m⁶A) mRNA modification pathway in the undifferentiated stem cell population to expand the number of undifferentiated stem cells without significant differentiation of the stem cell population.

According to yet another embodiment, a method for ex vivo expansion of an hematopoietic stem cell (HSC) population is provided, the HSC population being obtained from a tissue selected from the group consisting of peripheral blood, cord blood, and bone marrow, the method comprising modulating a $N^6$-Methyladenosine ($m^6A$) mRNA modification pathway in the HSC population to expand the HSC population to a sufficient quantity while maintaining a multilineage differentiation potential in the HSC population, which is sufficient for subsequent transplantation into a subject in need thereof.

According to yet another embodiment, a method for ex vivo expansion of hematopoietic stem cells (HSCs) by at least 2-fold is provided, the expanded HSCs being competent to reconstitute an HSC lineage upon transplantation into a mammal in need thereof, the method comprising introducing a mutation into the stem cells that results in deletion, replacement or reduced expression of a gene expressing a $m^6A$ mRNA modification reader and culturing the population of HSCs in a suitable culture medium.

According to a further embodiment, a kit for expanding an hematopoietic stem cell population (HSC) population for subsequent transplantation into a subject in need thereof is provided, the kit comprising a system for introducing a mutation into the HSC population that results in deletion, replacement or reduced expression of a gene expressing a $m^6A$ mRNA modification reader, and instructions for use thereof.

According to yet another embodiment, a kit for expanding an hematopoietic stem cell population (HSC) population for subsequent transplantation into a subject in need thereof is provided, the kit comprising an inhibitor of a $m^6A$ mRNA modification reader, and instructions for use thereof.

In yet a further embodiment, a method for administering an hematopoietic stem cell (HSC) to a subject in need thereof is provided, the method comprising: (a) introducing, into a sample containing an HSC population, a mutation that results in deletion, replacement or reduced expression of a gene expressing a $m^6A$ mRNA modification reader; (b) culturing the sample in a suitable culture media for a period of time sufficient to expand the number of HSCs in the sample to a number sufficient to transplant into the subject; and (c) administering the HSCs to the subject.

In yet a further embodiment, a method for administering an hematopoietic stem cell (HSC) to a subject in need thereof is provided, the method comprising: (a) culturing, in a suitable culture media, a sample containing an HSC population in the presence of an inhibitor of a $m^6A$ mRNA modification reader, for a period of time sufficient to expand the number of HSCs in the sample to a number sufficient to transplant into the subject; (b) removing from the culture the inhibitor of the $m^6A$ mRNA modification reader; and (c) administering the HSCs to the subject.

In another embodiment, a method for reconstituting bone marrow in a subject in need thereof is provided, comprising: (a) introducing, into a sample containing an HSC population, a mutation that results in deletion, replacement or reduced expression of a gene expressing a $m^6A$ mRNA modification reader; (b) culturing the sample in a suitable culture media for a period of time sufficient to expand the number of HSCs in the sample to a number sufficient to transplant into the subject; and (c) administering the HSCs to the subject.

In another embodiment, a method for reconstituting bone marrow in a subject in need thereof is provided, comprising: (a) culturing, in a suitable culture media, a sample containing an HSC population in the presence of an inhibitor of a $m^6A$ mRNA modification reader, for a period of time sufficient to expand the number of HSCs in the sample to a number sufficient to transplant into the subject; (b) removing from the culture the inhibitor of the $m^6A$ mRNA modification reader; and (c) administering the HSCs to the subject.

In one embodiment, a method for expanding a population of hematopoietic cells (HSCs) comprising culturing the population of HSCs under conditions sufficient to result in an expansion of the HSC population by at least 2-fold is provided, wherein the expanded population of HSCs is suitable for transplantation into a mammal in need thereof.

In a further embodiment, a method for expanding a population of hematopoietic stem cells (HSCs) is provided, comprising: (a) obtaining from a mammal a tissue sample comprising an HSC population; (b) expanding, in vitro, the HSC population from the sample, wherein: (i) the HSC population expands by at least 2-fold; and (ii) the expanded HSC population has at least a 5-fold increase in total colony-forming units.

In a further embodiment, a method for reconstituting a hematopoietic stem cell lineage in a subject in need thereof is provided, the method comprising: (a) obtaining from a mammal a tissue sample comprising an HSC population; (b) expanding, in vitro, the HSC population from the sample, wherein: (i) the HSC population expands by at least 2-fold; and (ii) the expanded HSC population has at least a 5-fold increase in total colony-forming units; and (c) transplanting the expanded HSC population into a subject in need thereof.

In yet another embodiment, a method for expanding a hematopoietic stem cell population in a mammal in need of such expansion is provided, comprising administering to the mammal a therapeutically effective amount of a modulator of a $N^6$-Methyladenosine ($m^6A$) mRNA modification pathway for a period of time sufficient to expand the HSC population by at least 2-fold with HSCs that possess the ability to reconstitute a hematopoietic lineage in the mammal.

According to yet another embodiment, a method for ex vivo expansion of a mesenchymal stem cell (MSC) population is provided, the MSC population being obtained from a tissue selected from the group consisting of peripheral blood, cord blood, and bone marrow, the method comprising modulating a $N^6$-Methyladenosine ($m^6A$) mRNA modification pathway in the MSC population to expand the MSC population to a sufficient quantity while maintaining a multilineage differentiation potential in the MSC population, which is sufficient for subsequent transplantation into a subject in need thereof.

According to yet another embodiment, a method for ex vivo expansion of mesenchymal stem cells (MSCs) by at least 2-fold is provided, the expanded MSCs being competent to reconstitute a MSC lineage upon transplantation into a mammal in need thereof, the method comprising introducing a mutation into the stem cells that results in deletion, replacement or reduced expression of a gene expressing a $m^6A$ mRNA modification reader and culturing the population of MSCs in a suitable culture medium.

According to a further embodiment, a kit for expanding a mesenchymal stem cell population (MSC) population for subsequent transplantation into a subject in need thereof is provided, the kit comprising a system for introducing a mutation into the MSC population that results in deletion, replacement or reduced expression of a gene expressing a m⁶A mRNA modification reader, and instructions for use thereof.

According to yet another embodiment, a kit for expanding an mesenchymal stem cell population (MSC) population for subsequent transplantation into a subject in need thereof is provided, the kit comprising an inhibitor of a m⁶A mRNA modification reader, and instructions for use thereof.

In yet a further embodiment, a method for administering a mesenchymal stem cell (MSC) to a subject in need thereof is provided, the method comprising: (a) introducing, into a sample containing a MSC population, a mutation that results in deletion, replacement or reduced expression of a gene expressing a m⁶A mRNA modification reader; (b) culturing the sample in a suitable culture media for a period of time sufficient to expand the number of MSCs in the sample to a number sufficient to transplant into the subject; and (c) administering the MSCs to the subject.

In yet a further embodiment, a method for administering a mesenchymal stem cell (MSC) to a subject in need thereof is provided, the method comprising: (a) culturing, in a suitable culture media, a sample containing a MSC population in the presence of an inhibitor of a m⁶A mRNA modification reader, for a period of time sufficient to expand the number of MSCs in the sample to a number sufficient to transplant into the subject; (b) removing from the culture the inhibitor of the m⁶A mRNA modification reader; and (c) administering the MSCs to the subject.

In another embodiment, a method for reconstituting bone marrow in a subject in need thereof is provided, comprising: (a) introducing, into a sample containing a MSC population, a mutation that results in deletion, replacement or reduced expression of a gene expressing a m⁶A mRNA modification reader; (b) culturing the sample in a suitable culture media for a period of time sufficient to expand the number of MSCs in the sample to a number sufficient to transplant into the subject; and (c) administering the MSCs to the subject.

In another embodiment, a method for reconstituting bone marrow in a subject in need thereof is provided, comprising: (a) culturing, in a suitable culture media, a sample containing a MSC population in the presence of an inhibitor of a m⁶A mRNA modification reader, for a period of time sufficient to expand the number of MSCs in the sample to a number sufficient to transplant into the subject; (b) removing from the culture the inhibitor of the m⁶A mRNA modification reader; and (c) administering the MSCs to the subject.

In one embodiment, a method for expanding a population of mesenchymal cells (MSCs) comprising culturing the population of MSCs under conditions sufficient to result in an expansion of the MSC population by at least 2-fold is provided, wherein the expanded population of MSCs is suitable for transplantation into a mammal in need thereof.

In a further embodiment, a method for expanding a population of mesenchymal stem cells (MSCs) is provided, comprising: (a) obtaining from a mammal a tissue sample comprising a MSC population; (b) expanding, in vitro, the MSC population from the sample, wherein: (i) the MSC population expands by at least 2-fold; and (ii) the expanded MSC population has at least a 5-fold increase in total colony-forming units.

In a further embodiment, a method for reconstituting a mesenchymal stem cell lineage in a subject in need thereof is provided, the method comprising: (a) obtaining from a mammal a tissue sample comprising a MSC population; (b) expanding, in vitro, the MSC population from the sample, wherein: (i) the MSC population expands by at least 2-fold; and (ii) the expanded MSC population has at least a 5-fold increase in total colony-forming units; and (c) transplanting the expanded MSC population into a subject in need thereof.

In yet another embodiment, a method for expanding a mesenchymal stem cell population in a mammal in need of such expansion is provided, comprising administering to the mammal a therapeutically effective amount of a modulator of a N⁶-Methyladenosine (m⁶A) mRNA modification pathway for a period of time sufficient to expand the MSC population by at least 2-fold with HSCs that possess the ability to reconstitute a mesenchymal lineage in the mammal.

According to year another embodiment, a method for ex vivo expansion of a mesenchymal stem cell (MSC) population is provided, the MSC population being obtained from a tissue selected from the group consisting of peripheral blood, cord blood, and bone marrow, the method comprising modulating a N⁶-Methyladenosine (m⁶A) mRNA modification pathway in the MSC population to expand the MSC population to a sufficient quantity while maintaining a multilineage differentiation potential in the MSC population, which is sufficient for subsequent transplantation into a subject in need thereof.

According to yet another embodiment, a method for ex vivo expansion of mesenchymal stem cells (MSCs) by at least 2-fold is provided, the expanded MSCs being competent to reconstitute a MSC lineage upon transplantation into a mammal in need thereof, the method comprising introducing a mutation into the stem cells that results in deletion, replacement or reduced expression of a gene expressing a m⁶A mRNA modification reader and culturing the population of MSCs in a suitable culture medium.

According to a further embodiment, a kit for expanding a mesenchymal stem cell population (MSC) population for subsequent transplantation into a subject in need thereof is provided, the kit comprising a system for introducing a mutation into the MSC population that results in deletion, replacement or reduced expression of a gene expressing a m⁶A mRNA modification reader, and instructions for use thereof.

According to yet another embodiment, a kit for expanding an mesenchymal stem cell population (MSC) population for subsequent transplantation into a subject in need thereof is provided, the kit comprising an inhibitor of a m⁶A mRNA modification reader, and instructions for use thereof.

In yet a further embodiment, a method for administering a mesenchymal stem cell (MSC) to a subject in need thereof is provided, the method comprising: (a) introducing, into a sample containing a MSC population, a mutation that results in deletion, replacement or reduced expression of a gene expressing a m⁶A mRNA modification reader; (b) culturing the sample in a suitable culture media for a period of time sufficient to expand the number of MSCs in the sample to a number sufficient to transplant into the subject; and (c) administering the MSCs to the subject.

In yet a further embodiment, a method for administering a mesenchymal stem cell (MSC) to a subject in need thereof is provided, the method comprising: (a) culturing, in a suitable culture media, a sample containing a MSC population in the presence of an inhibitor of a m⁶A mRNA modification reader, for a period of time sufficient to expand the number of MSCs in the sample to a number sufficient to transplant into the subject; (b) removing from the culture the inhibitor of the m⁶A mRNA modification reader; and (c) administering the MSCs to the subject.

In another embodiment, a method for reconstituting bone marrow in a subject in need thereof is provided, comprising: (a) introducing, into a sample containing a MSC population, a mutation that results in deletion, replacement or reduced expression of a gene expressing a $m^6A$ mRNA modification reader; (b) culturing the sample in a suitable culture media for a period of time sufficient to expand the number of MSCs in the sample to a number sufficient to transplant into the subject; and (c) administering the MSCs to the subject.

In another embodiment, a method for reconstituting bone marrow in a subject in need thereof is provided, comprising: (a) culturing, in a suitable culture media, a sample containing a MSC population in the presence of an inhibitor of a $m^6A$ mRNA modification reader, for a period of time sufficient to expand the number of MSCs in the sample to a number sufficient to transplant into the subject; (b) removing from the culture the inhibitor of the $m^6A$ mRNA modification reader; and (c) administering the MSCs to the subject.

In one embodiment, a method for expanding a population of mesenchymal cells (MSCs) comprising culturing the population of MSCs under conditions sufficient to result in an expansion of the HSC population by at least 2-fold is provided, wherein the expanded population of MSCs is suitable for transplantation into a mammal in need thereof.

In a further embodiment, a method for expanding a population of mesenchymal stem cells (MSCs) is provided, comprising: (a) obtaining from a mammal a tissue sample comprising a MSC population; (b) expanding, in vitro, the MSC population from the sample, wherein: (i) the MSC population expands by at least 2-fold.

In a further embodiment, a method for reconstituting a mesenchymal stem cell lineage in a subject in need thereof is provided, the method comprising: (a) obtaining from a mammal a tissue sample comprising a MSC population; (b) expanding, in vitro, the MSC population from the sample, wherein: (i) the MSC population expands by at least 2-fold; and (c) transplanting the expanded MSC population into a subject in need thereof.

In yet another embodiment, a method for expanding a mesenchymal stem cell population in a mammal in need of such expansion is provided, comprising administering to the mammal a therapeutically effective amount of a modulator of a $N^6$-Methyladenosine ($m^6A$) mRNA modification pathway for a period of time sufficient to expand the MSC population by at least 2-fold with MSCs that possess the ability to reconstitute a mesenchymal lineage in the mammal.

In a further embodiment, a method of isolating mesenchymal stem cells (MSCs) from a biological sample is provided, the method comprising contacting the biological sample having a population of MSCs with one or more N-cadherin antibodies.

In a further embodiment, an isolated population of mesenchymal stem cells is provided, as made by any of the processes described herein. According to yet another embodiment, an expanded, isolated population of mesenchymal stem cells is provided, as made by any of the processes described herein.

According to yet another embodiment, a kit for isolating a mesenchymal stem cell (MSC) population for subsequent transplantation into a subject in need thereof is provided. The kit comprises a system for contacting a biological sample comprising MSCs with one or more N-cadherin antibodies, and instructions for use thereof.

According to yet another embodiment, a method for administering a mesenchymal stem cell (MSC) to a subject in need thereof is provided. The method comprises: (a) isolating MSCs from a biological sample comprising a population of MSCs, by contacting the biological sample with one or more N-cadherin antibodies, and (b) administering the isolated MSCs to the subject.

According to yet another embodiment, a method for reconstituting bone marrow in a subject in need thereof is provided. The method comprises: (a) isolating mesenchymal stem cells (MSCs) from a biological sample comprising a population of MSCs, by contacting the biological sample with one or more N-cadherin antibodies, and (b) administering the isolated MSCs to the subject.

According to yet another embodiment, a method for treating a subject in need of a transplant, selected from the group consisting of a bone marrow transplant, a peripheral blood transplant and an umbilical cord blood transplant, is provided. The method comprises administering to the subject a population of isolated MSCs obtained by any of the methods described herein.

In yet another embodiment, a method for expanding a population of chimeric antigen receptor (CAR) T-cells prepared by modifying T-cells obtained from a tissue selected from the group consisting of peripheral blood, cord blood and bone marrow, is provided. The method comprises modulating a $N^6$-Methyladenosine ($m^6A$) mRNA modification pathway in the population of CAR T-cells, to expand the number of CAR-T cells.

In a further embodiment a method for ex vivo expansion of a chimeric antigen receptor (CAR) T-cell population is provided. The method comprises modulating a $N^6$-Methyladenosine ($m^6A$) mRNA modification pathway in the CAR T-cell population to expand the number of CAR T-cells.

According to yet another embodiment, a method for ex vivo expansion of a chimeric antigen receptor (CAR) T-cell population prepared by modifying T-cells obtained from a tissue selected from the group consisting of peripheral blood, cord blood, and bone marrow, is provided. The method comprises modulating a $N^6$-Methyladenosine ($m^6A$) mRNA modification pathway in the CAR T-cell population to expand the CAR T-cell population to a sufficient quantity which is sufficient for subsequent transplantation into a subject in need thereof.

In yet another embodiment, a method for ex vivo expansion of chimeric antigen receptor (CAR) T-cells, the expanded CAR T-cells being competent to treat a cancer and/or blood disorder upon transplantation into a mammal in need thereof, is provided. The method comprises introducing a mutation into the CAR T-cells that results in deletion, replacement or reduced expression of a gene expressing a $m^6A$ mRNA modification reader and culturing the population of CAR T-cells in a suitable culture medium.

In a further embodiment, a kit for expanding a chimeric antigen receptor (CAR) T-cell (HSC) population for subsequent transplantation into a subject in need thereof, is provided. The kit comprises a system for introducing a mutation into the CAR T-cell population that results in deletion, replacement or reduced expression of a gene expressing a $m^6A$ mRNA modification reader, and instructions for use thereof.

In yet a further embodiment, a method for administering chimeric antigen receptor (CAR) T-cell to a subject in need thereof is provided. The method comprises: (a) introducing, into a sample containing CAR T-cell population, a mutation that results in deletion, replacement or reduced expression of a gene expressing a $m^6A$ mRNA modification reader; (b) culturing the sample in a suitable culture media for a period of time sufficient to expand the number of CAR T-cells in the sample to a number sufficient to transplant into the subject; and (c) administering the CAR T-cells to the subject.

In another embodiment, a method for administering a CAR T-cell to a subject in need thereof, is provided. The method comprises: (a) culturing, in a suitable culture media, a sample containing a CAR T-cell population in the presence of an inhibitor of a m$^6$A mRNA modification reader, for a period of time sufficient to expand the number of CAR T-cells in the sample to a number sufficient to transplant into the subject; (b) removing from the culture the inhibitor of the m$^6$A mRNA modification reader; and (c) administering the CAR T-cells to the subject.

In a further embodiment, a method for treating cancer and/or a blood disorder in a subject in need thereof is provided. The method comprises: (a) introducing, into a sample containing a CAR T-cell population, a mutation that results in deletion, replacement or reduced expression of a gene expressing a m$^6$A mRNA modification reader; (b) culturing the sample in a suitable culture media for a period of time sufficient to expand the number of CAR T-cells in the sample to a number sufficient to transplant into the subject; and (c) administering the CAR T-cells to the subject.

In yet a further embodiment, a method for treating cancer and/or a blood disorder in a subject in need thereof, is provided. The method comprises: (a) culturing, in a suitable culture media, a sample containing a CAR T-cell population in the presence of an inhibitor of a m$^6$A mRNA modification reader, for a period of time sufficient to expand the number of CAR T-cells in the sample to a number sufficient to transplant into the subject; (b) removing from the culture the inhibitor of the m$^6$A mRNA modification reader; and (c) administering the CAR T-cells to the subject.

In one embodiment, a method for expanding a population of chimeric antigen receptor (CAR) T-cells is provided. The method comprises culturing the population of CAR T-cells under conditions sufficient to result in an expansion of the CAR T-cell population by at least 2-fold, wherein the expanded population of CAR T-cells is suitable for transplantation into a mammal in need thereof.

In yet another embodiment, a method for expanding a population of chimeric antigen receptor (CAR) T-cells is provided. The method comprises: (a) obtaining from a mammal a tissue sample comprising a T-cell population; (b) modifying the T-cell population with chimeric antigen receptors to provide CAR T-cell population; and (c) expanding, in vitro, the CAR T-cell population from the sample, wherein: (i) the CAR T-cell population expands by at least 2-fold.

In a further embodiment, a method for treating a subject suffering from cancer and/or a blood disorder is provided. The method comprises: (a) obtaining from a mammal a tissue sample comprising a T-cell population; (b) modifying the T-cell population with a chimeric antigen receptor (CAR) to form a CAR T-cell population; (c) expanding, in vitro, the CAR T-cell population from the sample, wherein: (i) the CAR T-cell population expands by at least 2-fold; and (d) transplanting the expanded CAR T-cell population into the subject.

In yet a further embodiment, a method for expanding a chimeric antigen receptor (CAR) T-cell population in a mammal in need of such expansion is provided. The method comprises administering to the mammal a therapeutically effective amount of a modulator of a N$^6$-Methyladenosine (m$^6$A) mRNA modification pathway for a period of time sufficient to expand the CAR T-cell population by at least 2-fold with CAR T-cells that possess the ability to treat cancer and/or a blood disorder in the mammal.

In yet another embodiment, a method of treating a subject suffering from a blood disorder is provided. The method comprises (a) obtaining a population of cells selected from the group consisting of stem cells and T-cells, from a tissue selected from the group consisting of peripheral blood, cord blood and bone marrow; (b) optionally, in a case where the population of cells comprises T-cells, modifying the T-cells with a chimeric antigen receptor (CAR) to provide CAR T-cells; (c) expanding the population of cells by modulating a N-Methyladenosine (m$^6$A) mRNA modification pathway in the cells, to expand the number of cells; and (d) transplanting the expanded cells to the subject to treat the blood disorder.

These and other aspects of the invention are further disclosed in the detailed description and examples which follow.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a schematic showing a deletion of Ythdf2 in the HSPCs of Mx1-cre;Ythdf2$^{f/f}$ conditional KO (cKO) mice; FIG. 1B shows a Western blot (left) and histogram (right) showing intracellular flow validation of knockout Ythdf2 in mouse HSPCs; FIG. 1C are representative flow cytometric analysis plots of HSPCs in BM from wt and Ythdf2 KO mice (n=5 for each group); FIGS. 1D and 1E are bar graphs showing the frequency in total nucleated cells (TNC) (1D) and absolute cell number (1E) of HSPCs in BM from wt and Ythdf2 KO mice (n=5 for each group); FIG. 1F is a bar graph showing the absolute number of BM TNC from wt and Ythdf2 KO mice (n=5 for each group); and FIGS. 1G and 1H are bar graphs showing the absolute number of committed progenitors (1G) and lineage cells (1H) in BM of wt and Ythdf2 KO mice (n=5 for each group). Data shown as mean±s.e.m. Unpaired t-test. n.s., nonsignificant FIG. 2A depicts an experimental scheme for limiting dilution transplantation assay (LDA) to determine the frequency of functional HSCs; FIG. 2B is a graph showing Primary LDA to determine the CRU frequency by ELDA (Extreme Limiting Dilution Analysis) (n=10 per group) at 16 weeks post transplantation; FIG. 2C is a graph showing a competitive reconstitution assay by transplanting 200K whole bone marrow (WBM) cells with 200K rescue cells into irradiated recipients. (n=10 for each group); FIGS. 2D and 2E are bar graphs showing the frequency in TNC (2D) and absolute cell number (2E) of donor derived HSPCs in BM from transplantation recipient mice as (2C) (n=10 for each group); FIGS. 2F and 2G are bar graphs showing absolute cell number of donor derived (CD45.2$^+$) committed progenitors (2F) and lineage cells (2G) in BM from primary 200K BM transplantation recipient mice (n=9-10 for each group); and FIG. 2H shows a plot with secondary LDA to determine the long-term CRU frequency by ELDA at 16 weeks after secondary transplantation (n=10); FIGS. 2I and 2J are, respectively, a bar graph showing quantification of functional mouse hematopoietic stem cells (HSCs) by transplantation assay with peripheral blood analysis for total engrafted donor cells at 4 weeks after transplantation (2I), and a bar graph showing quantification of functional mouse HSCs by transplantation assay with the percentage of B, T and myeloid lineage cells at 4 weeks after transplantation (2J). Data shown as mean±s.e.m. Unpaired t-test. n.s., nonsignificant.

FIG. 3A is a schematic of irCLIP-seq workflow; FIG. 3B is a schematic showing Ythdf2 binding motif (SEQ ID NO: 1) identified by MEME with all irCLIP peaks found in all three replicates; FIG. 3C is a pie chart depicting the fraction of Ythdf2 binding peaks in each of five transcript segments; FIG. 3D is a chart showing a GO enrichment analysis of Ythdf2 targets from intersect genes of three Ythdf2 irCLIP-seq replicates; FIG. 3E shows representative tracks of Tal1 harboring $m^6A$ peaks and Ythdf2 irCLIP peaks, with coverage of $m^6A$ immunoprecipitation and input fragments indicated in red and grey, respectively, and Ythdf2 irCLIP reads highlighted in yellow; FIG. 3F is a chart showing qPCR analysis of total mRNA of sorted LSK cells from wt and Ythdf2 KO mice. All Ct values were first normalized to Actb control (not $m^6A$-tagged). Then the ratio (Ythdf2 KO over wt) was calculated. (n=3); FIG. 3G shows representative images (left) and quantification via bar graph (right) of staining intensity of wt (n=65) and Ythdf2 KO (n=54) HSPCs for TAL1 (green); FIG. 3H shows images depicting fluorescence in situ hybridization of Tal1 mRNA (red) and fluorescence immunostaining of Dcp1a (P-body marker) (magenta), Ythdf2 (green) in wt and Ythdf2 KO HSPCs, where arrows indicate co-localized staining. Scale bars, 5 µm; FIG. 3I shows Quantification of Tal1 mRNA and DCP1a co-localization in sorted LSK cells from wt and Ythdf2 KO mice. Percentage indicates the average frequency of the Tal1 mRNA that co-localized with DCP1a over total Tal1 mRNA level in each LSK cells (n=9-17). Data shown as mean±s.e.m. Unpaired t-test.

FIG. 4A shows metagene profiles depicting sequence coverage in windows surrounding the TSS (left) and stop codon (right), where coverage of $m^6A$ IP and control (input) fragments indicated in red and grey, respectively; FIG. 4B depicts pie charts presenting the fraction of $m^6A$ peaks in each of five non-overlapping transcript segments; FIG. 4C depicts a Venn diagram showing shared and unique $m^6A$-tagged genes in mouse and hUCB HSPCs; FIG. 4D depicts a chart with a GO enrichment analysis of $m^6A$-tagged transcripts shared in both mouse and hUCB HSPCs; FIG. 4E shows representative tracks of HOXB4 harboring $m^6A$ peaks, where color codes are the same as in FIG. 4A; FIG. 4F depicts a schematic of lentivirus mediated YTHDF2 KD in hUCB CD34+ HSPCs for RNA-seq; FIG. 4G is a plot of a cumulative distribution of log 2 (fold change) for $m^6A$-marked genes (purple line) and non-$m^6A$-marked genes (black line), with control and YTHDF2 KD hUCB CD34+ cells; FIG. 4H shows representative coverage plots from the RNA-seq analysis, showing increased reads of $m^6A$-tagged gene HOXB4 but not a non-$m^6A$-tagged gene ACTB in YTHDF2 KD compared to control hUCB CD34+ cells; and FIG. 4I is a bar graph showing relative mRNA expression levels of non-$m^6A$ labeled ACTB (as control) and $m^6A$-marked transcription factor related to stem cell self-renewal in control and YTHDF2 KD hUCB CD34+ cells. RPKM from RNA-seq analysis were normalized to controls. Adjusted P value were indicated.

FIGS. 5A-5F: YTHDF2 KD facilitates expansion of human cord blood HSCs ex vivo. FIGS. 5A-5B are bar graphs depicting the fold change of frequency (5A) and absolute number (5B) of indicated cells in YTHDF2 KD over control cells after 7 days culture; FIG. 5C shows a bar graph depicting CFU output from transduced CD34+CD38− hUCB cells and images of CFU-granulocyte erythrocyte monocyte megakaryocyte (GEMMs) (scale bar, 200 µm); FIG. 5D includes images of burst forming unit-erythroid (BFU-E) (left) and colony-forming unit-granulocyte/macrophage (CFU-GM) (right) from 7-days cultured control or YTHDF2 KD hUCB cells (scale bar, 200 µm), where independent cord blood samples were used and repeated twice for the panels; FIG. 5E is a bar graph showing apoptosis analysis of CD34+CD38− cells in 7-day cultures of transduced CD34+ hUCB cells by Annexin V staining (n=3 independent CB samples); FIG. 5F is a bar graph showing the fold change of Tthdf2 knockdown (KD) to control in indicated human cord blood HSCs (n=3 individual human samples), where lentivirus was used to deliver control shRNA or human Ythdf2 shRNA into sorted CD34+CD38− blood cord HSCs. Dashed lines indicate 95% confidence intervals. Data shown as mean±s.e.m. Unpaired t-test. n.s., nonsignificant.

FIG. 6A is an image showing an experimental scheme for measuring frequency of HSCs after in vivo expansion; FIG. 6B includes representative flow plots of hCD45+ GFP+ reconstitution from primary recipient mice receiving the highest two cell doses. hCD45=human CD45; FIG. 6C is a plot showing hCD45+ GFP+ engraftment in BM from the primary recipient mice that received the highest two doses (n=8); FIG. 6D is a plot showing HSC frequency determined by primary LDA. Dashed lines indicate 95% confidence intervals; FIG. 6E includes representative flow plots of hCD45+ GFP+ reconstitution from secondary recipient mice receiving the highest two cell doses; FIG. 6F is a plot showing hCD45+ GFP+ engraftment in BM from the secondary recipient mice that received the highest two doses (n=6); FIG. 6D is a graph showing HSC frequency determined by secondary LDA. Dashed lines indicate 95% confidence intervals. Data shown as mean±s.e.m. Unpaired t-test. n.s., nonsignificant.

FIG. 7A is bar graph showing absolute cell number of HSPCs in BM from Mx1-cre−; Ythdf2$^{f/f}$ and Mx1-cre+; Ythdf2$^{f/f}$ mice without pI:pC injection (n=3 per group); FIG. 7B is a bar graph showing cell cycle analysis of HSPCs in wt (n=3) and Ythdf2 KO (n=4) mice; FIG. 7C is a bar graph showing apoptosis analysis of BM HSPCs in wt and Ythdf2 KO mice (n=5 for each group); FIG. 7D shows images of spleens from wt and Ythdf2 KO mice; FIGS. 7E-7H are bar graphs showing absolute number of TNC (7E), LSK CD48− CD150+ HSCs (7F), committed progenitors (7G) and lineage cells (7H) in the spleen of wt (n=3) and Ythdf2 KO (n=4) mice; FIG. 7I is a bar graph showing Homing ability of wt and Ythdf2 KO cells was determined by transplanting 1×10⁶ CFDA SE-labelled BM cells into lethally irradiated mice. 18 hours later, BM was analyzed for homed events (n=6 mice per group). Data shown as mean±s.e.m. Unpaired t-test. n.s., nonsignificant.

FIGS. 8A to 8C are bar graphs depicting absolute cell number of donor derived (CD45.2+) TNC (8A), committed progenitors (8B) and lineage cells (8C) in the BM from secondary 200K transplantation recipient mice at 16 weeks after secondary transplantation (n=7-10 for each group); FIGS. 8D to 8F are bar graphs depicting absolute cell number of donor derived (CD45.2+) TNC (8D), committed progenitors (8E), and lineage cells (8F) in the spleen from secondary 200K transplantation recipient mice at 16 weeks after secondary transplantation (n=7-10 for each group). Data shown as mean±s.e.m. Unpaired t-test. n.s., nonsignificant.

FIG. 9A is a schematic showing BM and spleen collected from wt and Ythdf2 KO mice were analyzed by flow cytometry at 5-7 months post pI:pC inductions; FIGS. 9B to 9E are bar graphs showing: absolute cell number of TNC (FIG. 9B), HSPCs (FIG. 9C), committed progenitors (FIG. 9D) and lineage cells (FIG. 9E) in the BM of wt and Ythdf2 KO mice at 5-7 months post induction. (n=4-7 mice per group); FIG. 9F is a bar graph showing the weight of spleens from wt and Ythdf2 KO mice at 5-7 months post induction. (n=4-7 mice per group); FIGS. 9G to 9J are bar graphs showing: absolute cell number of TNC (FIG. 9G), LSK CD48$^-$ CD150$^+$ HSCs (FIG. 9H), committed progenitors (FIG. 9I) and lineage cells (FIG. 9J) in the spleen of wt and Ythdf2 KO mice at 5-7 months post induction. (n=4-7 mice per group); FIG. 9K is a schematic and graph showing 5 months post pI:pC injection, 75 k WBM from wt and Ythdf2 KO mice were transplanted with 200K rescue cells into lethally irradiated recipients. Peripheral blood from transplantation recipients were analyzed every 4 weeks post transplantation to determine the donor derived engraftment (n=10 for each group). Data shown as mean±s.e.m. Unpaired t-test. n.s., nonsignificant.

FIG. 10A shows plots of metagene profiles depicting sequence coverage in windows surrounding the TSS (up) and stop codon (down), where coverage of $m^6A$ IP and control (input) fragments indicated in red and grey, respectively; FIG. 10B shows pie charts presenting the fraction of $m^6A$ peaks in each of five transcript segments; FIG. 10C shows plots of the fraction of genes in mouse HPSCs with $m^6A$ peaks in each of the segments as a function of expression level; FIG. 10D shows graphs of $m^6A$-tagged and non-$m^6A$-tagged mRNA degradation rates as determined by analysis of the expression level at 0 hour and 4 hours post actinomycin D treatment in HSPCs.

FIG. 11A is an image showing immunoprecipitation of Ythdf2 in control or Flag-Ythdf2 overexpressed HPC7 cells; FIG. 11B is an irCLIP membrane image showing IR800 labeled RNA-Ythdf2 complex, where red box indicate the RNA-Ythdf2 complex collected for library construction, and with samples without UV crosslinking serve as controls; FIG. 11C is a Venn diagram showing intersection genes identified in three independent Ythdf2 irCLIP-seq experiments; FIG. 11D is a Venn diagram showing overlap of Ythdf2 binding targets and $m^6A$ labeled mRNAs;

FIG. 11E shows representative tracks of Gata2 harboring $m^6A$ peaks and Ythdf2 irCLIP peaks, where coverage of $m^6A$ immunoprecipitation and input fragments are indicated in red and grey, respectively, and Ythdf2 irCLIP reads are highlighted in yellow.

FIG. 12A is a bar graph showing total RNA was extracted from 15,000 sorted BM LSK Flk2$^-$ cells; FIG. 12B shows quantification of $m^6A$ RNA methylation in wt and Ythdf2 KO Lin$^-$ cells (n=6); FIG. 12C shows quantification (right) and histogram (left) showing intracellular flow validation of increased expression of TAL1, GATA2, RUNX1 and STAT5 in Ythdf2 KO LT-HSCs comparing to wt LT-HSCs (n=3 mice per group); FIG. 12D shows fluorescence in situ hybridization of Gata2 mRNA (red) and fluorescence immunostaining of Dcp1a (P-body marker) (magenta), Ythdf2 (green) in wt and Ythdf2 KO HSPCs. Arrows indicate co-localized staining. Scale bars, 5 μm; FIG. 12E shows quantification of Gata2 mRNA and DCP1a co-localization in sorted LSK cells from wt and Ythdf2 KO mice. Percentage indicates the average frequency of the Gata2 mRNA that co-localized with DCP1a over total Gata2 mRNA level in each LSK cells (n=12-20); FIG. 12F shows percentage of GFP$^+$ cells in the CD45$^+$ population at 4 weeks post transplantation (n=10). Data shown as mean±s.e.m. Unpaired t-test. n.s., nonsignificant.

FIG. 13A is a Venn diagram showing intersection genes identified in three independent $m^6A$-seq experiments, using three independent cord blood samples; FIG. 13B shows pie charts with the percentage of mRNAs and non-coding RNAs containing $m^6A$ peaks; FIG. 13C is a bar graph showing GO enrichment analysis of the transcription factors harboring $m^6A$ modifications in hUCB CD34$^+$ cells; FIG. 13D shows images of Western blotting of YTHDF2 (up) and β-Actin (down) in sorted GFP$^+$ control and YTHDF2 KD hUCB cells, showing knockdown efficiency of YTHDF2; FIG. 13E shows a bar graph with expression level (left) and representative track plots (right) of YTHDF2 from RNA-seq analysis of control and YTHDF2 KD hUCB CD34$^+$ cells, showing knockdown efficiency of YTHDF2. FIGS. 13F through 13G are representative track plots of indicated transcription factors harboring $m^6A$ peaks (up) and their representative coverage plots from the RNA-seq analysis (bottom). Adjusted P values are indicated.

FIG. 14A depicts representative flow plots of GFP$^+$ CD34$^+$CD38$^-$ CD45RA$^-$ EPCR$^+$ HSCs in control and YTHDF2 KD hUCB cells post 7 days culture; FIG. 14B depicts confirmation of YTHDF2 protein knockdown and overexpression in transduced Hela cells; FIG. 14C depicts CFU production by YTHDF2 OE and control transduced CD34$^+$CD38$^-$ CB from day 10 cultures (n=3 independent human samples). Data shown as mean±s.e.m. Unpaired t-test. n.s., nonsignificant.

FIG. 15A includes representative flow plots of hCD45$^+$ GFP$^+$ monocyte, megakaryocyte (MK cell), B cell and erythrocyte in primary NSG recipient BM.; FIGS. 15B and 15C are bar graphs depicting the percentage of lineage cells in hCD45$^+$ GFP$^+$ (FIG. 15B) and in total CD45$^+$ (FIG. 15C) BM cells from primary NSG recipients at 10 weeks post transplantation (n=13-15); FIG. 15D is a bar graph depicting a summary of human donor derived lineage chimerisms in total CD45$^+$ BM cells from secondary NSG recipients at 12 weeks post transplantation (n=6). Data shown as mean±s.e.m. Unpaired t-test. n.s., nonsignificant.

FIG. 16 is a bar graph showing the frequency of N-Cad+ CD105+ in TNC with both wt Ythdf2 and a Ythdf2 knockout (KO).

FIG. 17A is a schematic representation of FACS sorting for rHSCs, pHSCs, ST-HSCs and MPPs; FIG. 17B shows a quantification of rHSCs and pHSCs function by transplantation assay. PB analysis for total engrafted donor cells at the indicated number of weeks post transplantation and the percentage of donor-derived B, T and myeloid lineage cells at 20 weeks post transplantation (n=10 mice per group); FIG. 17C shows donor derived cells from rHSCs or pHSCs transplanted mice at 40 weeks post transplantation; FIG. 17D H2B-GFP label retaining cells in rHSCs and pHSCs at 130 days post chasing (n=4 mice per group); FIG. 17E shows cell cycle gene expression in rHSCs and pHSCs (n=3 replicates from 20 mice); FIG. 17F shows rHSCs and pHSCs transplanted recipients received 5FU injection at 4 weeks post transplantation as indicated. PB analysis for donor engraft cells at indicated weeks post transplantation. The percentage of donor-derived B, T and myeloid lineage cells were shown at 20 weeks post transplantation (n=10 mice per group); FIG. 17G shows rHSCs and pHSCs at day 3 post 5FU treatment (pool from 15 mice); FIG. 17H shows DNA damage gene expression in rHSCs and pHSCs (n=3 replicated from 20 mice); FIG. 17I shows DNA damage genes in rHSCs from control mice and mice at day 3 post 5FU (n=20 in control mouse group, n=40 in D3 5FU mouse group). * P<0.05,  P<0.01, *P<0.001. Error bars, s.e.m; FIG. 17J shows heat map of stress response genes in rHSCs, pHSCs and 5FU rHSCs.

FIG. 18A shows representative whole-mount images of mouse sternal bone marrow (BM), with bone (white, generated by second harmonic generation, SHG), MKs (yellow, distinguished by size, morphology and CD41 expression). Green arrowheads denoted phenotypic $Lin^-CD48^-CD41^-CD150^+CD49b^-$rHSCs, White arrowheads denoted phenotypic $Lin^-CD48^-$ $CD41^-CD150^+CD49b+$ pHSCs; FIG. 18B shows representative image of rHSCs, pHSCs and 5FU rHSCs. White arrows denoted phenotypic $Lin^-CD48^-CD41^-CD150^+CD49b^-$rHSCs, phenotypic $Lin^-CD48^-CD41^-CD150^+CD49b^+$ pHSCs and phenotypic $Lin^-CD48^-CD41^-$ $CD150^+CD49b^-$ 5FU rHSCs; FIGS. 18C-E show relative distance between rHSCs, pHSCs and 5FU rHSCs to vessels, MKs or bones (n=144 rHSCs, n=685 pHSCs, n=707 5FU rHSCs); FIG. 18F shows absolute number of healthy, apoptotic and dead VE-Cad$^+$ CD31$^+$ vessel cells in control mice and mice at 1 day post 5FU treatment; FIGS. 18F-G show absolute number of Annex-inV$^+$ SytoxG$^-$ apoptotic Ve-Cad$^+$ CD31$^+$ endothelial cells in central marrow (CM) or N-cad– tomato+ cells in both CM and bone from control mice and mice 1 day post 5FU treatment. N=3 in each group. * P<0.05,  P<0.01, *P<0.001. Error bars, s.e.m; FIGS. 18H-I show representative image of N-cad– tomato+ and Ve-Cad$^+$ CD31$^+$ vessels in control mice and in mice at 3 days post 5FU treatment.

FIG. 19A shows a scheme for DT administration to N-cad-CreER$^T$;iDTR mice used for the experiments shown in B-G. D indicated day (e.g., D0 indicates day 0); FIG. 19B shows N-cad$^+$ cell ablation efficiency as indicated by Tomato$^+$ cells in N-cad-CreER$^T$;iDTR mice; FIGS. 19C-D show flow cytometric analyses to determine the absolute numbers of total nucleated cells (TNC) and HSPCs in the bone marrow (BM) from N-cad-CreER$^T$;iDTR mice post TMX and DT injections (n=5 mice per group); FIGS. 19E-H show quantification of functional HSCs by transplantation assay in primary 1° and secondary 2° transplantation. Total BM cells from PB analysis for total engrafted donor cells at the indicated number of weeks post transplantation and the percentage of donor-derived B, T and myeloid lineage cells at 16 weeks post transplantation (n=10 mice per group); FIGS. 19I-J show flow cytometric analyses to determine the absolute numbers of HSPCs in the bone marrow (BM) from N-cad-CreER$^T$;SCFf/f (N-cad-CreER$^T$_;SCFf/f, n=4 mice, N-cad-CreER$^{T+}$;SCFf/f, n=6 mice) and N-cad-CreER$^{T+}$;Cxcl12f/f mice (N-cad-CreER$^T$_;Cxcl12f/f, n=3 mice, N-cad-CreER$^{T+}$;Cxcl12f/f, n=6 mice) post TMX and DT injections. (* P<0.05,  P<0.01, *P<0.001. Error bars, s.e.m.).

FIGS. 20A-20K: transcriptome analysis for hematopoietic cells and niche cells. FIGS. 20A-B shows pearson distance tree and PCA analysis for hematopoietic stem and progenitor cells (HSPCs); FIGS. 20C-D show pearson distance tree and PCA analysis for BM niche cells; FIG. 20E shows HSC signature gene expression in hematopoietic stem and progenitor cells; FIG. 20F shows BM niche signature gene expression in niche cells; FIG. 20G shows term analysis for BM niche cells; FIG. 20H shows stromal cell development gene expression in niche cells from endosteal and perivascular zones; FIG. 20I shows lineage tracing for N-cad-CreER$^T$; R26-tdT; Nestin-GFP mice after 3 TMX injections, and N-cad-CreER$^T$; R26-ZsG; Cxcl12-DsR mice after 3 TMX injections; FIG. 20J shows enzymatically digested bone marrow cells from N-cad-CreERT; R26-tdT mice post TMX injections. LepR and Pdfgrα stained by antibodies shown as red peak. Isotype control shown as gray peak; FIG. 20K shows CFU-F activity in niche cells from endosteal and perivascular zones.

FIG. 21A shows experimental design; FIG. 21B shows live CFU-F colonies cultured from enzymatically digested bone marrow, stained with Cell Trace™ and Tomato$^+$ cells in one colony in high magnification; FIGS. 21C-E show in vitro differentiation of stromal cells derived from N-cad-CreER$^T$; R26-tdT mice: live tdTomato$^+$ cells and Alkaline Phosphatase staining of culture 21 days after osteo-differentiation (21C); live Tomato$^+$ cells and Oil Red O lipid staining 21 days after adipo-differentiation (21D); aggrecan antibody stained and toluidine blue stained chondrocytes at 21 days after chondro-differentiation of Tomato$^+$ cells (21E); FIGS. 21F-G show(F-G) experimental design.

FIGS. 22A-22K: N-cad$^+$ stromal cells give rise to osteoblasts and adipocytes in adult mice. FIG. 22A shows representative femur sections from N-cad-CreER$^T$; R26-tdT; Col2.3-GFP mice of different time points post TMX injection showing the anatomical distribution and increasing generation of Tomato$^+$Col2.3-GFP$^+$ osteoblasts. Scale bar, 100 µm; FIGS. 22B-C show higher-power images of N-cad-CreER$^T$; R26-tdT; Col2.3-GFP mice at early time points post TMX in region i, ii, iii, iv, v and vi shown in 6 hr (22B) and 14 hr (22C). Hollow arrowheads show Tomato$^+$ Col2.3GFP$^+$ osteoblasts (yellow cells) at 6 hours and 14 hours post TMX, whereas solid arrowheads indicate the N-cad recombined both in the trabecular (ii, iv, v) and cortical (iii, vi) region (green). These cells are potentially undifferentiated as shown by the absence of Col2.3-GFP. Scale bar, 50 µm; FIGS. 22D-E show image quantification showing percentage of Tomato$^+$Col2.3-GFP$^+$ and Tomato$^+$ Col2.3-GFP$^-$ cells in trabecular (22D) and compact bone (22E) at 6 hours, 14 hours, 24 hours, 2 weeks and 4 weeks post TMX injection; FIG. 22F shows image quantification comparing percentage of potential undifferentiated Tomato$^+$ Col2.3-GFP$^-$ between trabecular and compact bone. * P<0.05,  P<0.01, *P<0.001. Error bars, s.e.m; FIG. 22G shows representative image of trabecular bone (TB) and cortical bone (CB) in N-cad-CreER$^T$; R26-tdT; Col2.3-GFP mice at 4 weeks post TMX injection. Scale bar, 20 µm; FIG. 22H shows representative low and high-power image of femur section from N-cad-CreER$^T$; R26-tdT mice with Perilipin staining at 4 weeks post TMX injection. At periosteal region (i), bone marrow near trabecular region (ii) and central marrow(iii), solid arrowheads showed Tomato$^+$ Perilipin$^+$ derived from N-cad$^+$ MSCs; FIG. 22I shows BODIPY staining showed the lipid droplet (green) inside the Tomato$^+$Perilipin$^+$ adipocyte (arrowheads). Scale bar, 20 µm; FIGS. 22J-K show image quantification of Tomato$^+$ Perilipin$^+$ adipocytes in trabecular bone (22J) and periosteal region (22K) at 6 hours, 14 hours, 24 hours, 2 weeks and 4 weeks post TMX injection. (* P<0.05,  P<0.01, *P<0.001. Error bars, s.e.m.).

FIGS. 23A-23J: N-cad$^+$ MSCs give rise to chondrocytes during development and post injury. FIG. 23A shows experimental design; FIG. 23B shows tomato$^+$ partially colocalized with Aggrecan$^+$ chondrocytes in rib at E14.5(2 days post TMX induction); FIG. 23C shows an Illustration of chondrocyte development in femur; FIG. 23D shows a representative femur section from 2-day-old N-cad-CreER$^T$; R26-tdT mice with TMX induction at E12.5. Note that Tomato$^+$ cells gave rise to Aggrecan$^+$ cartilage cells in articular surface (i) and the developing secondary ossification center (ii). Arrowheads indicated Tomato$^+$ Aggrecan$^+$ cells; FIG. 23E shows a representative femur section from 10-month-old N-cad-CreER$^T$; R26-tdT mice with TMX induction at E12.5. Tomato$^+$ cells from early embryonic stage differentiated to Perilipin$^+$ adipocytes; FIG. 23F shows a representative femur section from 2-month-old N-cad-CreER$^T$; R26-tdT mice with TMX induction at E12.5. Tomato$^+$ cells from early embryonic stage differentiated to Osteopontin$_+$ hypertrophic chondrocytes (i and ii) and osteoblasts (iii, iv, v and vi); FIG. 23G shows an experimental design for femoral groove injury to N-cad-CreER$^T$; R26-tdT mice with TMX induction at E12.5; FIG. 23H shows quantification of Tomato$^+$ chondrocytes in control mice and in mice 3 weeks after knee cartilage injury. (1) Representative section of distal femur from N-cad-CreER$^T$; R26-tdT mice without cartilage injury or 3 weeks after cartilage injury. Note that the clustered Tomato$^+$ Aggrecan$^+$ cells at the knee surface of control mice (i) significantly increased at the correspondent region in mice 3 weeks after knee cartilage injury (ii); FIG. 23J shows AHO staining of the sections in FIG. 6H showing the Alcian blue positive chondrocytes in control (i) and in the location of cartilage injury(ii).

FIGS. 24A-24K: BrdU assay and N-cad reporter mouse line post 5FU. FIGS. 24A-F show representative images showing BrdU$^+$ cells in femur of mice at day 0, 2, 3, 4 and 6 post 5FU treatment. Note that BrdU$^+$ cells reduced at day 2 post 5FU, and reactivated from day 3 to day 6 post 5FU near bone (red dotted line) or vessel/adipose structure (green dotted line); FIG. 24G shows a model of dynamic of BrdU$^+$ cells; FIG. 24H shows a ratio of BrdU$^+$ cells in bone marrow to bone surface from day 3 to 6 post 5FU treatment; FIG. 24I shows a percentage of BrdU$^+$ cells near bone surface and near vessel/adipose structures from day 3 to 6 post 5FU treatment; FIG. 24J shows representative whole bone section showing N-cad driven tomato$^+$ cells in both bone surface and central marrow; FIG. 24K shows absolute number of N-cad driven tomato$^+$ cells in central marrow (CM) and in bone of N-cad-TdT mice of control group and mice 3 days post 5FU treatment. N=3 in each group. * P<0.05,  P<0.01, *P<0.001. Error bars, s.e.m.

FIG. 25A shows a generation of N-cad-CreER$^T$ mouse strain; FIG. 25B shows lineage tracing for N-cad-CreER$^T$, R26-tdT; Col2.3-GFP mice after three TMX injections; blood vessels stained by CD31 and Ve-cadherin antibodies.

FIG. 26A shows niche cells in endosteal zone harvested from digested bone cells; FIG. 26 B shows niche cells from Perivascular and sinusoid zones harvested from digested bone marrow cells; FIG. 26C shows localization of NG2-RFP$^+$ cells in endosteal and peri-arterial regions; FIGS. 26D-E show heatmaps of osteo-chondrogenic progenitor gene and adipogenic progenitor gene expression in niche cells.

FIGS. 27A-B show representative images of trabecular bone (TB) and cortical bone(CB) in N-cad-CreER$^T$; R26-tdT; Col2.3-GFP mice at 24 hours and 2 weeks post TMX induction. Scale bar, 20 µm; FIGS. 27C-E show representative femur section with high power images of N-cad-CreER$^T$; R26-tdT mice at 6 hours, 14 hours and 24 hours post TMX induction. Adipocytes shown with perilipin antibody staining.

FIG. 28A shows representative images of femur section showing N-cad$^+$ MSCs with Aggrecan staining in N-cad-CreER$^T$; R26-tdT 24 hours post TMX induction at postnatal D2; FIG. 28B shows a representative femur section from 2-month-old N-cad-CreER$^T$; R26-tdT mice with TMX induction at E12.5. Adipocytes shown with Perilipin antibody staining; FIG. 28C shows a representative femur section from 2-day-old N-cad-CreER$^T$; R26-tdT mice with TMX induction at E12.5. Developing bone cells shown with Osteopontin antibody staining; FIG. 28D shows a representative sagittal knee sections in E12.5 TMX induced N-cad-CreER$^T$; R26-tdT mice of control group and 2 weeks after knee cartilage injury. Scale bar, 1 mm.

DETAILED DESCRIPTION OF THE INVENTION

Figure 1A:
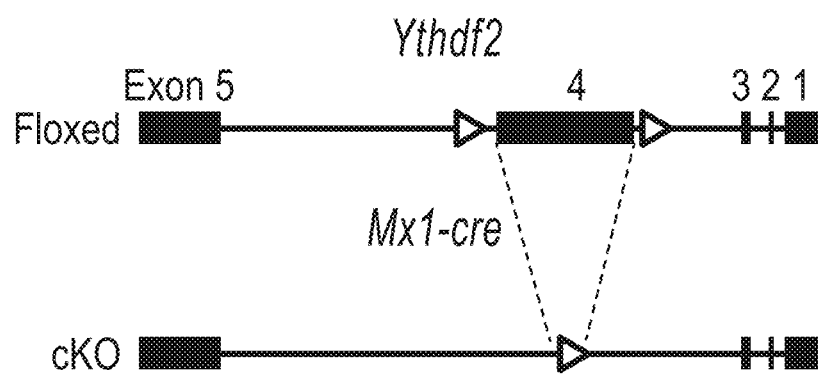
FIGS. 1A-1H: Ythdf2 KO leads to increase in phenotypic HSCs in mice.
Figure 1B:
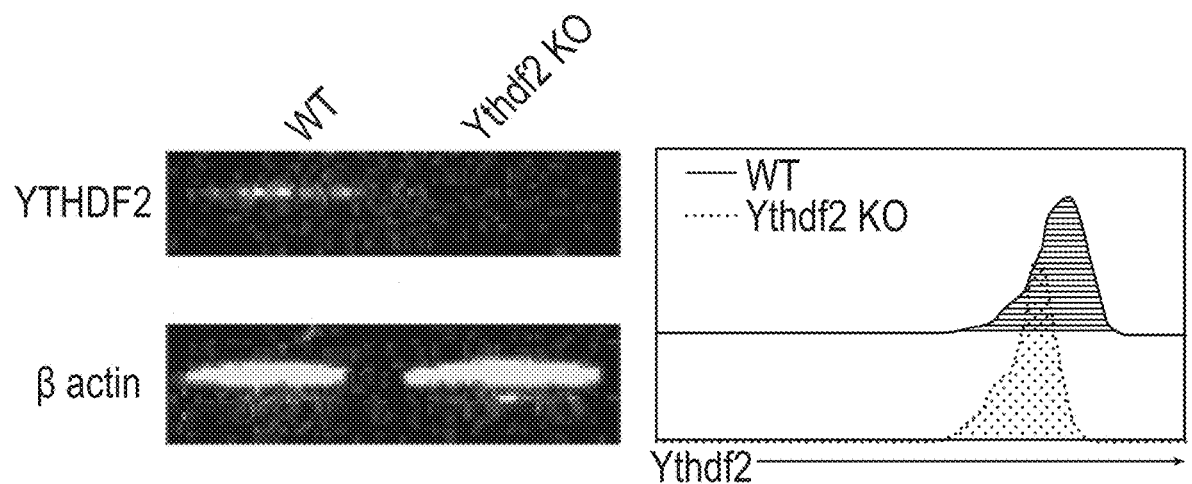

One embodiment of the invention is a method for expanding a population of stem cells obtained from a tissue selected from the group consisting of peripheral blood, cord blood, and bone marrow. This method comprises modulating a N6-methyladenosine (m$^6$A) mRNA modification pathway in the population of stem cells to expand the number of stem cells.

Another embodiment of the invention is a method for expanding a population of chimeric antigen receptor (CAR) T-cells cells obtained by modifying T-cells obtained from a tissue selected from the group consisting of peripheral blood, cord blood, and bone marrow. This method comprises modulating a N6-methyladenosine (m$^6$A) mRNA modification pathway in the population of CAR T-cells to expand the number of stem cells.

In the present invention the population of stem cells and/or T-cells may be obtained from any mammal, such as, e.g., a human, and from any tissue that contains stem cells and/or progenitor cells and/or T-cells. As noted above, in a preferred embodiment the tissue may be peripheral blood, cord blood or bone marrow.

As used herein, "expand", "expanding" and like terms means to increase the number of stem cells and/or CAR-T cells in the population relative to the number of stem cells and/or CAR T-cells in the original population either in vivo or ex vivo using any of the methods disclosed herein. The expansion may be at least 40-fold compared to the original number of stem cells and/or CAR T-cells in the population. More preferably, the expansion is at least 2-fold, 4-fold, 5-fold, 8-fold, 10-fold, 15-fold, 20-fold or more compared to the original number of stem cells.

In the present invention "a population of stem cells" means a group of substantially undifferentiated cells that possess the ability to give rise to many different types of cells and which have the ability to self-renew. Representative, non-limiting examples of stem cells according to the present invention include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoetic stem cells (HSCs), hematopoietic stem and progenitor cells (HSPCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs).

Hematopoietic stem cells, for example, have the ability to self-renew (i.e., expand) and can give rise to all the types of progenitor cells (such as, e.g., CMP, GMP, MEP and CLP) and ultimately all the types of blood cells (such as e.g., red blood cells, B lymphocytes, T lymphocytes, natural killer cells, neutrophils, basophils, eosinophils, monocytes, macrophages, and platelets) in the hematopoietic system. Mesenchymal stem cells, as another example, are multipotent stromal cells that can differentiate into a variety of cell types (such as, e.g., osteoblasts, chondrocytes, myocytes and adipocytes).

In the present invention "a population of chimeric antigen receptor (CAR) T-cells" means a group of T-cells that have been modified with chimeric antigen receptors capable of binding specific antigens, such as antigens on the surface of cancer cells, and may possess the ability to target and kill such cancer cells. The CAR T-cells can be prepared by modifying T-cells with the chimeric antigen receptors, such as by introducing DNA coding for the chimeric antigen receptors into the T-cells, to express the chimeric antigen receptors on the surface of the T-cells (Davila et al. *Sci Transl Med* 6(224), 224ra25 (2014); Tasian et al. *Ther Adv Hematol* 6(5), 228-241 (2015).

In the present invention, "modulating", "modulation" and like terms mean altering the signal transduction pathway, e.g., a protein in the m$^6$A mRNA modification pathway, including but not limited to lowering or increasing the expression level of a protein, altering the sequence of such a protein (by mutation, pre-translational or post-translational modification or otherwise), or inhibiting or activating such a protein (whether by binding, phosphorylation, glycosylation, translocation or otherwise). Such modulation may be achieved genetically or pharmacologically.

In one aspect of the present invention, modulating the m$^6$A mRNA modification pathway comprises introducing a mutation into a population of stem cells and/or CAR-T cells, which mutation results in modulation of a molecule in the m$^6$A mRNA modification pathway. In another aspect present invention, modulation of the m$^6$A mRNA modification pathway also includes contacting the stem cells and/or CAR T-cells with a modulator of a molecule in the m$^6$A mRNA pathway. Representative, non-limiting examples of such modulators include a small molecule, a biologic, an antisense RNA, a small interfering RNA (siRNA), and combinations thereof.

In the present invention, the phrase "modulation of a molecule in the m$^6$A mRNA modification pathway" means altering the function of a member of the m$^6$A mRNA modification pathway, which altered function may have an effect similar to inhibiting or decreasing the function of a molecule involved in a process upstream and/or downstream of m$^6$A modification of mRNA. Non-limiting examples of such "modulation" include increasing or decreasing the expression or function of proteins involved in any of: the incorporation of N$^6$-methyladenosine modifications in mRNA, removal of N$^6$-methyladenosine mRNA modifications to mRNA, and/or the recognizing and processing of N$^6$-methyladenosine modified mRNA. For example, the modulation may include increasing or decreasing N$^6$-methyladenosine modifications in mRNA, and/or affecting the type and/or distributions of such modifications in mRNA, such as by modulating the activity of one or more of a m$^6$A writer (e.g. methyltransferase) and m$^6$A eraser (e.g. demethylase). As another example, the modulation may increase or decreases expression or function of proteins that recognize N$^6$-methyladenosine modifications to mRNA to mediate m$^6$A-dependent functions, such as by modulating the activity of a m$^6$A reader (e.g., an RNA binding protein that recognizes methylated adenosine). Thus, modulation of the molecule in the m$^6$A mRNA modification pathway modulator may result in modulation of the activity and/or expression of a molecule upstream or downstream of an m$^6$A mRNA modification process.

In one aspect, the modulation of the m$^6$A mRNA modification pathway involves modulation of a molecule selected from the group consisting of m$^6$A mRNA modification readers, m$^6$A mRNA modification writers, m$^6$A mRNA modification erasers and combinations thereof. Non-limiting examples of m$^6$A modification writers include methyltransferases that are capable of post-transcriptionally installing the m$^6$A modification in messenger RNA, and can include any selected from the group consisting of METTL3, METTL14, WTAP, KIAA1429 and combinations thereof. Non-limiting examples of m$^6$A modification erasers include demethylases that are capable of reversing the methylation, and can include any selected from the group consisting of FTI, ALKBH5 and combinations thereof. M$^6$A modification readers include proteins that are capable of selectively binding m$^6$A-methylated mRNA to exert regulatory functions through selective recognition of methylated mRNA. Suitable m$^6$A modification readers can include any selected from the group consisting of Ythdf1, Ythdf2, Ythdf3, Ythdc1, Ythdc2, HNRNPC, HNRNPA2B1, elF3 and combinations thereof. According to one aspect, the m$^6$A modification readers comprise proteins of the YTH domain family of proteins, which includes Ythdf1, Ythdf2, Ythdf3, Ythdc1, Ythdc2 and combinations thereof. (see, e.g., Wang et al. *Nature*, 505(7481):117-120, 2014; Frayling et al.

Science, 316: 889-894, 2007; Zheng et al. *Mol. Cell.*, 49: 18-29, 2012; Cao et al. *Open Biol.*, 6(4): 160003, 2016; Maity et al. *The FEBS Journal*, 283(9): 1607-1630, 2016).

As used herein, "introducing a mutation" means any conventional method for producing an alteration in the genetic makeup of the stem cell population and/or CAR T-cell population. Non-limiting examples for introducing a mutation into a stem cell population and/or CAR T-cell population include mutagenesis via ultra-violet light irradiation, chemical mutagenesis, targeted mutagenesis such as site directed mutagenesis of a stem cell and/or CAR T-cell, and creation of a transgenic mouse. According to one aspect, a mutation may be introduced into the stem cell and/or CAR T-cell to delete, replace or reduce expression of a gene that expresses a molecule in the $m^6A$ mRNA modification pathway, such as a molecule selected from the group consisting of a $m^6A$ mRNA modification reader, a $m^6A$ mRNA modification writer, a $m^6A$ mRNA modification eraser and combinations thereof. In one aspect, the mutation is introduced to delete, replace or reduce expression of a gene that expresses a $m^6A$ mRNA modification reader, such as any selected from the group consisting of Ythdf1, Ythdf2, Ythdf3, Ythdc1, Ythdc2, HNRNPC, HNRNPA2B1, elF3 and combinations thereof. In a preferred aspect, a mutation is introduced to delete, replace or reduce expression of a gene that expresses Ythdf2. In yet another aspect, the mutation is introduced to delete, replace or reduce expression of a gene that expresses a $m^6A$ mRNA modification writer, such as any selected from the group consisting of METTL3, METTL14, WTAP, KIAA1429 and combinations thereof. In yet another aspect, the mutation is introduced to delete, replace or reduce expression of a gene that expresses a $m^6A$ mRNA modification eraser, such as any selected from the group consisting of FTI, ALKBH5 and combinations thereof.

In one aspect, the mutation can be introduced by exposing the stem cells and/or CAR T-cells to a Mx1-Cre targeting system (see, e.g., Kuhn et al. *Science*, 269(5229): 1427-1429, 1995) that inactivates or deletes at least a portion of a gene that expresses a molecule in the $m^6A$ mRNA modification pathway. In yet another aspect, a mutation is introduced that incorporates short hairpin RNA (shRNA) into the stem cells and/or CAR T-cells to reduce expression of a gene that expresses a molecule in the $m^6A$ mRNA modification pathway. For example, the shRNA may be introduced by exposing the stem cells and/or CAR T-cells to a vector to deliver shRNA, which may be a viral vector such as lentivirus (see, e.g., Chira et al. *Oncotarget*, 6(31): 30675-30703, 2015). The shRNA may be capable of triggering gene silencing to regulate gene expression (see, e.g., Paddison et al. *Genes Dev.*, 16(8): 948-958, 2002).

As used herein, "a modulator of a NM-Methyladenosine mRNA modification pathway" (or "$m^6A$ mRNA modification pathway modulator") is any agent that regulates the activity of any member of the $m^6A$ mRNA modification pathway, which results in, e.g., an increase or decrease in $N^6$-methyladenosine modifications in mRNA, and/or a change in the types and/or distributions of such modifications in mRNA, such as by modulating the activity of one or more of a $m^6A$ writer (e.g. methyltransferase) and $m^6A$ eraser (e.g. demethylase). As another example, the agent may be one that increases or decreases activity of proteins that recognize $N^6$-methyladenosine modifications to mRNA to mediate $m^6A$-dependent functions, such as by modulating the activity of a $m^6A$ reader (e.g., an RNA binding protein that recognizes methylated adenosine). Thus, the $m^6A$ mRNA modification pathway modulator may act on, or upstream of, or downstream of, an agent that affects the $m^6A$ modification to mRNA.

In one embodiment, the $m^6A$ mRNA modification pathway may be modulated by down-regulating and/or inhibiting a member of the $m^6A$ mRNA modification pathway, such as down-regulating and/or inhibiting a $m^6A$ mRNA modification reader. As used herein, "down-regulating" means inhibiting or reducing the amount of or inhibiting or decreasing the activity of a member of the $m^6A$ mRNA modification pathway. Such down-regulation may be accomplished using, e.g. antisense RNA, siRNA, antibodies, or small molecules. As another example, the $m^6A$ mRNA modification reader may be down-regulated by contacting the stem cells and/or CAR T-cells with an inhibitor of an $m^6A$ mRNA reader, to inhibit binding and/or recognizing of the $m^6A$ modified mRNA by the $m^6A$ mRNA reader. In one aspect, the $m^6A$ mRNA modification reader that is down-regulated is selected from the group consisting of Ythdf1, Ythdf2, Ythdf3, Ythdc1, Ythdc2, HNRNPC, HNRNPA2B1, elF3 and combinations thereof. In a preferred aspect, the $m^6A$ mRNA modification reader that is down-regulated is Ythdf2. Inhibitors of the $m^6A$ mRNA modification reader may be any selected from the group consisting of: (inhibitors of HNRNPC) hsa-let-7e-5p (MIRT051596), hsa-mir-455-3p (MIRT037890), hsa-mir-30c-5p (MIRT047904), hsa-mir-186-5p (MIRT045150), hsa-mir-744-5p (MIRT037494), hsa-mir-18a-3p (MIRT040851), hsa-mir-484 (MIRT042196), hsa-mir-505-5p (MIRT037959), hsa-mir-615-3p (MIRT039991), hsa-mir-342-3p (MIRT043694), hsa-miR-3607-3p, hsa-miR-30d, hsa-miR-3916, hsa-miR-3162-5p, hsa-miR-1273d, hsa-miR-3161, hsa-miR-30a, hsa-miR-629, hsa-miR-208b, hsa-miR-489, hsa-miR-3148, hsa-miR-2113, hsa-miR-877, hsa-miR-455-5p, hsa-miR-186, hsa-miR-548o, hsa-miR-3139, hsa-miR-320a, hsa-miR-4311, hsa-miR-555, hsa-miR-3605-5p, hsa-miR-515-5p, hsa-miR-144, hsa-miR-499-5p, hsa-miR-1323, hsa-miR-548x, hsa-miR-299-5p, hsa-miR-653, hsa-miR-576-5p, hsa-miR-548p, hsa-miR-586, hsa-miR-888, hsa-miR-3647-3p, hsa-miR-484, hsa-miR-320b, hsa-miR-620, hsa-miR-30b, hsa-miR-548q, hsa-miR-29b-1, hsa-miR-570, hsa-miR-183, hsa-miR-1276, hsa-miR-208a, hsa-miR-186, hsa-miR-28-5p, hsa-miR-330-3p, hsa-miR-548am, hsa-miR-320d, hsa-miR-3175, hsa-miR-3155, hsa-miR-548aa, hsa-miR-519e, hsa-miR-1270, hsa-miR-513b, hsa-miR-599, hsa-miR-518f, hsa-miR-4301, hsa-miR-30c, hsa-miR-3135, hsa-miR-4286, hsa-miR-202, hsa-miR-4263, hsa-miR-4299, hsa-miR-606, hsa-miR-3133, hsa-miR-583, hsa-miR-3125, hsa-miR-501-5p, hsa-miR-7-1, hsa-miR-514b-3p, hsa-miR-3155b, hsa-miR-548d-3p, hsa-miR-224, hsa-miR-7-2, hsa-miR-708, hsa-miR-3199, hsa-miR-514, hsa-miR-30e (see, e.g. Helwak et al. *Cell*, 153(3): 654-655, 2013; Whisnant et al., *M Bio* 4(2), 2013:e000193); (inhibitors of HNRNPA2B1) hsa-mir-92a-3p (MIRT049721), hsa-mir-30c-5p (MIRT048009), hsa-mir-191-5p (MIRT045809), hsa-let-7f-5p (MIRT051404), hsa-mir-27b-3p (MIRT046213), hsa-mir-877-3p (MIRT037116), hsa-mir-615-3p (MIRT040278), hsa-mir-1260b (MIRT052680), hsa-mir-103a-3p (MIRT027027), hsa-mir-16-5p (MIRT031508), hsa-mir-1296-5p (MIRT036075), hsa-mir-197-3p (MIRT048098), hsa-miR-548j, hsa-miR-3678-3p, hsa-miR-607, hsa-miR-188-5p, hsa-miR-15a, hsa-miR-3653, hsa-miR-371-5p, hsa-miR-550a, hsa-miR-3622b-3p, hsa-miR-548a-5p, hsa-miR-3170, hsa-miR-3148, hsa-miR-556-3p, hsa-miR-490-3p, hsa-miR-559, hsa-miR-200c, hsa-miR-130a, hsa-miR-548y, hsa-miR-548o, hsa-miR-23c, hsa-miR-491-3p, hsa-miR-335, hsa-miR-3667-3p, hsa-miR-466, hsa-miR-23b, hsamiR-4310, hsa-miR-127-5p, hsa-miR-548b-5p, hsa-miR-616, hsa-miR-16, hsa-miR-338-3p, hsa-miR-3200-5p, hsa-miR-362-3p, hsa-miR-448, hsa-miR-1306, hsa-miR-944, hsa-miR-3684, hsa-miR-373, hsa-miR-103a, hsa-miR-380, hsa-miR-499-5p, hsa-miR-1323, hsa-miR-323-5p, hsa-miR-3674, hsa-miR-1252, hsa-miR-33b, hsa-miR-580, hsa-miR-548c-3p, hsa-miR-103a-2, hsa-miR-548w, hsa-miR-600, hsa-miR-634, hsa-miR-586, hsa-miR-497, hsa-miR-720, hsa-miR-654-3p, hsa-miR-524-5p, hsa-miR-543, hsa-miR-548q, hsa-let-7f-2, hsa-miR-330-5p, hsa-miR-500a, hsa-miR-548I, hsa-miR-570, hsa-miR-374a, hsa-miR-1184, hsa-miR-649, hsa-miR-424, hsa-miR-3658, hsa-miR-186, hsa-miR-326, hsa-miR-548d-5p, hsa-miR-23a, hsa-miR-15b, hsa-miR-190, hsa-miR-203, hsa-miR-548h, hsa-miR-3136-5p, hsa-miR-618, hsa-miR-551b, hsa-miR-211, hsa-miR-1305, hsa-miR-513b, hsa-miR-96, hsa-miR-2117, hsa-miR-548n, hsa-miR-3910, hsa-miR-217, hsa-miR-892b, hsa-miR-502-5p, hsa-miR-548i, hsa-miR-520d-5p, hsa-miR-4299, hsa-miR-1285, hsa-miR-3133, hsa-miR-483-3p (see, e.g., Hafner et al. *Cell,* 141(1): 129-141, 2010; Helwak et al. *Cell,* 153(3): 654-655, 2013); (inhibitors of Ythdf1) hsa-miR-548g, hsa-miR-204, hsa-miR-3143, hsa-miR-521, hsa-miR-195, hsa-miR-3182, hsa-miR-3941, hsa-miR-34c-3p, hsa-miR-767-3p, hsa-miR-563, hsa-miR-548c-5p, hsa-miR-1911, hsa-miR-26b, hsa-miR-190b, hsa-miR-33a, hsa-miR-329, hsa-miR-221, hsa-miR-612, hsa-miR-3185, hsa-miR-3156-5p, hsa-miR-107, hsa-miR-664, hsa-miR-3657; (inhibitors of Ythdf2) hsa-mir-615-3p (MIRT040054), hsa-mir-106b-5p (MIRT044257), hsa-mir-1 (MIRT023842), miR-145, hsa-miR-3607-3p, hsa-miR-200a, hsa-miR-301a, hsa-miR-519a, hsa-miR-141, hsa-miR-130b, hsa-miR-181b, hsa-miR-301b, hsa-miR-3117-3p, hsa-miR-1236, hsa-miR-181a, hsa-miR-519c-3p, hsa-miR-551b, hsa-miR-519e, hsa-miR-519b-3p, hsa-miR-19b, hsa-miR-1303, hsa-miR-608, hsa-miR-145, hsa-miR-130a, hsa-miR-181c, hsa-miR-323b-3p, hsa-miR-421, hsa-miR-515-5p, hsa-miR-3666, hsa-miR-181d, hsa-miR-146a, hsa-miR-4295, hsa-miR-454, hsa-miR-3919, hsa-miR-19a, hsa-miR-543, hsa-miR-4262 (see, e.g. Helwak et al. *Cell,* 153(3): 654-655, 2013; Selbach et al. Nature, 455(7209): 58-63, 2008; Yang et al. *J Biol Chem.,* 292(9): 3614-3623, 2017); (inhibitors of Ythdf3) hsa-miR-582-3p, hsa-miR-579, hsa-miR-520e, hsa-miR-520f, hsa-miR-3152-3p, hsa-miR-106a, hsa-miR-30d, hsa-miR-30a, hsa-miR-93, hsa-miR-508-5p, hsa-miR-29a, hsa-miR-3148, hsa-miR-490-5p, hsa-miR-520b, hsa-miR-20a, hsa-miR-409-3p, hsa-miR-4255, hsa-let-7i, hsa-miR-373, hsa-let-7e, hsa-miR-520c-3p, hsa-miR-3920, hsa-miR-127-5p, hsa-miR-380, hsa-miR-616, hsa-miR-4277, hsa-miR-448, hsa-miR-16-2, hsa-let-7c, hsa-miR-340, hsa-miR-373, hsa-miR-520a-3p, hsa-miR-144, hsa-miR-1265, hsa-miR-548x, hsa-miR-362-5p, hsa-miR-33b, hsa-miR-26b, hsa-miR-17, hsa-miR-569, hsa-miR-3618, hsa-miR-576-5p, hsa-miR-922, hsa-miR-302a, hsa-miR-106b, hsa-miR-888, hsa-miR-484, hsa-let-7b, hsa-miR-582-5p, hsa-let-7f, hsa-miR-30b, hsa-miR-524-5p, hsa-miR-302d, hsa-let-7d, hsa-miR-513a-5p, hsa-miR-500a, hsa-miR-570, hsa-miR-548I, hsa-miR-105, hsa-miR-374c, hsa-let-7g hsa-miR-372, hsa-miR-3658, hsa-let-7a, hsa-miR-3908, hsa-miR-302b, hsa-miR-526b, hsa-miR-190, hsa-miR-181 b, hsa-miR-433, hsa-miR-98, hsa-miR-3606, hsa-miR-595, hsa-miR-548am, hsa-miR-187, hsa-miR-561, hsa-miR-181a, hsa-miR-3155, hsa-miR-655, hsa-miR-302c, hsa-miR-195, hsa-miR-26a, hsa-miR-590-3p, hsa-miR-30c, hsa-miR-502-5p, hsa-miR-495, hsa-miR-137, hsa-miR-181c, hsa-miR-520d-5p, hsa-miR-3942-5p, hsa-miR-202, hsa-miR-302e, hsa-miR-513c, hsa-miR-885-5p, hsa-miR-520a-5p, hsa-miR-583, hsa-miR-1297, hsa-miR-7-1, hsa-miR-520d-3p, hsa-miR-3155b, hsa-miR-3182, hsa-miR-519d, hsa-miR-550a, hsa-miR-7-2, hsa-miR-181d, hsa-miR-190b, hsa-miR-1912, hsa-miR-151-3p, hsa-miR-33a, hsa-miR-525-5p, hsa-miR-20b, hsa-miR-514b-5p, hsa-miR-30e, hsa-miR-4262, hsa-miR-636; (inhibitor of elF3) hsa-mir-92b-3p (MIRT040734), hsa-mir-16-5p (MIRT031705), hsa-mir-18a-3p (MIRT040974), hsa-mir-155-5p (MIRT020771), hsa-mir-484 (MIRT042324), hsa-let-7c-5p (MIRT051776), hsa-miR-3910, hsa-miR-148b, hsa-miR-136, hsa-miR-15a, hsa-miR-488, hsa-miR-500a, hsa-miR-1297, hsa-miR-3159, hsa-miR-374c, hsa-miR-424, hsa-miR-7-1, hsa-miR-186, hsa-miR-195, hsa-miR-15b, hsa-miR-26b, hsa-miR-505, hsa-miR-1206, hsa-miR-653, hsa-miR-1283, hsa-miR-7-2, hsa-miR-196a, hsa-miR-497, hsa-miR-33a, hsa-miR-655, hsa-miR-26a hsa-miR-16, hsa-mir-151a-3p (MIRT043600), hsa-mir-92a-3p (MIRT049064), hsa-mir-615-3p (MIRT039779), hsa-mir-877-3p (MIRT036964), hsa-mir-222-3p (MIRT046746), hsa-mir-423-3p (MIRT042468), hsa-mir-324-3p (MIRT042887), hsa-mir-124-3p (MIRT022932), hsa-miR-3140-3p, hsa-miR-124, hsa-miR-198, hsa-miR-525-5p, hsa-miR-506, hsa-miR-520a-5p, hsa-miR-196a* hsa-miR-3117-3p, hsa-mir-342-5p (MIRT038210), hsa-miR-378a-5p (MIRT043981), hsa-miR-615-3p (MIRT040086), hsa-let-7b-5p (MIRT052211), hsa-mir-455-3p (MIRT037879), hsa-miR-4267, hsa-miR-590-3p, hsa-mir-106b-5p (MIRT044355), hsa-mir-320a (MIRT044466), hsa-mir-16-5p (MIRT032018), hsa-mir-155-5p (MIRT021009), hsa-miR-4302, hsa-mir-191-5p (MIRT045793), hsa-mir-1303 (MIRT035890), hsa-mir-193b-3p (MIRT016316), hsa-mir-222-3p (MIRT046640), hsa-mir-532-3p (MIRT037924), hsa-mir-18a-3p (MIRT040929), hsa-mir-92a-3p (MIRT049001), hsa-miR-582-3p, hsa-miR-4265, hsa-miR-218-2, hsa-miR-1271, hsa-miR-340, hsa-miR-221, hsa-miR-20b, hsa-miR-508-3p, hsa-miR-141, hsa-miR-4325, hsa-miR-889, hsa-miR-29a, hsa-miR-129-3p, hsa-miR-129, hsa-miR-96, hsa-miR-3163, hsa-miR-187, hsa-miR-196a, hsa-miR-222, hsa-miR-1179, hsa-miR-182, hsa-miR-9* hsa-miR-32, hsa-miR-143, hsa-miR-4296 (see, e.g., Helwak et al. *Cell,* 153(3): 654-656, 2013; Selbach et al. *Nature,* 455 (7209):58-63, 2008; Baek et al, *Nature,* 455(7209):64-71, 2008; Leivonen et al. *Mol Cell Proteomics,* 10(7), 2011: M110.005322): (inhibitors of YTHDC1) hsa-mir-20a-3p (MIRT038967), hsa-mir-103a-3p (MIRT027037), hsa-mir-1 (MIRT023492), hsa-mir-19b-3p (MIRT031105), hsa-mir-100-5p (MIRT048400), hsa-mir-93-5p (MIRT027989), hsa-mir-16-5p (MIRT031379), hsa-let-7b-5p (MIRT052150), hsa-miR-520f, hsa-miR-300, hsa-miR-15a, hsa-miR-200a, hsa-miR-605, hsa-miR-30d, hsa-miR-30a, hsa-miR-3613-3p, hsa-miR-509-3-5p, hsa-miR-34c-5p, hsa-miR-324-3p, hsa-miR-1248, hsa-miR-152, hsa-miR-548t, hsa-miR-4310, hsa-miR-145, hsa-miR-516a-3p, hsa-miR-16, hsa-miR-3668, hsa-miR-4277, hsa-miR-448, hsa-miR-16-2, hsa-miR-148b, hsa-miR-509-5p, hsa-miR-103a, hsa-miR-1265, hsa-miR-2115, hsa-miR-548c-3p, hsa-miR-148a, hsa-miR-548p, hsa-miR-513a-3p, hsa-miR-497, hsa-miR-3647-3p, hsa-miR-382, hsa-miR-30b, hsa-miR-543, hsa-let-7f-2, hsa-miR-1269, hsa-miR-3164, hsa-miR-503, hsa-miR-500a, hsa-miR-449a, hsa-miR-141, hsa-miR-424, hsa-miR-3908, hsa-miR-889, hsa-miR-2116, hsa-miR-330-3p, hsa-miR-15b, hsa-miR-181b, hsa-miR-187, hsa-miR-1237, hsa-miR-449b, hsa-miR-101, hsa-miR-381, hsa-miR-618, hsa-miR-222, hsa-miR-181a, hsa-miR-432, hsa-miR-96, hsa-miR-19b, hsa-miR-195, hsa-miR-548n, hsa-miR-485-5p, hsa-miR-217, hsa-miR-30c, hsa-miR-495, hsa-miR-137, hsa-miR-1288, hsa-miR-181c, hsa-miR-3942-5p, hsa-miR-548v, hsa-miR-487a, hsa-miR-221, hsa-miR-891 b, hsa-miR-205, hsa-miR-195, hsa-miR-4271, hsa-miR-3611, hsamiR-516b, hsa-miR-181d, hsa-miR-154, hsa-miR-646, hsa-miR-153, hsa-miR-34a, hsa-miR-19a, hsa-miR-107, hsa-miR-30e and hsa-miR-4262 (see, e.g. Helwak et al. *Cell*, 153(3): 654-655, 2013; Hafner et al. Cell, 141(1): 129-141, 2010; Kishore et al, Nat Methods, 8(7):559-64, 2011; Memczak et al. *Nature*, 495(7441):333-8, 2013; Selbach et al. *Nature*, 455(7209):58-63, 2008; Chi et al. Nature. 460 (7254):479-86, 2009).

In the present invention, the term "small molecule" includes any chemical or other moiety, other than polypeptides and nucleic acids, that can act to affect biological processes, particularly to modulate members of the $m^6A$ mRNA modification pathway. Small molecules can include any number of therapeutic agents presently known and used, or that can be synthesized in a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

As used herein, the term "biologic" means products derived from living sources as opposed to a chemical process. Non-limiting examples of a "biologic" include proteins, conditioned media, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No. 20070065447.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64(8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253(5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307(1): 198-205. Additional discussion of related principles, methods, etc., that may be applicable in the context of this invention are provided in, e.g., Fassina, Immunomethods. October 1994; 5(2):121-9.

As used herein, "peptide" includes targeted proteases, which are capable of, e.g., substrate-targeted inhibition of post-translational modification such as disclosed in, e.g., U.S. Patent Application Publication No. 20060275823.

"Antisense" molecules as used herein include antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry, which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described, e.g., in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described, e.g., in WO 90/10448.

The term small interfering RNA ("siRNA") refers to small inhibitory RNA duplexes that induce the RNA interference (RNAi) pathway. (Elbashir, S. M. et al. Nature 411:494-498 (2001); Caplen, N. J. et al. Proc. Natl. Acad. Sci. USA 98:9742-9747 (2001); Harborth, J. et al. J Cell Sci. 114: 4557-4565 (2001).) These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region. As used herein, siRNA molecules are not limited to RNA molecules but further encompass chemically modified nucleotides and non-nucleotides. siRNA gene-targeting may be carried out by transient siRNA transfer into cells (achieved by such classic methods as liposome-mediated transfection, electroporation, or microinjection).

In an additional aspect of the present invention, the number of stem cells and/or CAR T-cells is increased by a factor of at least 2-fold. Preferably, the number of stem cells and/or CAR T-cells is increased by a factor of at least 2.5 fold, at least 3 fold, at least 3.5 fold, at least 4-fold, such as at least 5-fold, including at least 8-fold, at least 10-fold, at least 15-fold, at least 20-fold, or more. Surprisingly and unexpectedly such levels of stem cell and/or CAR T-cell expansion are achieved using the methods of the present invention.

As noted above, the methods of the present invention may be used to expand any population of stem cells. Preferably, the stem cells that may be expanded according to the methods of the present invention may selected from hematopoietic stem cells (HSCs), hematopoietic stem and progenitor cells (HSPCs), endothelial progenitor cells (EPCs), mesenchymal stem cells (MSCs), cardiac stem cells (CSCs), neuronal stem cells (NSCs), and combinations thereof. According to one aspect, the stem cells are HSCs. According to yet another aspect, the stem cells are MSCs.

The methods of the present invention may also be capable of expanding stem cells such that the expanded cells have at least a 5-fold increase in total colony-forming units (CFU), such as an 8-fold, 10-fold, and even 15-fold or more increase. Further, the methods may be capable of providing an increase in CFU-granulocyte erythrocyte monocyte megakaryocyte (GEMM) colonies of at least 3.8-fold, such as at least 4-fold, 5-fold, and even at least 8-fold or more.

Another embodiment of the invention is a method for ex vivo expansion of a substantially undifferentiated stem cell population. This method comprises modulating a $N^6$-methyladenosine mRNA modification pathway in the undifferentiated stem cell population to expand the number of undifferentiated stem cells without significant differentiation of the stem cell population.

In this embodiment, a stem cell population is "substantially undifferentiated" if a sufficient number of cells in that population retain the ability to self-renew and can give rise to various differentiated cell types when transplanted into a recipient, for example, in the case of an HSC population, repopulating the HSC lineage when transplanted (or in the case of an MSC population, repopulating the MSC lineage when transplanted). As used herein, "without significant differentiation" means the expanded stem cell population has a sufficient number of cells that maintain a multi-lineage differentiation potential so that the full scope of a target stem lineage may be regenerated upon transplantation of the expanded stem cell population into a recipient. Thus, e.g., in the case of an HSC population, the expanded HSC population, when transplanted into a recipient, is capable of regenerating the entire hematopoietic cell lineage. In the case of a MSC population, the expanded MSC population, when transplanted into a recipient, is capable of regenerating the entire mesenchymal cell lineage.

Another embodiment is a method for ex vivo expansion of a chimeric antigen receptor (CAR) T-cell population. This method comprises modulating a $N^6$-Methyladenosine ($m^6A$) mRNA modification pathway in the CAR T-cell population to expand the number of CAR T-cells.

A further embodiment of the invention is a method for ex vivo expansion of an hematopoietic stem cell (HSC) population obtained from a tissue selected from the group consisting of peripheral blood, cord blood, and bone marrow. This method comprises modulating a $N^6$-methyladenosine mRNA modification pathway in the HSC population to expand the HSC population to a sufficient quantity while maintaining a multilineage differentiation potential in the HSC population, which is sufficient for subsequent transplantation into a subject in need thereof.

A further embodiment of the invention is a method for ex vivo expansion of a mesenchymal stem cell (MSC) population obtained from a tissue selected from the group consisting of peripheral blood, cord blood, and bone marrow. This method comprises modulating a $N^6$-methyladenosine mRNA modification pathway in the MSC population to expand the MSC population to a sufficient quantity while maintaining a multilineage differentiation potential in the MSC population, which is sufficient for subsequent transplantation into a subject in need thereof.

A further embodiment of the invention is a method for ex vivo expansion of a chimeric antigen receptor (CAR) T-cell population prepared by modifying T-cells obtained from a tissue selected from the group consisting of peripheral blood, cord blood, and bone marrow. The method comprising modulating a $N^6$-Methyladenosine ($m^6A$) mRNA modification pathway in the CAR T-cell population to expand the CAR T-cell population to a sufficient quantity which is sufficient for subsequent transplantation into a subject in need thereof.

As used herein, "obtained" from a tissue means any conventional method of harvesting or partitioning tissue from a donor. As noted previously, the tissue may be any tissue that contains a stem cell such as an HSC and/or MSC, and/or a T-cell that is capable of being modified with chimeric antigen receptors. Thus, for example, the tissue may be obtained from a blood sample, such as a peripheral or cord blood sample, or harvested from bone marrow. Methods for obtaining such samples are well known to the artisan. In the present invention, the samples may be fresh, i.e., obtained from the donor without freezing. Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Such samples may be obtained from any suitable donor. Preferably, the donor is a mammal, for example, a primate, such as a human. Furthermore, the sample may be obtained from an autologous or allogeneic donor or source. Preferably, the sample is obtained from an autologous source.

In this method, "maintaining a multilineage differentiation potential" means that the expanded HSC and/or MSC population has the ability, when transplanted into a subject in need of such a transplant, to regenerate all the types of progenitor cells e.g., CMP, GMP, MEP, and CLP, and ultimately all the types of blood cells including, e.g., red blood cells, B lymphocytes, T lymphocytes, natural killer cells, neutrophils, basophils, eosinophils, monocytes, macrophages, and platelets in the hematopoietic system.

In the present invention, that quantity of expanded HSCs and/or MSCs and/or CAR T-cells, which is "sufficient for subsequent transplantation" generally corresponds to that number of HSCs and/or MSCs and/or CAR T-cells, which would result in greater than about 1% engraftment after transplantation. This is one accepted measure of a successful transplant. In the present invention, any conventional method may be used to determine the % engraftment, including the one set forth in the Examples. Such a measure may be carried out with or without competitor cells, typically and preferably, without competitor cells. (Zhang, C. C., et al., *Nat Med*, 12(2): 240-5, 2006. Zhang, C. C. and H. F. Lodish, *Blood*, 105(11): 4314-20, 2005).

In the above described ex vivo expansion methods, modulating the $N^6$-methyladenosine mRNA modification pathway may be achieved as previously set forth. Modulating the $N^6$-methyladenosine mRNA modification pathway may include introducing a mutation into the stem cells and/or CAR T-cells that results in modulation of a molecule in the $m^6A$ mRNA modification pathway, or contacting the stem cells and/or CAR T-cells with a modulator of a molecule in the $m^6A$ mRNA modification pathway selected from the group consisting of a small molecule, a biologic, an antisense RNA, a small interfering RNA (siRNA), and combinations thereof.

In one aspect of the ex vivo expansion methods, the modulation of the $m^6A$ mRNA modification pathway involves modulation of a molecule selected from the group consisting of $m^6A$ mRNA modification readers, $m^6A$ mRNA modification writers, $m^6A$ mRNA modification erasers, and combinations thereof. Non-limiting examples of $m^6A$ modification writers include methyltransferases that are capable of post-transcriptionally installing the $m^6A$ modification in messenger RNA, and can include any selected from the group consisting of METTL3, METTL14, WTAP, KIAA1429 and combinations thereof. Non-limiting examples of $m^6A$ modification erasers include demethylases that are capable of reversing the methylation, and can include any selected from the group consisting of FTI, ALKBH5 and combinations thereof. $M^6A$ modification readers include proteins that are capable of selectively binding $m^6A$-methylated mRNA to exert regulatory functions through selective recognition of methylated mRNA. Suitable $m^6A$ modification readers can include any selected from the group consisting of Ythdf1, Ythdf2, Ythdf3, Ythdc1, Ythdc2, HNRNPC, HNRNPA2B1, elF3 and combinations thereof. According to one aspect, the $m^6A$ modification readers comprise proteins of the YTH domain family of proteins, which includes Ythdf1, Ythdf2, Ythdf3, Ythdc1, Ythdc2 and combinations thereof. (see, e.g., Wang et al. *Nature*, 505(7481):117-120, 2014; Frayling et al. *Science*, 316: 889-894, 2007; Zheng et al. *Mol. Cell.*, 49: 18-29, 2012; Cao et al. *Open Biol.*, 6(4): 160003, 2016; Maity et al. *The FEBS Journal*, 283(9): 1607-1630, 2016).

In one aspect of the ex vivo methods, modulating the $m^6A$ mRNA modification pathway comprises introducing a mutation into the stem cells and/or CAR-T cells to delete, replace, or reduce expression of a gene that expresses a molecule in the $m^6A$ mRNA modification pathway. For example, the mutation deletes, replaces or reduces expression of a gene that expresses a molecule selected from the group consisting of a $m^6A$ mRNA modification reader, a $m^6A$ mRNA modification writer, a $m^6A$ mRNA eraser, and combinations thereof. In one aspect, the mutation deletes, replaces or reduces expression of a gene that expresses a $m^6A$ mRNA modification reader, such as a $m^6A$ mRNA modification reader selected from the group consisting of Ythdf1, Ythdf2, Ythdf3, Ythdc1, HNRNPC, HNRNPA2B1, elF3, and combinations thereof. In a preferred aspect, the mutation deletes, replaces or reduces expression of a gene that expresses Ythdf2. In yet another aspect, the mutation deletes, replaces or reduces expression of a gene that expresses a $m^6A$ mRNA modification eraser, such as a $m^6A$ mRNA modification eraser selected from the group consisting of FTO, ALKBH5 and combinations thereof. In yet another aspect, the mutation deletes, replaces or reduces expression of a gene that expresses a $m^6A$ mRNA modification writer, such as a $m^6A$ mRNA modification writer selected from the group consisting of METTL3, METTL14, WTAP, KIAA1429 and combinations thereof.

In one aspect of the ex vivo expansion methods, the mutation can be introduced by any of the methods previously disclosed herein. For example, the mutation can be introduced by exposing the stem cells and/or CAR T-cells to a Mx1-Cre targeting system (see, e.g., Kuhn et al. *Science*, 269(5229): 1427-1429, 1995) that inactivates or deletes at least a portion of a gene that expresses a molecule in the $m^6A$ mRNA modification pathway. In yet another aspect, a mutation is introduced that incorporates short hairpin RNA (shRNA) into the stem cells and/or CAR T-cells to reduce expression of a gene that expresses a molecule in the $m^6A$ mRNA modification pathway. For example, the shRNA may be introduced by exposing the stem cells and/or CAR-T cells to a vector to deliver shRNA, which may be a viral vector such as lentivirus (see, e.g., Chira et al. *Oncotarget*, 6(31): 30675-30703, 2015). The shRNA may be capable of triggering gene silencing to regulate gene expression (see, e.g., Paddison et al. *Genes Dev.*, 16(8): 948-958, 2002).

In these ex vivo expansion methods, according to one aspect, modulating of the $m^6A$ mRNA modification pathway comprises down-regulating and/or inhibiting a member of the m⁶A mRNA modification pathway, such as down-regulating and/or inhibiting a m⁶A mRNA modification reader. As used herein, "down-regulating" means inhibiting or reducing the amount of or inhibiting or decreasing the activity of a member of the m⁶A mRNA modification pathway. Such down-regulation may be accomplished using, e.g. antisense RNA, siRNA, antibodies, or small molecules. As another example, the m⁶A mRNA modification reader may be down-regulated by contacting the stem cells and/or CAR T-cells with an inhibitor of an m⁶A mRNA reader, to inhibit binding and/or recognizing of the m⁶A modified mRNA by the m⁶A mRNA reader. In one aspect, the m⁶A mRNA modification reader that is down-regulated is selected from the group consisting of Ythdf1, Ythdf2, Ythdf3, Ythdc1, Ythdc2, HNRNPC, HNRNPA2B1, elF3 and combinations thereof. In a preferred aspect, the m⁶A mRNA modification reader that is down-regulated is Ythdf2. The RNA decay role of Ythdf2 has been previously elucidated (see, e.g., Wang et al. *Nature* 505(7481): 117-120, 2014). Inhibitors of the m⁶A mRNA modification reader may be any selected from the group consisting of: (inhibitors of HNRNPC) hsa-let-7e-5p (MIRT051596), hsa-mir-455-3p (MIRT037890), hsa-mir-30c-5p (MIRT047904), hsa-mir-186-5p (MIRT045150), hsa-mir-744-5p (MIRT037494), hsa-mir-18a-3p (MIRT040851), hsa-mir-484 (MIRT042196), hsa-mir-505-5p (MIRT037959), hsa-mir-615-3p (MIRT039991), hsa-mir-342-3p (MIRT043694), hsa-miR-3607-3p, hsa-miR-30d, hsa-miR-3916, hsa-miR-3162-5p, hsa-miR-1273d, hsa-miR-3161, hsa-miR-30a, hsa-miR-629, hsa-miR-208b, hsa-miR-489, hsa-miR-3148, hsa-miR-2113, hsa-miR-877, hsa-miR-455-5p, hsa-miR-186, hsa-miR-548o, hsa-miR-3139, hsa-miR-320a, hsa-miR-4311, hsa-miR-555, hsa-miR-3605-5p, hsa-miR-515-5p, hsa-miR-144, hsa-miR-499-5p, hsa-miR-1323, hsa-miR-548x, hsa-miR-299-5p, hsa-miR-653, hsa-miR-576-5p, hsa-miR-548p, hsa-miR-586, hsa-miR-888, hsa-miR-3647-3p, hsa-miR-484, hsa-miR-320b, hsa-miR-620, hsa-miR-30b, hsa-miR-548q, hsa-miR-29b-1, hsa-miR-570, hsa-miR-183, hsa-miR-1276, hsa-miR-208a, hsa-miR-186, hsa-miR-28-5p, hsa-miR-330-3p, hsa-miR-548am, hsa-miR-320d, hsa-miR-3175, hsa-miR-3155, hsa-miR-548aa, hsa-miR-519e, hsa-miR-1270, hsa-miR-513b, hsa-miR-599, hsa-miR-518f, hsa-miR-4301, hsa-miR-30c, hsa-miR-3135, hsa-miR-4286, hsa-miR-202, hsa-miR-4263, hsa-miR-4299, hsa-miR-606, hsa-miR-3133, hsa-miR-583, hsa-miR-3125, hsa-miR-501-5p, hsa-miR-7-1, hsa-miR-514b-3p, hsa-miR-3155b, hsa-miR-548d-3p, hsa-miR-224, hsa-miR-7-2, hsa-miR-708, hsa-miR-3199, hsa-miR-514, hsa-miR-30e (see, e.g. Helwak et al. *Cell*, 153(3): 654-655, 2013; Whisnant et al., *M Bio* 4(2), 2013:e000193); (inhibitors of HNRNPA2B1) hsa-mir-92a-3p (MIRT049721), hsa-mir-30c-5p (MIRT048009), hsa-mir-191-5p (MIRT045809), hsa-let-7f-5p (MIRT051404), hsa-mir-27b-3p (MIRT046213), hsa-mir-877-3p (MIRT037116), hsa-mir-615-3p (MIRT040278), hsa-mir-1260b (MIRT052680), hsa-mir-103a-3p (MIRT027027), hsa-mir-16-5p (MIRT031508), hsa-mir-1296-5p (MIRT036075), hsa-mir-197-3p (MIRT048098), hsa-miR-548j, hsa-miR-3678-3p, hsa-miR-607, hsa-miR-188-5p, hsa-miR-15a, hsa-miR-3653, hsa-miR-371-5p, hsa-miR-550a, hsa-miR-3622b-3p, hsa-miR-548a-5p, hsa-miR-3170, hsa-miR-3148, hsa-miR-556-3p, hsa-miR-490-3p, hsa-miR-559, hsa-miR-200c, hsa-miR-130a, hsa-miR-548y, hsa-miR-548o, hsa-miR-23c, hsa-miR-491-3p, hsa-miR-335, hsa-miR-3667-3p, hsa-miR-466, hsa-miR-23b, hsa-miR-4310, hsa-miR-127-5p, hsa-miR-548b-5p, hsa-miR-616, hsa-miR-16, hsa-miR-338-3p, hsa-miR-3200-5p, hsa-miR-362-3p, hsa-miR-448, hsa-miR-1306, hsa-miR-944, hsa-miR-3684, hsa-miR-373, hsa-miR-103a, hsa-miR-380, hsa-miR-499-5p, hsa-miR-1323, hsa-miR-323-5p, hsa-miR-3674, hsa-miR-1252, hsa-miR-33b, hsa-miR-580, hsa-miR-548c-3p, hsa-miR-103a-2, hsa-miR-548w, hsa-miR-600, hsa-miR-634, hsa-miR-586, hsa-miR-497, hsa-miR-720, hsa-miR-654-3p, hsa-miR-524-5p, hsa-miR-543, hsa-miR-548q, hsa-let-7f-2, hsa-miR-330-5p, hsa-miR-500a, hsa-miR-548I, hsa-miR-570, hsa-miR-374a, hsa-miR-1184, hsa-miR-649, hsa-miR-424, hsa-miR-3658, hsa-miR-186, hsa-miR-326, hsa-miR-548d-5p, hsa-miR-23a, hsa-miR-15b, hsa-miR-190, hsa-miR-203, hsa-miR-548h, hsa-miR-3136-5p, hsa-miR-618, hsa-miR-551b, hsa-miR-211, hsa-miR-1305, hsa-miR-513b, hsa-miR-96, hsa-miR-2117, hsa-miR-548n, hsa-miR-3910, hsa-miR-217, hsa-miR-892b, hsa-miR-502-5p, hsa-miR-548i, hsa-miR-520d-5p, hsa-miR-4299, hsa-miR-1285, hsa-miR-3133, hsa-miR-483-3p (see, e.g., Hafner et al. *Cell*, 141(1): 129-141, 2010; Helwak et al. *Cell*, 153(3): 654-655, 2013); (inhibitors of Ythdf1) hsa-miR-548g, hsa-miR-204, hsa-miR-3143, hsa-miR-521, hsa-miR-195, hsa-miR-3182, hsa-miR-3941, hsa-miR-34c-3p, hsa-miR-767-3p, hsa-miR-563, hsa-miR-548c-5p, hsa-miR-1911, hsa-miR-26b, hsa-miR-190b, hsa-miR-33a, hsa-miR-329, hsa-miR-221, hsa-miR-612, hsa-miR-3185, hsa-miR-3156-5p, hsa-miR-107, hsa-miR-664, hsa-miR-3657; (inhibitors of Ythdf2) hsa-mir-615-3p (MIRT040054), hsa-mir-106b-5p (MIRT044257), hsa-mir-1 (MIRT023842), miR-145, hsa-miR-3607-3p, hsa-miR-200a, hsa-miR-301a, hsa-miR-519a, hsa-miR-141, hsa-miR-130b, hsa-miR-181b, hsa-miR-301b, hsa-miR-3117-3p, hsa-miR-1236, hsa-miR-181a, hsa-miR-519c-3p, hsa-miR-551b, hsa-miR-519e, hsa-miR-519b-3p, hsa-miR-19b, hsa-miR-1303, hsa-miR-608, hsa-miR-145, hsa-miR-130a, hsa-miR-181c, hsa-miR-323b-3p, hsa-miR-421, hsa-miR-515-5p, hsa-miR-3666, hsa-miR-181d, hsa-miR-146a, hsa-miR-4295, hsa-miR-454, hsa-miR-3919, hsa-miR-19a, hsa-miR-543, hsa-miR-4262 (see, e.g. Helwak et al. *Cell*, 153(3): 654-655, 2013; Selbach et al. *Nature*, 455(7209): 58-63, 2008; Yang et al. *J Biol Chem.*, 292(9): 3614-3623, 2017); (inhibitors of Ythdf3) hsa-miR-582-3p, hsa-miR-579, hsa-miR-520e, hsa-miR-520f, hsa-miR-3152-3p, hsa-miR-106a, hsa-miR-30d, hsa-miR-30a, hsa-miR-93, hsa-miR-508-5p, hsa-miR-29a, hsa-miR-3148, hsa-miR-490-5p, hsa-miR-520b, hsa-miR-20a, hsa-miR-409-3p, hsa-miR-4255, hsa-let-7i, hsa-miR-373, hsa-let-7e, hsa-miR-520c-3p, hsa-miR-3920, hsa-miR-127-5p, hsa-miR-380, hsa-miR-616, hsa-miR-4277, hsa-miR-448, hsa-miR-16-2, hsa-let-7c, hsa-miR-340, hsa-miR-373, hsa-miR-520a-3p, hsa-miR-144, hsa-miR-1265, hsa-miR-548x, hsa-miR-362-5p, hsa-miR-33b, hsa-miR-26b, hsa-miR-17, hsa-miR-569, hsa-miR-3618, hsa-miR-576-5p, hsa-miR-922, hsa-miR-302a, hsa-miR-106b, hsa-miR-888, hsa-miR-484, hsa-let-7b, hsa-miR-582-5p, hsa-let-7f, hsa-miR-30b, hsa-miR-524-5p, hsa-miR-302d, hsa-let-7d, hsa-miR-513a-5p, hsa-miR-500a, hsa-miR-570, hsa-miR-548I, hsa-miR-105, hsa-miR-374c, hsa-let-7g hsa-miR-372, hsa-miR-3658, hsa-let-7a, hsa-miR-3908, hsa-miR-302b, hsa-miR-526b, hsa-miR-190, hsa-miR-181 b, hsa-miR-433, hsa-miR-98, hsa-miR-3606, hsa-miR-595, hsa-miR-548am, hsa-miR-187, hsa-miR-561, hsa-miR-181a, hsa-miR-3155, hsa-miR-655, hsa-miR-302c, hsa-miR-195, hsa-miR-26a, hsa-miR-590-3p, hsa-miR-30c, hsa-miR-502-5p, hsa-miR-495, hsa-miR-137, hsa-miR-181c, hsa-miR-520d-5p, hsa-miR-3942-5p, hsa-miR-202, hsa-miR-302e, hsa-miR-513c, hsa-miR-885-5p, hsa-miR-520a-5p, hsa-miR-583, hsa-miR-1297, hsa-miR-7-1, hsa-miR-520d-3p, hsa-miR-3155b, hsa-miR-3182, hsa-miR-519d, hsa-miR-550a, hsa-miR-7-2, hsa-miR-181d, hsa-miR-190b, hsa-miR-1912, hsa-miR-151-3p, hsa-miR-33a, hsa-miR-525-5p, hsa-miR-20b, hsa-miR-514b-5p, hsa-miR-30e, hsa-miR-4262, hsa-miR-636; (inhibitor of elF3) hsa-mir-92b-3p (MIRT040734), hsa-mir-16-5p (MIRT031705), hsa-mir-18a-3p (MIRT040974), hsa-mir-155-5p (MIRT020771), hsa-mir-484 (MIRT042324), hsa-let-7c-5p (MIRT051776), hsa-miR-3910, hsa-miR-148b, hsa-miR-136, hsa-miR-15a, hsa-miR-488, hsa-miR-500a, hsa-miR-1297, hsa-miR-3159, hsa-miR-374c, hsa-miR-424, hsa-miR-7-1, hsa-miR-186, hsa-miR-195, hsa-miR-15b, hsa-miR-26b, hsa-miR-505, hsa-miR-1206, hsa-miR-653, hsa-miR-1283, hsa-miR-7-2, hsa-miR-196a, hsa-miR-497, hsa-miR-33a, hsa-miR-655, hsa-miR-26a hsa-miR-16, hsa-mir-151a-3p (MIRT043600), hsa-mir-92a-3p (MIRT049064), hsa-mir-615-3p (MIRT039779), hsa-mir-877-3p (MIRT036964), hsa-mir-222-3p (MIRT046746), hsa-mir-423-3p (MIRT042468), hsa-mir-324-3p (MIRT042887), hsa-mir-124-3p (MIRT022932), hsa-miR-3140-3p, hsa-miR-124, hsa-miR-198, hsa-miR-525-5p, hsa-miR-506, hsa-miR-520a-5p, hsa-miR-196a* hsa-miR-3117-3p, hsa-mir-342-5p (MIRT038210), hsa-mir-378a-5p (MIRT043981), hsa-mir-615-3p (MIRT040086), hsa-Iet-7b-5p (MIRT052211), hsa-mir-455-3p (MIRT037879), hsa-miR-4267, hsa-miR-590-3p, hsa-mir-106b-5p (MIRT044355), hsa-mir-320a (MIRT044466), hsa-mir-16-5p (MIRT032018), hsa-mir-155-5p (MIRT021009), hsa-miR-4302, hsa-mir-191-5p (MIRT045793), hsa-mir-1303 (MIRT035890), hsa-mir-193b-3p (MIRT016316), hsa-mir-222-3p (MIRT046640), hsa-mir-532-3p (MIRT037924), hsa-mir-18a-3p (MIRT040929), hsa-mir-92a-3p (MIRT049001), hsa-miR-582-3p, hsa-miR-4265, hsa-miR-218-2, hsa-miR-1271, hsa-miR-340, hsa-miR-221, hsa-miR-20b, hsa-miR-508-3p, hsa-miR-141, hsa-miR-4325, hsa-miR-889, hsa-miR-29a, hsa-miR-129-3p, hsa-miR-129, hsa-miR-96, hsa-miR-3163, hsa-miR-187, hsa-miR-196a, hsa-miR-222, hsa-miR-1179, hsa-miR-182, hsa-miR-9* hsa-miR-32, hsa-miR-143, hsa-miR-4296 (see, e.g., Helwak et al. *Cell,* 153(3): 654-656, 2013; Selbach et al. *Nature,* 455 (7209):58-63, 2008; Baek et al, *Nature,* 455(7209):64-71, 2008; Leivonen et al. *Mol Cell Proteomics,* 10(7), 2011: M110.005322): (inhibitors of YTHDC1) hsa-mir-20a-3p (MIRT038967), hsa-mir-103a-3p (MIRT027037), hsa-mir-1 (MIRT023492), hsa-mir-19b-3p (MIRT031105), hsa-mir-100-5p (MIRT048400), hsa-mir-93-5p (MIRT027989), hsa-mir-16-5p (MIRT031379), hsa-let-7b-5p (MIRT052150), hsa-miR-520f, hsa-miR-300, hsa-miR-15a, hsa-miR-200a, hsa-miR-605, hsa-miR-30d, hsa-miR-30a, hsa-miR-3613-3p, hsa-miR-509-3-5p, hsa-miR-34c-5p, hsa-miR-324-3p, hsa-miR-1248, hsa-miR-152, hsa-miR-548t, hsa-miR-4310, hsa-miR-145, hsa-miR-516a-3p, hsa-miR-16, hsa-miR-3668, hsa-miR-4277, hsa-miR-448, hsa-miR-16-2, hsa-miR-148b, hsa-miR-509-5p, hsa-miR-103a, hsa-miR-1265, hsa-miR-2115, hsa-miR-548c-3p, hsa-miR-148a, hsa-miR-548p, hsa-miR-513a-3p, hsa-miR-497, hsa-miR-3647-3p, hsa-miR-382, hsa-miR-30b, hsa-miR-543, hsa-let-7f-2, hsa-miR-1269, hsa-miR-3164, hsa-miR-503, hsa-miR-500a, hsa-miR-449a, hsa-miR-141, hsa-miR-424, hsa-miR-3908, hsa-miR-889, hsa-miR-2116, hsa-miR-330-3p, hsa-miR-15b, hsa-miR-181b, hsa-miR-187, hsa-miR-1237, hsa-miR-449b, hsa-miR-101, hsa-miR-381, hsa-miR-618, hsa-miR-222, hsa-miR-181a, hsa-miR-432, hsa-miR-96, hsa-miR-19b, hsa-miR-195, hsa-miR-548n, hsa-miR-485-5p, hsa-miR-217, hsa-miR-30c, hsa-miR-495, hsa-miR-137, hsa-miR-1288, hsa-miR-181c, hsa-miR-3942-5p, hsa-miR-548v, hsa-miR-487a, hsa-miR-221, hsa-miR-891 b, hsa-miR-205, hsa-miR-195, hsa-miR-4271, hsa-miR-3611, hsa-miR-516b, hsa-miR-181d, hsa-miR-154, hsa-miR-646, hsa-miR-153, hsa-miR-34a, hsa-miR-19a, hsa-miR-107, hsa-miR-30e and hsa-miR-4262 (see, e.g. Helwak et al. *Cell,* 153(3): 654-655, 2013; Hafner et al. Cell, 141(1): 129-141, 2010; Kishore et al, Nat Methods, 8(7):559-64, 2011; Memczak et al. *Nature,* 495(7441):333-8, 2013; Selbach et al. *Nature,* 455(7209):58-63, 2008; Chi et al. Nature. 460 (7254):479-86, 2009).

In these ex vivo expansion methods, it is preferred that the stem cell is selected from HSCs, hematopoietic stem and progenitor cells (HSPCs), endothelial progenitor cells, (EPCs), mesenchymal stem cells (MSCs), cardiac stem cells (CSCs), neuronal stem cells (NSCs), and combinations thereof. According to certain aspects, the stem cell is an HSC. According to other aspects, the stem cell is a MSC. The ex vivo expansion methods can also use a population of cells comprising CAR T-cells. In these methods, the HSC and/or MSC is obtained from a mammalian, e.g., primate or human, tissue selected from the group consisting of cord blood, peripheral blood, and bone marrow, although any HSC and/or MSC-containing tissue may be used.

In another aspect of the method for ex vivo expansion of an hematopoietic stem cell (HSC) population, the expansion of the number of stem cells is by at least 2-fold, such as e.g., by at least 2.5-fold, at least 3-fold, at least 3.5-fold, at least 4-fold, and including at least 5-fold, at least 8-fold, at least 10-fold, at least 15-fold, or at least 20-fold or more.

In another aspect of the method for ex vivo expansion of a mesenchymal stem cell (MSC) population, the expansion of the number of stem cells is by at least 2-fold, such as e.g., by at least 2.5-fold, at least 3-fold, at least 3.5 fold, at least 4-fold, and including at least 5-fold, at least 8-fold, at least 10-fold, at least 15-fold, or at least 20-fold or more.

In another aspect of the method for ex vivo expansion of CAR T-cell population, the expansion of the number of CAR T-cells is by at least 2-fold, such as e.g., by at least 2.5-fold, at least 3-fold, at least 3.5 fold, at least 4-fold, and including at least 5-fold, at least 8-fold, at least 10-fold, at least 15-fold, or at least 20-fold or more.

Yet another embodiment of the present invention is an expanded, substantially undifferentiated stem cell population made by a method of the present invention, such as, e.g., the method for ex vivo expansion of a substantially undifferentiated stem cell population or the method for ex vivo expansion of an hematopoietic stem cell (HSC) population.

Yet another embodiment of the present invention is an expanded, substantially undifferentiated stem cell population made by a method of the present invention, such as, e.g., the method for ex vivo expansion of a substantially undifferentiated stem cell population or the method for ex vivo expansion of an mesenchymal stem cell (MSC) population.

Yet another embodiment of the present invention is an expanded, CAR T-cell population made by a method of the present invention, such as, e.g., the method for ex vivo expansion of a CAR T-cell population.

An additional embodiment of the present invention is a method for ex vivo expansion of hematopoietic stem cells (HSCs) by at least 2-fold, wherein the expanded HSCs, are competent to reconstitute an HSC lineage upon transplantation into a mammalian subject in need thereof. This method comprises introducing a mutation into the stem cells that results in deletion, replacement or reduced expression of a gene expressing a m$^6$A mRNA modification reader and culturing the population of HSCs in a suitable culture medium.

An additional embodiment of the present invention is a method for ex vivo expansion of mesenchymal stem cells (MSCs) by at least 2-fold, wherein the expanded MSCs, are competent to reconstitute a MSC lineage upon transplantation into a mammalian subject in need thereof. This method comprises introducing a mutation into the stem cells that results in deletion, replacement or reduced expression of a gene expressing a $m^6A$ mRNA modification reader and culturing the population of HSCs in a suitable culture medium.

An additional embodiment of the present invention is a method for ex vivo expansion of chimeric antigen receptor (CAR) T-cells by at least 2-fold, wherein the expanded CAR T-cells are competent to treat a cancer and/or blood disorder upon transplantation into a mammalian subject in need thereof. This method comprises introducing a mutation into the CAR T-cells that results in deletion, replacement or reduced expression of a gene expressing a $m^6A$ mRNA modification reader and culturing the population of CAR T-cells in a suitable culture medium.

In this aspect of the invention, "competent to reconstitute an HSC lineage" means that the expanded HSCs, when transplanted into a suitable mammalian subject, result in greater than 1% engraftment in the recipient, which engrafted cells are able to differentiate into the cell lineages necessary to have a normal functioning hematopoietic system. In this aspect of the invention, "competent to reconstitute a MSC lineage" means that the expanded MSCs, when transplanted into a suitable mammalian subject, result in greater than 1% engraftment in the recipient, which engrafted cells are able to differentiate into the cell lineages necessary to have a normal functioning hematopoietic system. In this aspect of the invention "competent to treat a cancer and/or blood disorder" means that the expanded CAR T-cells, when transplanted into a suitable mammalian subject, are capable of providing treatment of a cancer and/or blood disorder from which the mammalian subject is suffering, such as for example at least one of leukemia and lymphoma. In this method, a "suitable culture medium", "fluid media" and "media" which are used interchangeably herein, mean physiologically balanced salt solutions that can maintain a stem cell population and/or CAR T-cell population for a required period of time, which solution may optionally be supplemented with suitable $m^6A$ mRNA modification pathway modulators of the present invention. Such base culture media are well known in the arts. A non-limiting example of a suitable base culture medium for HSCs is StemSpan Media (Stem Cell Technologies, Cat. No. 09600), which is supplemented with 10 ug/ml Heparin, 5× Penicillin/Streptomycin, 10 ng/ml recombinant mouse (rm) Stem Cell Factor, and 20 ng/ml rm-Thrombopoietin.

In one aspect of the invention, the ex vivo expansion of HSCs and/or MSCs and/or CAR T-cells by at least 2-fold can be performed by any of the methods that have been described herein. For example, the method may involve introducing a mutation that deletes, replaces or reduces expression of a gene expressing a $m^6A$ mRNA modification reader, such as Ythdf2. Further, the mutation may be introduced by any of the methods described herein, such as by exposing the stem cells and/or CAR T-cells to a Mx1-Cre targeting system that inactivates or deletes at least a portion of a gene that expresses a $m^6A$ mRNA modification reader. The mutation may also be introduced by incorporating shRNA into the stem cells and/or CAR-T cells to reduce expression of a gene that expresses a $m^6A$ mRNA modification reader. Other methods of introducing a mutation, and mutations that target other $m^6A$ mRNA modification readers that are described herein may also be provided.

In one aspect of this embodiment, the HSCs and/or MSCs and/or CAR T-cells are obtained from a mammalian tissue, preferably primate or human tissue, which is selected from cord blood, peripheral blood, and bone marrow. In this embodiment, the number of HSCs and/or MSCs and/or CAR T-cells is expanded by a factor of at least 2-fold, such as at least 2.5-fold, at least 3-fold, at least 3.5-fold, at least 4-fold, and including at least 5-fold, at least 8-fold, at least 10-fold, at least 15-fold, at least 20-fold or more.

Yet another embodiment of the present invention is a kit for expanding an hematopoietic stem cell (HSC) population, mesenchymal stem cell (MSC) population, and/or CAR T-cell population for subsequent transplantation into a subject in need thereof. The kit comprises a system for introducing a mutation into the HSC, MSC and/or CAR T-cell population that results in deletion, replacement or reduced expression of a gene expressing a $m^6A$ mRNA modification reader, and instructions for use thereof. Preferably, in the kit, the system for introducing a mutation into the HSC, MSC and/or CAR-T cell population includes one or more reagents capable of introducing a mutation into the HSC, MSC and/or CAR-T cell population that results in deletion, replacement or reduced expression of a gene expressing Ythdf2. For example, the kit can include a system for introducing a mutation into the HSC, MSC and/or CAR-T cell population that comprises a Mx1-Cre targeting system that inactivates or deletes at least a portion of a gene that expresses a $m^6A$ mRNA modification reader. The kit can also include a system for introducing a mutation into the HSC, MSC and/or CAR T-cell population that comprises reagents for delivering a lentivirus that incorporates shRNA into the HSC, MSC and/or CAR T-cell population to reduce expression of a gene that expresses a $m^6A$ mRNA modification reader. The kit may further comprise other systems/methods set forth herein for introducing the mutation to modulate a $m^6A$ mRNA modification pathway, such as by deleting, replacing, or reducing expression of a gene expressing a $m^6A$ mRNA modification reader, including Ythdf2. The kit and the components therein may be packaged in any suitable manner for distribution and/or storage.

In yet another embodiment, a kit for expanding an hematopoietic stem cell population (HSC) population and/or mesenchymal stem cell (MSC) population and/or CAR-T cell population for subsequent transplantation into a subject in need thereof is provided. The kit comprises an inhibitor of a $m^6A$ mRNA modification reader, and instructions for use thereof, where the inhibitor may be any of the inhibitors disclosed herein, such as, e.g., an inhibitor of Ythdf2.

In one aspect of this embodiment, the kits may be able to provide an expansion of the number of stem cells and/or CAR T-cells by a factor selected from the group consisting of at least 2-fold, at least 2.5 fold, at least 3-fold, at least 3.5-fold, at least 4-fold, at least 5-fold, at least 8-fold, at least 10-fold, at least 15-fold, at least 20-fold or more.

A further embodiment of the present invention is a method for administering an hematopoietic stem cell (HSC) to a subject in need thereof. The method comprises (a) introducing, into a sample containing an HSC population, a mutation that results in deletion, replacement or reduced expression of a gene expressing a $m^6A$ mRNA modification reader; (b) culturing the sample in a suitable culture media for a period of time sufficient to expand the number of HSCs in the sample to a number sufficient to transplant into the subject; and (c) administering the HSCs to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the HSC population that reduces expression of a gene expressing Ythdf2. Furthermore, the HSCs may be obtained from any appropriate tissue such as, e.g., a tissue selected from the group consisting of cord blood, peripheral blood, and bone marrow, and the subject may be a mammal, such as a human.

A further embodiment of the present invention is a method for administering a mesenchymal stem cell (MSC) to a subject in need thereof. The method comprises (a) introducing, into a sample containing a MSC population, a mutation that results in deletion, replacement or reduced expression of a gene expressing a $m^6A$ mRNA modification reader; (b) culturing the sample in a suitable culture media for a period of time sufficient to expand the number of MSCs in the sample to a number sufficient to transplant into the subject; and (c) administering the MSCs to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the MSC population that reduces expression of a gene expressing Ythdf2. Furthermore, the MSCs may be obtained from any appropriate tissue such as, e.g., a tissue selected from the group consisting of cord blood, peripheral blood, and bone marrow, and the subject may be a mammal, such as a human.

A further embodiment of the present invention is a method for administering a chimeric antigen receptor (CAR) T-cell to a subject in need thereof. The method comprises (a) introducing, into a sample containing a CAR T-cell population, a mutation that results in deletion, replacement or reduced expression of a gene expressing a $m^6A$ mRNA modification reader; (b) culturing the sample in a suitable culture media for a period of time sufficient to expand the number of CAR T-cells in the sample to a number sufficient to transplant into the subject; and (c) administering the CAR T-cells to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the CAR T-cell population that reduces expression of a gene expressing Ythdf2. Furthermore, the CAR T-cells may be obtained from any appropriate tissue such as, e.g., a tissue selected from the group consisting of cord blood, peripheral blood, and bone marrow, and the subject may be a mammal, such as a human.

A further embodiment of the present invention is a method for administering an hematopoietic stem cell (HSC) to a subject in need thereof. The method comprises: (a) culturing, in a suitable culture media, a sample containing an HSC population in the presence of an inhibitor of a $m^6A$ mRNA modification reader, for a period of time sufficient to expand the number of HSCs in the sample to a number sufficient to transplant into the subject; (b) removing from the culture the inhibitor of the $m^6A$ mRNA modification reader; and (c) administering the HSCs to the subject. In this method, the inhibitor is as previously disclosed, such as, e.g., an inhibitor of Ythdf2. Furthermore, the HSCs may be obtained from any appropriate tissue, such as, e.g., a tissue selected from the group consisting of cord blood, peripheral blood, and bone marrow, and the subject may be a mammal, such as a human.

A further embodiment of the present invention is a method for administering a mesenchymal stem cell (MSC) to a subject in need thereof. The method comprises: (a) culturing, in a suitable culture media, a sample containing an MSC population in the presence of an inhibitor of a $m^6A$ mRNA modification reader, for a period of time sufficient to expand the number of MSCs in the sample to a number sufficient to transplant into the subject; (b) removing from the culture the inhibitor of the $m^6A$ mRNA modification reader; and (c) administering the MSCs to the subject. In this method, the inhibitor is as previously disclosed, such as, e.g., an inhibitor of Ythdf2. Furthermore, the MSCs may be obtained from any appropriate tissue, such as, e.g., a tissue selected from the group consisting of cord blood, peripheral blood, and bone marrow, and the subject may be a mammal, such as a human.

A further embodiment of the present invention is a method for administering a chimeric antigen receptor (CAR) T-cell to a subject in need thereof. The method comprises: (a) culturing, in a suitable culture media, a sample containing an CAR T-cell population in the presence of an inhibitor of a $m^6A$ mRNA modification reader, for a period of time sufficient to expand the number of CAR T-cells in the sample to a number sufficient to transplant into the subject; (b) removing from the culture the inhibitor of the $m^6A$ mRNA modification reader; and (c) administering the CAR T-cells to the subject. In this method, the inhibitor is as previously disclosed, such as, e.g., an inhibitor of Ythdf2. Furthermore, the CAR T-cells may be obtained from any appropriate tissue, such as, e.g., a tissue selected from the group consisting of cord blood, peripheral blood, and bone marrow, and the subject may be a mammal, such as a human.

An additional embodiment of the present invention is a method for reconstituting bone marrow in a subject in need thereof. The method comprises (a) introducing, into a sample containing an HSC population, a mutation that results in deletion, replacement or reduced expression of a gene expressing a $m^6A$ mRNA modification reader; (b) culturing the sample in a suitable culture media for a period of time sufficient to expand the number of HSCs in the sample to a number sufficient to transplant into the subject; and (c) administering the HSCs to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the HSC population that reduces expression of a gene expressing Ythdf2. Furthermore, the HSCs may be obtained from any appropriate tissue, such as, e.g., a tissue selected from the group consisting of cord blood, peripheral blood, and bone marrow, and the subject may be a mammal, such as a human.

An additional embodiment of the present invention is a method for reconstituting bone marrow in a subject in need thereof. The method comprises (a) introducing, into a sample containing a MSC population, a mutation that results in deletion, replacement or reduced expression of a gene expressing a $m^6A$ mRNA modification reader; (b) culturing the sample in a suitable culture media for a period of time sufficient to expand the number of MSCs in the sample to a number sufficient to transplant into the subject; and (c) administering the MSCs to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the MSC population that reduces expression of a gene expressing Ythdf2. Furthermore, the MSCs may be obtained from any appropriate tissue, such as, e.g., a tissue selected from the group consisting of cord blood, peripheral blood, and bone marrow, and the subject may be a mammal, such as a human.

An additional embodiment of the present invention is a method for treating cancer and/or a blood disorder in a subject in need thereof. The method comprises (a) introducing, into a sample containing a CAR T-cell population, a mutation that results in deletion, replacement or reduced expression of a gene expressing a $m^6A$ mRNA modification reader; (b) culturing the sample in a suitable culture media for a period of time sufficient to expand the number of CAR T-cells in the sample to a number sufficient to transplant into the subject; and (c) administering the CAR T-cells to the subject. In this embodiment, the method of introducing the mutation, and the mutation targeted at the $m^6A$ mRNA modification reader, are as previously disclosed, such as, for example, a mutation that results in deletion of a gene expressing Ythdf2, or a mutation that results in incorporation of shRNA into the CAR T-cell population that reduces expression of a gene expressing Ythdf2. Furthermore, the CAR T-cells may be obtained from any appropriate tissue, such as, e.g., a tissue selected from the group consisting of cord blood, peripheral blood, and bone marrow, and the subject may be a mammal, such as a human.

In yet another embodiment, there is provided a method for reconstituting bone marrow in a subject in need thereof. This method comprises (a) culturing, in a suitable culture media, a sample containing an HSC population in the presence of an inhibitor of a $m^6A$ mRNA modification reader, for a period of time sufficient to expand the number of HSCs in the sample to a number sufficient to transplant into the subject; (b) removing from the culture the inhibitor of the $m^6A$ mRNA modification reader; and (c) administering the HSCs to the subject. In this method, the inhibitor is as previously disclosed, such as an inhibitor of Ythdf2. Furthermore, the HSCs may be obtained from any appropriate tissue, such as, e.g., a tissue selected from the group consisting of cord blood, peripheral blood, and bone marrow, and the subject may be a mammal, such as a human.

In yet another embodiment, there is provided another method for reconstituting bone marrow in a subject in need thereof. This method comprises (a) culturing, in a suitable culture media, a sample containing an MSC population in the presence of an inhibitor of a $m^6A$ mRNA modification reader, for a period of time sufficient to expand the number of MSCs in the sample to a number sufficient to transplant into the subject; (b) removing from the culture the inhibitor of the $m^6A$ mRNA modification reader; and (c) administering the MSCs to the subject. In this method, the inhibitor is as previously disclosed, such as an inhibitor of Ythdf2. Furthermore, the MSCs may be obtained from any appropriate tissue, such as, e.g., a tissue selected from the group consisting of cord blood, peripheral blood, and bone marrow, and the subject may be a mammal, such as a human.

In these methods, "reconstituting bone marrow" means restoration of all or a portion of the bone marrow in a subject suffering from a disease in which normal bone marrow function has been compromised. Non-limiting examples of such diseases include blood disorders such as aplastic anemia, myelodysplastic syndromes (MDS), paroxysmal nocturnal hemoglobinuria (PNH), and blood cancers, such as leukemia. Thus, as used herein, "reconstituted" means that the transplanted HSCs and/or MSCs are able to successfully engraft in the host and differentiate into all the cell lineages typically found in or derived from bone marrow. Aspects of the methods herein may involve transplantation of HSCs and/or MSCs obtained from tissue selected from the group consisting of cord blood, peripheral blood, and bone marrow, to the subject, for the treatment of blood disorders such as leukemia and lymphoma.

In yet another embodiment, there is provided another method for treating cancer and/or a blood disorder in a subject in need thereof. This method comprises (a) culturing, in a suitable culture media, a sample containing a chimeric antigen receptor (CAR) T-cell population in the presence of an inhibitor of a $m^6A$ mRNA modification reader, for a period of time sufficient to expand the number of CAR T-cells in the sample to a number sufficient to transplant into the subject; (b) removing from the culture the inhibitor of the $m^6A$ mRNA modification reader; and (c) administering the CAR T-cells to the subject. In this method, the inhibitor is as previously disclosed, such as an inhibitor of Ythdf2. Furthermore, the T-cells that are modified to prepare the CAR T-cells may be obtained from any appropriate tissue, such as, e.g., a tissue selected from the group consisting of cord blood, peripheral blood, and bone marrow, and the subject may be a mammal, such as a human.

In these methods, "treating cancer and/or a blood disorder in a subject" means eradicating cancer cells, alleviating symptoms, or otherwise reducing a disease state in a subject suffering from the cancer and/or blood disorder. Non-limiting examples of cancers and/or blood disorders include blood disorders such as aplastic anemia, myelodysplastic syndromes (MDS), paroxysmal nocturnal hemoglobinuria (PNH), and blood cancers, such as leukemia and lymphoma.

In these methods, "a period of time sufficient to expand the number of HSCs" means the minimum amount of time to expand the HSCs in culture to a point where there is a sufficient number of HSCs for one or more transplantations, and "a period of time sufficient to expand the number of MSCs" means the minimum amount of time to expand the MSCs in culture to a point where there is a sufficient number of MSCs for one or more transplantations. Similarly, "a period of time sufficient to expand the number of CAR T-cells" means the minimum amount of time to expand the CAR T-cells in culture to a point where there is a sufficient number of CAR T-cells for one or more transplantations. Typically, such a period of time may be at least about 10 days in culture. Under certain circumstances, it may be desirable to expand the stem cell and/or CAR T-cell, e.g., HSC and/or MSC, population beyond what is required for a single transplantation. For example, it may be desirable to expand the stem cell and/or CAR T-cell, e.g., HSC and/or MSC, population to a number sufficient for multiple transplantations, such as e.g., from about 2 to about 100 transplantations. In these circumstances, the excess cells may be preserved for later use by any conventional method, such as e.g., by cryo-preservation.

As indicated previously, "a number sufficient to transplant" means the minimum number of stem cells, e.g., HSCs and/or MSCs and/or CAR T-cells, necessary to achieve greater than 1% engraftment in a recipient. "Administering the HSCs to the subject" means conventional methods for delivering HSCs to the subject, including but not limited to, delivering the HSCs surgically and/or intravenously. "Administering the MSCs to the subject" means conventional methods for delivering MSCs to the subject, including but not limited to, delivering the MSCs surgically and/or intravenously. "Administering the CAR T-cells to the subject" means conventional methods for delivering CAR T-cells to the subject, including but not limited to, delivering the MSCs surgically and/or intravenously. In these embodiments, the tissue the HSCs and/or MSCs and/or T-cells are obtained from, and the $m^6A$ mRNA modification reader inhibitors are as previously disclosed.

An additional embodiment of the present invention is a method for expanding a population of hematopoietic stem cells (HSCs). This method comprises culturing a population of HSCs under conditions sufficient to result in an expansion of the HSC population by at least 2-fold, wherein the expanded population of HSCs is suitable for transplantation into a mammal in need thereof. In this embodiment the "conditions sufficient to result in an expansion of the HSC population" are those conditions that can result in expansion of HSCs in culture by, e.g., at least 2-fold, such as, e.g., by at least 2.5-fold, at least 3-fold, at least 3.5 fold, at least 4-fold, at least 5-fold, at least 8-fold, at least 10-fold, at least 15-fold, at least 20-fold or more. "Suitable for transplantation into a mammal" means that the number and quality of HSCs is sufficient to support greater than 1% engraftment in a mammalian recipient, such as, e.g., a primate recipient, including an human recipient, in need thereof.

An additional embodiment of the present invention is a method for expanding a population of mesenchymal stem cells (MSCs). This method comprises culturing a population of MSCs under conditions sufficient to result in an expansion of the MSC population by at least 2-fold, wherein the expanded population of MSCs is suitable for transplantation into a mammal in need thereof. In this embodiment the "conditions sufficient to result in an expansion of the MSC population" are those conditions that can result in expansion of MSCs in culture by, e.g., at least 2-fold, such as, e.g., by at least 2.5-fold, at least 3-fold, at least 3.5 fold, at least 4-fold, at least 5-fold, at least 8-fold, at least 10-fold, at least 15-fold, at least 20-fold or more. "Suitable for transplantation into a mammal" means that the number and quality of MSCs is sufficient to support greater than 1% engraftment in a mammalian recipient, such as, e.g., a primate recipient, including an human recipient, in need thereof.

An additional embodiment of the present invention is a method for expanding a population of chimeric antigen receptor (CAR) T-cells. This method comprises culturing a population of CAR T-cells under conditions sufficient to result in an expansion of the CAR T-cell population by at least 2-fold, wherein the expanded population of CAR T-cells is suitable for transplantation into a mammal in need thereof. In this embodiment the "conditions sufficient to result in an expansion of the CAR T-cell population" are those conditions that can result in expansion of CAR T-cells in culture by, e.g., at least 2-fold, such as, e.g., by at least 2.5-fold, at least 3-fold, at least 3.5 fold, at least 4-fold, at least 5-fold, at least 8-fold, at least 10-fold, at least 15-fold, at least 20-fold or more. "Suitable for transplantation into a mammal" means that the number and quality of CAR T-cells is sufficient to support greater than 1% engraftment in a mammalian recipient, such as, e.g., a primate recipient, including an human recipient, in need thereof.

Yet another embodiment of the present invention is a method for treating a subject in need of a bone marrow transplant, a peripheral blood transplant, or a cord blood transplant comprising administering to the subject a population of HSCs obtained by a method disclosed herein, particularly the methods for expanding a population of hematopoietic stem cells (HSCs). The subject may be a mammal, such as a human.

Yet another embodiment of the present invention is a method for treating a subject in need of a bone marrow transplant, a peripheral blood transplant, or a cord blood transplant comprising administering to the subject a population of MSCs obtained by a method disclosed herein, particularly the methods for expanding a population of mesenchymal stem cells (MSCs). The subject may be a mammal, such as a human.

Yet another embodiment of the present invention is a method for treating a subject suffering from cancer and/or a blood disorder, comprising administering to the subject a population of CAR T-cells obtained by a method disclosed herein, particularly the methods for expanding a population of CAR T-cells. The subject may be a mammal, such as a human.

A further embodiment of the present invention is a method for expanding a population of hematopoietic stem cells (HSCs). The method comprises (a) obtaining from a mammal a tissue sample comprising an HSC population; (b) expanding, in vitro, the HSC population from the sample, wherein (i) the HSC population expands by at least 2-fold; and (ii) the expanded HSC population has at least a 5-fold increase in total colony forming units. In one aspect of this embodiment, the HSC population expands by at least 4-fold, such as e.g., at least 5-fold, including at least 8-fold, at least 10-fold, at least 15-fold, at least 20-fold or more. In another aspect of this embodiment, the mammal is a primate, including a human. Preferably, the human requires a peripheral blood transplant, a cord blood transplant, or a bone marrow transplant. In a further aspect, the tissue sample is obtained from any appropriate tissue, such as, e.g., a tissue selected from the group consisting of cord blood, peripheral blood, and bone marrow.

A further embodiment of the present invention is a method for expanding a population of mesenchylam stem cells (MSCs). The method comprises (a) obtaining from a mammal a tissue sample comprising a MSC population; (b) expanding, in vitro, the MSC population from the sample, wherein (i) the MSC population expands by at least 2-fold. In one aspect of this embodiment, the MSC population expands by at least 2.5-fold, such as at least 3-fold, at least 3.5 fold, at least 4-fold, such as e.g., at least 5-fold, including at least 8-fold, at least 10-fold, at least 15-fold, at least 20-fold or more. In another aspect of this embodiment, the mammal is a primate, including a human. Preferably, the human requires a peripheral blood transplant, a cord blood transplant, or a bone marrow transplant. In a further aspect, the tissue sample is obtained from any appropriate tissue, such as, e.g., a tissue selected from the group consisting of cord blood, peripheral blood, and bone marrow.

A further embodiment of the present invention is a method for expanding a population of chimeric antigen receptor (CAR) T-cells. The method comprises (a) obtaining from a mammal a tissue sample comprising a T-cell population; (b) modifying the T-cell population with chimeric antigen receptors to provide CAR T-cell population; (c) expanding, in vitro, the CAR T-cell population from the sample, wherein (i) the CAR T-cell population expands by at least 2-fold. In one aspect of this embodiment, the CAR T-cell population expands by at least 2.5-fold, such as at least 3-fold, at least 3.5 fold, at least 4-fold, such as e.g., at least 5-fold, including at least 8-fold, at least 10-fold, at least 15-fold, at least 20-fold or more. In another aspect of this embodiment, the mammal is a primate, including a human. Preferably, the human is suffering from a cancer and/or a blood disorder. In a further aspect, the tissue sample is obtained from any appropriate tissue, such as, e.g., a tissue selected from the group consisting of cord blood, peripheral blood, and bone marrow.

An additional embodiment of the present invention is a method for reconstituting an hematopoietic stem cell lineage in a recipient in need thereof. The method comprises (a) obtaining from a mammal a tissue sample comprising an HSC population; (b) expanding, in vitro, the HSC population from the sample, wherein: (i) the HSC population expands by at least 2-fold, such as for example, by at least 4-fold, including at least 8-fold, at least 10-fold, at least 15-fold, at least 20-fold or more, and (ii) the expanded HSC population has at least at 5-fold increase in total colony forming units; and (c) transplanting the expanded HSC population into a subject in need thereof, such as a mammal, including a primate or human. In this embodiment, the human recipient requires a peripheral blood transplant, a cord blood transplant or a bone marrow transplant. Thus, in a further aspect, the tissue sample is obtained from any appropriate tissue such as, e.g., a tissue selected from the group consisting of cord blood, peripheral blood, and bone marrow. The sample may be obtained from an autologous or allogeneic source. Preferably, the sample is obtained from an autologous source.

An additional embodiment of the present invention is a method for reconstituting a mesenchymal stem cell (MSC) lineage in a recipient in need thereof. The method comprises (a) obtaining from a mammal a tissue sample comprising a MSC population; (b) expanding, in vitro, the MSC population from the sample, wherein: (i) the MSC population expands by at least 2-fold, such as for example, by at least 4-fold, including at least 8-fold, at least 10-fold, at least 15-fold, at least 20-fold or more; and (c) transplanting the expanded MSC population into a subject in need thereof, such as a mammal, including a primate or human. In this embodiment, the human recipient requires a peripheral blood transplant, a cord blood transplant or a bone marrow transplant. Thus, in a further aspect, the tissue sample is obtained from any appropriate tissue such as, e.g., a tissue selected from the group consisting of cord blood, peripheral blood, and bone marrow. The sample may be obtained from an autologous or allogeneic source. Preferably, the sample is obtained from an autologous source.

An additional embodiment of the present invention is a method for treating a subject suffering from cancer and/or a blood disorder. The method comprises (a) obtaining from a mammal a tissue sample comprising a T-cell population; (b) modifying the T-cell population with a chimeric antigen receptor (CAR) to form a CAR T-cell population; (c) expanding, in vitro, the CAR T-cell population from the sample, wherein: (i) the CAR T-cell population expands by at least 2-fold, such as for example, by at least 4-fold, including at least 8-fold, at least 10-fold, at least 15-fold, at least 20-fold or more; and (c) transplanting the expanded CAR-T cell population into a subject in need thereof, such as a mammal, including a primate or human. In this embodiment, the human recipient may be suffering from, e.g., leukemia and/or lymphoma. Thus, in a further aspect, the tissue sample is obtained from any appropriate tissue such as, e.g., a tissue selected from the group consisting of cord blood, peripheral blood, and bone marrow. The sample may be obtained from an autologous or allogeneic source. Preferably, the sample is obtained from an autologous source.

In aspects of the present invention, it is preferred that the expanded HSC population comprises HSCs that have a phenotype selected from the group consisting of CD34$^-$ or CD34$^+$/CD38$^{-/low}$/Thy-1$^+$/CD90$^+$/Kit$^{-/lo}$/Lin$^-$/CD133$^+$ VEGFR2$^+$, which are markers for the most primitive and long-term undifferentiated human HSCs; CD150$^+$/CD48$^-$/CD244$^-$, which is a marker for human HSCs and their progenitors; and/or CD150$^-$/CD48$^-$/CD244$^+$ and CD150$^-$/CD48$^+$/CD244$^+$, which are markers for non-self-renewing multipotent hematopoietic progenitors, and combinations thereof. (See, e.g., Mimeault, M., et al., Stem Cells: A Revolution in Therapeutics—Recent Advances in Stem Cell Biology and Their Therapeutic Applications in Regenerative Medicine and Cancer Therapies. Clin Pharmacol Ther., 82(3):252-64 (2007)). In aspects of the present invention, it is preferred that the expanded MSC population and/or MSC population subject to expansion, comprises MSCs that have a phenotype selected from the group consisting of N-cadherin+ and CD105+, and combinations thereof. That is, the MSC population of any of the embodiments described herein can comprise at least one MSC selected from the group consisting of N-cadherin+ MSCs and CD105+ MSCs. In one embodiment, the MSC population comprises N-cadherin+ MSCs.

The exact proportions of HSCs and/or MSCs having these markers in the population is not critical, so long as the expanded HSC and/or MSC population as a whole is sufficient to result in at least 1% engraftment in a recipient.

In another embodiment, the invention is a method for expanding a hematopoietic stem cell population in a mammal in need of such expansion. This method comprises administering to the mammal a therapeutically effective amount of a modulator of a N$^6$-methyladenosine (m$^6$A) mRNA modification pathway, for a period of time sufficient to expand the HSC population by at least 2-fold with HSCs that possess the ability to reconstitute an hematopoietic lineage in the mammal.

In another embodiment, the invention is a method for expanding a mesenchymal stem cell population in a mammal in need of such expansion. This method comprises administering to the mammal a therapeutically effective amount of a modulator of a N$^6$-methyladenosine (m$^6$A) mRNA modification pathway, for a period of time sufficient to expand the MSC population by at least 2-fold with MSCs that possess the ability to reconstitute a mesenchymal lineage in the mammal.

In another embodiment, the invention is a method for expanding a chimeric antigen receptor (CAR) T-cell population in a mammal in need of such expansion. This method comprises administering to the mammal a therapeutically effective amount of a modulator of a N$^6$-methyladenosine (m$^6$A) mRNA modification pathway, for a period of time sufficient to expand the CAR T-cell population by at least 2-fold with CAR T-cells that possess the ability to treat cancer and/or a blood disorder in the mammal.

In these methods, the modulators may be as previously disclosed herein, and/or modulation may be performed by any method disclosed herein. For example, the modulator may comprise a system for introducing a mutation into the HSC and/or MSC and/or CAR T-cell population that deletes, replaces or reduces expression of a gene expressing a N$^6$-methyladenosine (m$^6$A) mRNA modification reader, such as Ythdf2. As yet another example, the modulator may comprise an inhibitor of a N6-methyladenosine (m6A) mRNA modification reader, such as an inhibitor of Ythdf2. The mammal in need of expansion may be a human.

In another embodiment, the invention includes a method of isolating mesenchymal stem cells (MSCs) from a biological sample, the method comprising contacting the biological sample having a population of MSCs with one or more N-cadherin antibodies. For example, according to certain aspects, the biological sample comprises a tissue selected from the group consisting of peripheral blood, cord blood and bone marrow. Furthermore, in certain embodiments, the method of isolating the MSCs can further comprise one or more steps of expanding the population of MSCs from the biological sample, by modulating a N$^6$-Methyladenosine (m$^6$A) mRNA modification pathway in the population of MSCs, to expand the number of mesenchymal stem cells, such as by any of the methods described herein. In one embodiment, the population of MSCs is expanded after isolating from the biological sample. In another embodiment, the population of MSCs in the biological sample is expanded before isolation of the MSCs from the biological sample. In one embodiment, the MSC population is expanded to a sufficient quantity while maintaining a multilineage differentiation potential in the MSC population, which is sufficient for subsequent transplantation into a subject in need thereof, such that the MSCs isolated by the method can be used for such transplantation. For example, the isolated MSCs may be transplanted into a human subject. According to yet another embodiment, the MSCs may be further isolated from the biological sample by contacting with CD105 antibodies, either in addition to or as an alternative to the N-cadherin antibodies. In yet a further embodiment, the N-cadherin antibodies may be used to identify the MSCs in the biological sample, by contacting the biological sample with the N-cadherin antibodies and detecting those cells that bind to the N-cadherin antibodies.

In one embodiment, the method of isolating the MSCs comprises expanding the MSC population, by modulating the $m^6A$ mRNA modification pathway by introducing a mutation into the stem cells that results in modulation of a molecule in the $m^6A$ mRNA modification pathway or contacting the stem cell with a modulator of a molecule in the $m^6A$ mRNA modification pathway selected from the group consisting of a small molecule, a biologic, an antisense RNA, a small interfering RNA (siRNA), and combinations thereof, such as by any of the modulation methods described herein. For example, in one embodiment, modulating the $m^6A$ mRNA modification pathway comprises introducing a mutation into the stem cells to delete, replace, or reduce expression of a gene that expresses a molecule in the $m^6A$ mRNA modification pathway. In one embodiment, the mutation deletes, replaces or reduces expression of a gene that expresses a molecule selected from the group consisting of a $m^6A$ mRNA modification reader, a $m^6A$ mRNA modification writer, and a $m^6A$ mRNA eraser. In yet another embodiment, the mutation deletes, replaces or reduces expression of a gene that expresses a $m^6A$ mRNA modification reader. In one embodiment, the mutation deletes, replaces or reduces expression of a gene that expresses a $m^6A$ mRNA modification reader selected from the group consisting of Ythdf1, Ythdf2, Ythdf3, Ythdc1, Ythdc2, HNRNPC, HNRNPA2B1, and eIF3. In another embodiment, the mutation deletes, replaces or reduces expression of a gene that expresses Ythdf2. In one embodiment, the mutation deletes, replaces or reduces expression of a gene that expresses a $m^6A$ mRNA modification eraser. In one embodiment, the mutation deletes, replaces or reduces expression of a gene that expresses a $m^6A$ mRNA modification eraser selected from the group consisting of FTO and ALKBH5. In another embodiment, the mutation deletes, replaces or reduces expression of a gene that expresses a $m^6A$ mRNA modification writer. In one embodiment, the mutation deletes, replaces or reduces expression of a gene that expresses a $m^6A$ mRNA modification writer selected from the group consisting of METTL3, METTL14, WTAP and KIAA1429.

In another embodiment, the method of isolating MSCs comprises expanding the population of MSCS by modulating the $m^6A$ mRNA modification pathway, by exposing the stem cells to a Mx1-Cre targeting system that inactivates or deletes at least a portion of a gene that expresses a molecule in the $m^6A$ mRNA modification pathway. In one embodiment, modulating the $m^6A$ mRNA modification pathway comprises introducing a mutation that incorporates shRNA into the stem cells to reduce expression of a gene that expresses a molecule in the $m^6A$ mRNA modification pathway. For example, in one embodiment, the shRNA is introduced by exposing the stem cells to a lentivirus to deliver the shRNA. According to yet another embodiment, modulating the $m^6A$ mRNA modification pathway comprises downregulating a $m^6A$ mRNA modification reader. In one embodiment, the $m^6A$ mRNA modification reader is selected from the group consisting of Ythdf1, Ythdf2, Ythdf3, Ythdc1, Ythdc2, HNRNPC, HNRNPA2B1, and eIF3. For example, in one embodiment, the $m^6A$ mRNA modification reader comprises Ythdf2.

In one embodiment, the method of isolating MSCs further comprise expanding the population of MSCs by downregulating the $m^6A$ mRNA modification reader, by contacting the stem cells with an inhibitor of the $m^6A$ mRNA modification reader that is any of those described herein, such as any of those selected from the group consisting of: (inhibitors of HNRNPC) hsa-let-7e-5p (MIRT051596), hsa-mir-455-3p (MIRT037890), hsa-mir-30c-5p (MIRT047904), hsa-mir-186-5p (MIRT045150), hsa-mir-744-5p (MIRT037494), hsa-mir-18a-3p (MIRT040851), hsa-mir-484 (MIRT042196), hsa-mir-505-5p (MIRT037959), hsa-mir-615-3p (MIRT039991), hsa-mir-342-3p (MIRT043694), hsa-miR-3607-3p, hsa-miR-30d, hsa-miR-3916, hsa-miR-3162-5p, hsa-miR-1273d, hsa-miR-3161, hsa-miR-30a, hsa-miR-629, hsa-miR-208b, hsa-miR-489, hsa-miR-3148, hsa-miR-2113, hsa-miR-877, hsa-miR-455-5p, hsa-miR-186, hsa-miR-548o, hsa-miR-3139, hsa-miR-320a, hsa-miR-4311, hsa-miR-555, hsa-miR-3605-5p, hsa-miR-515-5p, hsa-miR-144, hsa-miR-499-5p, hsa-miR-1323, hsa-miR-548x, hsa-miR-299-5p, hsa-miR-653, hsa-miR-576-5p, hsa-miR-548p, hsa-miR-586, hsa-miR-888, hsa-miR-3647-3p, hsa-miR-484, hsa-miR-320b, hsa-miR-620, hsa-miR-30b, hsa-miR-548q, hsa-miR-29b-1, hsa-miR-570, hsa-miR-183, hsa-miR-1276, hsa-miR-208a, hsa-miR-186, hsa-miR-28-5p, hsa-miR-330-3p, hsa-miR-548am, hsa-miR-320d, hsa-miR-3175, hsa-miR-3155, hsa-miR-548aa, hsa-miR-519e, hsa-miR-1270, hsa-miR-513b, hsa-miR-599, hsa-miR-518f, hsa-miR-4301, hsa-miR-30c, hsa-miR-3135, hsa-miR-4286, hsa-miR-202, hsa-miR-4263, hsa-miR-4299, hsa-miR-606, hsa-miR-3133, hsa-miR-583, hsa-miR-3125, hsa-miR-501-5p, hsa-miR-7-1, hsa-miR-514b-3p, hsa-miR-3155b, hsa-miR-548d-3p, hsa-miR-224, hsa-miR-7-2, hsa-miR-708, hsa-miR-3199, hsa-miR-514, hsa-miR-30e; (inhibitors of HNRNPA2B1) hsa-mir-92a-3p (MIRT049721), hsa-mir-30c-5p (MIRT048009), hsa-mir-191-5p (MIRT045809), hsa-let-7f-5p (MIRT051404), hsa-mir-27b-3p (MIRT046213), hsa-mir-877-3p (MIRT037116), hsa-mir-615-3p (MIRT040278), hsa-mir-1260b (MIRT052680), hsa-mir-103a-3p (MIRT027027), hsa-mir-16-5p (MIRT031508), hsa-mir-1296-5p (MIRT036075), hsa-mir-197-3p (MIRT048098), hsa-miR-548j, hsa-miR-3678-3p, hsa-miR-607, hsa-miR-188-5p, hsa-miR-15a, hsa-miR-3653, hsa-miR-371-5p, hsa-miR-550a, hsa-miR-3622b-3p, hsa-miR-548a-5p, hsa-miR-3170, hsa-miR-3148, hsa-miR-556-3p, hsa-miR-490-3p, hsa-miR-559, hsa-miR-200c, hsa-miR-130a, hsa-miR-548y, hsa-miR-548o, hsa-miR-23c, hsa-miR-491-3p, hsa-miR-335, hsa-miR-3667-3p, hsa-miR-466, hsa-miR-23b, hsa-miR-4310, hsa-miR-127-5p, hsa-miR-548b-5p, hsa-miR-616, hsa-miR-16, hsa-miR-338-3p, hsa-miR-3200-5p, hsa-miR-362-3p, hsa-miR-448, hsa-miR-1306, hsa-miR-944, hsa-miR-3684, hsa-miR-373, hsa-miR-103a, hsa-miR-380, hsa-miR-499-5p, hsa-miR-1323, hsa-miR-323-5p, hsa-miR-3674, hsa-miR-1252, hsa-miR-33b, hsa-miR-580, hsa-miR-548c-3p, hsa-miR-103a-2, hsa-miR-548w, hsa-miR-600, hsa-miR-634, hsa-miR-586, hsa-miR- 497, hsa-miR-720, hsa-miR-654-3p, hsa-miR-524-5p, hsa-miR-543, hsa-miR-548q, hsa-let-7f-2, hsa-miR-330-5p, hsa-miR-500a, hsa-miR-548I, hsa-miR-570, hsa-miR-374a, hsa-miR-1184, hsa-miR-649, hsa-miR-424, hsa-miR-3658, hsa-miR-186, hsa-miR-326, hsa-miR-548d-5p, hsa-miR-23a, hsa-miR-15b, hsa-miR-190, hsa-miR-203, hsa-miR-548h, hsa-miR-3136-5p, hsa-miR-618, hsa-miR-551b, hsa-miR-211, hsa-miR-1305, hsa-miR-513b, hsa-miR-96, hsa-miR-2117, hsa-miR-548n, hsa-miR-3910, hsa-miR-217, hsa-miR-892b, hsa-miR-502-5p, hsa-miR-548i, hsa-miR-520d-5p, hsa-miR-4299, hsa-miR-1285, hsa-miR-3133, hsa-miR-483-3p; (inhibitors of Ythdf1) hsa-miR-548g, hsa-miR-204, hsa-miR-3143, hsa-miR-521, hsa-miR-195, hsa-miR-3182, hsa-miR-3941, hsa-miR-34c-3p, hsa-miR-767-3p, hsa-miR-563, hsa-miR-548c-5p, hsa-miR-1911, hsa-miR-26b, hsa-miR-190b, hsa-miR-33a, hsa-miR-329, hsa-miR-221, hsa-miR-612, hsa-miR-3185, hsa-miR-3156-5p, hsa-miR-107, hsa-miR-664, hsa-miR-3657; (inhibitors of Ythdf2) hsa-mir-615-3p (MIRT040054), hsa-mir-106b-5p (MIRT044257), hsa-mir-1 (MIRT023842), miR-145, hsa-miR-3607-3p, hsa-miR-200a, hsa-miR-301a, hsa-miR-519a, hsa-miR-141, hsa-miR-130b, hsa-miR-181b, hsa-miR-301b, hsa-miR-3117-3p, hsa-miR-1236, hsa-miR-181a, hsa-miR-519c-3p, hsa-miR-551b, hsa-miR-519e, hsa-miR-519b-3p, hsa-miR-19b, hsa-miR-1303, hsa-miR-608, hsa-miR-145, hsa-miR-130a, hsa-miR-181c, hsa-miR-323b-3p, hsa-miR-421, hsa-miR-515-5p, hsa-miR-3666, hsa-miR-181d, hsa-miR-146a, hsa-miR-4295, hsa-miR-454, hsa-miR-3919, hsa-miR-19a, hsa-miR-543, hsa-miR-4262; (inhibitors of Ythdf3) hsa-miR-582-3p, hsa-miR-579, hsa-miR-520e, hsa-miR-520f, hsa-miR-3152-3p, hsa-miR-106a, hsa-miR-30d, hsa-miR-30a, hsa-miR-93, hsa-miR-508-5p, hsa-miR-29a, hsa-miR-3148, hsa-miR-490-5p, hsa-miR-520b, hsa-miR-20a, hsa-miR-409-3p, hsa-miR-4255, hsa-let-7i, hsa-miR-373, hsa-let-7e, hsa-miR-520c-3p, hsa-miR-3920, hsa-miR-127-5p, hsa-miR-380, hsa-miR-616, hsa-miR-4277, hsa-miR-448, hsa-miR-16-2, hsa-let-7c, hsa-miR-340, hsa-miR-373, hsa-miR-520a-3p, hsa-miR-144, hsa-miR-1265, hsa-miR-548x, hsa-miR-362-5p, hsa-miR-33b, hsa-miR-26b, hsa-miR-17, hsa-miR-569, hsa-miR-3618, hsa-miR-576-5p, hsa-miR-922, hsa-miR-302a, hsa-miR-106b, hsa-miR-888, hsa-miR-484, hsa-let-7b, hsa-miR-582-5p, hsa-let-7f, hsa-miR-30b, hsa-miR-524-5p, hsa-miR-302d, hsa-let-7d, hsa-miR-513a-5p, hsa-miR-500a, hsa-miR-570, hsa-miR-548I, hsa-miR-105, hsa-miR-374c, hsa-let-7g hsa-miR-372, hsa-miR-3658, hsa-let-7a, hsa-miR-3908, hsa-miR-302b, hsa-miR-526b, hsa-miR-190, hsa-miR-181 b, hsa-miR-433, hsa-miR-98, hsa-miR-3606, hsa-miR-595, hsa-miR-548am, hsa-miR-187, hsa-miR-561, hsa-miR-181a, hsa-miR-3155, hsa-miR-655, hsa-miR-302c, hsa-miR-195, hsa-miR-26a, hsa-miR-590-3p, hsa-miR-30c, hsa-miR-502-5p, hsa-miR-495, hsa-miR-137, hsa-miR-181c, hsa-miR-520d-5p, hsa-miR-3942-5p, hsa-miR-202, hsa-miR-302e, hsa-miR-513c, hsa-miR-885-5p, hsa-miR-520a-5p, hsa-miR-583, hsa-miR-1297, hsa-miR-7-1, hsa-miR-520d-3p, hsa-miR-3155b, hsa-miR-3182, hsa-miR-519d, hsa-miR-550a, hsa-miR-7-2, hsa-miR-181d, hsa-miR-190b, hsa-miR-1912, hsa-miR-151-3p, hsa-miR-33a, hsa-miR-525-5p, hsa-miR-20b, hsa-miR-514b-5p, hsa-miR-30e, hsa-miR-4262, hsa-miR-636; (inhibitor of elF3) hsa-mir-92b-3p (MIRT040734), hsa-mir-16-5p (MIRT031705), hsa-mir-18a-3p (MIRT040974), hsa-mir-155-5p (MIRT020771), hsa-mir-484 (MIRT042324), hsa-let-7c-5p (MIRT051776), hsa-miR-3910, hsa-miR-148b, hsa-miR-136, hsa-miR-15a, hsa-miR-488, hsa-miR-500a, hsa-miR-1297, hsa-miR-3159, hsa-miR-374c, hsa-miR-424, hsa-miR-7-1, hsa-miR-186, hsa-miR-195, hsa-miR-15b, hsa-miR-26b, hsa-miR-505, hsa-miR-1206, hsa-miR-653, hsa-miR-1283, hsa-miR-7-2, hsa-miR-196a, hsa-miR-497, hsa-miR-33a, hsa-miR-655, hsa-miR-26a hsa-miR-16, hsa-mir-151a-3p (MIRT043600), hsa-mir-92a-3p (MIRT049064), hsa-mir-615-3p (MIRT039779), hsa-mir-877-3p (MIRT036964), hsa-mir-222-3p (MIRT046746), hsa-mir-423-3p (MIRT042468), hsa-mir-324-3p (MIRT042887), hsa-mir-124-3p (MIRT022932), hsa-miR-3140-3p, hsa-miR-124, hsa-miR-198, hsa-miR-525-5p, hsa-miR-506, hsa-miR-520a-5p, hsa-miR-196a* hsa-miR-3117-3p, hsa-mir-342-5p (MIRT038210), hsa-mir-378a-5p (MIRT043981), hsa-mir-615-3p (MIRT040086), hsa-let-7b-5p (MIRT052211), hsa-mir-455-3p (MIRT037879), hsa-miR-4267, hsa-miR-590-3p, hsa-mir-106b-5p (MIRT044355), hsa-mir-320a (MIRT044466), hsa-mir-16-5p (MIRT032018), hsa-mir-155-5p (MIRT021009), hsa-miR-4302, hsa-mir-191-5p (MIRT045793), hsa-mir-1303 (MIRT035890), hsa-mir-193b-3p (MIRT016316), hsa-mir-222-3p (MIRT046640), hsa-mir-532-3p (MIRT037924), hsa-mir-18a-3p (MIRT040929), hsa-mir-92a-3p (MIRT049001), hsa-miR-582-3p, hsa-miR-4265, hsa-miR-218-2, hsa-miR-1271, hsa-miR-340, hsa-miR-221, hsa-miR-20b, hsa-miR-508-3p, hsa-miR-141, hsa-miR-4325, hsa-miR-889, hsa-miR-29a, hsa-miR-129-3p, hsa-miR-129, hsa-miR-96, hsa-miR-3163, hsa-miR-187, hsa-miR-196a, hsa-miR-222, hsa-miR-1179, hsa-miR-182, hsa-miR-9* hsa-miR-32, hsa-miR-143, hsa-miR-4296: (inhibitors of YTHDC1) hsa-mir-20a-3p (MIRT038967), hsa-mir-103a-3p (MIRT027037), hsa-mir-1 (MIRT023492), hsa-mir-19b-3p (MIRT031105), hsa-mir-100-5p (MIRT048400), hsa-mir-93-5p (MIRT027989), hsa-mir-16-5p (MIRT031379), hsa-let-7b-5p (MIRT052150), hsa-miR-520f, hsa-miR-300, hsa-miR-15a, hsa-miR-200a, hsa-miR-605, hsa-miR-30d, hsa-miR-30a, hsa-miR-3613-3p, hsa-miR-509-3-5p, hsa-miR-34c-5p, hsa-miR-324-3p, hsa-miR-1248, hsa-miR-152, hsa-miR-548t, hsa-miR-4310, hsa-miR-145, hsa-miR-516a-3p, hsa-miR-16, hsa-miR-3668, hsa-miR-4277, hsa-miR-448, hsa-miR-16-2, hsa-miR-148b, hsa-miR-509-5p, hsa-miR-103a, hsa-miR-1265, hsa-miR-2115, hsa-miR-548c-3p, hsa-miR-148a, hsa-miR-548p, hsa-miR-513a-3p, hsa-miR-497, hsa-miR-3647-3p, hsa-miR-382, hsa-miR-30b, hsa-miR-543, hsa-let-7f-2, hsa-miR-1269, hsa-miR-3164, hsa-miR-503, hsa-miR-500a, hsa-miR-449a, hsa-miR-141, hsa-miR-424, hsa-miR-3908, hsa-miR-889, hsa-miR-2116, hsa-miR-330-3p, hsa-miR-15b, hsa-miR-181 b, hsa-miR-187, hsa-miR-1237, hsa-miR-449b, hsa-miR-101, hsa-miR-381, hsa-miR-618, hsa-miR-222, hsa-miR-181a, hsa-miR-432, hsa-miR-96, hsa-miR-19b, hsa-miR-195, hsa-miR-548n, hsa-miR-485-5p, hsa-miR-217, hsa-miR-30c, hsa-miR-495, hsa-miR-137, hsa-miR-1288, hsa-miR-181c, hsa-miR-3942-5p, hsa-miR-548v, hsa-miR-487a, hsa-miR-221, hsa-miR-891b, hsa-miR-205, hsa-miR-195, hsa-miR-4271, hsa-miR-3611, hsa-miR-516b, hsa-miR-181d, hsa-miR-154, hsa-miR-646, hsa-miR-153, hsa-miR-34a, hsa-miR-19a, hsa-miR-107, hsa-miR-30e and hsa-miR-4262.

According to one embodiment, the invention comprises an isolated population of mesenchymal stem cells made by any of the processes described herein. For example, the invention in certain embodiments can comprise an expanded, isolated population of mesenchymal stem cells made by any of the expansion and/or isolation processes described herein.

In one embodiment, a kit for isolating a mesenchymal stem cell (MSC) population for subsequent transplantation into a subject in need thereof is provided. The kit comprises a system for contacting a biological sample comprising MSCs with one or more N-cadherin antibodies, and instructions for use thereof. In one embodiment, the kit further comprises a system for expanding the population of MSCs by introducing a mutation into the MSC population that results in deletion, replacement or reduced expression of a gene expressing a $m^6A$ mRNA modification reader, and instructions for use thereof. In yet another embodiment, the system for introducing a mutation into the MSC population includes one or more reagents capable of introducing a mutation into the MSC population that results in deletion, replacement or reduced expression of a gene expressing Ythdf2. In yet another embodiment, the system for introducing a mutation into the MSC population comprises a Mx1-Cre targeting system that inactivates or deletes at least a portion of a gene that expresses a $m^6A$ mRNA modification reader. In one embodiment, the system for introducing a mutation into the MSC population comprises reagents for delivering a lentivirus that incorporates shRNA into the MSC population to reduce expression of a gene that expresses a $m^6A$ mRNA modification reader.

According to another embodiment of the invention, a method for administering a mesenchymal stem cell (MSC) to a subject in need thereof is provided. The method comprises isolating MSCs from a biological sample comprising a population of MSCs, by contacting the biological sample with one or more N-cadherin antibodies, and administering the isolated MSCs to the subject. Furthermore, in one embodiment, the method further comprises introducing, into the biological sample containing the MSC population, a mutation that results in deletion, replacement or reduced expression of a gene expressing a $m^6A$ mRNA modification reader, and culturing the biological sample in a suitable culture media for a period of time sufficient to expand the number of MSCs in the sample to a number sufficient to transplant into the subject. In one embodiment, wherein the mutation results in deletion a gene expressing Ythdf2. In one embodiment, the mutation results in incorporation of shRNA into the HSC population that reduces expression of a gene expressing Ythdf2. According to yet another aspect, the MSCs are obtained from a biological sample comprising a tissue selected from the group consisting of cord blood, peripheral blood, and bone marrow.

According to yet another embodiment, a method for reconstituting bone marrow in a subject in need thereof is provided. The method comprises isolating mesenchymal stem cells (MSCs) from a biological sample comprising a population of MSCs, by contacting the biological sample with one or more N-cadherin antibodies, and administering the isolated MSCs to the subject. Furthermore, according to one aspect, the method further comprises introducing, into the biological sample containing the MSC population, a mutation that results in deletion, replacement or reduced expression of a gene expressing a $m^6A$ mRNA modification reader, and culturing the sample in a suitable culture media for a period of time sufficient to expand the number of MSCs in the sample to a number sufficient to transplant into the subject. In one embodiment, the MSCs are obtained from a biological sample comprising a tissue selected from the group consisting of cord blood, peripheral blood, and bone marrow.

According to yet another embodiment, a method for treating a subject in need of a transplant, selected from the group consisting of a bone marrow transplant, a peripheral blood transplant and an umbilical cord blood transplant comprising administering to the subject a population of isolated MSCs obtained by any of the methods described herein. According to embodiment, the sample is from an autologous or allogeneic source. According to yet another embodiment, the sample is from an autologous source.

In the present invention, a "therapeutically effective amount" is an amount sufficient to effect beneficial or desired results. In terms of treatment of a mammal, a "therapeutically effective amount" of a modulator and/or expanded cells is an amount sufficient to treat, manage, palliate, ameliorate, or stabilize a condition, such as a bone marrow disease, in the mammal. A therapeutically effective amount can be administered in one or more doses.

The therapeutically effective amount is generally determined by a physician on a case-by-case basis and is within the skill of one in the art. Several factors are typically taken into account when determining an appropriate dosage. These factors include age, sex and weight of the subject, the condition being treated, the severity of the condition and the form of the drug being administered.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of a modulator according to the invention will be that amount of the modulator, which is the lowest dose effective to produce the desired effect. The effective dose of a modulator maybe administered as two, three, four, five, six or more sub-doses, administered separately at appropriate intervals throughout the day.

A modulator may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a modulator of the present invention may be administered in conjunction with other treatments. A modulator of the present invention maybe encapsulated or otherwise protected against gastric or other secretions, if desired.

While it is possible for a modulator of the invention to be administered alone, it is preferable to administer the modulator as a pharmaceutical formulation (composition). Such pharmaceutical formulations typically comprise one or more modulators as an active ingredient in admixture with one or more pharmaceutically-acceptable carriers and, optionally, one or more other compounds, drugs, ingredients and/or materials. Regardless of the route of administration selected, the modulator of the present invention may be formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition comprising a modulator of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

Pharmaceutical compositions comprising a modulator of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more modulator in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug containing a modulator of the present invention, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods and compositions of the present invention. These examples are illustrative only and are not intended to limit the scope of the invention in any way.

EXAMPLES

The examples herein examine Ythdf2, a well-recognized $m^6A$ reader promoting targeted mRNA decay (Wang et al. Blood, 505: 17-120, 2014), at least partly with the purpose of investigating its role in the context of HSC maintenance. Without being limited to any particular theory, it is believed that manipulation of Ythdf2 might potentially influence the life span of a great number $m^6A$-marked mRNAs, thus impacting adult HSC self-renewal versus differentiation and facilitating HSC expansion. As shown in the examples below, Ythdf2 depletion specifically expands mouse and human HSCs without skewing lineage fate. Accordingly, it is believed that Ythdf2 may play an essential role in regulating HSC self-renewal, and provide a novel approach to enhance hUCB HSCs ex vivo expansion, including in clinical applications.

The examples also show functional definition of the drug-resistant rHSC population, and a finding that rHSCs are maintained in the endosteal niche largely by $N-cad^+$ cells during homeostasis and under chemotherapeutic stress. It is further shown that $N-cad^+$ cells in endosteal zone are mesenchymal stem cells and contribute to rHSC maintenance.

Example A

The following protocols were used in the "A" Examples below.

Mice. Ythdf2 conditional KO mice were generated by Chuan He and Bin Shen group. Mice were housed in the animal facility at Stowers Institute for Medical Research (SIMR) and handled according to Institute and NIH guidelines. All procedures were approved by the IACUC of SIMR.

Flow cytometry and HSPC sorting. Mouse HSPCs, progenitors, and lineage cells were harvested from BM (femur and tibia) and spleen. Red blood cells were lysed using a 0.16 M ammonium chloride solution, and the cells were filtered with 70 µm strainers to generate single cell suspensions. For mouse HSC identification, cells were stained with antibodies against Sca-1 (D7), c-Kit (2B8), CD34 (RAM34), Flk2 (A2F10), CD48 (HM48-1), CD150 (TC15-12F12.2), together with lineage cocktail including CD3 (145-2C11), CD4 (RM4-5), CD8 (53-6.7), Mac-1 (M1/70), Gr1 (RB6-8C5), CD45R (B220, RA3-6B2), IgM (II-41) and Ter119 (TER-119). For progenitors and lineage cells, cells were stained with antibodies as previously described (Qian, P. et al. Cell Stem Cell, 18:214-228, 2016, doi:10.1016/j.stem.2015.11.001). 7-aminoactinomycin D (7-AAD) (A1310, Life technologies) was used to exclude dead cells. Human cord blood samples were acquired from the St. Louis Cord Blood Bank. Mononuclear cells were isolated with Lymphoprep™ (StemCell technologies), followed by isolation of human $CD34^+$ cord blood cells by human CD34 MicroBead Kit UltraPure (Miltenyi Biotec). To quantify human HSPCs, cells were stained with antibodies against CD34 (581), CD38 (HIT2), CD45RA (HI100), CD90 (5E10), CD49f (GoH3), EPCR/CD201 (RCR-401). Cell sorting and analyses were performed on MoFlo (Dako), InFlux Cell Sorter (BD Biosciences), and/or MACSQuant (Miltenyi Biotec). Data analysis was performed using FlowJo software.

Homing assay. In vivo homing assays were performed as previously described (He et al. Methods in Molecular Biology, 1185: 279-284, 2014). Basically, whole bone marrow (WBM) cells from CD45.2 mice were labelled with 5 µM 5-(and −6)-carboxyfluorescein diacetate succinimidyl ester (CFDA SE) (Molecular Probes) at 37° C. for 10 mins, washed three times, and $1 \times 10^6$ WBM were transplanted into lethally irradiated ptprc mice. After 18 hours, femurs and tibias were flushed, and CFDA SE+ cells were determined.

Competitive reconstitution assay. Competitive reconstitution assays were performed by intravenous transplantation of $2 \times 10^5$, $7.5 \times 10^4$ or $2.5 \times 10^4$ donor-derived WBM cells from wt or Ythdf2 KO mice (CD45.2), together with $2 \times 10^5$ rescue cells (CD45.1) into groups of ten lethally irradiated (10 Gy) ptprc recipient mice. For secondary transplantation, primary transplant recipients were sacrificed. BM cells were dissected from femur and tibia, and then transplanted mouse-to-mouse at a dosage of $1 \times 10^6$ cells into irradiated secondary recipient mice. Baytril water was given to recipient mice three days before irradiation and continued for another two weeks after irradiation. Primary and secondary CRU frequencies were measured using ELDA software (Hu et al. *Journal of Immunological Methods,* 347: 70-78, 2009), in which successful engraftment was defined as the presence of a distinct CD45.2$^+$ CD45.1$^-$ population ≥5% and ≥1% of total hematopoietic cells in peripheral blood, respectively (Purton et al. *Cell Stem Cell,* 1: 263-270, 2007). Also, the secondary transplantation recipient mice that died before 16 weeks post transplantation were counted for failed engraftment.

Cell cycle and apoptosis assays. Cell cycle analysis was performed with FITC mouse anti-human Ki67 set (BD Pharmingen) according to the manufacturer's instructions. Briefly, 5×10$^6$ BM cells were isolated and stained with HSC antibodies as described above. Cells were fixed by 4% paraformaldehyde at 4° C. overnight or room temperature (RT) for 1 hour, and then permeabilized with 0.2% triton X-100 on ice for 15 mins. Cells were washed with PBS containing 2% FBS, and then were incubated with Ki-67 antibody at RT for 1 hour in the dark, and SYTOX Red (Invitrogen) at RT for another 5 mins, followed by flow cytometric analysis with InFlux Cell Sorter (BD Biosciences). For apoptosis analysis, Annexin V (Invitrogen) and SYTOX Red staining of 5×10$^6$ BM cells was performed according to the manufacturer's protocol.

m$^6$A RNA-IP-seq. Two replicates of 10$^5$ LT-HSC, ST-HSC (LSK CD34$^+$ FLK2$^-$) and MPP (LSK CD34$^+$ FLK2$^+$) from C57BL/6J mouse were sorted into TRIzol (Invitrogen), and total RNA was isolated according to the manufacturer's instructions. RNA was fragmented to ~100 nucleotide fragments with Ambion fragmentation reagent (2 mins incubation at 70° C.). The samples were then subjected to Turbo DNase treatment (Ambion), followed by a phenol-chloroform extraction, and resuspension in 85 µl of nuclease-free water, and 5 µl was saved as input. Then, the remaining 80 µl RNA fragments were diluted into IPP buffer (150 mM NaCl, 0.1% NP-40, 10 mM Tris-HCl, pH 7.5). RNA was incubated with 25 µl of protein-G magnetic beads, previously bound to 3 µg of anti-m$^6$A plyclonal antibody (Synaptic Systems), for 3 hours at 4° C. in IPP buffer. Beads were washed twice with 200 µl IPP buffer, twice with 200 µl low-salt buffer (50 mM NaCl, 0.1% NP-40, 10 mM Tris-HCl, pH 7.5) and twice with 200 µl high-salt buffer (500 mM NaCl, 0.1% NP-40, 10 mM Tris-HCl, pH 7.5). Beads were then treated with 300 µl Elution Buffer (5 mM Tris-HCL pH 7.5, 1 mM EDTA pH 8.0, 0.05% SDS, 4.2 µl Proteinase K (20 mg/ml)) for 1.5 hours at 50° C., and RNA was recovered with phenol:chloroform extraction followed by ethanol precipitation. Three human CD34$^+$ umbilical cord blood cells were isolated as described above and isolated total RNA with TRIzol. RNA was fragmented to ~100 nucleotide fragments with Ambion fragmentation reagent (2 mins 50 secs incubation at 70° C.). The samples were then subjected to Turbo DNase treatment (Ambion), followed by a phenol:chloroform extraction, and resuspension in 18 µl of nuclease-free water, and 1 µl was saved as input. m$^6$A RNA IP was performed with EpiMark® N6-Methyladenosine Enrichment Kit following manufacturer's instructions.

Following m$^6$A preparation of RNA, quality was assessed on Agilent 2100 Bioanalyzer, and 1 ng (mouse) or 10 ng (human) RNA was used to generate RNAseq libraries according to the manufacturer's directions for the SMARTer Stranded Total RNA-Seq Kit—Pico Input Mammalian (Takara Bio Inc) using 16 cycles (mouse) or 13 cycles (human) PCR2 amplification. The method uses random priming and a template switching oligo to generate complimentary DNA, followed by the ligation of barcoded adapters; ribosomal-derived cDNA is then removed through probe-directed enzyme cleavage and subsequent enrichment of un-cleaved fragments.

The protocol was modified to retain lower molecular weight sample fragments by using a 1.2×SPRI bead concentration for PCR1 cleanup. To remove dimerized adapters, libraries underwent 160-600 bp size selection with a Pippin Prep (Sage Science) 2% gel. The resulting libraries were checked for quality and quantity using the Bioanalyzer and Qubit Fluorometer (Life Technologies). Then equal molar libraries were pooled and requantified. For mouse m$^6$A-seq, libraries were sequenced as 50 bp single read on the Illumina HiSeq 2500 instrument using HiSeq Control Software 2.2.58. Following sequencing, Illumina Primary Analysis version RTA 1.18.64 and Secondary Analysis version bcl2fastq2 v2.18 were run to demultiplex reads for all libraries and generate FASTQ files. For human m$^6$A-seq, libraries were sequenced as 75 bp single read on the Illumina NextSeq instrument using NextSeq Control Software 2.1.2. Following sequencing, Illumina Primary Analysis version NextSeq RTA 2.4.11 and Secondary Analysis version bcl2fastq2 v2.18 were run to demultiplex reads for all libraries and generate FASTQ files.

Plasmid construction and stable cell line generation. Mouse Ythdf2 (mYthdf2) was cloned from commercial cDNA clone (ORIGENE #MC200730) into vector pcDNA5/FRT/Flag plasmid using primers listed: mYthdf2 ORF Clone BamhI F: 5'-CGC GGA TCC TCG GCC AGC AGC CTC TTG GA-3' (SEQ ID NO: 2) and mYthdf2 ORF Clone NotI R: 5'-ATA AGA ATG CGG CCG CCT ATT TCC CAC GAC CTT GAC GT-3' (SEQ ID NO: 3). Then Flag-mYthdf2 was subcloned under EF1a promoter in pSicoR-EF1a-IRES-EGFP lentiviral construct (Gibson Assembly®, forward primer: 5'-GTC GAC GGT ACC GCG GGC CCA TGG ATT ACA AGG ATG ACG ACG-3' (SEQ ID NO: 4) and reverse primer: 5'-GAG GGA GAG GGG CGG ATC CCC TAT TTC CCA CGA CCT TGA CGT-3' (SEQ ID NO: 5)). Human Ythdf2 (hYthdf2) was cloned from plasmid provided by the Chuan He lab using primers indicated: Forward 5'-CGT TCG AAA TGT CGG CCA GCA GCC TCT-3' (SEQ ID NO: 6); Reverse 5'-TCC CCC GGG TTA TTT CCC ACG ACC TT-3' (SEQ ID NO: 7). Then hYthdf2 was cloned into pSicoR-EF1a-IRES-EGFP constructs under EF1a promoter by BstBI and XmaI restriction digestions and ligation. To generate Flag-mYthdf2 HPC7 stable cell line, lentiviruses were generated by transfection of pSicoR-EF1a-Flag-mYthdf2-IRES-EGFP constructs together with the psPAX2 and pMD2.G plasmids at a ratio of 10:7.5:2.5 into 293T cells using calcium phosphate transfection. The virus particles were harvested 48, 72, and 96 hours post transfection, filtered by 0.45 micrometers filter unit (Millipore), and then centrifuged at 18,000 RPM, 4° C. for 2 hours. HPC7 cells were infected with recombinant lentivirus-transducing units in the presence of 4 µg/mL polybrene (Sigma). 48 hours after infection, GFP$^+$ cells were sorted and cultured for experiments.

irCLIP-seq and data analysis. For irCLIP-seq, the procedure was modified from the previously reported methods (Zarneger et al. *Nature Methods,* 13: 489-492, 2016); Simsek et al. *Cell,* 169: 1051-1065 e1018, 2017). In brief, irCLIP was performed on ~3×10$^8$ Flag-Ythdf2 HPC7 cells by UV crosslinking cells at 0.4 J/cm$^2$ for 3 times. Whole-cell lysates were generated in lysis buffer (150 mM KCl, 10 mM HEPES pH 7.6, 2 mM EDTA, 0.5% NP-40, 0.5 mM DTT, 1:100 protease inhibitor cocktail, 400 U/ml RNase inhibitor; 1 ml cell pellet and 2 ml lysis buffer). Pipetted up and down several times, and then the mRNP lysate was incubated on ice for 5 mins and shock-frozen at −80° C. with liquid nitrogen. The mRNP lysate was thawed on ice and centrifuged at 15,000 g for 15 mins to clear the lysate. Flag-Ythdf2 was isolated with 30 µl of protein-G magnetic beads per 1 ml lysate, previously bound to 2 µg of anti-Flag monoclonal antibody (Sigma) for 2 hours at 4° C. on rotation. The beads were collected, washed eight times with 1 ml ice-cold NT2 buffer (200 mM NaCl, 50 mM HEPES pH 7.6, 2 mM EDTA, 0.05% NP-40, 0.5 mM DTT, 200 U/ml RNase inhibitor) and one time with 200 µl irCLIP NT2 buffer (50 mM Tris, pH 7.5; 150 mM NaCl; 1 mM $MgCl_2$; 0.0005% NP-40). mRNP complex was digested with RNase 1 (Thermo Fisher #AM2294) at 0.4 U/µl in irCLIP NT2 buffer (aqueous volume of 30 µl and supplemented with 6 µl of PEG400 (16.7% final)). The nuclease reaction was incubated at 30° C. for 15 mins in an Eppendorf Thermomixer, 15 s 1,400 r.p.m., 90 s rest. Nuclease digestions were stopped by addition of 0.5 mL of ice-cold high-stringency buffer (20 mM Tris, pH 7.5; 120 mM NaCl; 25 mM KCl; 5 mM EDTA; 1% Trition-X100; 1% Na-deoxycholate). Immunoprecipitates were then quickly rinsed with 0.25 mL then with 0.05 mL of ice-cold irCLIP NT2 buffer. The irCLIP adaptor ligation and library construction followed previously reported protocol (Zarneger et al. *Nature Methods,* 13: 489-492, 2016).

Data were demultiplexed using FAST-iCLIP version 0.9.3 and aligned to mouse genome mm10 from UCSC using STAR (2.4.2a) with parameters "-outFilterScoreMinOverLread 0 -outFilterMatchNminOverLread 0 -outFilterMatchNmin 0". RPM-normalized genome browser tracks were created in R (3.4.1) and plotted using the Gviz package (1.20.0). Enriched motifs were identified by taking midpoints of each binding site found in all three replicates, adding 20 bases up and downstream, and running MEME (4.11.1) with parameters "-dna -mod zoops -revcomp -minw 5-maxw 10-nmotifs 10-maxsize 1000000". After motifs were identified, we ran tomtom (4.11.1) against transfac (1-2017) to identify known binding sites. GO enrichment analysis was performed using a hypergeometric test in R. GO terms were considered enriched if they had a BH-adjusted p-value less than 0.05. Selected terms of interest are shown in the bar plot. Bars in the bar plot indicate percentage of genes in the list being tested having the term divided by the percentage of genes in the genome having the term. Peaks found by FAST-iCLIP in all three replicates were assigned to various features in the genome. Promoters were defined as upstream 150 bases from the TSS. "trans_stop" was defined as upstream and downstream 200 bases from the transcript start site.

Cord blood transduction. Cord blood transduction was conducted as described previously (Rentas, S. et al. *Nature,* 532:508-511, 2016, doi:10.1038/nature17665). Briefly, fresh CD34$^+$ cord blood cells or flow-sorted CD34$^+$CD38$^-$ cells were prestimulated for 12-18 h in StemSpan medium (StemCell Technologies) supplemented with growth factors interleukin 6(IL-6; 20 ng/ml, Peprotech), stem cell factor (SCF; 100 ng/ml, Peprotech), Flt3 ligand (FLT3-L; 100 ng/ml, Peprotech) and thrombopoietin (TPO; 20 ng/ml, Peprotech). Lentiviruses were then added in the same medium at a multiplicity of infection (MOI) of 50-200 for 24 hours. Cells were then given 2 days after transduction before in vitro or in vivo assays. Human YTHDF2 was targeted for knockdown by shRNA targeting 5'-AAGGACGTTCC-CAATAGCCAA-3' (SEQ ID NO: 8) near the N terminus of CDS, as used in a previous report (Wang, X. et al. *Nature* 505:117-120, 2014, doi:10.1038/nature12730). Scramble shRNA (seed sequence 5'-GCGCGATAGCGCTAATAAT-3' (SEQ ID NO: 9)) were used as control.

Clonogenic progenitor assays. Flow-sorted GFP$^+$ cord blood cells from day 10 cultured transduced cells (12,000 per ml) were resuspended in semi-solid methylcellulose medium (Methocult H4034; StemCell Technologies). Colony counts were carried out after 14 days of incubation.

Human umbilical cord blood HSPC culture. 2 days after transduction, human cord blood CD34$^+$ or CD34$^+$ CD38$^-$ cells were collected and the GFP$^+$ percentage was determined by flow cytometry. To ensure that equal numbers of GFP$^+$ cells were cultured before expansion, identically cultured GFP$^-$ cells were added to the one with higher GFP$^+$ percentage to match the % GFP$^+$ between control and hYthdf2 KD. Then cells were seeded at a density of 105 per ml in StemSpan medium (StemCell Technologies) supplemented with growth factors IL-6 (20 ng/ml), SCF (100 ng/ml), FLT3-L (100 ng/ml), TPO (20 ng/ml) and CHIR99021 (250 nM) (Stemgent) (Perry et al. *Genes and Development,* 25: 1928-1942, 2011).

Human HSC xenotransplantation. For human cord blood HSC ex vivo expansion analysis, 10$^5$ sorted CD34$^+$ CD38$^-$ cells were transduced with human YTHDF2 shRNA or control shRNA for 3 days and then analyzed for transduction efficiency (% GFP$^{-/+}$) and stem cell markers. On day 10, cultured cells were collected for stem cell marker analysis. For hUBC HSC primary LDA assay, CD34$^+$ cells were enriched as described above and transduced with human YTHDF2 shRNA or control shRNA at 50 MOI. Media were changed at 24 hours post infection. Equal number of GFP$^+$ cells were sorted out from control or YTHDF2 KD cells on 3 days post infection and cultured overnight. Three doses, 50K, 20K and 10K, of sorted GFP$^+$ cells were transplanted into sublethally irradiated (3.25 Gy) NSG mice, respectively. The cut-off for HSC engraftment was an exhibition of more than 1% human CD45$^+$ GFP$^+$ cells out of total CD45$^+$ cells in BM of primary transplantation recipients. For hUCB HSC secondary LDA assay, BM cells from highest two doses primary recipients were collected and mixed together at 10 weeks post transplantation. Three doses, 1.2×10$^7$, 8×10$^6$, 4×10$^6$, of BM cells were transplanted into sublethally irradiated (3.25 Gy) NSG mice, respectively. The cut-off for HSC engraftment was an exhibition of more than 0.2% human CD45$^+$ GFP$^+$ cells out of total CD45$^+$ cells in BM of secondary transplantation recipients. HSC frequency was assessed using ELDA software (Hu et al. *Journal of Immunological Methods,* 347: 70-78, 2009). For all human cord blood xenotransplantation experiments, female NSG mice aged 6-8 weeks were used.

m$^6$A-seq data analysis. Human and mouse m$^6$A-seq data were aligned to the transcriptome of hg19 and mm10. In order to identify m$^6$A peaks, hg19 and mm10 transcriptome was divided into 25 nucleotide-wide tiles. The number of reads in the m$^6$A IP and non-IP (control) sample was counted in each tile, and p value was calculated with Fisher exact test and adjusted for multiple testing. Tiles with significant m$^6$A signal enrichment (adjust-Pval <=0.05) were merged into bigger regions. Regions smaller than 100 bp were discarded, and regions over 200 bp were divided into 100 to 200 bp sub-regions; m$^6$A signal over control was calculated at each region; and regions with at least 2-fold enrichment in all replicates were identified as m$^6$A peaks. m$^6$A peaks distribution and m$^6$A marked genes were determined by overlapping all m$^6$A peaks with hg19 and mm10 RefGene annotation. m$^6$A marked genes were identified by overlapping m$^6$A peaks with hg19 RefGene. To filter for transcription factors, genes marked by m$^6$A in all three samples were compared against human transcription factor database fantom.gsc.riken.jp/5/sstar/Browse_Transcription_Factors_hg19. GO term analysis was then performed using R package enrich GO. m⁶A marked human transcription factors were used as searching list, and all the expressed genes were used as background. Hemopoiesis related BP terms with significant enrichment were used to generate FIG. 3C.

RNA-seq. Human cord blood CD34$^+$ cells were transduced with control or human YTHDF2 KD lentivirus and sorted out for GFP$^+$ CD34$^+$ 10 days later. Three replicates of 12,000 GFP$^+$ CD34$^+$ cells were sorted for each group and were used to extract total RNA. Four nanograms of high quality total RNA was used for cDNA synthesis and library preparation according to the manufacturer's directions with the SMART-Seq v4 Ultra Low Input RNA Kit for Sequencing (Takara, 634891) and Nextera XT (Illumina, FC-131-1096). Resulting short fragment libraries were checked for quality and quantity using an Agilent 2100 Bioanalyzer and Invitrogen Qubit Fluorometer. Equal molar libraries were pooled, requantified, and sequenced as 75 base pair single reads on a High Output flow cell on the Illumina NextSeq 500 instrument. Following sequencing, Illumina Primary Analysis version NextSeq RTA 2.4.11 and Secondary Analysis version bcl2fastq2 2.18 were run to demultiplex reads for all libraries and generate FASTQ files.

For RNA-seq analysis, reads were aligned to UCSC genome hg38 with Tophat version 2.0.13 with default parameters, using Ensembl 87 gene models. Read counts were generated using HTSeq-count with -m intersection-nonempty. Reads were also aligned to ERCC control sequences and counts tabulated. A scaling factor was calculated based on the median of the ERCC counts for each sample and used for normalization. Differentially expressed genes were found using the edgeR package (3.18.1) in R (3.4.1). Differentially expressed genes were required to have a BH-adjusted p-value <0.05 and a 2-fold change in expression.

RNA stability assay. 15,000 sorted LT-, ST-HSCs and MPPs were cultured in StemSpan SFEM medium (Stem Cell Technologies) supplemented with 10 μg/mL heparin (Sigma), 0.5× penicillin/streptomycin (Sigma), 10 ng/mL recombinant mouse (rm) SCF (Biovision, Inc.), and 20 ng/mL Tpo (Cell Sciences, Inc.) (Perry et al. *Genes and Development*, 25: 1928-1942 (2011)) at 37° C. 5% $CO_2$ 5% $O_2$. Sorted cells were treated with 5 μM actinomycin D (Sigma) for inhibition of mRNA transcription. Cells were harvested at 0 hour or 4 hours post treatment, and total RNA was extracted and used for RNA-seq.

m⁶A RNA Methylation Quantification.

Mouse BM Lineage negative cells from wt and Ythdf2 KO mice were enriched with mouse Lineage Cell Depletion Kit (Miltenyi Biotec), followed by total RNA extraction with TRIzol (Invitrogen). The quantification of m⁶A RNA methylation in Lin$^-$ cells were performed with m⁶A RNA Methylation Quantification Kit (Abcam ab185912) following manufacturer's protocol. 200 ng total RNA were used per replicates for either group.

Qpcr Analysis.

$10^5$ LSK cells were sorted from wt and Ythdf2 KO mice. Total RNA were extracted with TRIzol (Invitrogen). cDNA synthesis was conducted with High-Capacity RNA-to-cDNA™ Kit (Thermo) following manufacturer's protocol. qPCR primers used are listed in Table S5, qPCR primers used to verify the expressional levels of transcription factors in wt and Ythdf2 KO HSPCs.

Figure 14A:
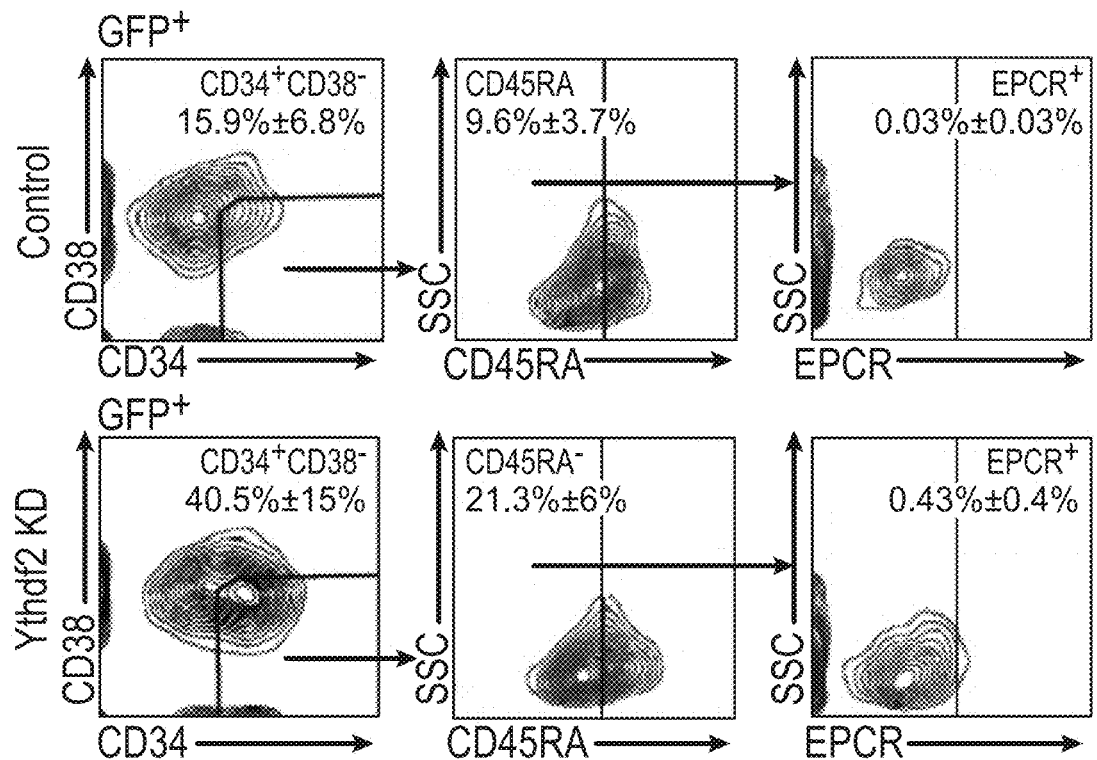
FIGS. 14A-14C: YTHDF2 KD in hUCB cells resulted in HSC expansion without changing lineage output.
Figure 14B:
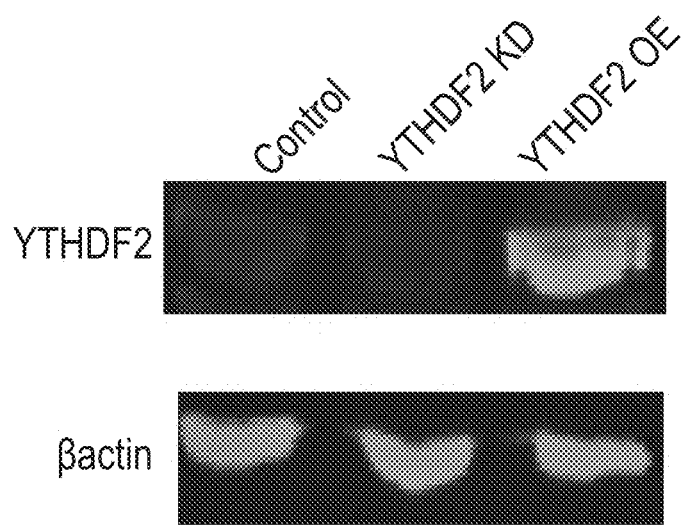

Western blot and intracellular staining. To validate the KO or KD efficiency in Ythdf2 KO mouse model or hUCB, 33,000 cKit$^+$ cells or 120,000 GFP$^+$ cells were sorted from BM or transfected hUCB samples, respectively. Hela cells transduced to overexpress human YTHDF2 were used validate overexpression efficiency as shown in FIG. 14B. Immunoblotting was performed with anti-YTHDF2 rabbit polyclonal antibody (MBL, RN123PW) and β-actin mouse monoclonal antibody (NOVUS, NB600-501). Secondary antibodies used were IRDye 8000 W Goat anti-Mouse IgG and IRDye 8000 W Goat anti-Rabbit IgG antibodies (LI-COR). For intracellular staining, BM cells from wt and Ythdf2 KO mice were stained with HSC markers as above, then fixed with the Cytofix/Cytoperm kit (BD Biosciences) according to the manufacturer's instructions. Fixed and permeabilized cells were immunostained with anti YTHDF2 antibody (MBL RN123PW), anti TAL1 antibody (Santacruz sc-393287), anti GATA2 antibody (Santacruz sc-267), anti RUNX1 antibody (Santacruz sc-365644), anti STAT5 antibody (Santacruz sc-74442) and detected by Alexa-488 donkey anti-rabbit IgG antibody (Invitrogen).

Single cell immunostaining. 10,000 LSKs from wt and Ythdf2 KO mice were sorted onto Poly-L-lysine coating slides, which were placed in a moisture chamber and incubated at 4° C. for 30 mins to allow cells settling onto the slides. Cells were fixed with chilled methanol at RT for 10 mins, blocked with universal blocking reagent (BioGenex) at RT for 30 mins, and stained with mouse TAL1 antibody (Santa Cruz, SC393287) or mouse IgG control (Abcam) at 4° C. overnight. Cells were then stained with Alexa Fluor 488 donkey anti-mouse IgG (Thermo Fisher Scientific) at 4° C. for 30 mins. Images were taken on a PerkinElmer Ultraview spinning disk system with Yokagawa CS-X1 disk. All emission was collected onto a C9100-23 Hamamatsu EM-CCD using Velocity software (PerkinElmer). For Z-stacks, the step size was set at 400 nm. Staining intensity per image was quantified by ImageJ program.

FISH in conjugation with fluorescent immunostaining. Sorted LSKs were spun onto microscope glass slide (Fisher Scientific Cat. No. 12-544-4) using a Cytospin™ 4 Cytocentrifuge at 800 rpm for 1 min with medium acceleration (Thermo Scientific, cat. no. A78300003), followed by an immediate immersion into 4% PFA (diluted from 16% (wt/vol) aqueous solution, Electron Microscopy Sciences, cat. no. 15710). Cells were fixed at RT (25±2° C.) for 30 mins. RNA in situ hybridization was performed using RNA-scope multiplex fluorescent detection kit according to the manufacturer's instructions (Advanced Cell Diagnostics) with a couple of modifications: Antigen retrieval was unnecessary, and digestion was performed with 1:15 diluted proteinase Ill solution for 10 mins at RT. RNAscope probes targeting mouse Tal1 and Gata2 were designed and produced by ACDbio. After the in situ hybridization was completed, slides were rinsed twice with PBST and directly processed with background blocking (Background buster solution, Innovex, cat. no. NB306) and primary antibody incubation. Anti-YTHDF2 (MBL, 1:500) and anti-Dcp1a (Santa Cruz, SC100706, 1:200) antibodies were diluted with antibody diluent reagent buffer (Life technologies, cat. no. 003118) and incubated at 4° C. overnight. Donkey anti-rabbit Alexa Fluor 488 (Invitrogen, 1:500) and donkey anti-mouse Alexa Fluor 633 (Invitrogen, 1:500) were used for protein target multiplexing.

Example A-1

Ythdf2 KO Leads to Increase in Phenotypic HSCs in Primary Mice.

Figure 1C:
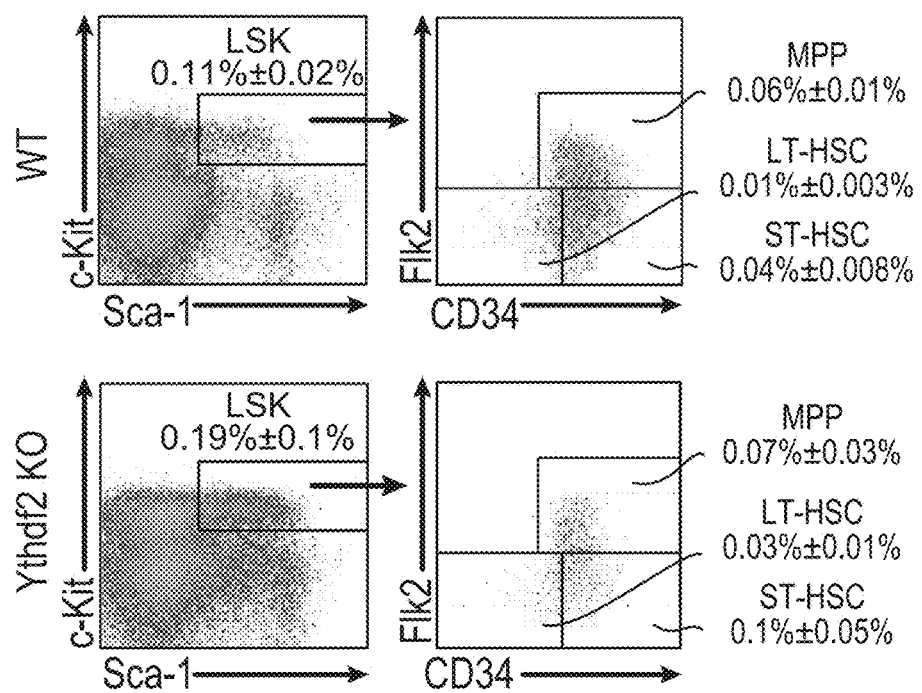
Figure 1D:
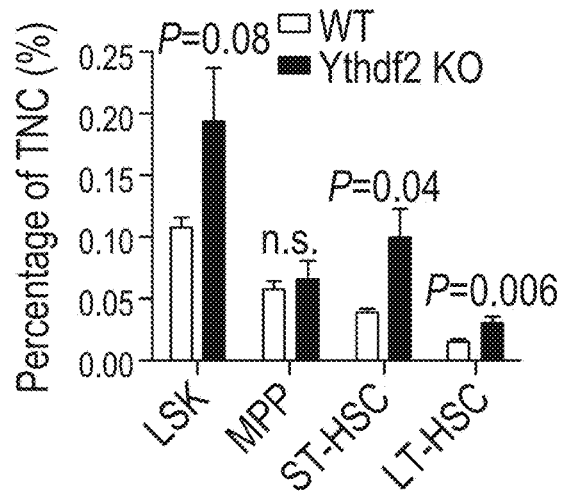
Figure 1E:
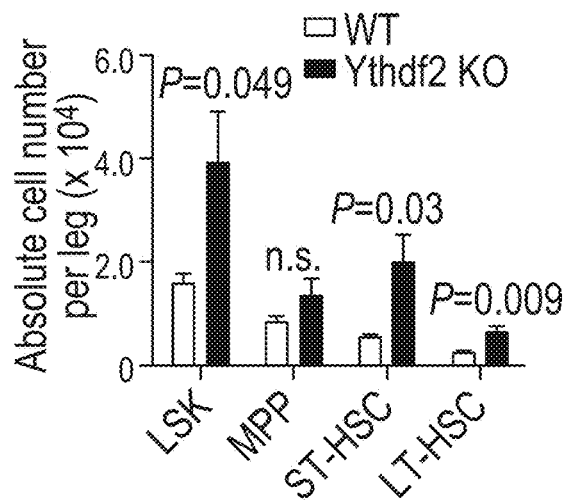
Figure 1F:
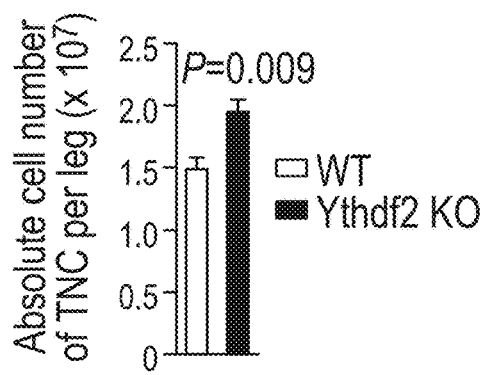
Figure 1G:
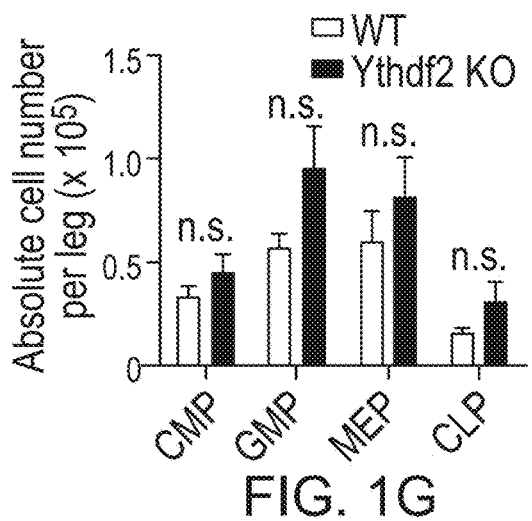
Figure 1H:
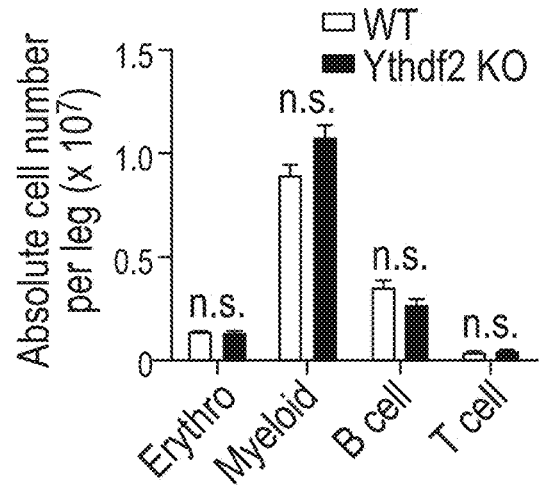
Figure 7A:
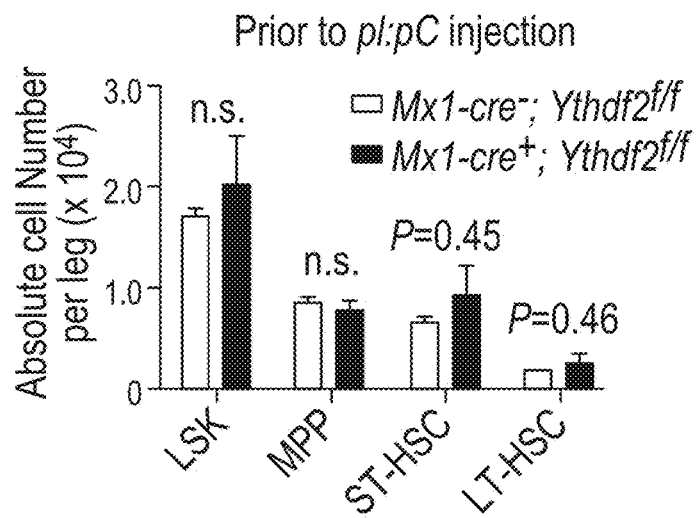
FIGS. 7A-7I: Ythdf2 KO HSCs show no signs of lineage bias or differences in quiescence and homing ability but exhibit lower apoptotic rate.
Figure 7B:
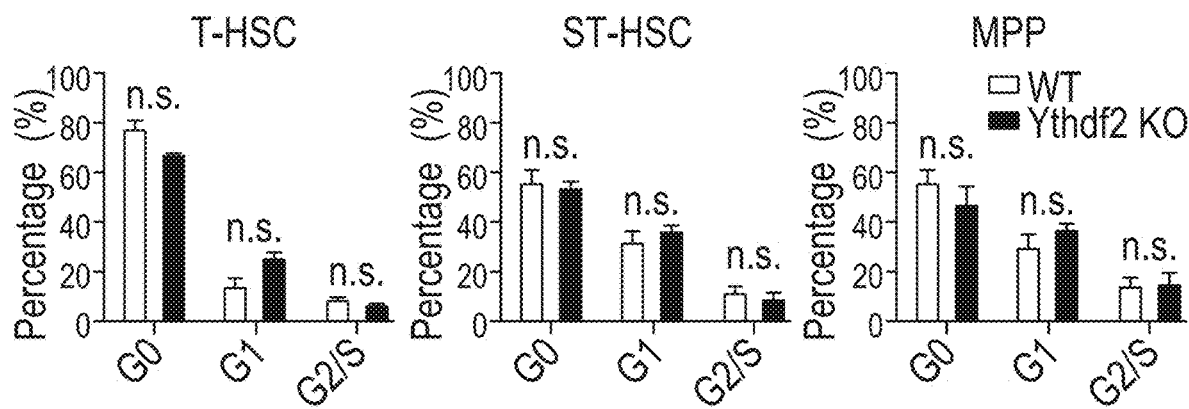
Figure 7C:
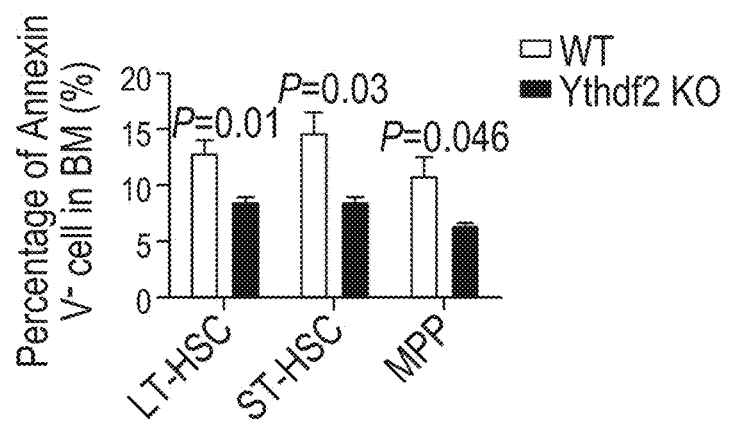
Figure 7D:
Figure 7E:
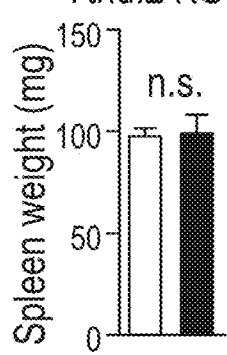
Figure 7F:
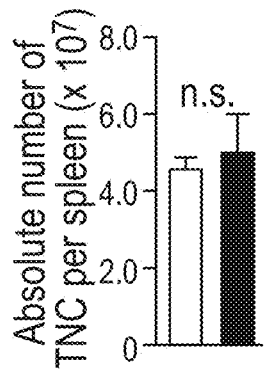
Figure 7F:
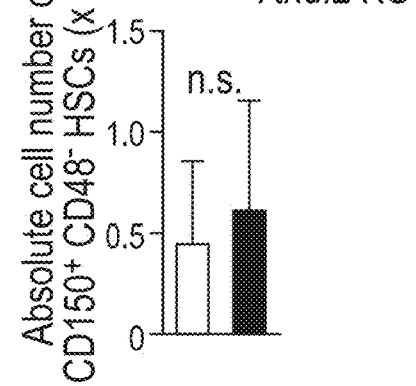
Figure 7G:
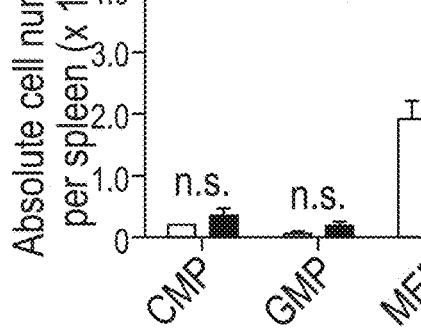
Figure 7H:
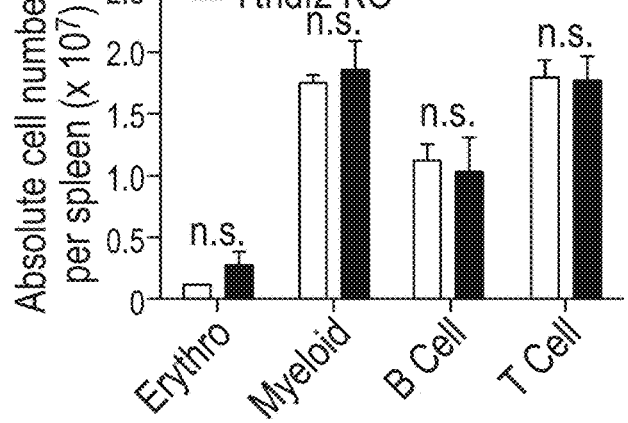

To investigate the effects of Ythdf2 on phenotypic HSCs, Crispr-Cas9 technology was utilized to generate Ythdf2$^{f/f}$ conditional knockout mice, and then crossed with Mx1-Cre mice to specifically reduce Ythdf2 expression in hematopoietic cells (hereafter Ythdf2 KO mice) (FIG. 1A and B). BM HSPCs showed no discernible difference at the absence of pI:pC (FIG. 7A). Four weeks after pI:pC injections, a significant increase was observed in both frequency and absolute number of long-term HSCs (Lin$^-$ Sca1$^+$ cKit$^+$ (LSK) CD34$^-$ Flk2$^-$; LT-HSCs) and short-term HSCs (LSK CD34$^+$ Flk2$^-$; ST-HSCs), but not multipotent progenitors (LSK CD34$^+$ Flk2$^+$; MPPs) in Ythdf2 KO mice compared to littermate wild type (wt) mice (FIG. 1C to 1E). It was found that the frequency and absolute cell number of Long Term HSCs (LT-HSCs) and ST-HSCs increased by over 2-fold while MPP exhibited milder response (FIGS. 1C and 1E). Although Ythdf2 KO led to increased BM cellularity, the absolute number of committed progenitors, including common myeloid progenitors (CMPs), granulocyte-macrophage progenitors (GMPs), megakaryocyte-erythrocyte progenitors (MEPs) and common lymphoid progenitors (CLPs), as well as mature lineage cells, erythrocytes, myeloid cells, B cells and T cells, showed no significant difference between Ythdf2 KO and wt mice (FIG. 1F to H). Cell cycle analysis revealed no discernible change of quiescence in HSCs or MPPs after Ythdf2 KO (FIG. 7B). Notably, the percentage of apoptotic cells in Ythdf2 KO LT-, ST-HSCs and MPPs significantly reduced compared to wt controls (FIG. 7C). To further identify any potential HSC defects in Ythdf2 KO mice, the number of HSCs, committed progenitors, and mature lineages in the spleen were examined, and no significant differences were found between wt and Ythdf2 KO mice (FIGS. 7D to 7H). In summary, Ythdf2 KO in primary mice specifically increases HSC numbers with no bias or defects in either progenitor or lineage cells.

Example A-2

Ythdf2 KO Expands Functional HSCs in Mice.

Figure 2A:
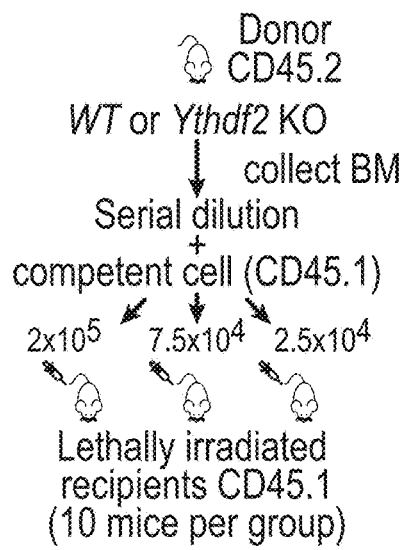
FIGS. 2A-2J: Ythdf2 KO results in expansion of functional HSCs in mice.
Figure 2B:
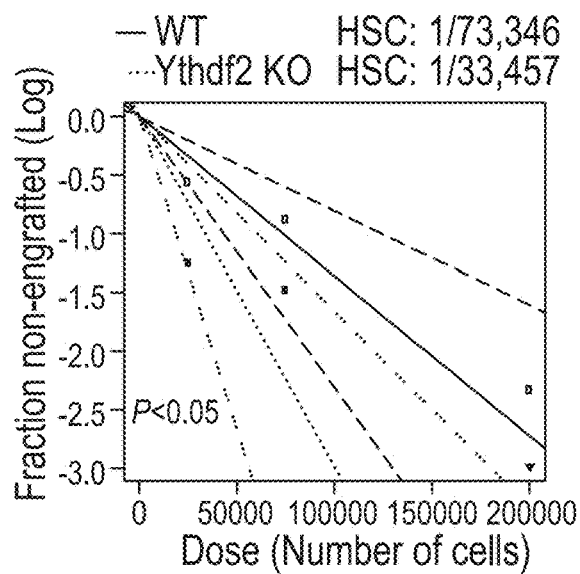
Figure 2C:
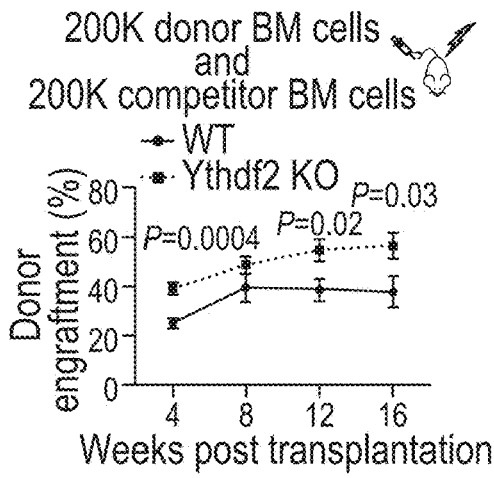
Figure 2D:
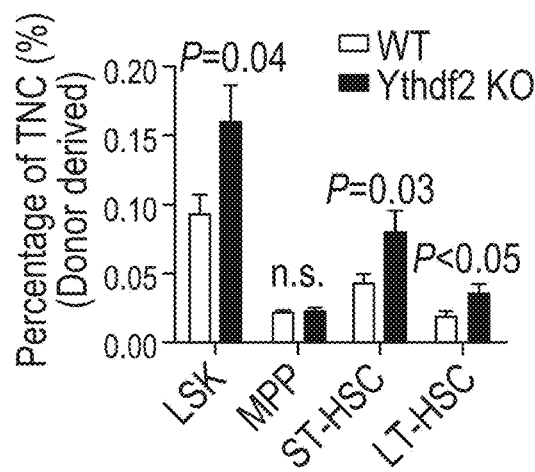
Figure 2E:
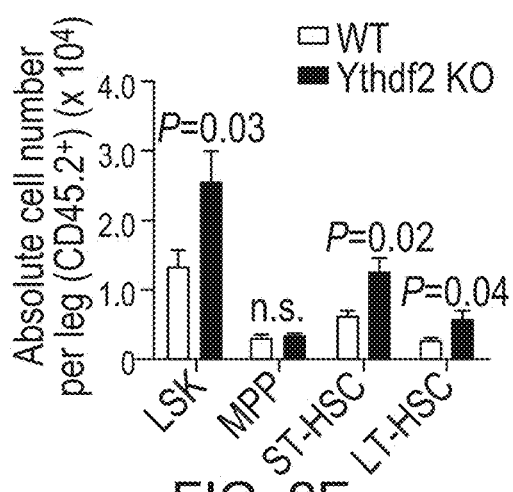
Figure 2F:
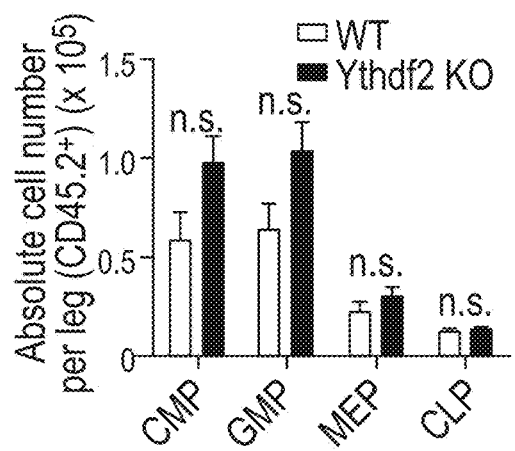
Figure 2G:
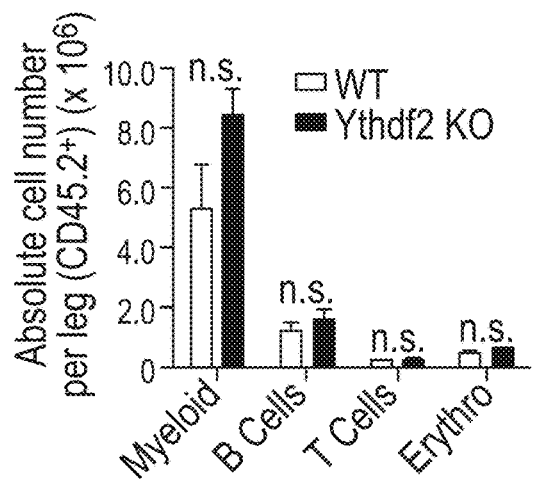
Figure 2H:
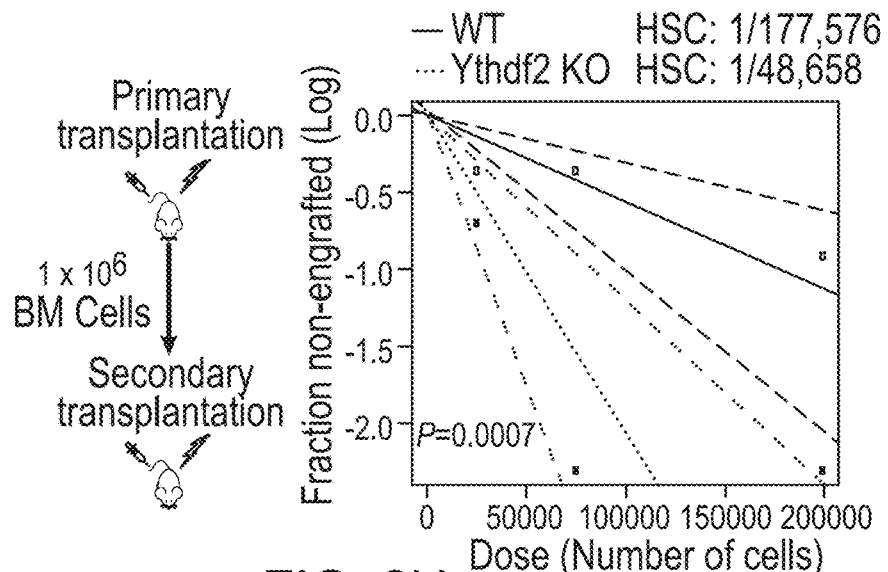
Figure 2I:
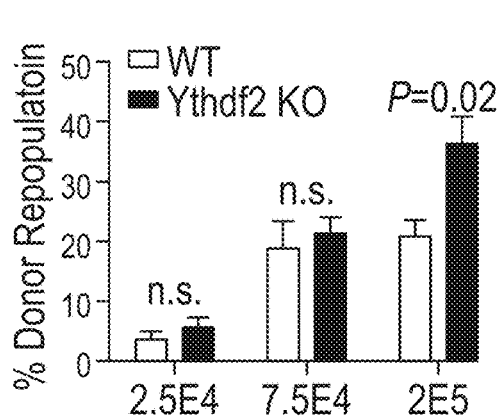
Figure 2J:
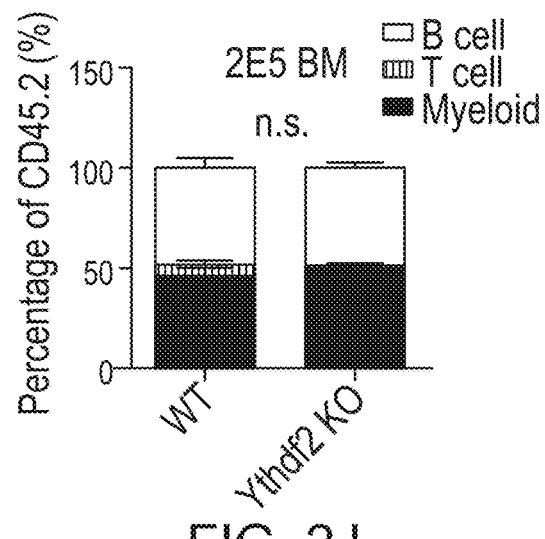
Figure 7I:
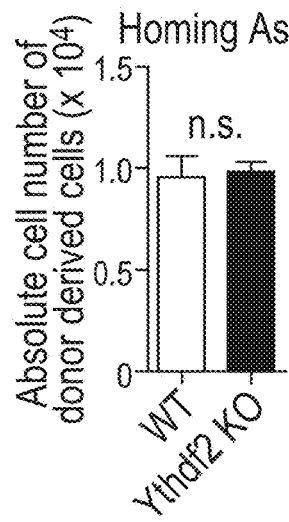
Figure 8A:
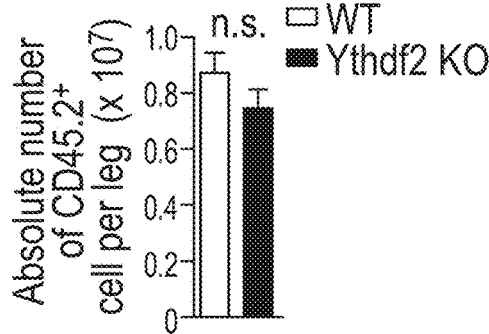
FIGS. 8A-8F: Transplantation recipient mice of Ythdf2 KO BM display no lineage changes or defects 16 weeks post transplantation.
Figure 8B:
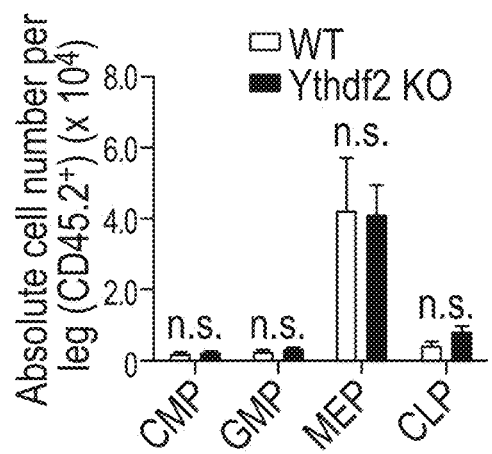
Figure 8C:
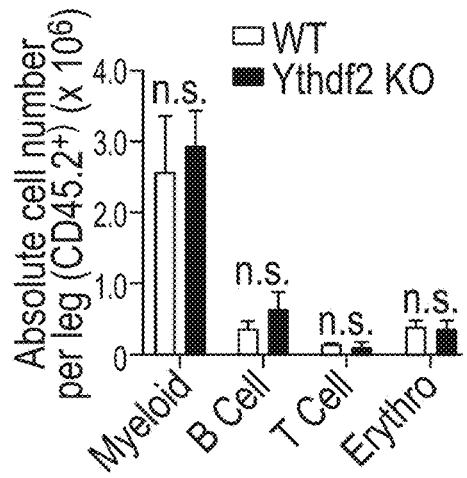
Figure 8D:
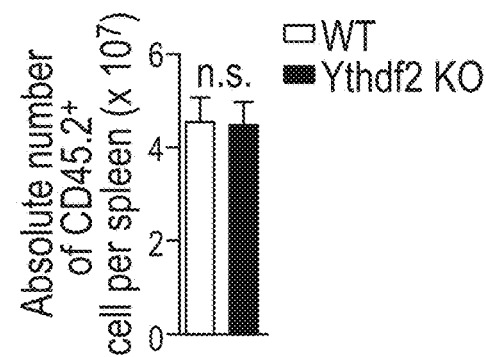
Figure 8E:
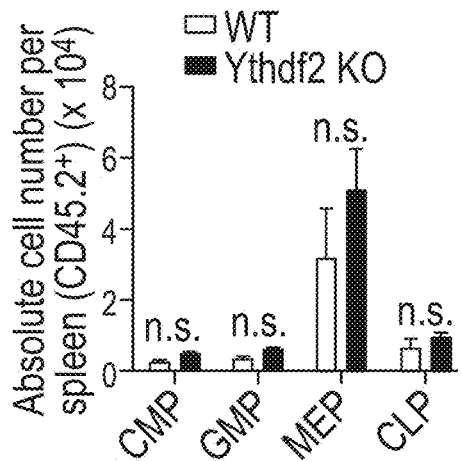
Figure 8F:
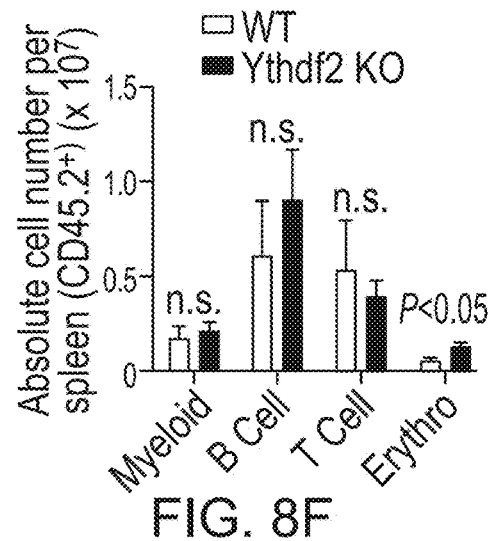

To determine whether Ythdf2 KO expands functional HSCs, a short-term homing assay was initially performed by transplanting 1×10$^6$ carboxyfluorescein diacetate succinimidyl ester (CFDA SE)-labelled BM cells from KO mice or their control littermates into lethally irradiated recipient mice, and no significant difference was found in their homing capacity between mutant and wt controls (FIG. 7I). Limited dilution, competitive repopulation unit assay (LDA) was then executed by transplanting 2×10$^5$, 7.5×10$^4$ or 2.5×10$^4$ donor BM cells (CD45.2), together with 2×10$^5$ recipient BM cells derived from the ptprc mutant strain (CD45.1), into lethally irradiated recipient mice (FIG. 2A). Consistent with an increased number of phenotypic HSCs in Ythdf2 KO mice, it was found that competitive repopulating units (CRUs) increased 2.2-fold in Ythdf2 KO HSCs compared to controls (FIG. 2B). In the 2×10$^5$ group, compared to controls, and a significant increase was observed in the overall repopulation rate from Ythdf2 KO donor cells at 16 weeks post transplantation (FIG. 2C). Moreover, recipients of Ythdf2 KO BM cells, compared to that of controls, exhibited markedly higher frequency and absolute number of donor derived LT-HSCs and ST-HSCs, but not MPPs in BM (FIGS. 2D and 2E). Furthermore, it was found that donor derived committed progenitors and mature lineages in BM from transplantation recipients of mutant and wt cells showed no significant changes (FIGS. 2F and 2G). To determine the long-term repopulation ability of HSCs from Ythdf2 KO mice, the secondary transplantation with BM cells derived from primary recipients was conducted. Notably, it was found that compared to controls, CRUs from Ythdf2 KO cells revealed a 3.5-fold increase (FIG. 2H) and exhibited no signs of leukemia in both BM and spleen at 16 weeks after secondary transplantation (FIGS. 9A to 9F). Furthermore, in FIGS. 2I and 2J, a limiting dilution assay was conducted by transplanting total bone marrow (BM) from WT or Ythdf2 KO mice with 3 different dosages. Four weeks post transplantation, it was observed that the engraftment of donor cells increased in the mice transplanted with 200,000 Ythdf2 KO BM cells, as compared to that with WT BM cells. Furthermore, this increase did not generate lineage bias in the transplantation recipients.

Figure 9A:
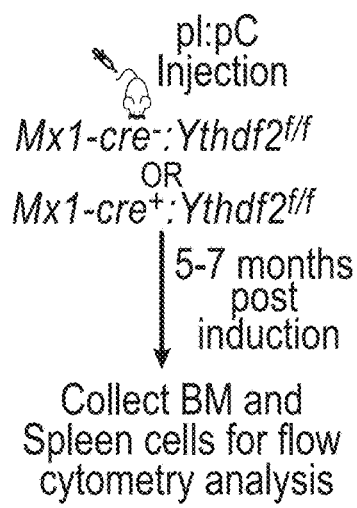
FIGS. 9A-9K: Ythdf2 KO has long-term effect on mouse HSC expansion in vivo without inducing lineage bias.
Figure 9B:
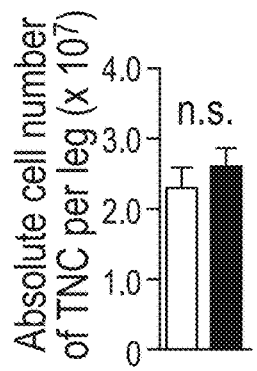
Figure 9C:
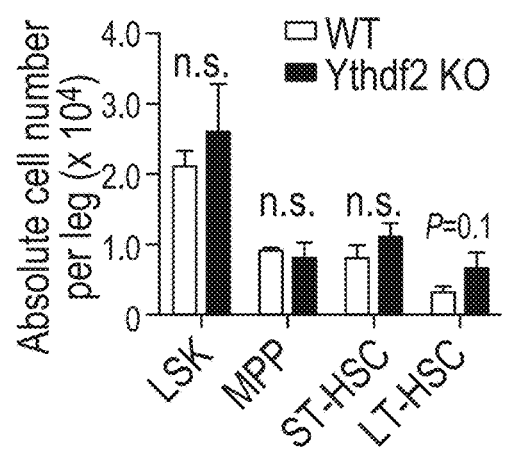
Figure 9D:
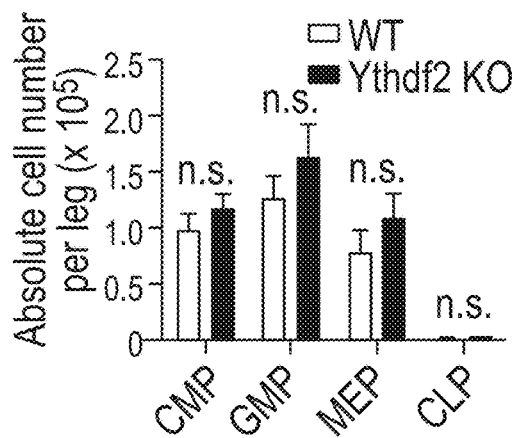
Figure 9E:
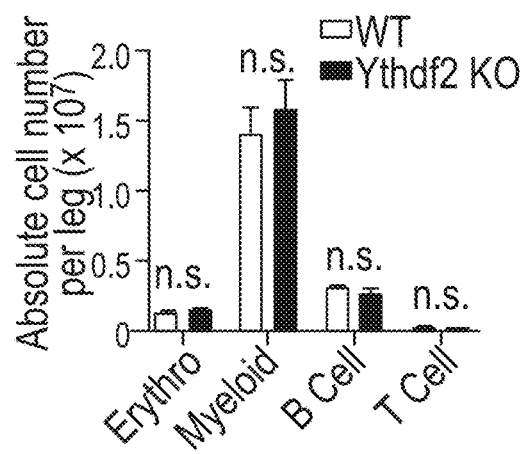
Figure 9F:
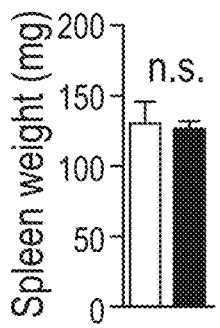
Figure 9G:
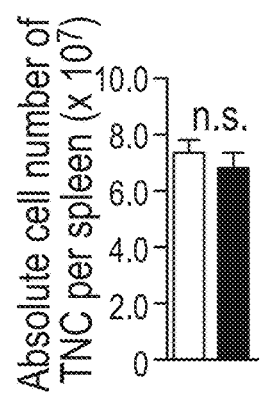
Figure 9H:
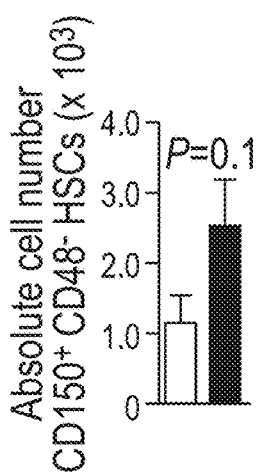
Figure 9I:
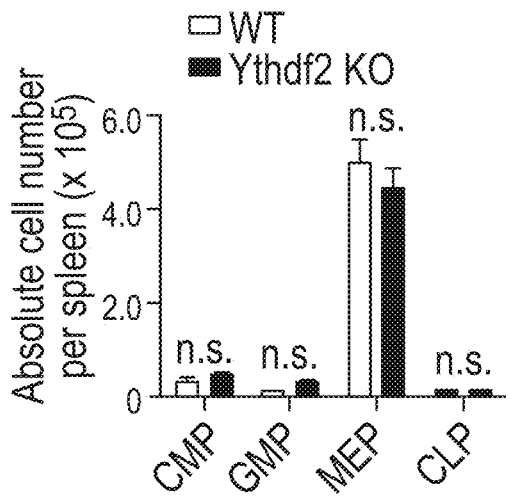
Figure 9J:
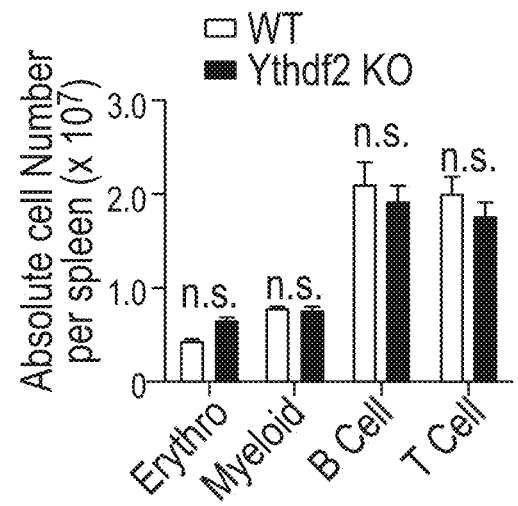
Figure 9K:
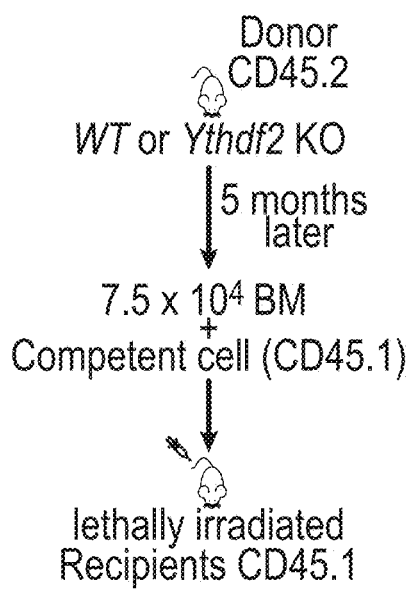
Figure 9K:
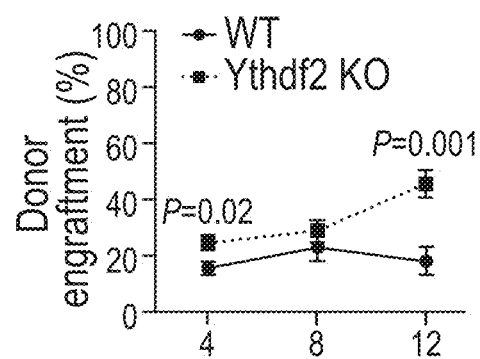

We also investigated the long-term effect of Ythdf2 KO on hematopoiesis under homeostasis condition by examining the stem cells, progenitor cells, and lineages in both BM and spleen at over 5 months post pI:pC injections (FIG. 9A). Although we observed a modest increase in LT-HSCs in BM from Ythdf2 KO mice compared to that of controls (FIG. 9C), there were no discernible differences between Ythdf2 KO and control mice in progenitors and lineage cells from either BM or spleen (FIGS. 9D to 9J). These observations indicate that long-term effect of Ythdf2 KO in vivo neither skews lineage differentiation nor facilitates aberrant proliferation, which is in line with previous reports that Ythdf2 is not required for leukemogenesis. To verify the frequency of functional HSCs in the BM at 5 moths post pI:pC induction, we transplanted 7.5×10$^4$ BM cells from wt and Ythdf2 KO mice with competent cells into lethally irradiated recipients. We found that Ythdf2 KO led to significantly higher engraftment in recipients comparing to wt controls, suggesting that Ythdf2 KO has long-term capability on mouse HSC expansion in vivo (FIG. 9K). Taken together, these data reveal that Ythdf2 KO results in specific and significant mouse HSC expansion in vivo without affecting lineage commitment.

Example A-3

Ythdf2 Regulates HSC Self-Renewal Gene Expression by m$^6$A-Mediated mRNA Decay.

Figure 3A:
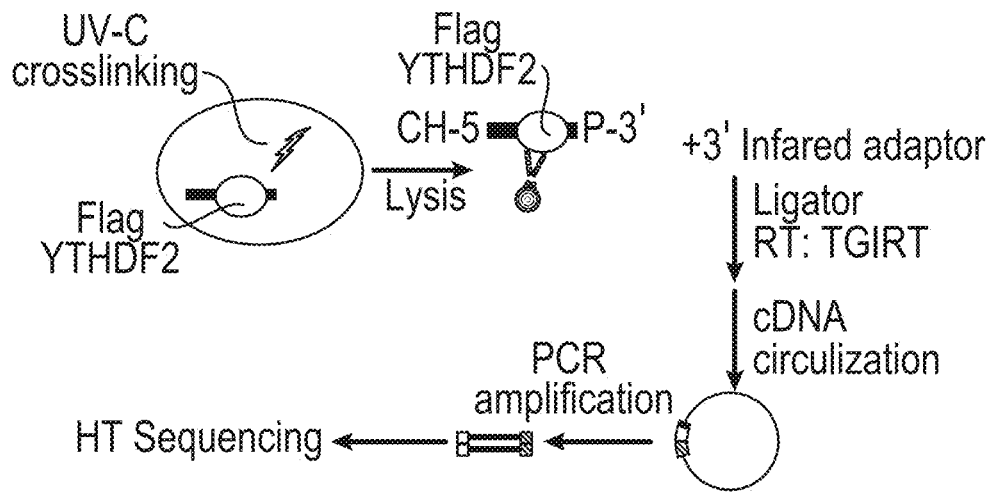
FIGS. 3A-3I: Ythdf2 functions as an $m^6A$ reader and regulates HSC gene expression by mediating mRNA decay.
Figure 3B:
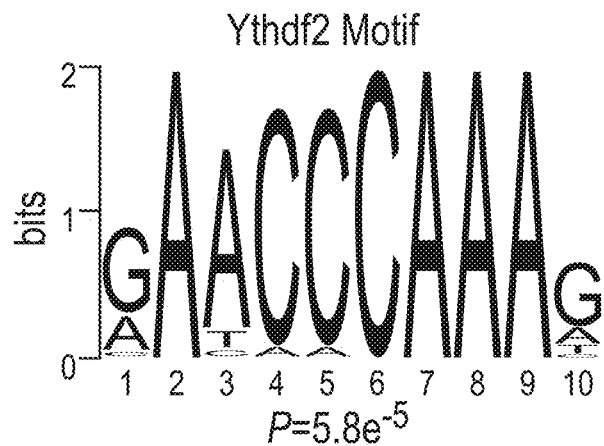
Figure 3C:
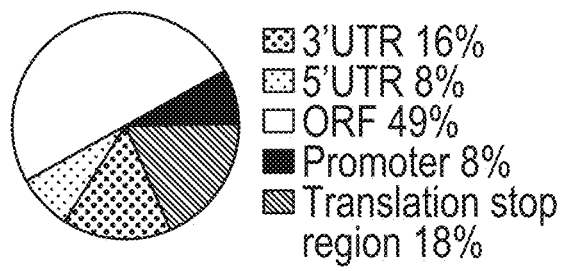
Figure 3D:
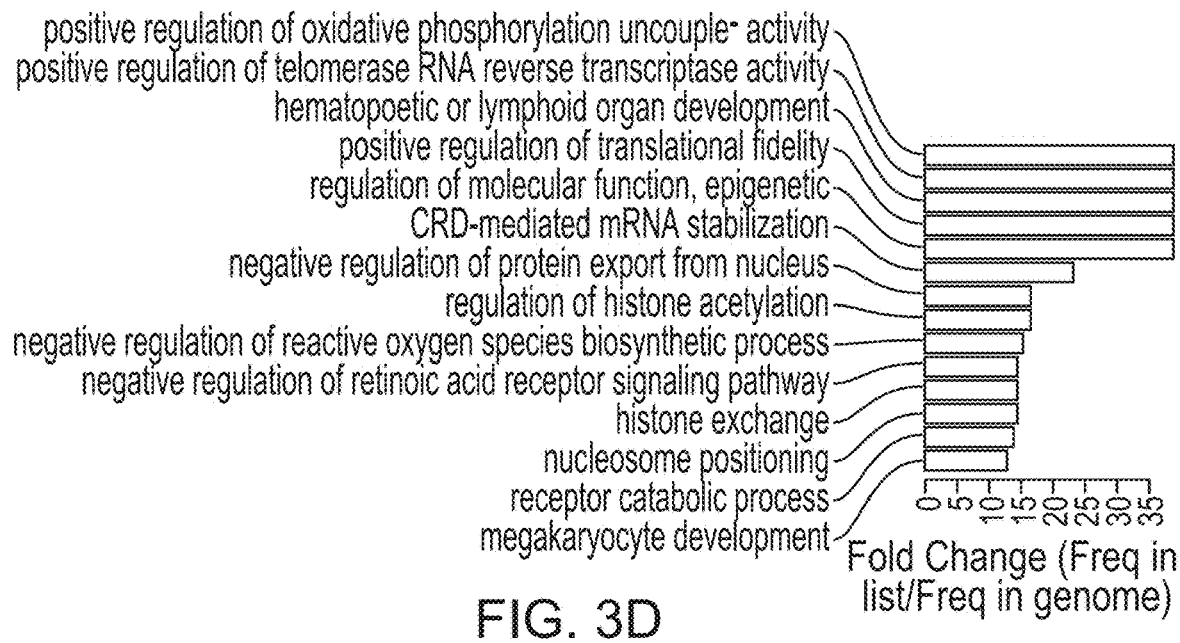
Figure 3E:
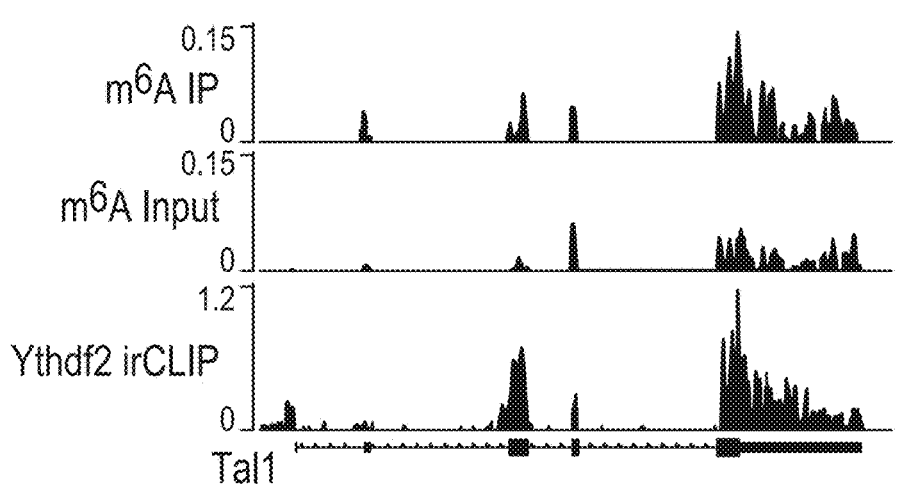
Figure 3F:
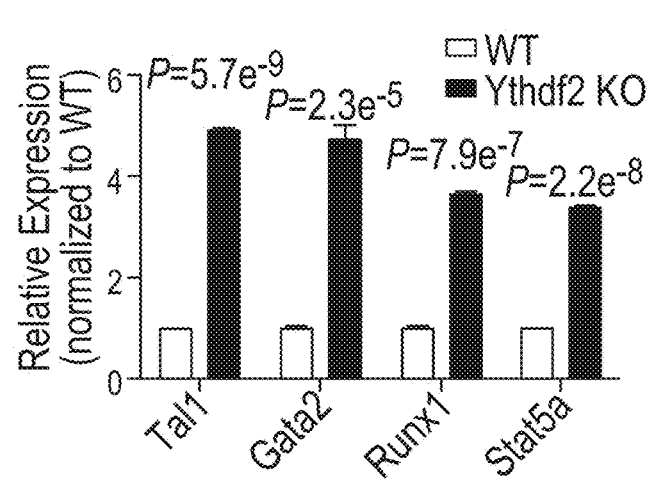
Figure 3G:
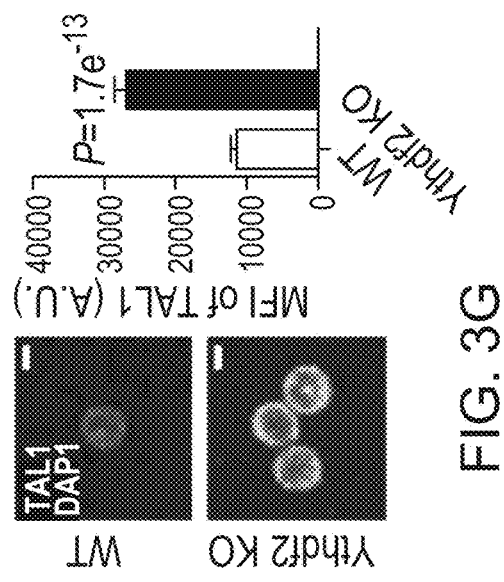
Figure 3H:
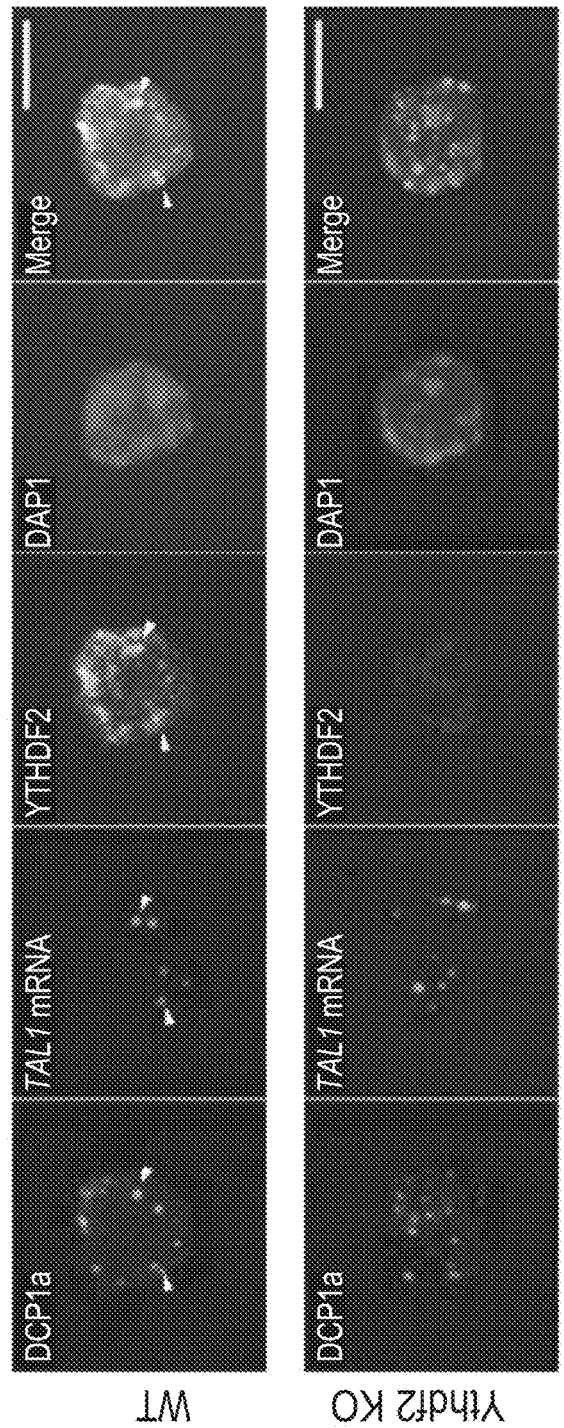
Figure 3I:
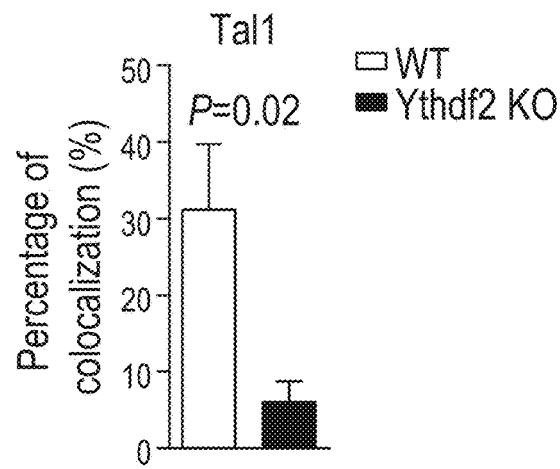
Figure 10A:
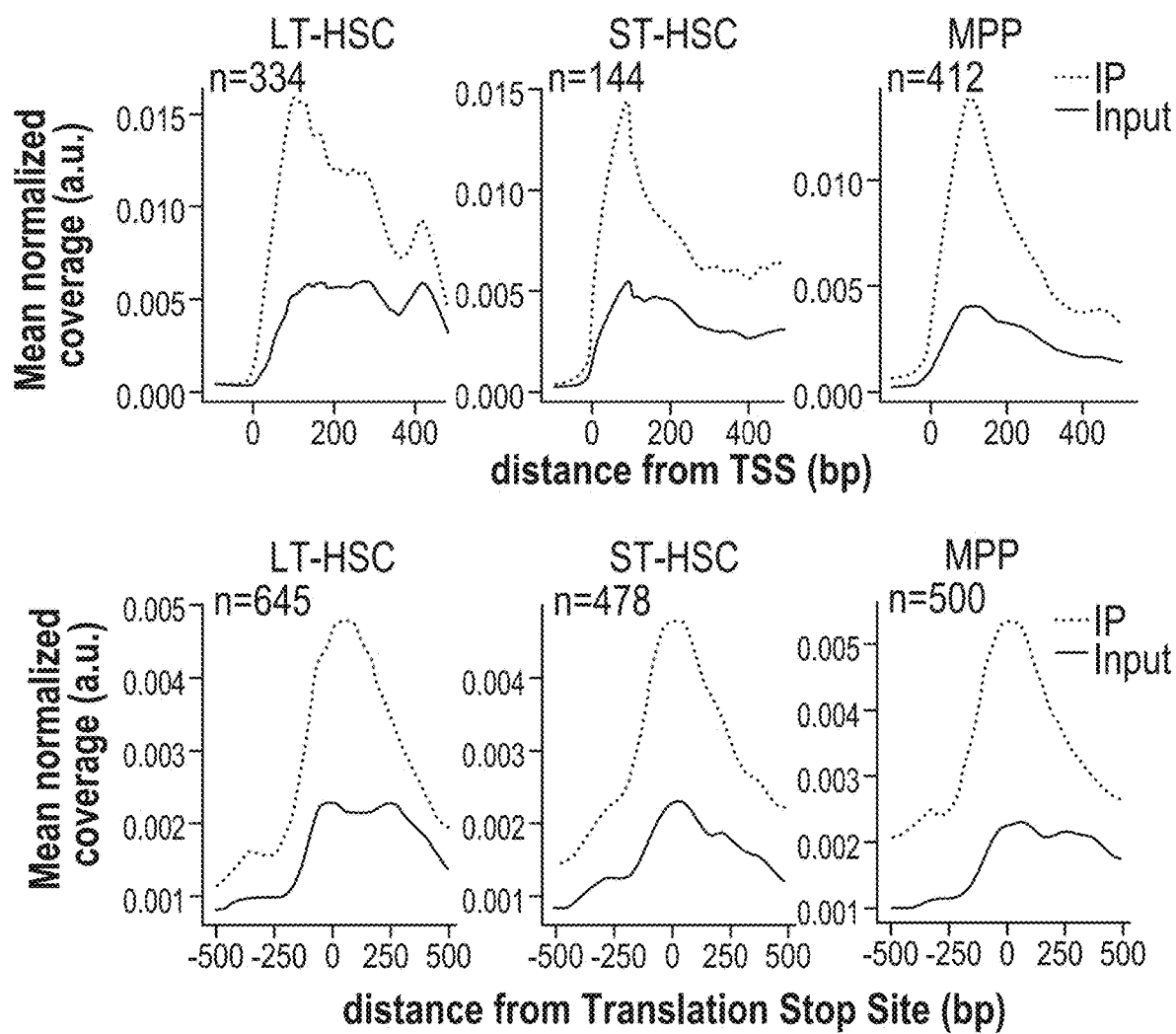
FIGS. 10A-10D: Molecular characterization of $m^6A$ modification in mouse HSPCs.
Figure 10B:
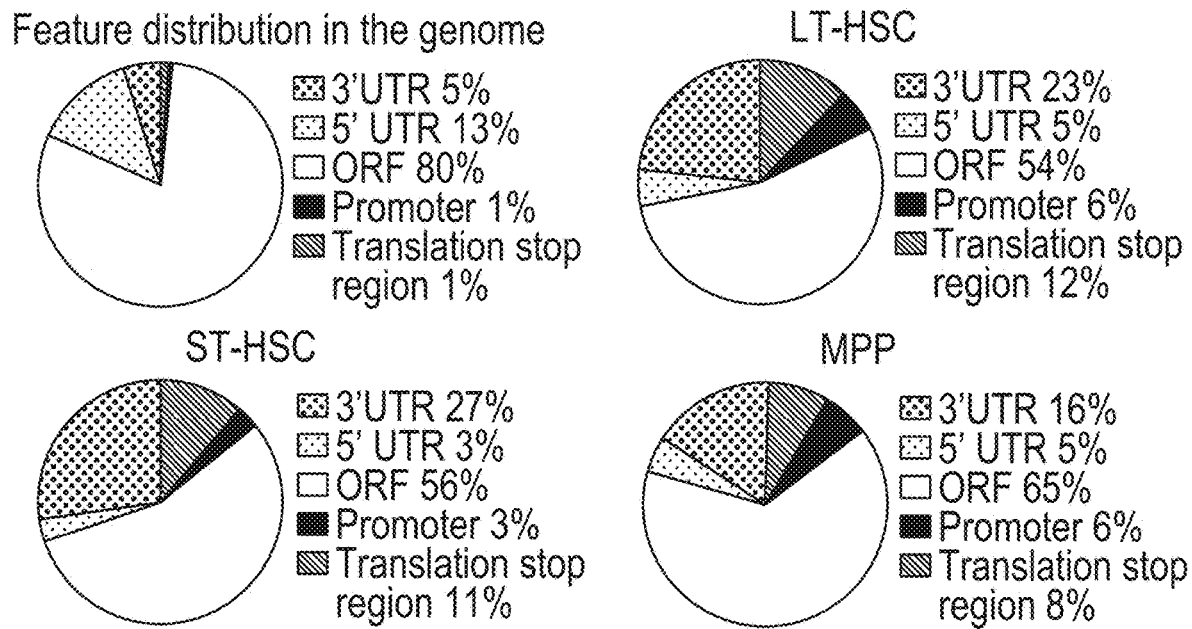
Figure 10C:
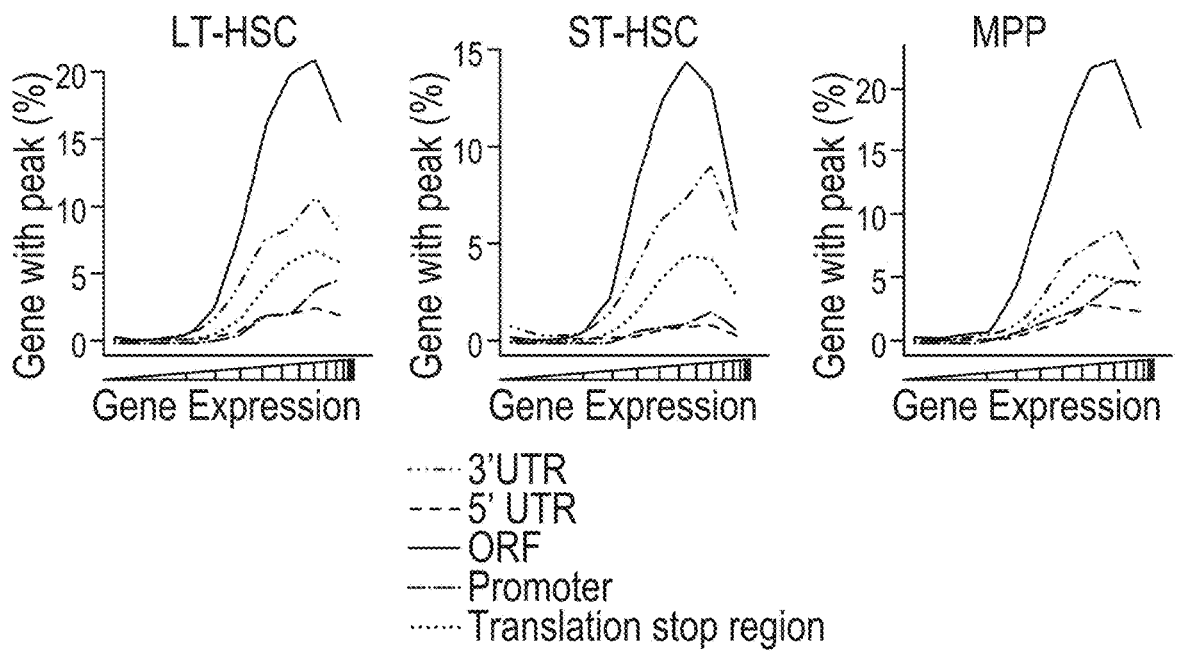
Figure 10D:
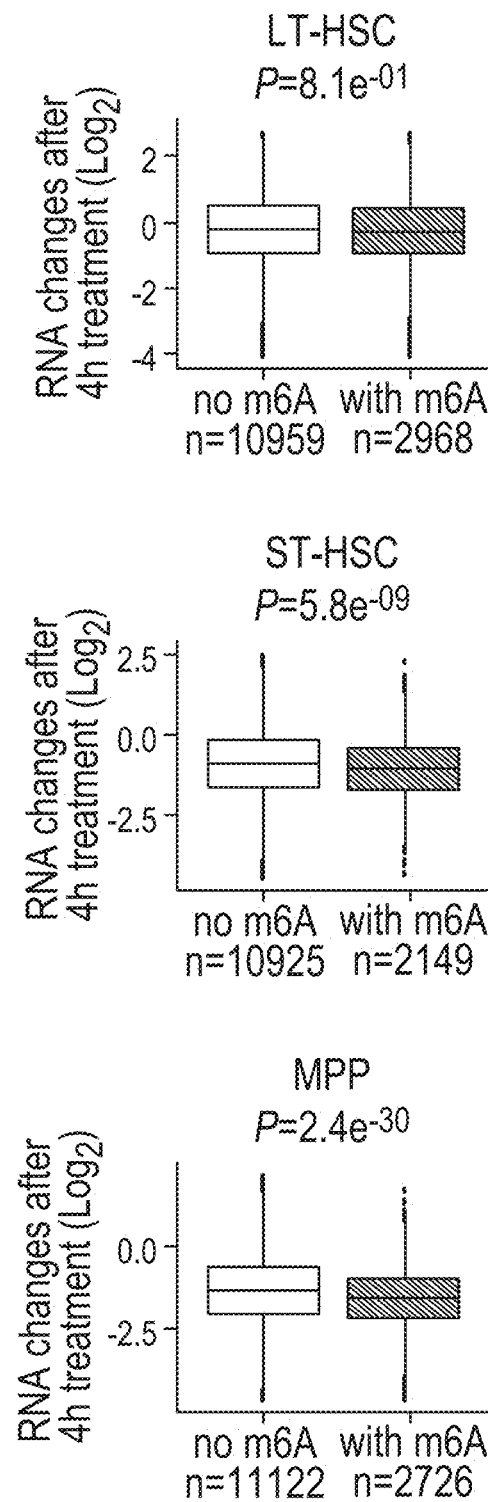
Figure 11A:
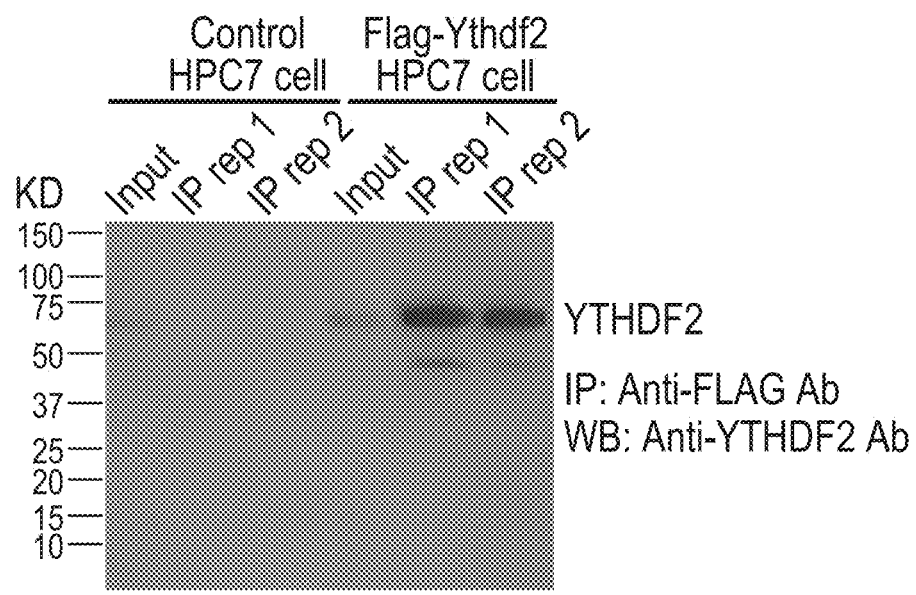
FIGS. 11A-11E: Define Ythdf2 functionality in mouse HSPCs by irCLIP-seq.
Figure 11B:
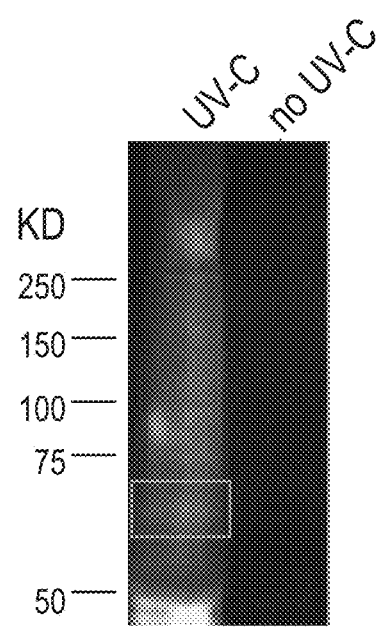
Figure 11C:
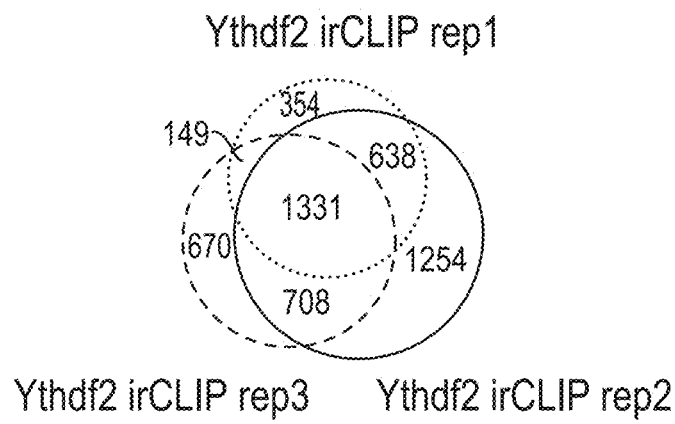
Figure 11D:
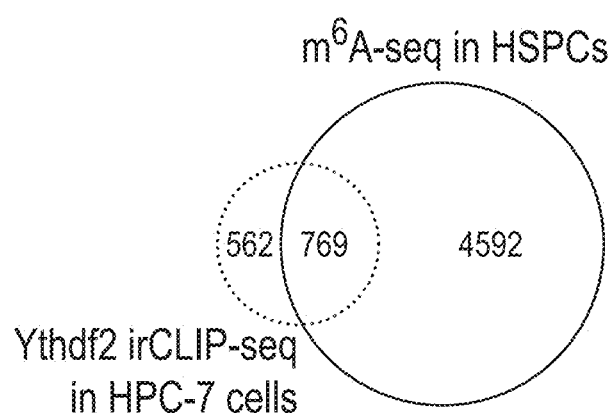
Figure 11E:
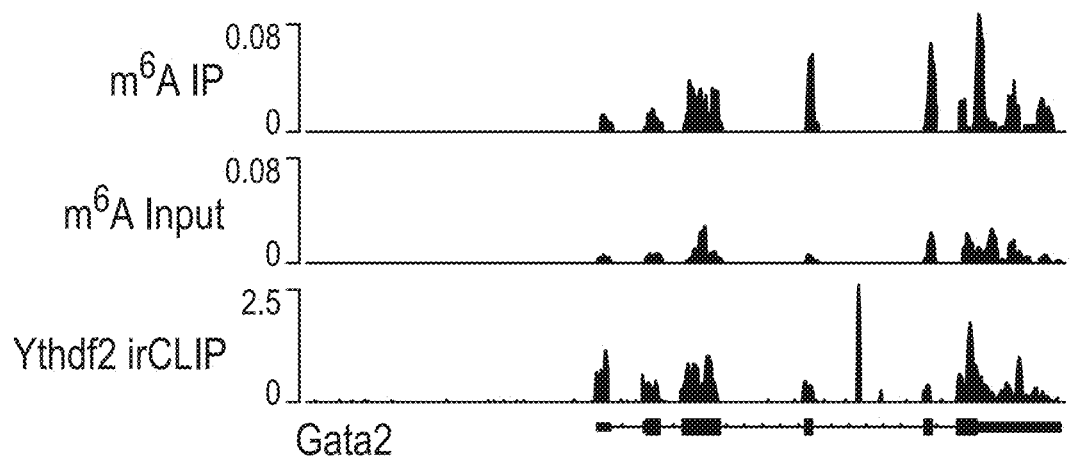
Figure 12A:
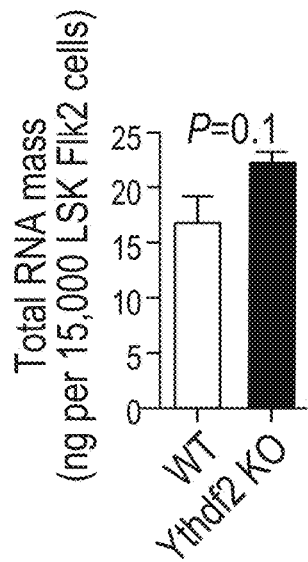
FIGS. 12A-12F: Ythdf2 KO increased $m^6A$-tagged mRNA expression, contributing to HSC expansion.
Figure 12B:
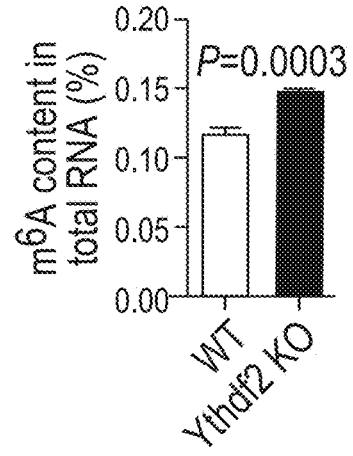
Figure 12C:
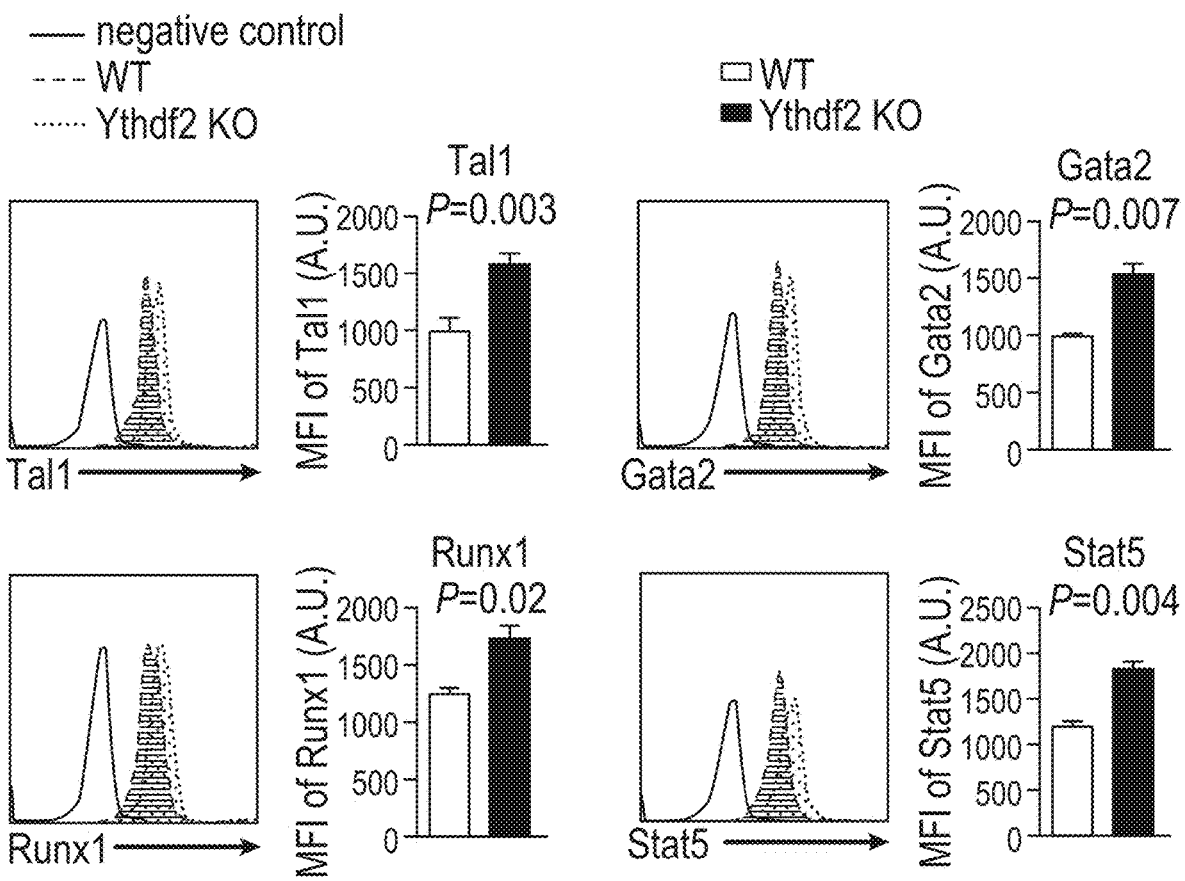
Figure 12D:
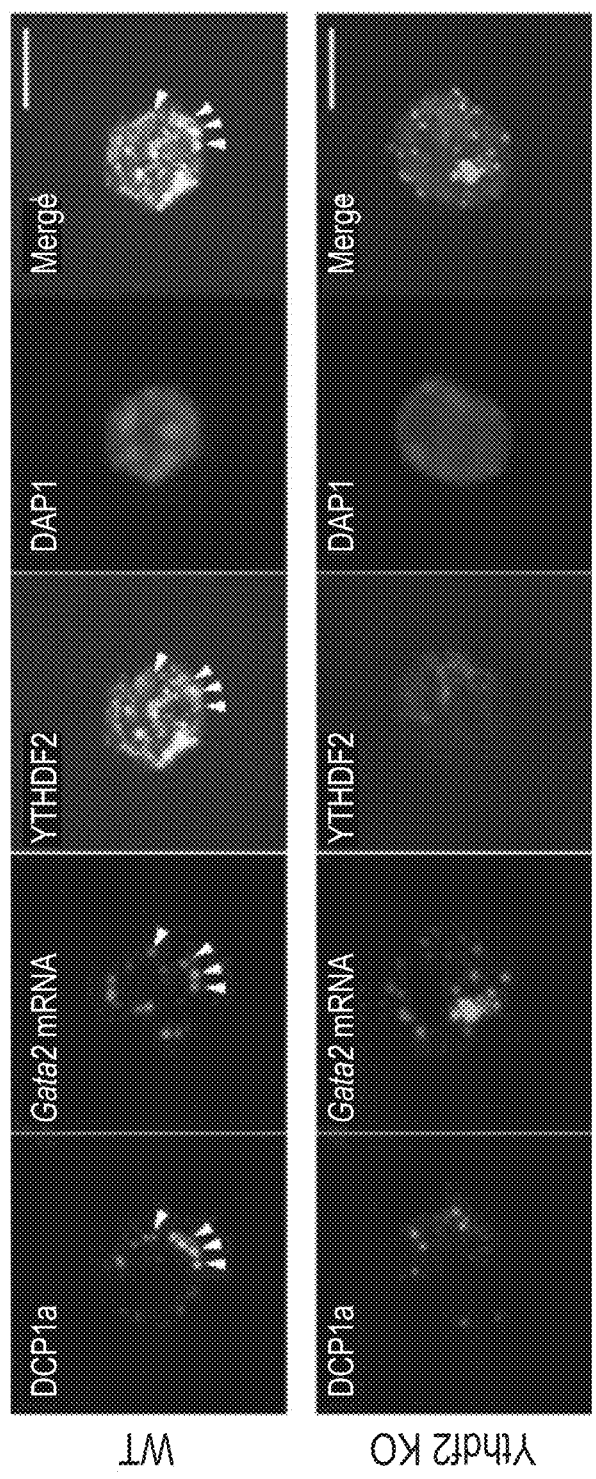
Figure 12E:
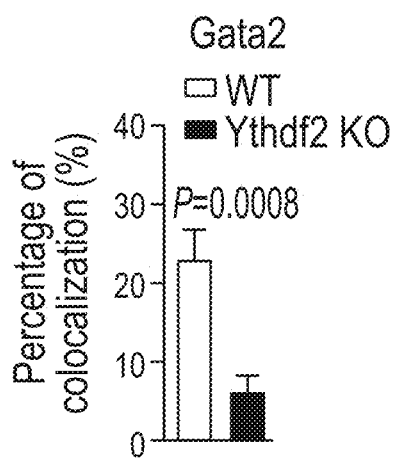
Figure 12F:
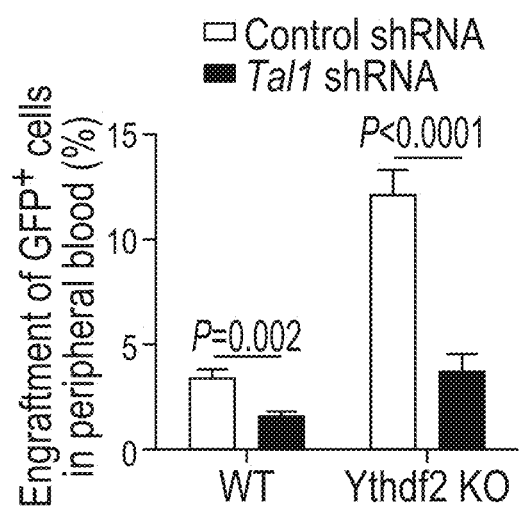

To explore the underlying mechanisms of how Ythdf2 KO expands HSCs, mapping was performed of the m$^6$A methylome by methylated RNA immunoprecipitation combined with high-throughput sequencing (MeRIP-seq or m$^6$A-seq) in LT-HSCs, ST-HSCs, and MPPs sorted from adult C57BL/6J mice (Meyer et al. *Cell*, 149: 1635-1646, 2012; Schwartz et al. *Cell*, 155: 1409-1421, 2013; Dominissini et al. *Nature*, 485: 201-206, 2012). m$^6$A peaks were selected by identifying significantly enriched overlapping peaks from two independent replicates. Consistent with previous studies (Meyer et al. *Cell*, 149: 1635-1646, 2012); Dominissini et al. *Nature*, 485: 201-206, 2012), it was found that m$^6$A peaks were abundant in mRNA open reading frame (ORF), in 3' untranslated regions (UTRs), and around the stop codon in all three HSPC populations. Transcripts of moderately expressed genes were more likely to be methylated (FIGS. 10A to 10C). Intriguingly, it was found that m$^6$A modifications were enriched in the mRNAs of transcription factors, such as Gata2, Etv6, Stat5 and Tal1, which have been documented to be critical for HSC self-renewal and stem cell state maintenance (Wang et al. *Blood*, 113: 4856-5865, 2009; Ebina et al. *The EMBO Journal*, 34: 694-709, 2015; Orkin et al. *Cell*, 132: 631-644, 2008: de Pater et al. *The Journal* of *Experimental Medicine*, 210: 2843-2850, 2013; Hock et al. *Genes and Development*, 18: 2336-2341, 2004; Lim et al. *The Journal of Clinical Investigation* 122: 3705-3717, 2012; Reynaud et al. *Blood*, 106: 2318-2328, 2005; and Kato et al. *The Journal of Experimental Medicine*, 202: 169-179, 2005), suggesting the m$^6$A modification could play critical roles in the regulation of HSCs (Table S1, Key transcription factors critical for HSC self-renewal and maintenance are labeled by m$^6$A in HSPCs). Given the accumulating evidence that m$^6$A mRNA methylation regulates stem cell fate determination by facilitating the decay of mRNAs coding for transcription factors and genes in key signaling pathways involved in self-renewal and differentiation (Batista et al. *Cell Stem Cell*, 15: 707-719, 2014; (Geula et al. *Science* 347: 1001-1006, 2015; Yoon et al. *Cell*, 2017; Zhang et al. *Nature*, 549: 273-276, 2017; Zhao et al. *Nature*, 542: 475-478, 2017; Li et al. *Cancer Cell*, 31: 127-141, 2017; Li et al. *Nature*, 548: 338-342, 2017) the mRNA degradation rates were next measured in LT-, ST-HSCs, and MPPs by monitoring mRNA levels after transcription inhibition with actinomycin D. It was found that degradation rates of methylated mRNAs were significantly faster than unmethylated mRNAs in ST-HSCs, and MPPs (FIG. 10D). As Ythdf2 is a well-recognized m$^6$A "reader" that mediates mRNA decay (Wang et al. *Nature*, 505: 117-120, 2014), the targets of Ythdf2 were further determined by performing infrared UV-crosslinking immunoprecipitation sequencing (irCLIP-seq) in the mouse multipotent hematopoietic precursor cell line HPC-7 (Pinto do et al. *The EMBO Journal*, 17: 5744-5756, 1998; Zarnegar et al. *Nature Methods*, 13: 489-492, 2016) (FIG. 3A; FIGS. 11A to 11C). The results showed that 57.8% of Ythdf2 target mRNAs contained m$^6$A peaks (FIG. 11D). Ythdf2 binding sites were enriched with the conserved m$^6$A motif and exhibited the characteristic of m$^6$A distribution features (FIGS. 3B and 3C). Gene ontology (GO) analysis of Ythdf2 target transcripts revealed enrichment of genes related to hematopoietic or lymphoid organ development, suggesting the involvement of Ythdf2 in the regulation of hematopoiesis (FIG. 3D). Notably, it was found that Ythdf2 bound to transcription factor mRNAs, such as that of Tal1 and Gata2, on sites largely overlapping with m$^6$A peaks (FIG. 3E; FIG. 5E and Table S2, Ythdf2 targeted mRNAs from three irCLIP-seq replicates). Significant change was not observed in the total RNA mass in LSK Flk2$^-$ cells from wt and Ythdf2 KO mice. Though m$^6$A modification only constitute 0.1-0.4% of adenosine nucleotide in mammal cells, it was found that Ythdf2 KO led to increased level of m$^6$A content in total RNA from BM Lin$^-$ cells, suggesting that Ythdf2 specifically regulates the stability of m$^6$A-marked mRNAs (FIGS. 12A and 12B). Consistently, qPCR analysis of total mRNA revealed increased levels of Tal1, Gata2, Runx1 and Stat5a, whose mRNAs have shown to be modified by m$^6$A, in Ythdf2 KO LSK cells compared to wt controls (FIG. 3F). Single cell immunofluorescence staining and intracellular flow cytometry further revealed that Ythdf2 KO HSPCs exhibited significant increases in the intensities of m6A-labeled transcription factors involved in stem cell self-renewal, such as TAL1, GATA2, RUNX1 and STAT5, indicative of a suppressive role of Ythdf2 in HSC self-renewal (FIG. 3G; FIG. 12C). A previous study has shown that Ythdf2 regulates RNA metabolism through localizing the bound mRNAs to mRNA decay sites (Wang et al. *Nature*, 505: 117-120, 2014). To further explore the mechanism of Ythdf2 in regulating HSC self-renewal, fluorescence in situ hybridization (FISH) was performed of Tal1 mRNA and fluorescence immunostaining of Ythdf2 and Dcp1a, a marker of mRNA decay sites (Sheth et al. *Science*, 30:805-808, 2003; Kedersha et al. *Methods in Enzymology*, 431: 61-81, 2007), and their relative spatial distribution was analyzed in sorted wt and Ythdf2 KO HSPCs. Co-localization of Tal1 mRNA, Dcp1a and Ythdf2 was observed in wt cells while substantially reduced in Ythdf2 KO controls (FIGS. 3H and 3I). Furthermore, similar observation was confirmed by co-staining Gata2 mRNA FISH with Ythdf2 and Dcp1a in wt or Ythdf2 KO HSPCs (FIGS. 12D and 12E). To determine whether the increased transcription factors, such as Tal1, expression accounts for the HSC expansion in Ythdf2 KO mice, rescue experiments were performed using short hairpin (sh) RNA-mediated Tal1 knock down (KD) in wt and Ythdf2 KO LSK cells, followed by transplanting into lethally irradiated recipients. Depletion of Tal1 in HSPCs significantly impaired the reconstitution capacity of wt cells as reported previously and also rescued the increased engraftment of Ythdf2 KO cells (FIG. 12F). Overall, these data indicate that Ythdf2 regulates HSC self-renewal by enabling the degradation of mRNAs encoding transcription factors essential for stem-cell renewal.

Example A-4

Dissecting the Role of Ythdf2 in Human UCB HSPCs by m$^6$A-Seq and RNA-Seq.

Figure 4A:
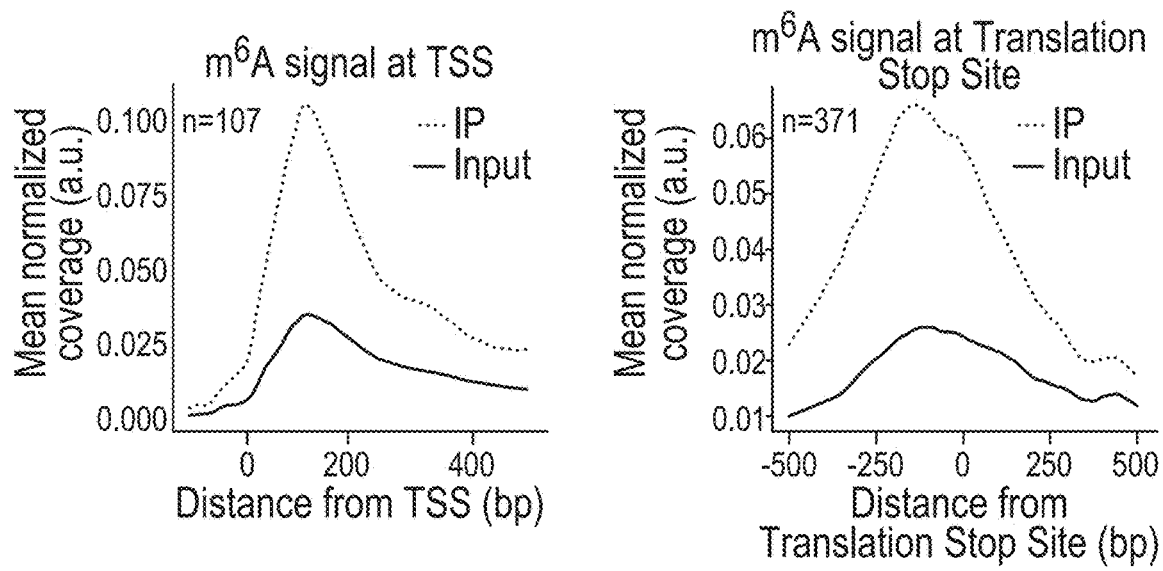
FIGS. 4A-4I: Role of YTHDF2 in human cord blood HSCs by $m^6A$-seq and RNA-seq analysis.
Figure 4B:
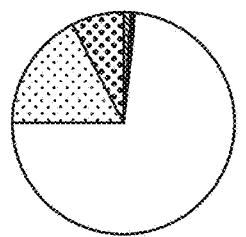
Figure 4B:
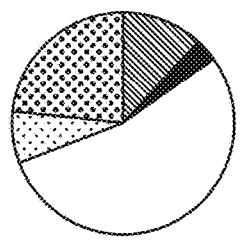
Figure 4C:
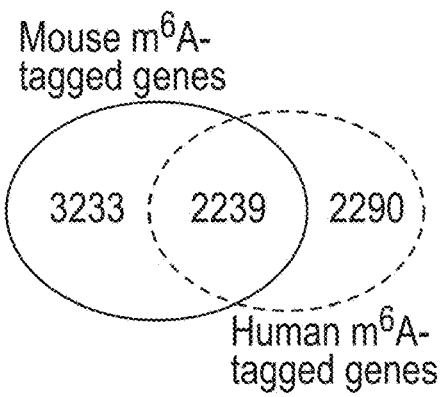
Figure 4D:
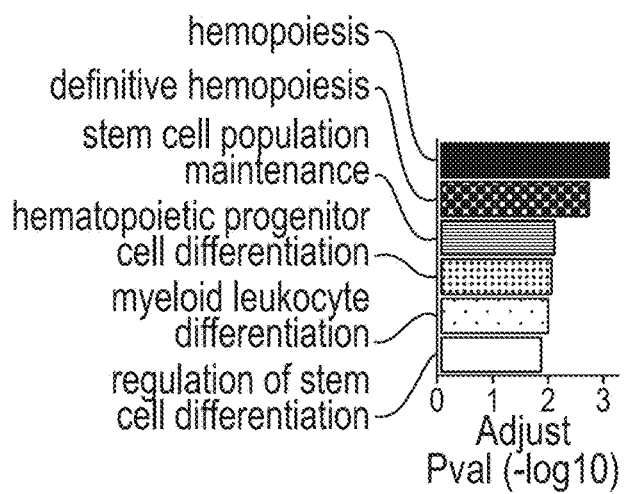
Figure 4E:
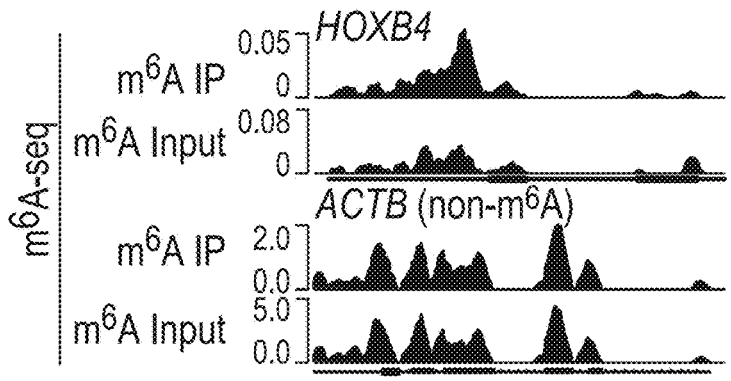
Figure 13A:
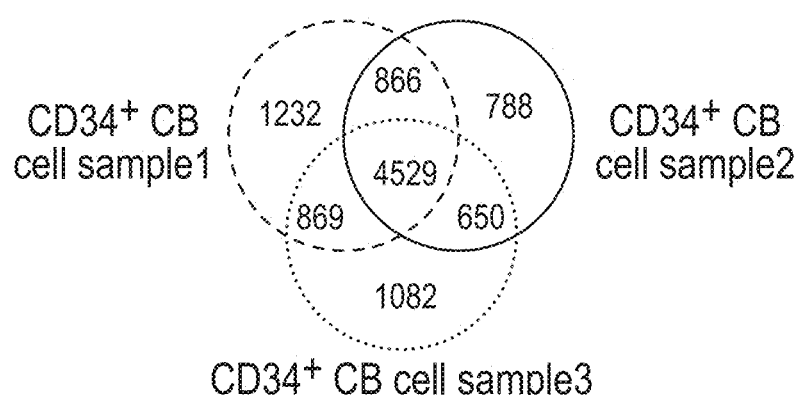
FIGS. 13A-13G: YTHDF2 regulates expression of transcription factors related to stem cell self-renewal in human cord blood stem cells.
Figure 13B:
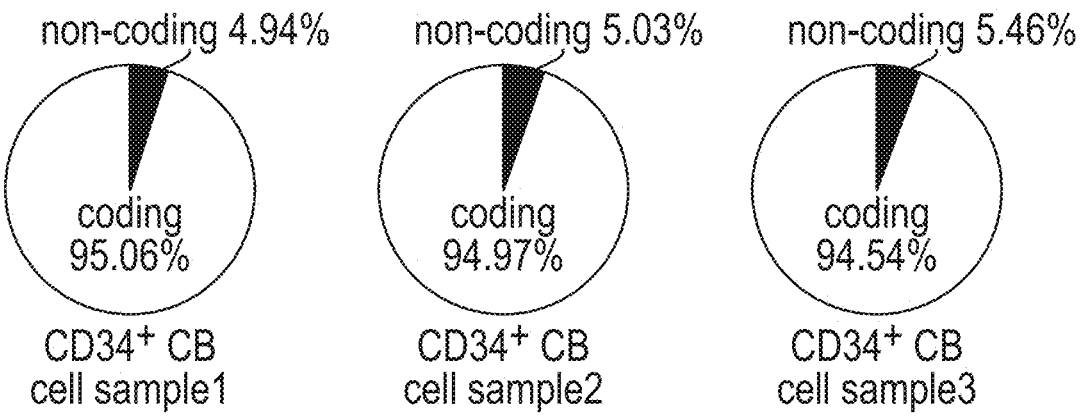
Figure 13C:
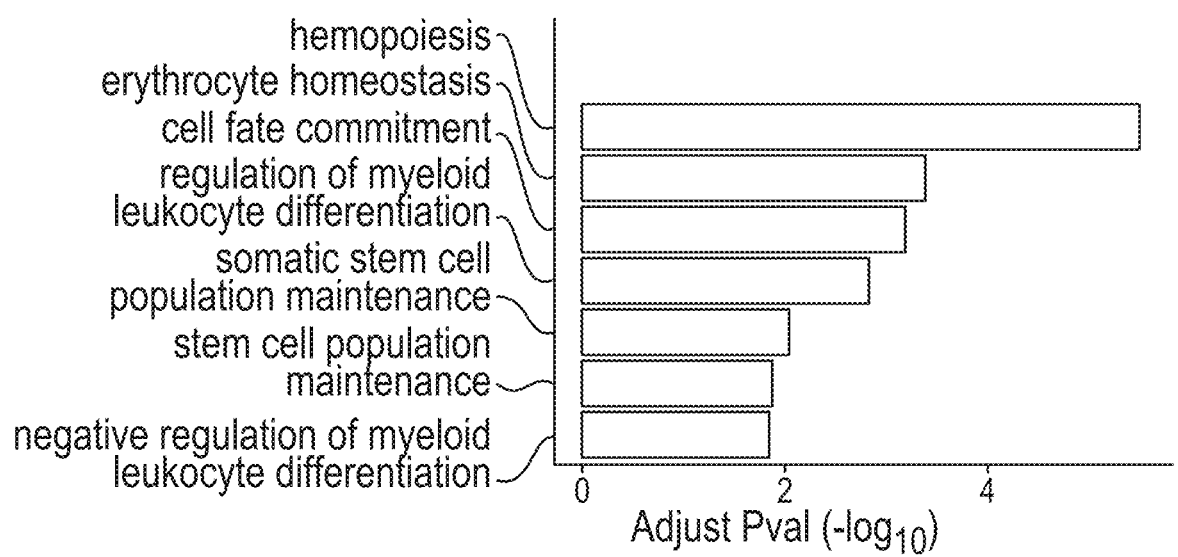
Figure 13D:
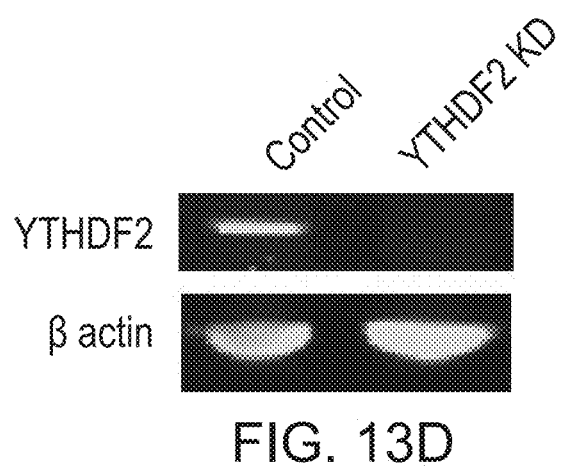
Figure 13E:
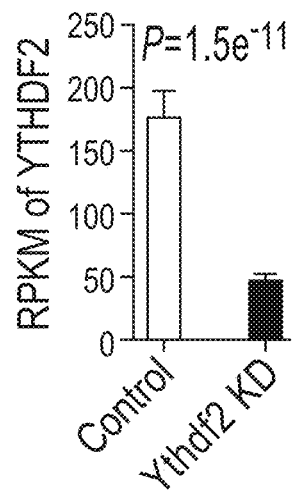
Figure 13F:
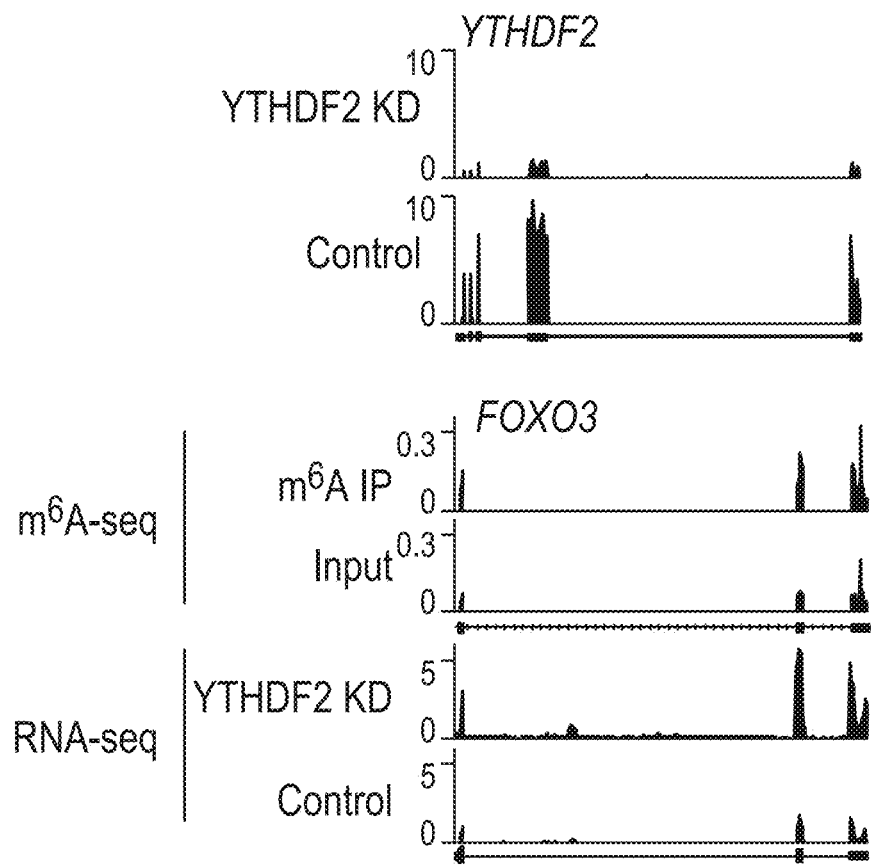
Figure 13G:
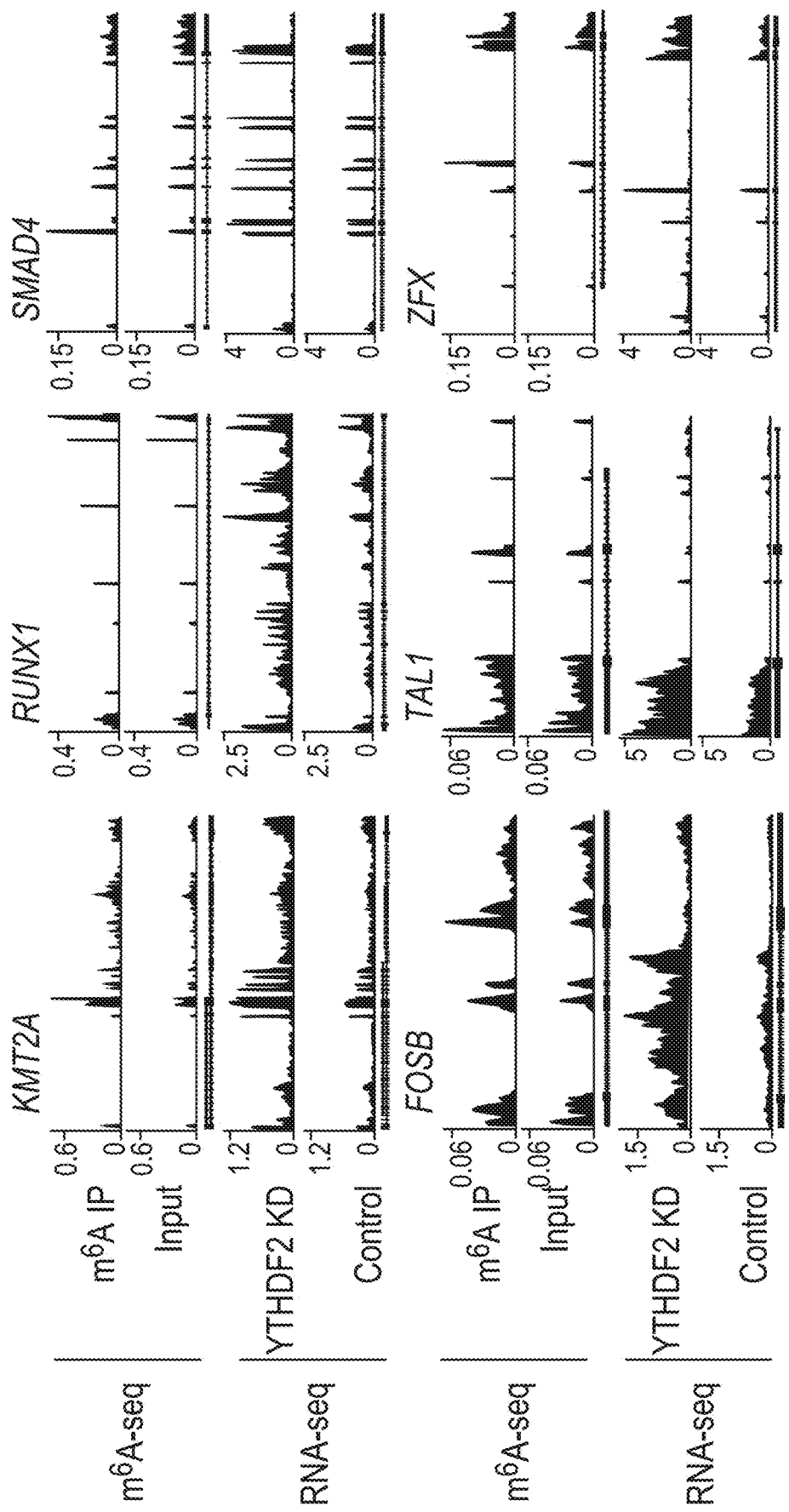

The limited number of HSCs in a single human umbilical cord blood unit has been an obstacle for clinical applications, such as HSC transplantation (Walasek et al. *Annals of the New York Academy of Sciences*, 1266: 138-150, 2012). The observation that Ythdf2 KO resulted in an increase of phenotypic and functional mouse HSCs prompted a test whether YTHDF2 knockdown (KD) could facilitate human UCB HSC expansion. First, m$^6$A-seq with CD34$^+$ cells isolated from 3 individual hUCB samples was performed (FIG. 13A). m$^6$A modifications predominantly occurred in mRNAs (~95%), preferential in mRNA ORF regions, 3'UTRs, and near the stop codon, as expected (~90%) (FIGS. 4A and 4B; FIG. 13B). m$^6$A landscapes in mouse and hUCB HSPCs were compared, and it was found that 2,239 genes were commonly m$^6$A tagged (FIG. 4C). These commonly m$^6$A-tagged transcripts were enriched for genes related to hematopoiesis and stem cell maintenance (FIG. 4D). Due to the enrichment of m$^6$A labeling in the mRNAs of transcription factors responsible for mouse HSC self-renewal, the m$^6$A-marked transcription factor transcripts in hUCB CD34$^+$ cells were next characterized by performing GO term analysis. Among the 722 identified m$^6$A-labeled transcription factor mRNAs, major GO terms were related to cell fate commitment and stem cell maintenance (FIG. 13C). For example, HOXB4, overexpression of which has been reported to expand human and mouse HSCs ex vivo (Amsellem et al. *Nature Medicine*, 9: 1423-1427, 2003; Antonchuck et al. *Cell*, 109: 39-45, 2002), was marked by m$^6$A in hUCB CD34$^+$ cells (FIG. 4E). Other transcription factors required for HSC self-renewal and critical to induce HSCs from other cell types (Ebina et al. *The EMBO Journal*, 34: 694-709, 2015; Galan-Caridad et al. *Cell*, 129: 345-357, 2007, such as Zfx, RUNX1 and FOSB, were also m$^6$A-tagged in hUCB CD34$^+$ cells (FIGS. 13F and 13G and see also Supplementary Table S3 of article "Supression of m6A Reader Ythdf2 Prmotd Hematopoeitic Stem Cell Expansion" by Li et al, *Cell Research* 28, 904-917 (2018), which article (and including the Supplementary Tables thereof) is hereby incorporated by reference herein in its entirety, Genes marked by m$^6$A in human UCB CD34$^+$ HSPCs from individual samples). To further dissect the role of YTHDF2 in hUCB HSPCs, RNA-seq was performed with control or YTHDF2 KD hUCB CD34+ cells (FIG. 4F; FIGS. 13D and 13E). Remarkably, transcripts marked by m6A, including HOXB4 and other HSC self-renewal related transcription factors, showed significant increases of input mRNA reads in the YTHDF2 KD cells compared to the control, without noticeable changes for non-m6A labelled genes (FIGS. 4G to 4I; FIGS. 13F and 13G). These results support the role of YTHDF2 in regulating hUCB HSC self-renewal through RNA degradation.

Example A-5

Expansion of hUCB HSCs by YTHDF2 KD.

Figure 4F:
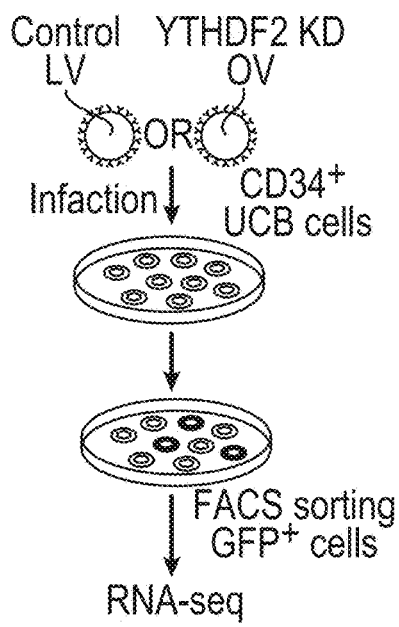
Figure 4G:
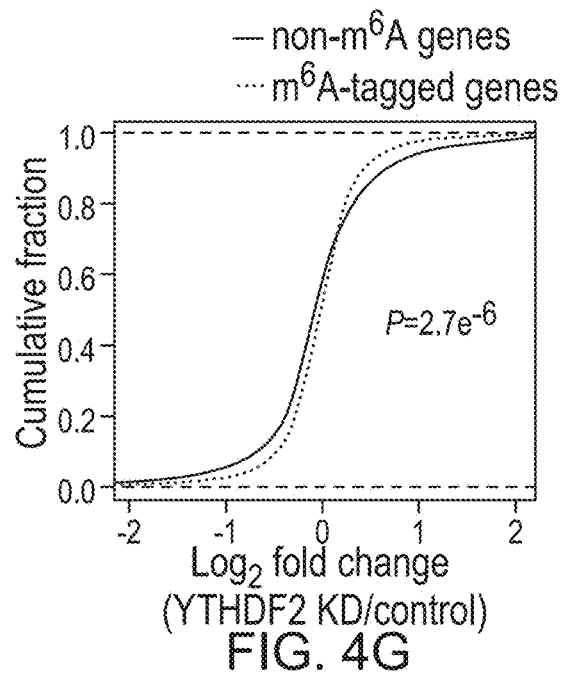
Figure 4H:
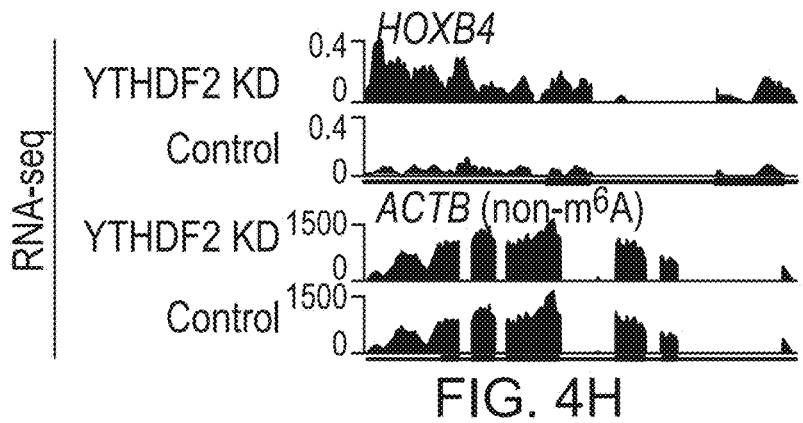
Figure 4I:
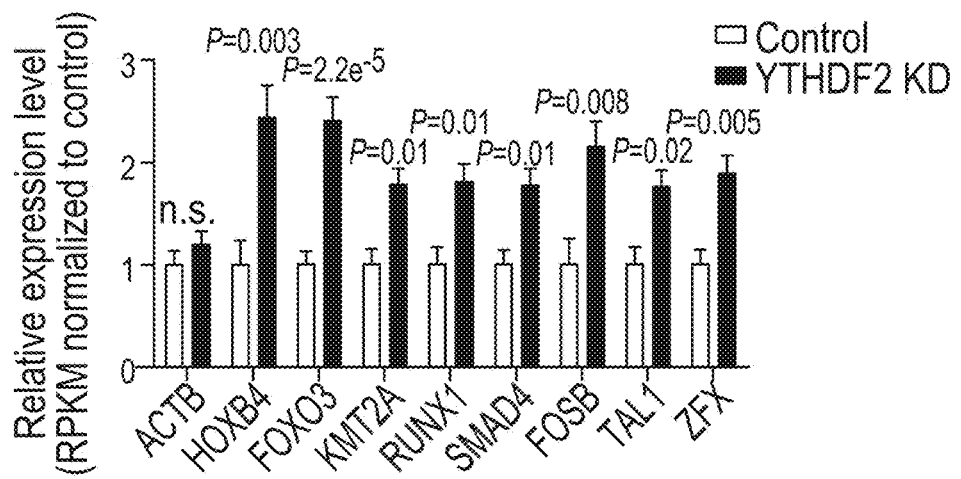
Figure 5A:
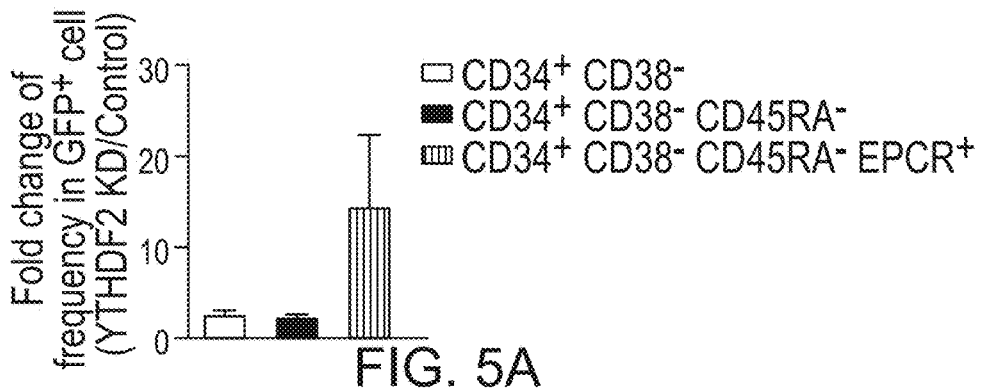
Figure 5B:
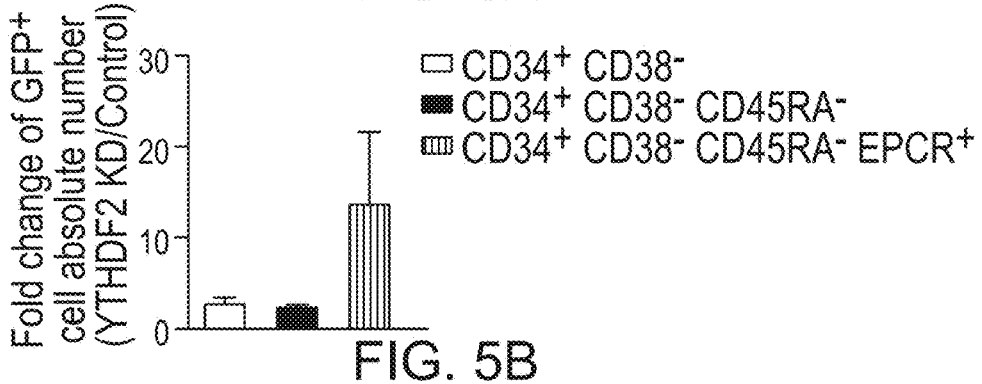
Figure 5F:
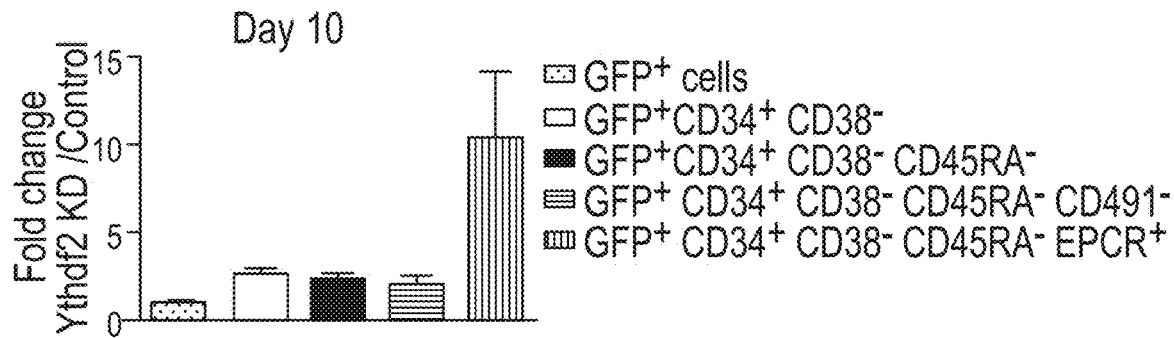
Figure 14C:
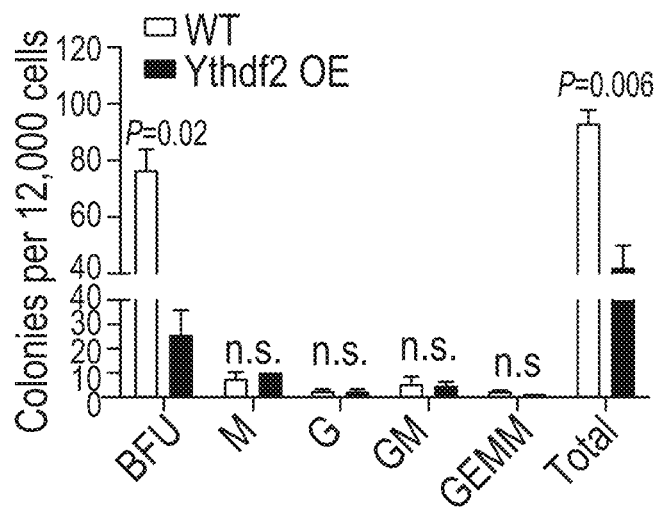

To further explore whether suppression of YTHDF2 can expand human HSCs, short hairpin (sh) RNA-induced YTHDF2 KD in hUCB HSPCs was performed as above (FIG. 4F). After 7 days ex vivo culture, lentiviral knockdown of YTHDF2 resulted in an average 14.3-fold and 13.6-fold increase, respectively, in the frequency and absolute number of CD34+ CD38− CD45RA− EPCR+ phenotypic HSCs and a 5.1-fold increase in CFUs relative to control cells, especially the most primitive CFU-granulocyte erythrocyte monocyte megakaryocyte (GEMM) colony type and burst forming unit-erythroid (BFU-E), reflecting higher expression level of key transcription factors for hematopoiesis, such as TAL1, in YTHDF2 KD hUCB cells (FIGS. 5A to 5D; FIG. 14A). Interestingly, the apoptotic rate was significantly reduced in YTHDF2 KD hUCB HSPCs compared to control cells, similar to the trend of HSCs in Ythdf2 KO mouse (FIG. 5E). Also, FIG. 5F shows that the Ythdf2 knockdown (KD) HSCs exhibited up to a 10-fold increase compared to control HSCs 10 days post transduction. Next, the effect of overexpression (OE) YTHDF2 on HSPC function was explored. Overexpression of YTHDF2 reduced clonogenic potential of hUCB HSPCs by 2.2 fold, suggesting YTHDF2 negatively regulates HSC maintenance ex vivo (FIGS. 14B and 14C).

Figure 6A:
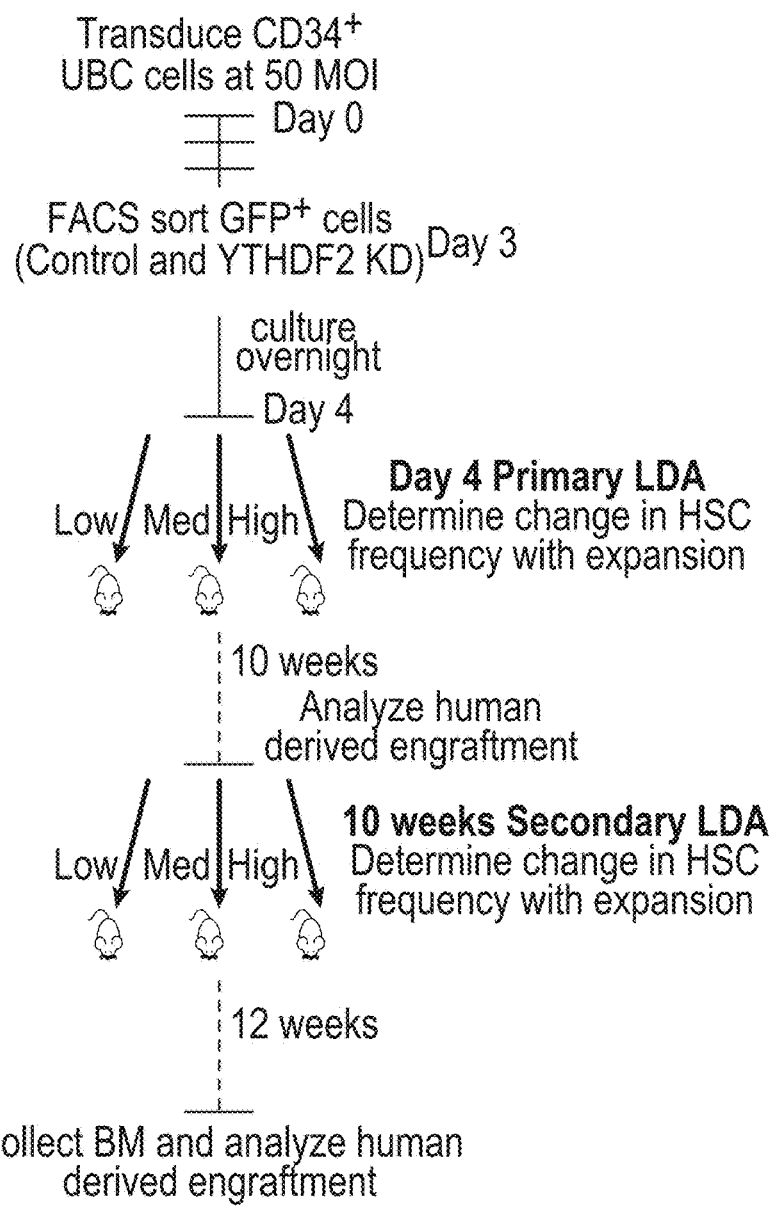
FIGS. 6A-6G: YTHDF2 KD facilitates expansion of human cord blood functional long-term HSCs.
Figure 6B:
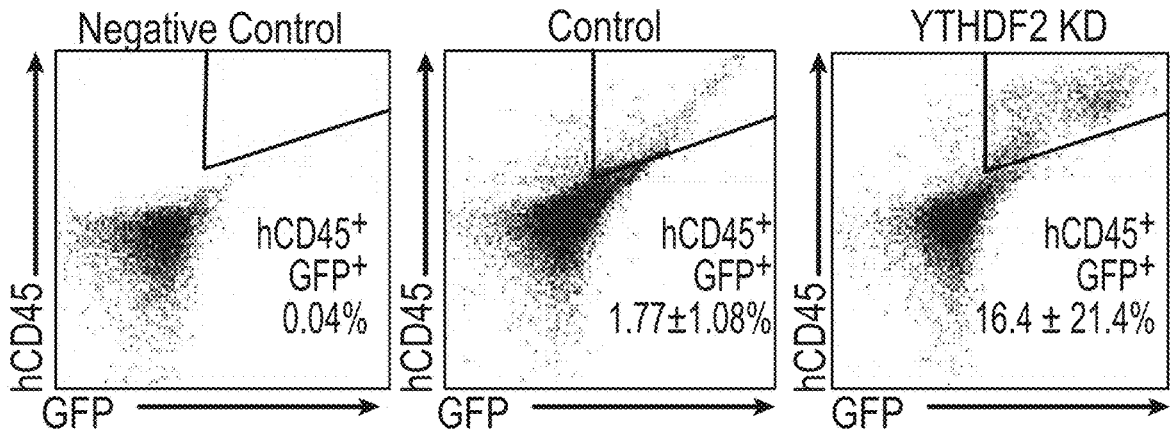
Figure 6C:
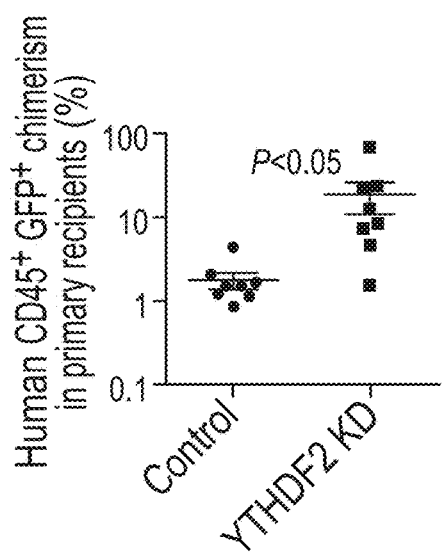
Figure 6D:
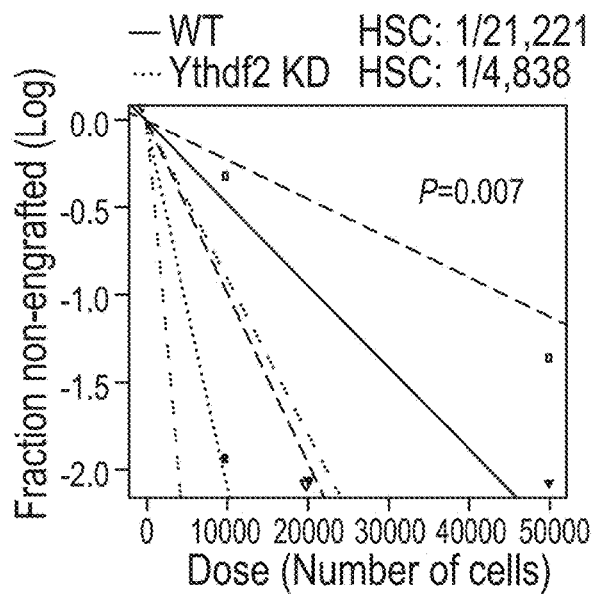
Figure 6E:
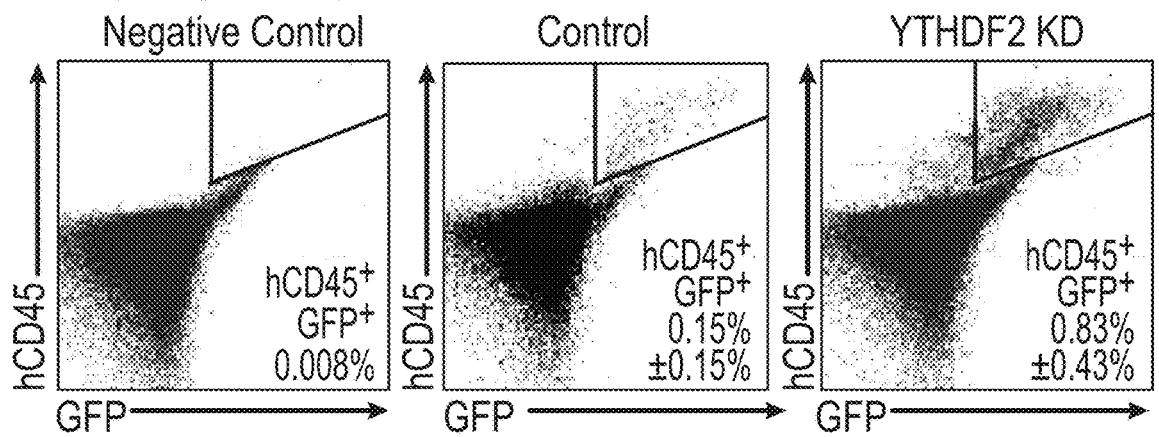
Figure 6F:
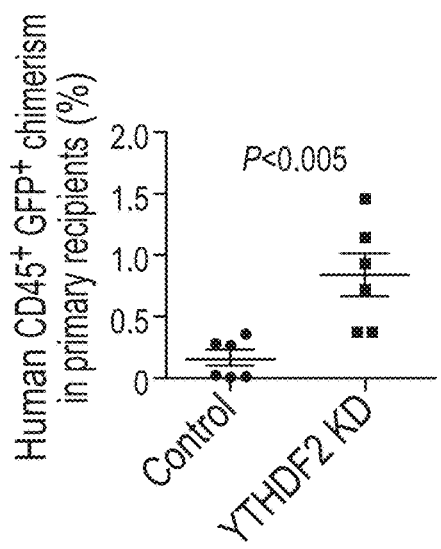
Figure 6G:
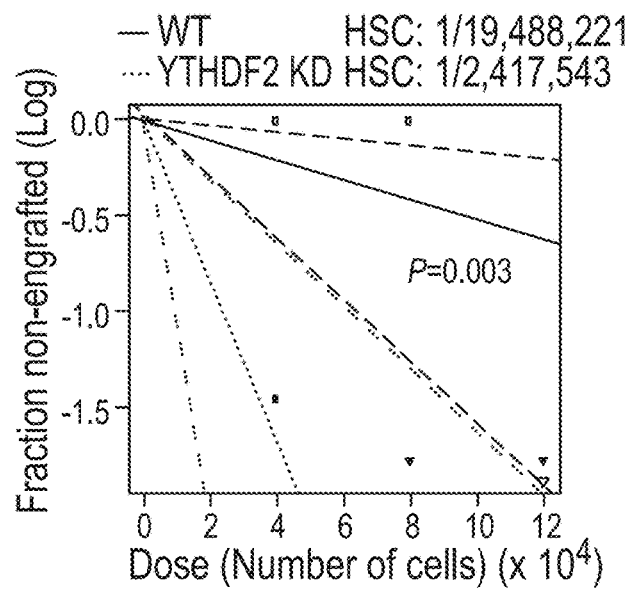
Figure 15A:
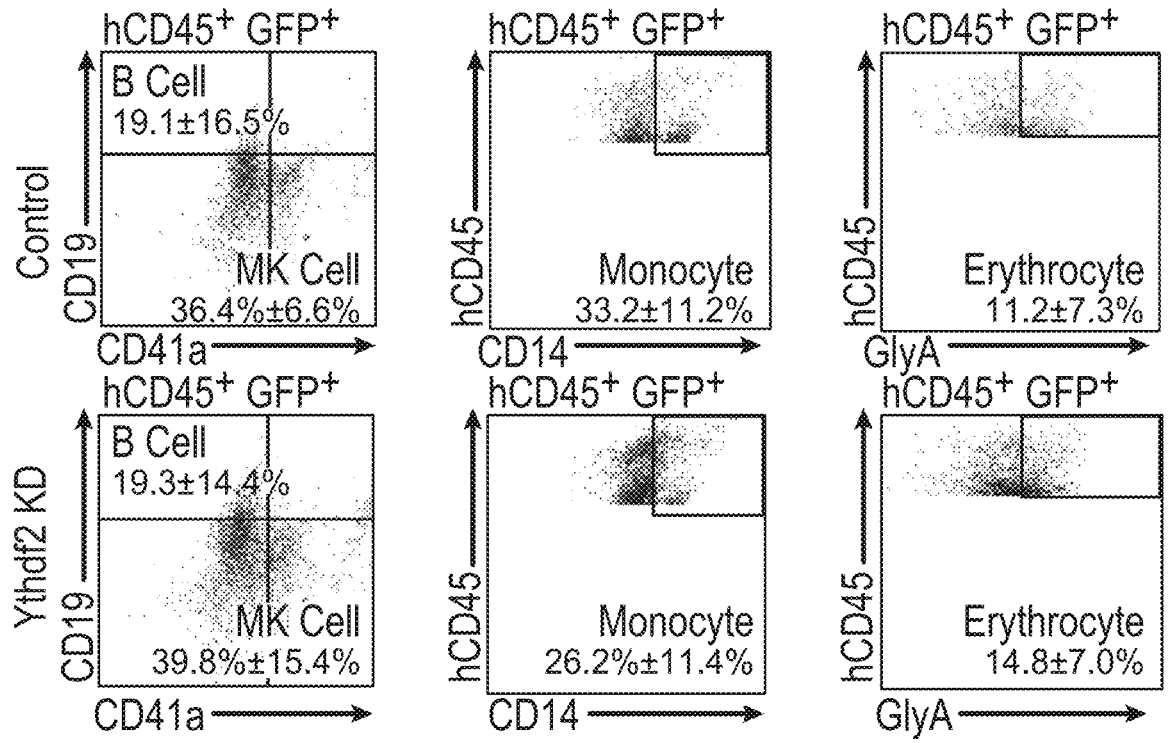
FIGS. 15A-15D: YTHDF2 KD in hUCB cells resulted in HSC expansion without changing lineage output.
Figure 15B:
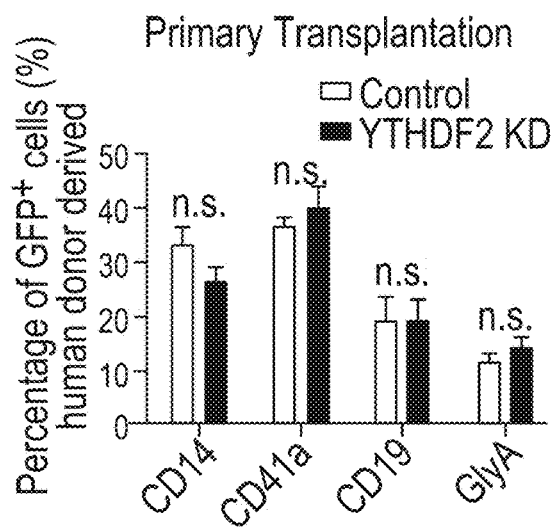
Figure 15C:
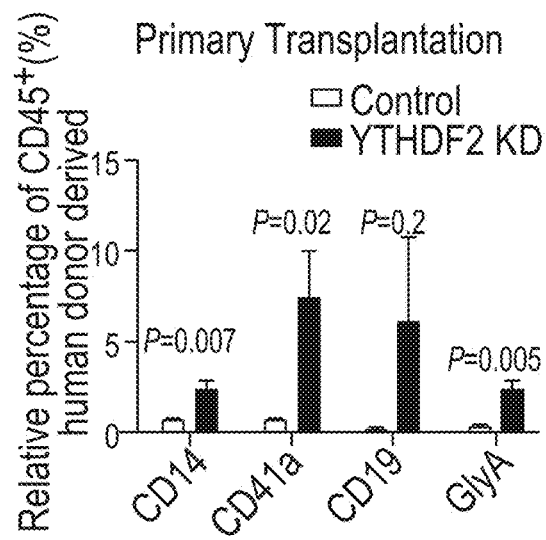
Figure 15D:
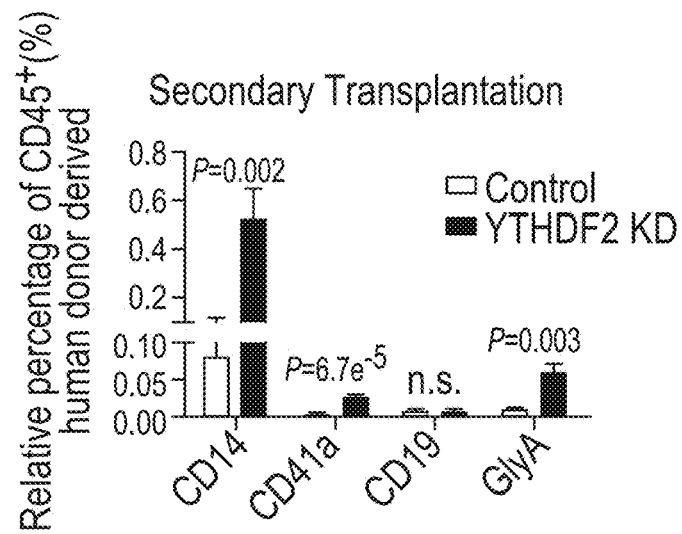

To determine whether YTHDF2 KD can expand human HSCs in vivo, LDA was performed by transplanting GFP+ cells sorted from hUCB CD34+ cells infected with control and YTHDF2 shRNA at day 4 post infection (FIG. 6A). At 10 weeks post transplantation, we analyzed BM cells were analyzed from recipient NOD/SCID //2rg$^{null}$ (NSG) mice and measured the functional HSC frequency after in vivo expansion. Notably, compared to control group, recipients of YTHDF2 KD cells displayed a 9-fold increase in human hematopoietic cell (hCD45+ GFP+) engraftment in BM without changes in the proportions of each lineage (FIGS. 6B and 6CH; FIGS. 15A and 15B). YTHDF2 KD significantly increased the percentage of myeloid, megakaryocyte and erythrocyte in the BM of primary recipients (FIG. 15C). Accordingly, it was found that the HSC frequency in YTHDF2 KD cells was increased 4.4-fold relative to that in control cells (FIG. 6D). It was confirmed the long-term capability of YTHDF2 KD hUCB cells to be reconstituted and undergo self-renewal; 12 weeks after transplantation of BM from primary recipients into sublethally irradiated secondary NSG recipient mice, human hematopoietic cell chimerism in BM were higher in the YTHDF2 KD group, as compared to that in the control group (FIGS. 6E, 6F; FIG. 15D). CRUs from YTHDF2 KD cells revealed an 8-fold increase relative to that in control cells (FIG. 6G). These data demonstrate that YTHDF2 KD remarkably facilitates the expansion of both phenotypic and functional hUCB HSCs ex vivo.

Example A-6

Figure 16:
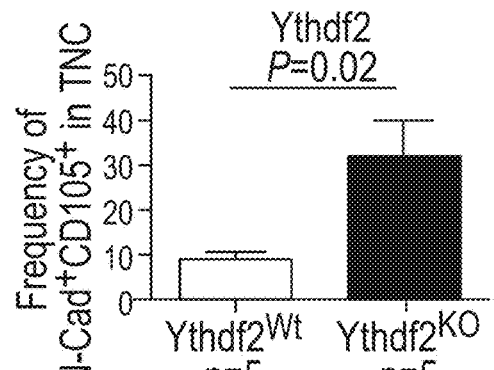
FIG. 16: expansion of mesenchymal stem cells in vivo.

The examples herein demonstrate that conditional deletion of Ythdf2, m6A reader, lead to expansion of phenotypic and functional HSCs without lineage bias. To investigate if there is concomitant increase in mesenchymal stem cells in vivo, Ythdf2$^{f/f}$ if mice were crossed with Mx1-Cre mice to conditionally delete Ythdf2 expression from mesenchymal cells. Nine-months post pI:pc injection bone marrow cells were isolated from Ythdf2$^{KO}$ and their wild type littermates. Single-cell suspension of total bone marrow cells were immuno-stained with flow antibodies. Hematopoietic (CD45, Ter119) and endothelial cells (CD31) were excluded using specific markers. Mesenchymal stem cell present within the total bone marrow stromal cells were further purified by inclusion of N-Cadherin and CD105 antibodies. Mesenchymal stem cells marking both N-Cadherin+ and CD105+ were quantitated. Conditional deletion of Ythdf2 led to 3.6-fold expansion in frequency of mesenchymal stem cells (FIG. 16). Our study clearly demonstrates that loss of Ythdf2 can expand bone marrow mesenchymal stem cells in vivo.

DISCUSSION

Although recent studies explore the biological functions of mRNA m6A modifications (Zheng et al. *Molecular Cell*, 49: 18-29, 2013; Zhou et al. *Nature*, 526: 591-594, 2015; Alarcon et al. *Cell*, 162: 1299-1308, 2015; Zhang et al. *Cancer Cell*, 31: 591-606 e596, 2017; Lence et al. *Nature*, 540: 242-247, 2016; Haussmann et al. *Nature*, 540: 301-302, 2016; Chen et al. *Cell Stem Cell*, 16: 289-301, 2015; Alarcon et al. *Nature*, 519: 482-485, 2015; Xiao et al. *Molecular Cell*, 61: 507-519, 2016; Wojtas et al. *Molecular Cell*, 68: 374-387 e312, 2017; Ivanovna et al. *Molecular Cell*, 67: 1059-1067 e1054, 2017; Fustin et al. *Cell*, 155: 793-806, 2013; Slobodin et al. *Cell*, 169: 326-337 e312, 2017; Schwartz et al. *Cell*, 159: 148-162, 2014; Pendleton et al. *Cell*, 169: 824-835 e814, 2017; Shi et al. *Cell Research*, 27: 315-328, 2017; Huang et al. *Nature Cell Biology*, 20: 285-295, 2018; Bertero et al. *Nature*, 2018; Liu et al. *Nature*, 518: 560-564, 2015), embodiments herein identify Ythdf2 as an important regulator of human and mouse HSC self-renewal by coupling the post-transcriptional m6A modification to the degradation of mRNAs encoding key transcription factors for self-renewal. Repression of Ythdf2 in mouse HSPCs and hUCB HSCs can lead to increased expression of multiple key TFs critical for self-renewal, thereby facilitating ex vivo expansion of both phenotypic and functional HSCs without noticeable lineage bias and leukemia potential. In addition, stem cell niches, to some extent, may contribute to Ythdf2 suppression-mediated mouse HSC expansion as Mx1-cre can be activated in mesenchyme stromal cells. It would be intriguing to study the function of Ythdf2 on mesenchymal stem cells (MSCs) and how repression of Ythdf2 in both HSCs and MSCs may synergistically expand HSCs in vivo.

Given the broad and complicated impact of m6A writer complex Mettl3 and Mettl14 on mRNA splicing, translation, and pri-miRNA processing (Barbieri et al. *Nature*, 2017; Alarcon et al. *Nature*, 519: 482-485, 2015; Liu et al. *Nature*, 518: 560-564, 2015), Mettl3 or Mettl14 depletion results in distinct outcomes in normal stem cells and leukemia. Recent studies have demonstrated that Mettl3 and Mettl14 play essential roles in leukemia development and leukemia stem cell maintenance (Vu et al. *Nature Medicine*, 2017; Barbieri et al. *Nature*, 2017; Weng et al. *Cell Stem Cell*, 22: 191-205 e199, 2018). In contrast, Ythdf2 is believed to be mainly involved in m6A-mediated mRNA decay (Batista et al. *Cell Stem Cell*, 15: 707-719, 2014; Yoon et al. *Cell*, 2017; Zhang et al. *Nature*, 549: 273-276, 2017; Wang et al. *Nature*, 505:

117-120, 2014). According to certain embodiments herein, it is believed that manipulating Ythdf2 may extend the half-life of specific m⁶A-marked mRNAs encoding TFs critical for stem cell self-renewal without affecting other aspects of mRNA processing. The Examples herein show that Ythdf2 depletion in HSCs neither skews the lineage commitment nor induces hematological malignancies, reducing the risk of leukemogenesis with expanded HSCs. Furthermore, stem cell self-renewal is a complexed process comprised of cell division, survival, prevention of differentiation and stemness retention. The observation that Ythdf2-deficient HSCs exhibited lower apoptotic rate indicates embodiments of methods herein also benefit another feature of stem cell self-renewal.

A major limitation in using hUCB HSC transplantation is the insufficient number of HSCs in one hUCB unit. Albeit previous studies have revealed that Dlk1, SR1, Musashi2 and UM171 can expand hUCB HSCs by targeting Notch, AHR signaling or other unknown pathway (Boitano et al. *Science*, 329: 1345-1348, 2010; Fares et al. *Science*, 345: 1509-1512, 2014; Rentas et al. *Nature*, 532: 508-511, 2016; Chou et al. *Experimental Hematologyl*, 41: 479-490 e474, 2013). Accordingly, embodiments herein provide a novel and potent way to target multiple key TFs critical for HSC self-renewal and to enhance the expansion of HSCs. For example, reducing Ythdf2 level and function during in vitro culture via small chemicals or AAV-mediated KD may allow the Ythdf2 level and function to restore after transplantation in vivo, and thus not affect normal HSC maintenance and function in human patients. Furthermore, in certain embodiments, methods described herein may be combined with other methods to facilitate the expansion of not only human HSCs, but also other stem cells, rendering an approach for stem cell-based therapies.

Example B

The following protocols were used in the "B" Examples below.

Animals. C57BL/6-Gt(ROSA)26Sortm1(HBEGF)Awai/J (iDTR), B6.Cg-Gt(ROSA)26Sortm14(CAG-tdTomato)Hze/J(R26RtdT), Tg(Cspg4-DsRed.T1)1Akik/J, Cxcl12tm2.1Sjm/J, Kitltm2.1Sjm/J (SCF$^{f/f}$), Cxcl12tm1.1Sjm/J (CXCL12$^{f/f}$) mice were obtained from the Jackson Laboratory. N-cad-CreER$^T$, and N-cad-TdT mice were generated by Applied StemCell, Inc. To induce N-cad-CreER$^T$; R26-tdT mouse, tamoxifen (Sigma) was injected intraperitoneally at 2 mg per injection for 3 days. To induce N-cad-CreER$^T$; R26-tdT at embryonic stage, a single dose of 1.5 mg of TMX was injected intraperitoneally (IP) into the E12.5 pregnant dam. Cesarean section was performed at E19.5 and the neonatal mice were transferred to foster mice. To induce N-Cad$^+$ cells ablation in N-cad-CreER$^T$;iDTR mice, DT (Sigma) was injected intraperitoneally every other day at a dose of 50 ng per g body as indicated. 5FU (Sigma-Aldrich) was injected once in the tail vein at 150 μg per g body weight. After 5FU injection, mice were analyzed as described in the text. All mouse strains used in this study had a C57BL/6J genetic background. Animals were randomly included in the experiments according to genotyping results. Animal experiments were conducted in a blinded fashion with respect to the investigator. The numbers of animals used per experiment are stated in the figure legends. All mice used in this study were housed in the animal facility at the Stowers Institute for Medical Research (SIMR) and were handled according to SIMR and National Institutes of Health (NIH) guidelines. All procedures were approved by the Institutional Animal Care and Use Committee (IACUC) of the SIMR.

Flow cytometry. For phenotype analysis, hematopoietic cells were harvested from bone marrow (femur and tibia). Red blood cells were lysed using a 0.16 M ammonium chloride solution. For cell surface phenotyping, a lineage cocktail (Lin, phycoerythrin (PE)-Cy5) was used, including anti-CD3 (145-2C11), anti-CD4 (RM4-5), anti-CD8 (53-6.7), anti-Mac-1 (M1/70), anti-Gr1 (RB6-8C5), anti-B220 (RA3-6B2), anti-IgM (II/41) and anti-TER119 (TER-119) (100 ng antibody cocktail per million bone marrow cells, eBioscience). Monoclonal antibodies to SCA1 (D7, eBioscience), c-KIT (2B8, eBioscience), FLK2 (A2F10, eBioscience), CD34 (RAM34, eBioscience), CD48 (HM48-1, eBioscience), CD150 (TC15-12F12.2, BioLegend) and CD49b (HMa2, Biolegend) (all used as 50 ng per million bone marrow cells) were also used where indicated. For lineage analysis of peripheral blood, monoclonal antibodies to CD45.1 (A20, eBioscience), CD45.2 (104, eBioscience), CD3, B220, Mac-1 and Gr1 were used. 7-aminoactinomycin D (7-AAD) (A1310, Life technologies) was used to exclude dead cells. For stromal niche cell analysis, CD45 (30-F11, eBioscience), CD31 (390, eBioscience), PDGFRα-biotin (APB5, eBioscience), LepR-Bio (R&D), CD51 (clone RM7-V, Biolegend). Samples stained with biotin conjugated antibodies were washed with staining medium, then incubated with streptavidin brilliant violet 421TM (Biolegend, 1:500). Cell sorting and analysis were performed using MoFlo (Dako), InFlux Cell Sorter (BD Biosciences), MACSQuant (Miltenyi Biotec) or CyAn ADP (Dako) instruments. Data analysis was performed using FlowJo software.

Whole-mount sternum HSC immunostaining. Sternal bones were collected and transected with a surgical blade into 3-4 fragments. The fragments were bisected sagittally to expose bone marrow cavity, fixed in 4% PFA. blocked/permeabilized in PBS containing 20% normal goat serum and 0.5% Triton X100, and stained with primary antibodies for 3 days. The tissues were incubated with secondary antibodies for 2 hours (Bruns et al., 2014; Kunisaki et al., 2013). Fluorescence imaging was performed on a spinning-disk confocal microscope (UltraVIEW; PerkinElmer), including an inverted microscope (Axiovert 200 M; Carl Zeiss Microimaging, Jena, Germany), attached to a spinning-disk confocal system (CSU-X1; Yokogawa Corporation of America) and Orca-R2 camera (Hamamatsu) with Volocity acquisition software (PerkinElmer) and a 20×/0.8 Plan-Apochromat objective (Carl Zeiss). Images were collected as a series of optical sections, with a step size of 4 μm. Images were collected in a tile pattern (overlap 10%) sufficient to cover the entire sample. Channels were collected sequentially. (Blue dye) was excited using 405 nm light (50 mW diode laser, OEM) and (red dye) was excited using 561 nm light (50 mW solid state laser, OEM), and each was collected using a multibandpass emission filter with 415 nm-775 nm 580 nm-650 nm bands. (Green dye) was excited using 488 nm light (50 mW solid state laser, OEM) and collected using a multibandpass emission filter of 500 nm-550 nm, and (far red dye) was excited using 640 nm light (50 mW solid state laser, OEM) and collected using a multibandpass emission filter with 455 nm-515 nm and 660 nm-750 nm. Exposure times and laser powers were adjusted to compensate for variations in staining.

Second Harmonic Generation (SHG) imaging was performed immediately following fluorescence imaging. SHG images were collected on a LSM-780 laser scanning confocal microscope (Carl Zeiss) equipped with a QUASAR detection unit, a 10×0.45 Plan-Apochromat objective (Carl Zeiss), and Zen 2012 acquisition software (v8.1.3, Carl Zeiss). Images were collected as a series of optical sections, with a step size of 8 µm and a pixel size (1.32 µm/pixel) an integer multiple of four times the fluorescence pixel size. SHG images were taken with a laser light wavelength of 900 nm and collected at 371-420 nm. As a reference for image alignment, images of Cd150-PE were taken using the 561 nm line of a DPSS laser (Melles Griot) and collected at 566-735 nm concurrently with the SHG images. Images were collected in a tile pattern (no overlap) sufficient to cover the entire sample. Tiles were stitched into a complete 3D image using Zen software.

Images were analyzed using Fiji software (1.51 g National Institutes of Health). To align SHG and fluorescence images, fluorescence images were first background subtracted, and image tiles were stitched into a complete 3D image using the Grid/Collection stitching plugin (reference bioinformatics.oxfordjournals.org/content/25/11/1463.abstract). Given that the transfer of the sample from the fluorescence microscope to the SHG microscope involved a small amount of sample rotation, it was necessary to realign the SHG and fluorescence images in 3 dimensions. Alignment of SHG and fluorescence image sets was carried out using a custom plugin available at research.stowers.org/imagejplugins. Firstly, a minimum of 8 common landmarks were identified by visual inspection of both the SHG and fluorescence data sets. Next the Kabsch algorithm was used to find the best scaled rotation to transform the fluorescence coordinates to the SHG image coordinates. Finally, each 3D voxel in the fluorescence image was transformed to the corresponding SHG position and trilinear interpolation was used the find the SHG intensity at that position to create the realigned composite image.

Image analysis was conducted by researchers unfamiliar with the hypotheses of the study. HSCs were identified by eye. Cells were considered negative for staining if the shape of the cell could not be discerned by eye, or if the shape of the cell formed a dark region in a field of positive signal. Distance measurements to niche components were made using Fiji and Microsoft Excel software. The locations of the HSC and nearest point of each of the three niche components were marked using point ROIs in Fiji and locations were transferred to excel, where distances in 3D were then calculated using the 3D Pythagorean Theorem. To calculate distances for randomly distributed HSCs, random point ROIs were generated using a custom plugin in FIJI in the same images analyzed for observed HSCs. The randomly generated points were considered simulated HSCs if they appeared in a reasonable HSC location (as assessed by the presence of $Lin^+$ cells in the surrounding regions). Niche distance measurements for simulated HSCs were then made in the same manner as for observed HSCs.

The statistical significance of differences in the distribution of distances was assessed by Kolmogorov-Smirnov analysis using Origin software. Statistical significance of changes in percentages of HSCs at 5 µm were assessed using a Student's T test in Microsoft Excel. Changes were considered significant if $P<0.05$.

Final images shown in figures are maximum projections that have been background subtracted and contrast adjusted for clarity.

Transplantation and Repopulation assay. 100 sorted pHSCs or rHSC cells together with $1.0 \times 10^5$ CD45.1 rescue bone marrow cells were transplanted to lethally irradiated (10 Gy) CD45.1 recipients. $2.0 \times 10^5$ CD45.2 BM cells from N-cad-CreER$^T$;iDTR and control mice together with $2.0 \times 10^5$ CD45.1 rescue bone marrow cells were transplanted into lethally irradiated (10 Gy) CD45.1 recipients. Every 4 weeks post transplantation, peripheral blood was collected from the submandibular vein. Hematopoietic repopulation was measured from donor-derived blood cells (CD45.2).

RNA sequencing and analysis. cDNA was generated from 1000 purified cells using SMARTer Ultra Low Input RNA kit (Clonetech) and library was generated by the Nextera XT DNA Library Preparation Kit (Illumina), followed by sequencing on an Illumina HiSeq2500 for 50 bp single reads. Raw reads were demultiplexed into Fastq format allowing up to one mismatch using Illumina bcl2fastq2 v2.18. Reads were aligned to UCSC genome mm10 with TopHat v2.0.13, default parameters. FPKM values were generated using Cufflinks v2.2.1 with "-u—max-bundle-frags 100000000". Read counts were generated using HTSeq-count with "-m intersection-nonempty". Three or four replicates were sequenced for each population. Data are accessible at NCBI GEO: GSE104887

CFU-F assay and in vitro differentiation. Cells were sorted directly into culture at a 96-well plate. The cultures were incubated at 37° C. in a humidified atmosphere with 5% $O_2$ and 10% $CO_2$ for 7-10 days. Colonies were stained by CellTracker™ Green CMFDA (Life technologies) and image was acquired by Celigo Imaging Cytometer (Nexcelom). For in vitro differentiation, clonally expanded Ncad-CreER$^T$ driven Tomato$^+$ BM/Bone stromal cells were isolated from CFU-F cultures by digesting with 0.25% Trypsin/EDTA, split into 3 aliquots, and seeded into separate cultures permissive for differentiation: StemPro Osteogenesis kit Gibco A10072-01, Adipogenesis kit A10070-01 and Chondrogenesis differentiation kit A10071-01. The osteoblastic differentiation was assessed by VECTOR Red Alkaline Phosphatase; the adipogenic differentiation was detected by Oil Red O (Sigma); and the chondrogenic differentiation was detected by Toluidine blue (Sigma, 0.1 g T Blue/100 mL distilled water).

Bone Sectioning, Immunostaining and Imaging.

Freshly isolated femurs were fixed in 4% paraformaldehyde overnight, followed by 1 to 3 days decalcification in 10% EDTA. For paraffin section, bone samples were processed with Sakura Tissue Tek VIP 5 Tissue Processor (Sakura America, Torrance, CA), and paraffin sections were cut in 5 µm thickness. Sections were deparaffinized with xylene, followed by Alcian Blue/Hematoxylin/Orange G staining. For frozen section, bone samples were processed with the CryoJane tape-transfer system. Sections were blocked with Power Block™ Universal Blocking Reagent for 30 minutes to 1 hour and then stained overnight with rabbit-anti-Aggrecan (Millipore, 1:300), rabbit-anti-Perilipin (Cell Signaling, 1:300) and goat-anti-Osteopontin (R&D, 1:300). Donkey-anti-goat Alexa Fluor 488 and Donkey-anti-goat Alexa Fluor 647 were used as secondary antibodies (all from Invitrogen, 1:300). Antibodies were diluted with Antibody Diluent Solution (Invitrogen 00-3218). Slides were mounted with FLUORO-GEL (Electron Microscopy Science 1798510), and images were acquired with an Olympus slide scanner.

Femoral groove surgery. Mice were anesthetized with 2.5% isoflurane, and buprenorphine was administered for analgesia. The skin of the right leg was shaved and scrubbed with alcohol and iodine. A small incision was made in the skin, lateral to the knee joint. After sliding the skin medially for visualization, an internal incision was made medial to the patella, extending into the quadriceps muscle and along the patella tendon to release the tissue. The patella was subluxated laterally, and the distal femur was exposed. The subchondral bone was perforated using a microsaw to penetrate the articular cartilage at the knee joint. The extensor mechanism (quadriceps, patella tendon and patella) was returned to its original anatomical location. The internal incision was sutured with absorbable suture, and the skin sutured with non-absorbable suture.

Statistics.

Values are shown as the mean±s.e.m. All statistical analyses were generated using GraphPad Prism 5 (GraphPad Software). Student's t test was used for comparisons between two groups. Statistical significance was defined as $p<0.05$.

Example B-1

Figure 17A:
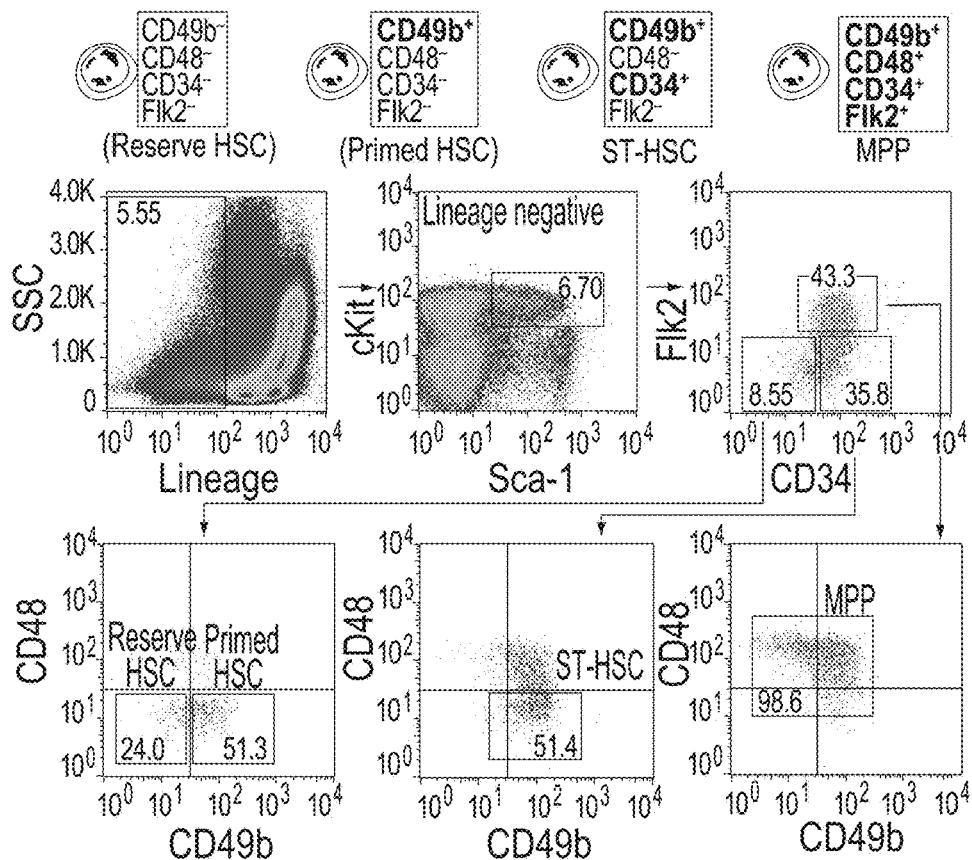
FIGS. 17A-17J: functional identification of rHSC population.
Figure 17B:
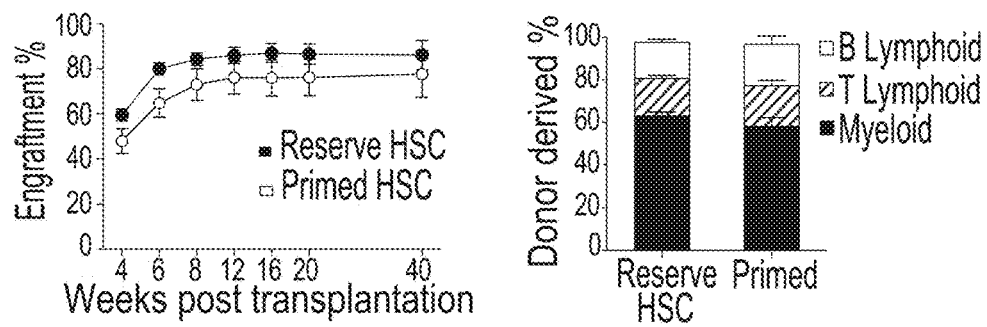
Figure 17C:
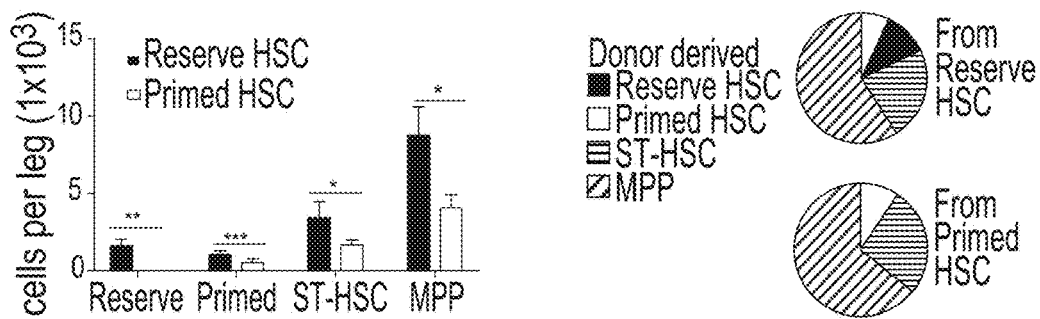
Figure 17D:
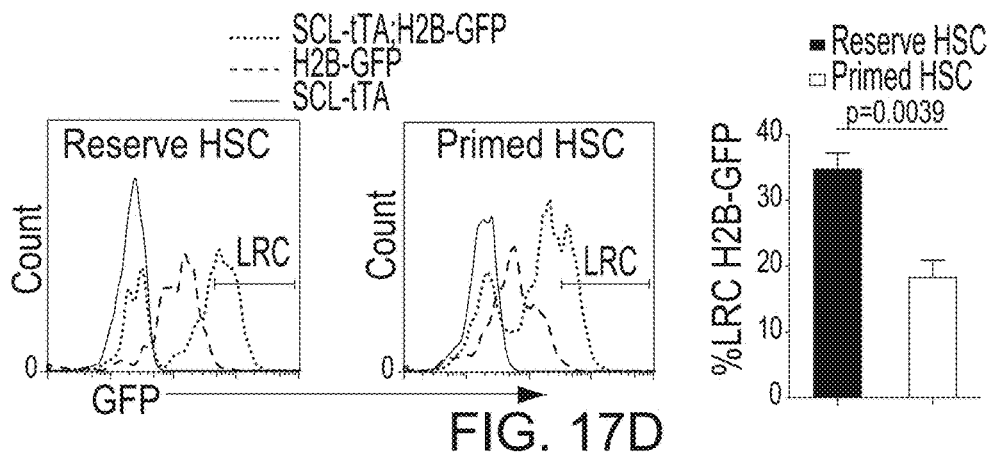
Figure 17E:
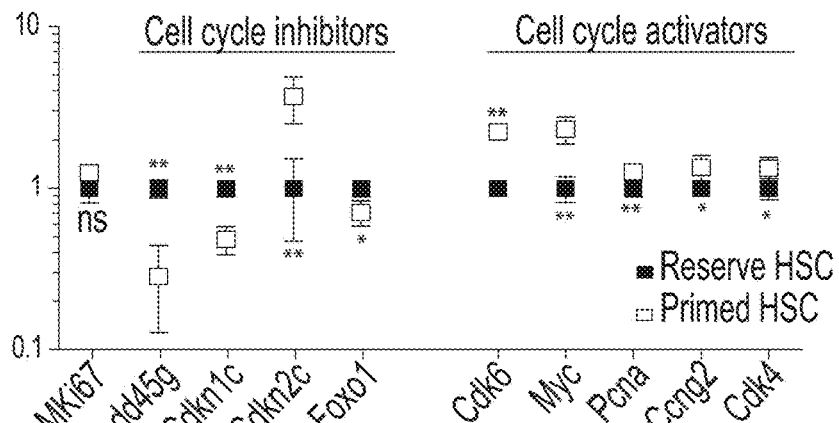

Functionally distinguished reserve and primed HSCs in mouse bone marrow. To explore the reserve HSC (hereafter rHSC(s)) subpopulation, a cell surface marker was adapted, CD49b (Integrin $\alpha 2$), which can distinguish intermediate-term from permanently long-term HSCs (LT-HSCs) (Benveniste et al., 2010; Qian et al., 2015; Wagers and Weissman, 2005; Yang et al., 2005). Intriguingly, it was found a $CD48^-$ $CD49b^-$ subpopulation which exists only in conventional LT-HSCs ($CD34^-Flk2^-Lineage^-$ $Sca-1^+c-Kit^+$ (LSK) cells) but not in short-term HSCs (ST-HSCs; $CD34^+FLK2^-LSK$) or multipotent progenitor cells (MPPs; $CD34^+FLK2^+LSK$). It was proposed that the $CD48^-$ $CD49b^-$ LT-HSCs subpopulation enriches rHSCs and that the $CD48^-CD49b^+$ LT-HSCs subpopulation enriches primed HSCs (hereafter pHSC(s)) (FIG. 17A) and tested with a repopulation assay. It was found that both rHSCs and pHSCs supported hematopoiesis in lethally irradiated mice for up to 40 weeks after transplantation without significant difference (FIG. 17B), consistent with a previous report (Benveniste et al., 2010). However, transplanted pHSCs had very low efficiency in generating rHSCs (95.4% reduction) as well as ST-HSCs and MPPs (~78% reduction for both populations) in recipients compared to transplanted rHSCs, suggesting that rHSCs hierarchically precede pHSCs (FIG. 17C). Using the Scl-tTA-induced H2B-GFP label-retaining model, it was found that rHSCs significantly enriched more H2B-GFP$^{high}$ cells compared to pHSCs (P=0.0039), indicating that rHSCs have slower cell cycle compared to pHSCs (FIG. 17D). Molecularly, it was found that rHSCs had higher expression of Gadd45 g, Cdkn1c (encoding p57), and Foxo1 that are all involved in maintaining Go phase of HSCs, and lower expression of cell cycle activators such as Myc, Pcna, Ccng2, and Cdk4. There was no difference in Ki67 expression between rHSCs and pHSCs, indicating that Ki67 expression alone is insufficient to distinguish the two HSC subpopulations (FIG. 17E).

Figure 17F:
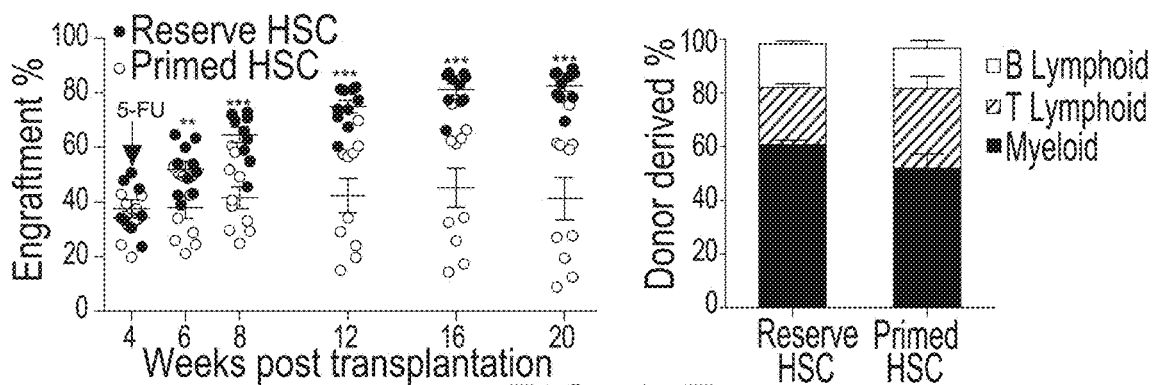

Because the functional definition for rHSC is drug-resistance, rHSCs or pHSCs were transplanted into recipient mice and the mice were challenged with 5FU at 4 weeks post transplantation. As shown in FIG. 17F, rHSCs were insensitive to 5FU treatment; however, pHSCs dramatically reduced their reconstitution ability (44% reduction at 20 weeks post transplantation). Taken together, the data indicated that $CD48^-CD49b^-$ LT-HSC indeed enriched rHSCs that were resistant to chemotherapeutic treatment, whereas $CD48^-CD49b^+$ LT-HSC enriched pHSCs that were sensitive to chemotherapy; furthermore, the former gave rise to the latter but not vice versa in the transplantation assay.

Figure 17G:
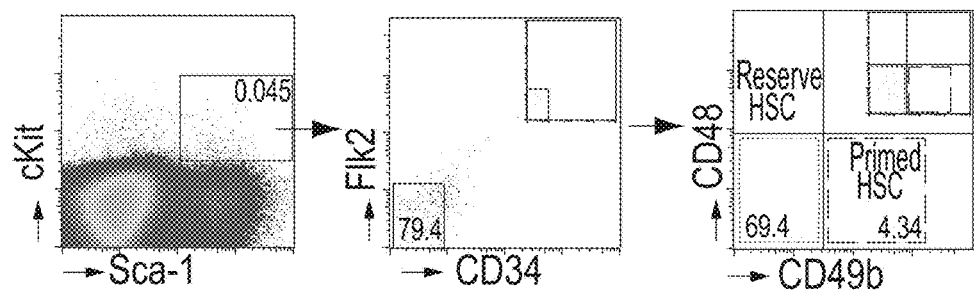
Figure 17H:
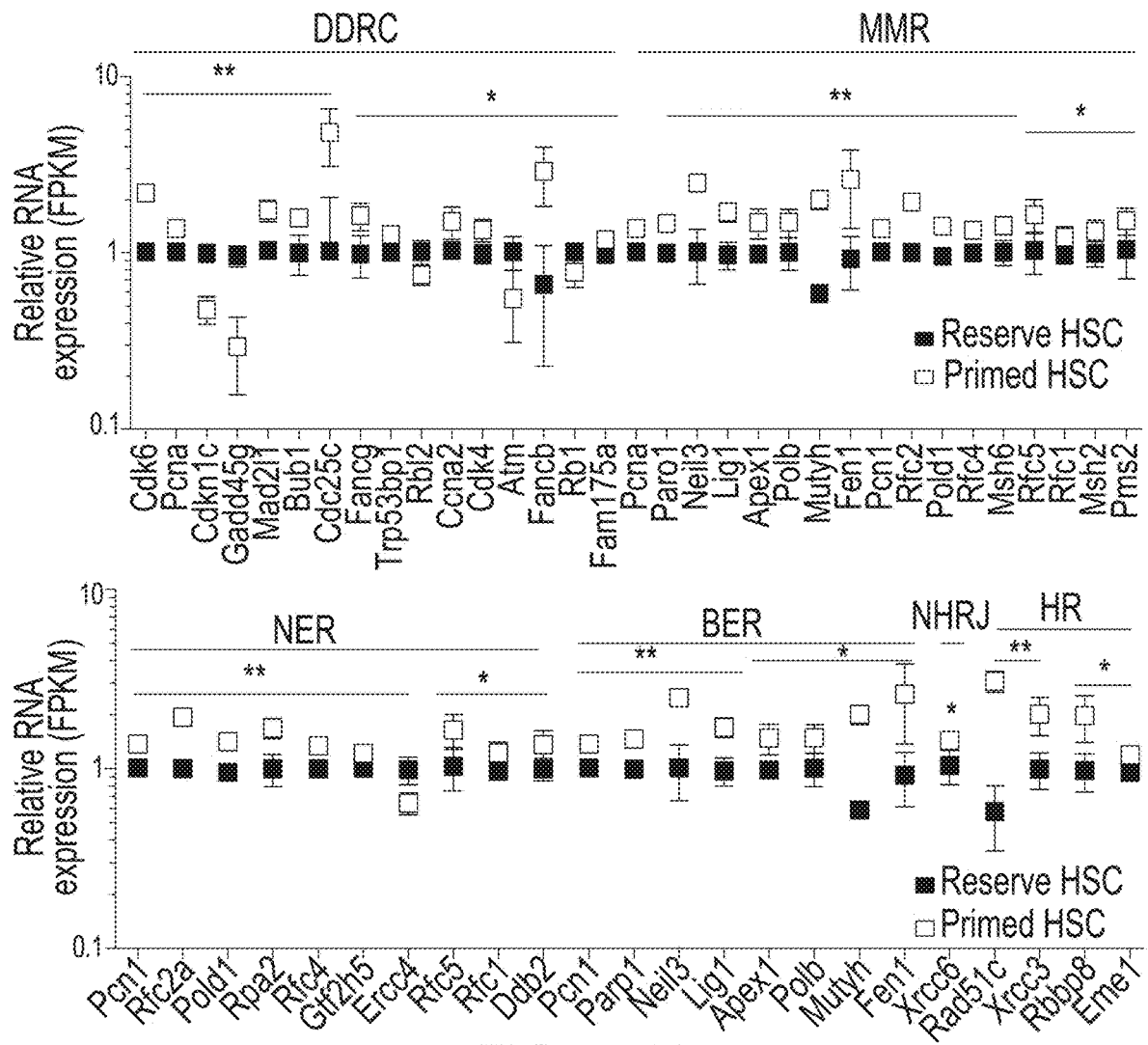
Figure 17I:
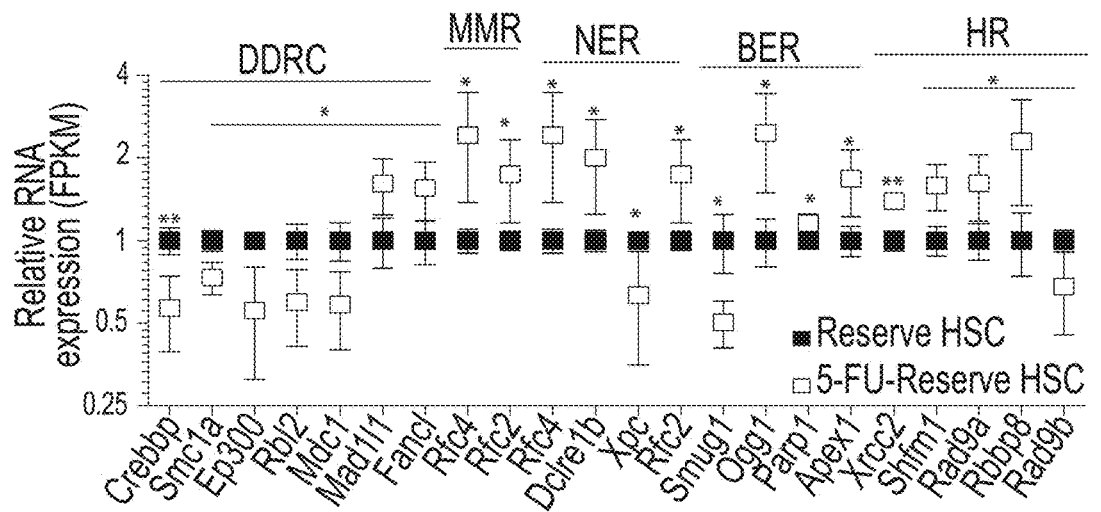
Figure 17J:
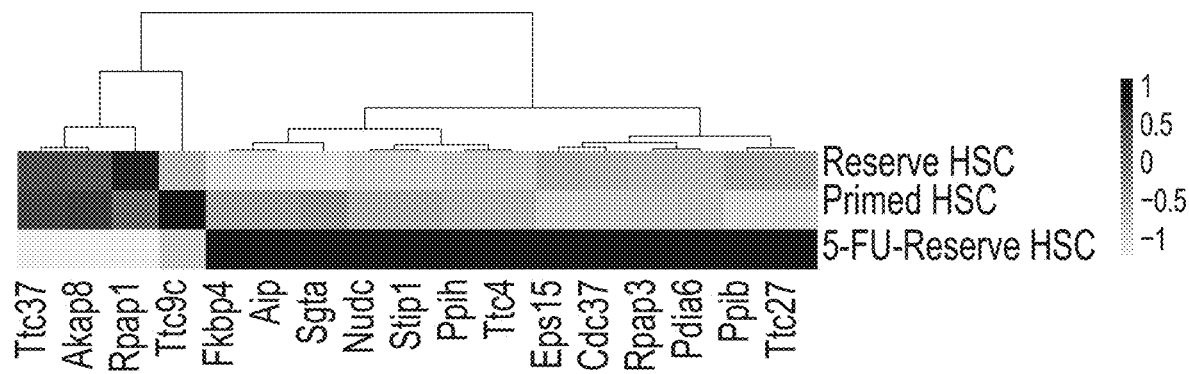

The direct consequences of acute 5FU challenge on rHSCs and pHSCs were further analyzed. As shown in FIG. 17G, at 3 days post 5FU, around 92% of pHSCs were eliminated and only rHSCs survived, suggesting that rHSCs must have specifically turned on their DNA repair system to overcome the chemotherapeutic stress. To test this hypothesis, the transcriptome profiling of DNA damage response genes in rHSCs, pHSCs and rHSCs post 5FU treatment was analyzed. It was observed that rHSCs maintained a lower expression of genes involving the DNA damage repair system compared to pHSCs during homeostasis (FIG. 17H), but that most DNA repair pathways, such as DNA mismatch repair (MMR), nucleotide excision repair (NER), base excision repair (BER), and homologous recombination, (HR) were significantly activated in rHSCs under 5FU challenge (FIG. 17I). Furthermore, in parallel, a great number of stress response genes (Rodina et al., 2016), which primarily belong to Hsp90 and Hsp70 family, were also upregulated (1.8±0.17-fold and 1.4±0.1-fold respectively) (FIG. 17J), which partially explained how rHSCs survived and reconstituted the hematopoietic system under chemotherapeutic stress.

Taken together, the coexistence of pHSCs and rHSCs were functionally demonstrated in BM. Even with their quiescent state and active DNA-repairing pathways, pHSCs were still sensitive to chemotherapy, whereas rHSCs activated their DNA damage repair and stress response genes to survive chemotherapeutic stress and give rise to pHSCs; thus, rHSCs play a critical role in supporting hematopoietic regeneration under severe stress.

Example B-2

Figure 18A:
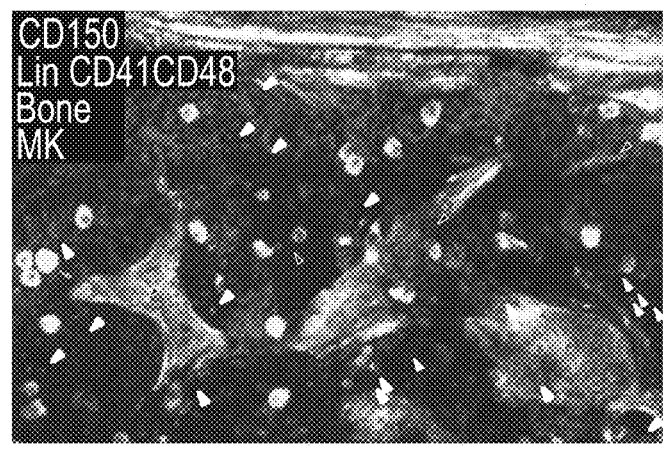
FIGS. 18A-18I: rHSCs located by endosteal region in BM niche.
Figure 18B:
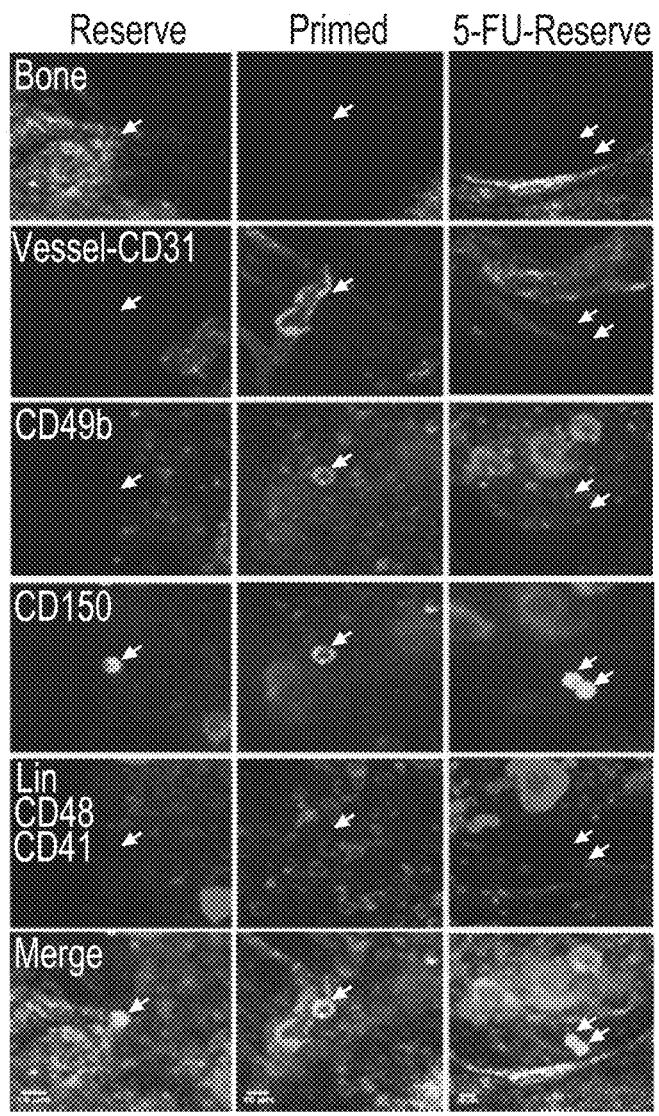

Drug-Resistant rHSCs Predominantly Localize in the Endosteal Region of Bone Marrow Whether extrinsic mechanisms from the BM niche contributed to rHSC maintenance during hemostasis and under chemotherapeutic stress was further examined. To this end, whole mount HSC staining was performed, which simultaneously detected the relative distribution of rHSCs and pHSCs to bones (achieved by second-harmonic generation, SHG), megakaryocytes (MKs) or vessels within ~75 μm thickness bone cavity (FIG. 18A-B). Our quantification data showed that 43.4% rHSCs and 31.0% pHSCs were located within 10 μm distance from vessels, and that 22.6% rHSCs and 24.6% pHSCs were located within 10 μm from MKs (FIG. 18C-D), consistent with previous reports that the bulk of the HSC population resides in perivascular and sinusoid zones (Acar et al., 2015; Bruns et al., 2014; Chen et al., 2016; Zhao et al., 2014). Interestingly, it was noticed that 16.4% rHSCs compared to only 3.69% pHSCs located within 10 μm from the bone surface (FIG. 2E). These data showed that both rHSCs and pHSCs were unbiasedly distributed to vessels and MKs, but that rHSCs were located significantly closer to endosteal bone surface compared to pHSCs (P=0.00182).

Figure 18C:
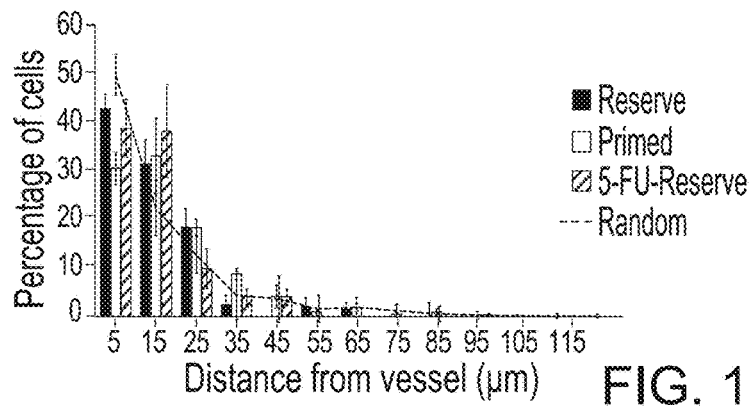
Figure 18D:
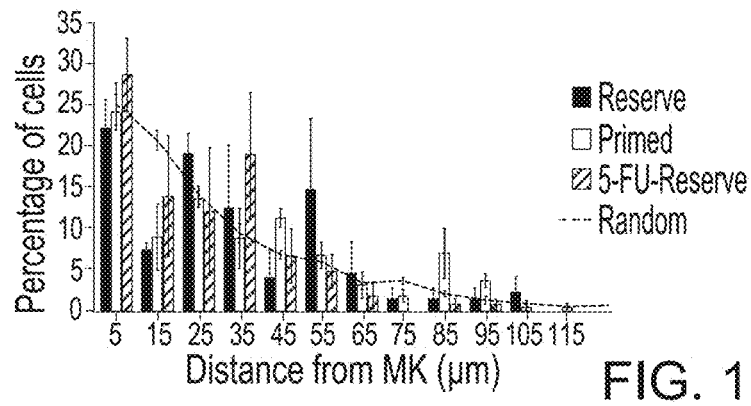
Figure 18E:
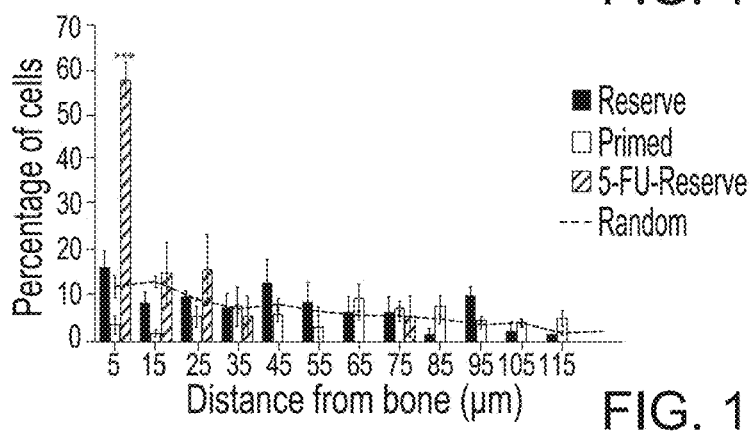
Figure 29:
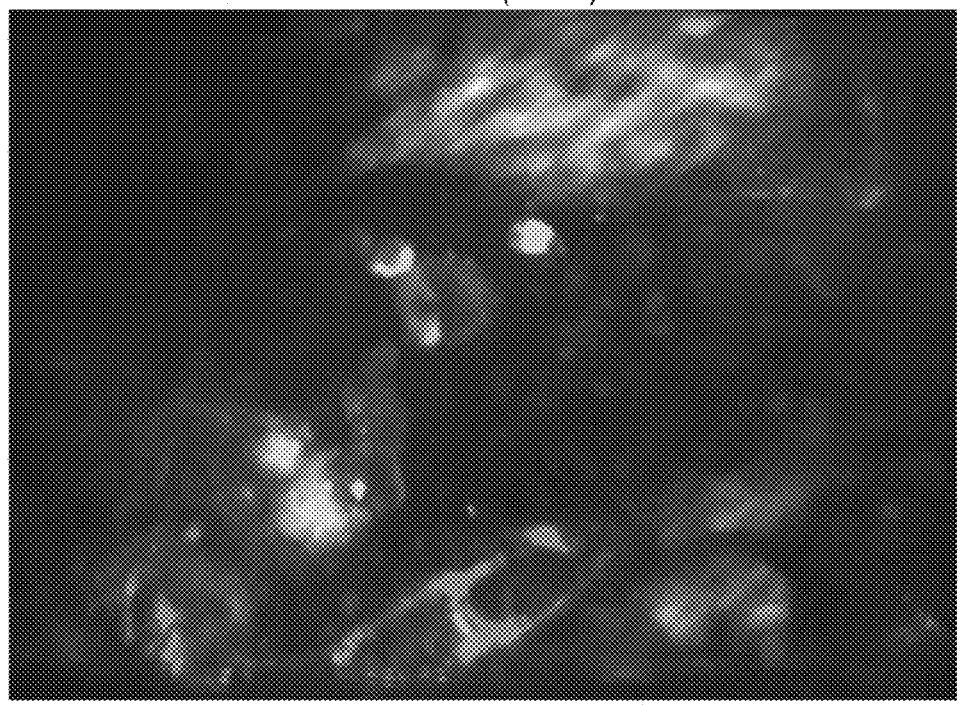
FIG. 29: Image of surviving rHSCs (green, CD150$^+$ Lin$^-$ CD49b$^-$) at day 3 post 5FU treatment were often detected as single cells adjacent to the bone surface (white, SHG), and proliferating HSCs were often associated with MKs (CD150$^+$ Lin$^+$) or near the vessels (red, CD31+).

To test whether the endosteal region preserved rHSCs during chemotherapeutic stress, the distribution of rHSCs was examined at day 3 post 5FU treatment when pHSCs were eliminated (FIG. 18B). Interestingly, we found that ~55% of surviving rHSCs were preserved by the endosteal niche upon acute 5FU stress, which is a ~3.5-fold enrichment compared to homeostasis (FIG. 18E). However, there was no significant difference in frequency of surviving rHSCs observed near vessels or MKs (FIG. 18C-D). Consistently, it was observed that only 4.24% of pHSCs survived acute 5FU stress as shown in FIG. 17G. Next, the dynamic process of BM damage and the subsequent recovery after 5FU stress was studied by examining the BrdU-labeled surviving and proliferation cells. It was noticed that at day 2 post 5FU treatment, there was a large loss of the BrdU-labeled cells, indicating an active apoptosis induced by 5FU. At day 3 post 5FU treatment, it was observed that surviving BrdU$^+$ cells (mostly single cells) were mainly detected adjacent to bone lining cells in the endosteal region (FIG. 24A-D). At day 3.5, it was observed that pairs of BrdU$^+$ cells appeared at the endosteal surface, indicating activation and division of surviving cells. Starting and continuing at days 4 and 5, the number of proliferating cells gradually increased, and these cells were very often detected as clusters close to either vessels or potential adipocyte structures (~55% at day 4 and ~65% at day 6) (FIG. 24E-I). This observation suggested that bone surface was the niche where cells post 5FU initially survived. These cells were then activated and gave rise to daughter cells, the latter of which underwent expansion mainly in vessels or adjacent to megakaryocytes (Zhao et al., 2014). It was further confirmed that surviving 5FU-rHSCs were indeed detected often as single cells adjacent to the bone surface, and proliferating HSCs often associated with MKs or near the vessels. Surviving rHSCs (green, CD150+ Lin− CD49b−) at day 3 post 5FU treatment were often detected as single cells adjacent to the bone surface (white, SHG), and proliferating HSCs were often associated with MKs (CD150+ Lin+) or near the vessels (red, CD31+) (FIG. 29).

Figure 18F:
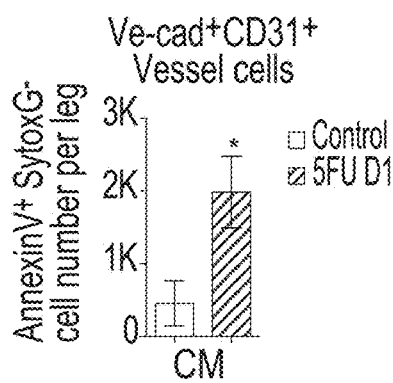
Figure 18G:
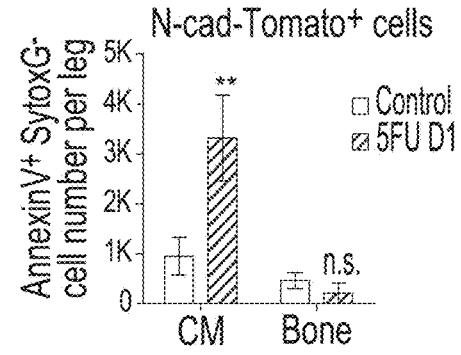
Figure 18H:
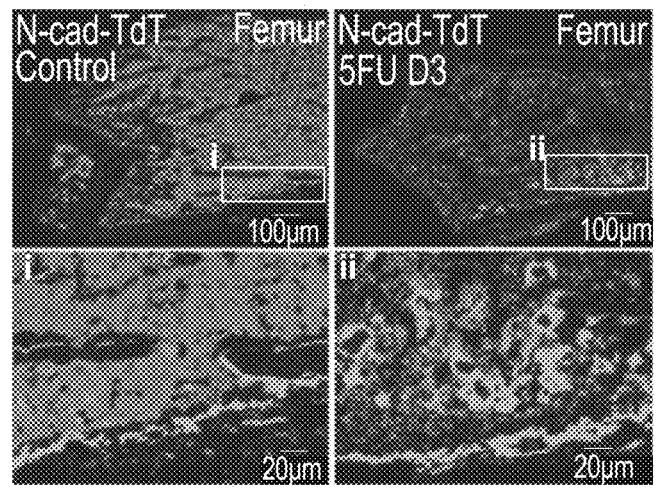
Figure 18I:
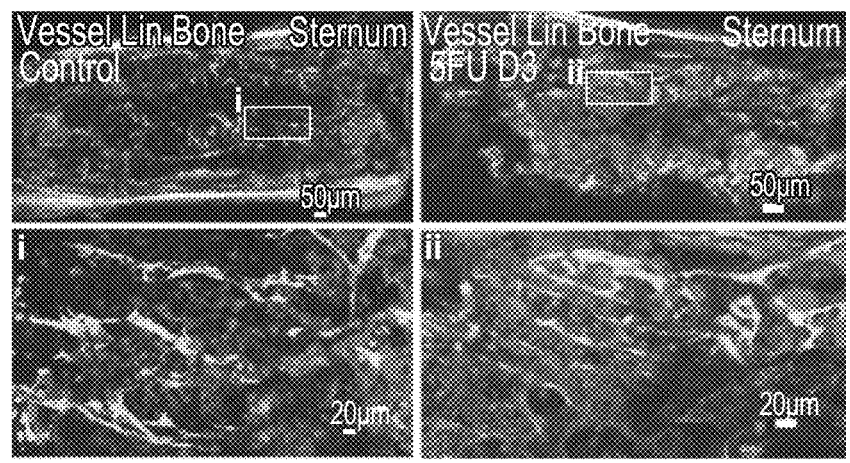
Figure 24G:
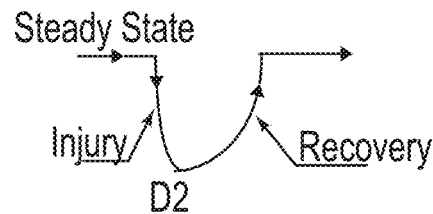
Figure 24H:
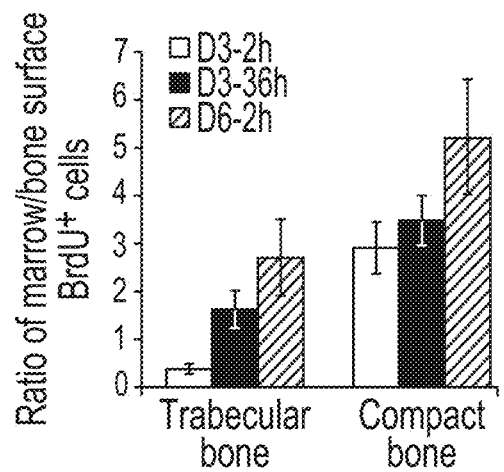
Figure 24I:
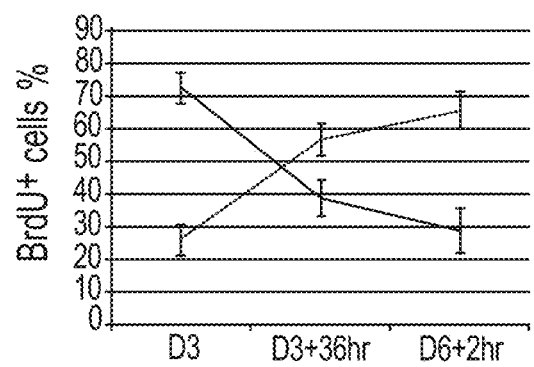
Figure 24J:
Figure 24K:
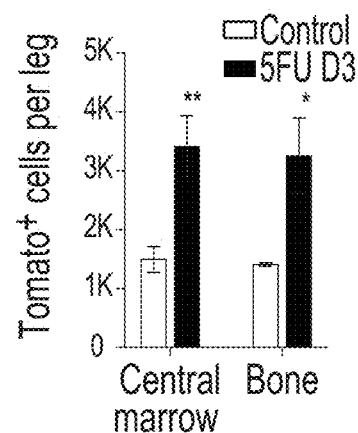

N-cad$^+$ pre-osteoblastic cells in bone surface have been found resistant, whereas Osx$^+$ osteoblasts have been found to be sensitive to 5FU treatment and N-cad$^+$ stromal cells have been found to give rise to Osx$^+$ osteoblasts during recovery post 5FU treatment (Sugimura et al., 2012). A recent study showed dramatic depletion of LepR$^+$ stromal cells in central marrow due to cell death 1 day following irradiation (Zhou et al., 2017). To track the early changes in vascular and endosteal niches, an apoptotic assay was performed at day 1 post 5FU treatment. It was found that the apoptotic CD31$^+$VE-cadherin$^+$ cells greatly increased 1 day post 5FU (FIG. 18F), consistent with previous reports of disrupted blood vessel structure post 5FU (Dominici et al., 2009; Sugimura et al., 2012). To study the endosteal niche, the N-cad-tdTomato (N-cad-TdT) mouse line was established in which the Tomato$^+$ cells report N-cad expression in both central marrow and bone surface (FIG. 24J). A marked increase of apoptotic N-Cad driven Tomato$^+$ cells in the central marrow was noticed, whereas the Tomato$^+$ cells in endosteal zone remained stable 1 day post 5FU (FIG. 18G). At day 3 post 5FU treatment when hematopoietic regeneration started, N-Cad driven Tomato$^+$ cells in central marrow as well as in bone surface increased by 2.2-fold and 1.7-fold respectively (FIG. 18H, FIG. 24K). The number of CD31$^+$ vessel cells also increased but showed a dilated and damaged architecture (FIG. 18I). Taken together, previous reports and this data showed that vessels and associated stromal cells in the perivascular niche, including LepR$^+$ and N-cad$^+$ cells, suffered immediate damage and were sensitive to 5FU stress, whereas N-cad$^+$ endosteal stromal cells remained stable.

The data partially explain previous findings that most HSCs are predominantly distributed in perivascular and sinusoidal zones (Acar et al., 2015; Chen et al., 2016; Kunisaki et al., 2013). pHSCs which account for 51.3% of the quiescent HSC population are near perivascular and sinusoid zones in homeostasis. Under stress, however, rHSCs reside closer to the bone surface survive chemotherapeutic stress. Collectively, the data indicate that the endosteal niche plays a critical role in protecting rHSCs from chemotherapy.

Example B-3

N-Cad$^+$ Niche Cells Maintain Functional HSCs Including rHSCs in Bone Marrow

Figure 19A:
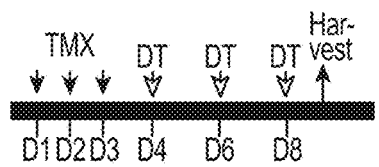
FIGS. 19A-19J: N-cad$^+$ cells maintain functional HSCs in BM niche.
Figure 19B:
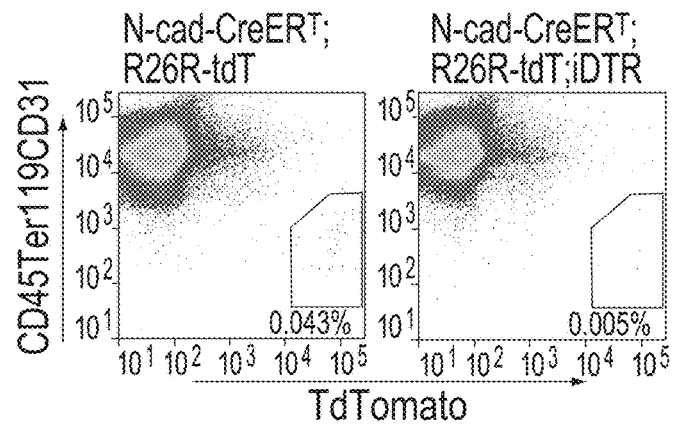
Figure 19C:
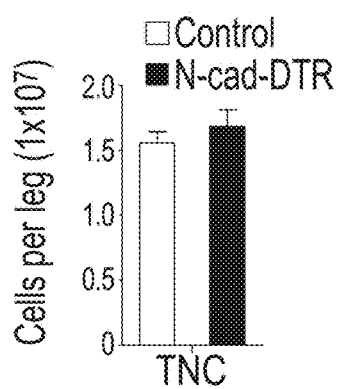
Figure 19D:
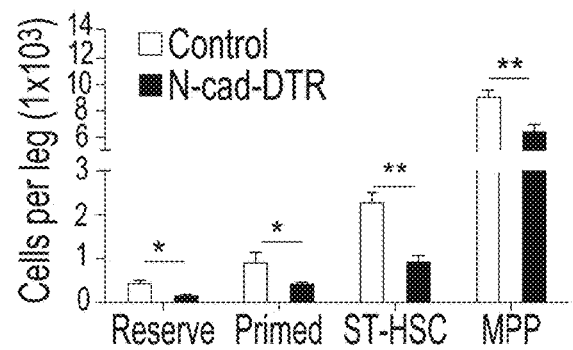
Figure 25A:
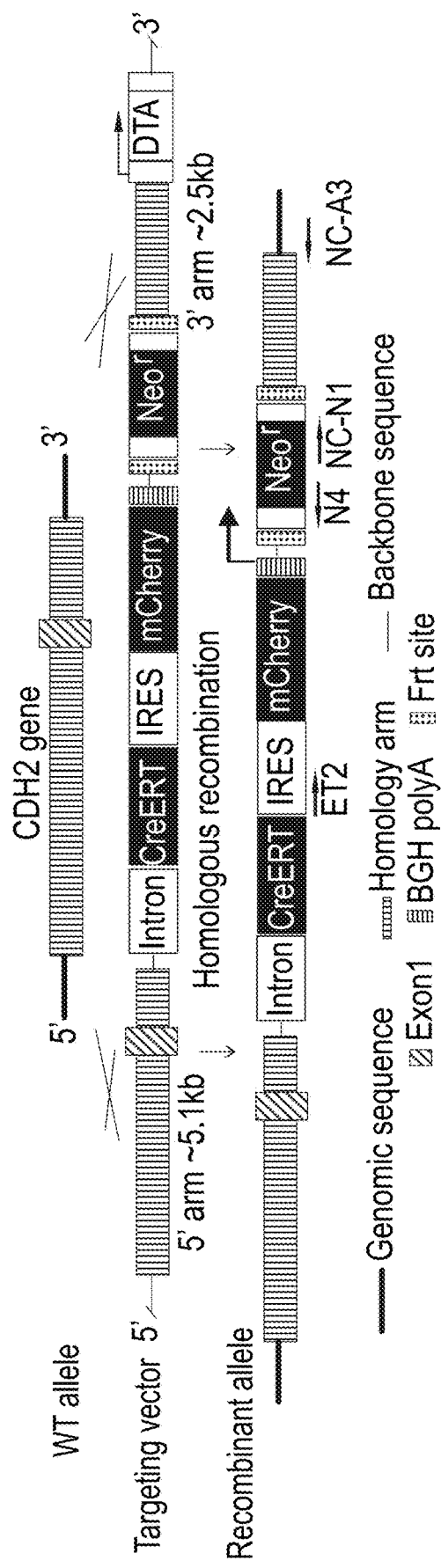
FIGS. 25A-25B: generation of N-cad-CreER$^T$ mouse strain.
Figure 25B:
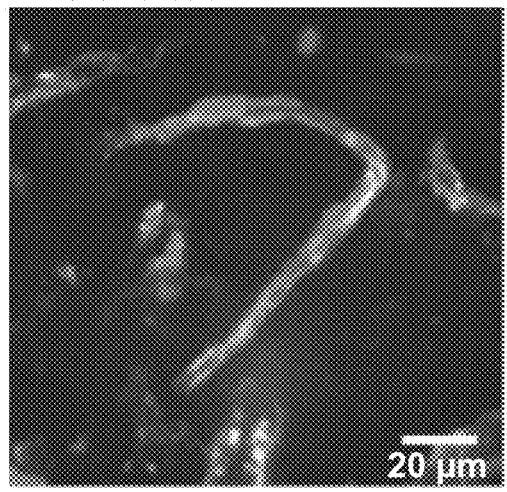
Figure 25B:
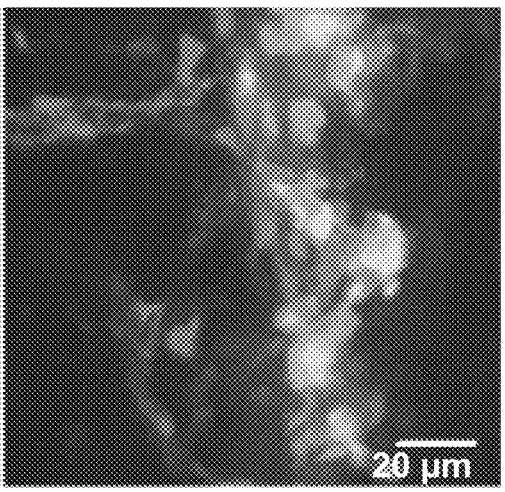

Though N-cad$^+$ stromal cells were the first identified HSC niche cells, and though N-cad$^+$ stromal cells at the endosteal niche were resistant while Osx$^+$ osteoblasts were sensitive to chemotherapy, a direct evidence for N-cad$^+$ functionally supporting HSCs was still missing due to lack of proper genetic mouse lines. According to aspects herein, the N-cad-CreER$^T$ line was generated (FIG. 25A) and showed that N-cad$^+$ stromal cells gave rise to both Col2.3-GFP$^+$ osteoblastic cells and perivascular cells (FIG. 25B). A previous study showed that depleting the mature Col2.3-GFP$^+$ osteoblasts did not affect overall engraftment of BM cells (Ding et al., 2012; Greenbaum et al., 2013), but only caused impaired regenerative capacity of a subset of LT-HSCs (Bowers et al., 2015). Though N-cad$^+$ stromal cells developmentally proceed Osx$^+$ osteoprogenitor cells, which further give rise to mature Col2.3$^+$ osteoblasts, a functional contribution to HSC maintenance by N-cad$^+$ stromal cells is unknown. To investigate the HSC niche role of N-cad$^+$ cells, N-cad-CreER$^T$induced DTR (encoding diphtheria toxin receptor) line (N-cad-CreER$^T$;iDTR) was generated, in which N-cad$^+$ niche cells were rendered sensitive to diphtheria toxin (DT). Three tamoxifen (TMX) injections were administered and followed with intraperitoneal injections of DT (one injection every other day) to the N-cad-CreER$^T$; iDTR mice and analyzed them on the first day after the last injection (FIG. 19A). The efficient ablation was observed of N-cad$^+$ stromal cells in N-cad-CreER$^T$;iDTR; R26-tdT compared to N-cad-CreER$^T$; R26-tdT mice treated concurrently with DT (FIG. 19B). Whether N-cad$^+$ cell ablation would affect HSCs in vivo was further examined. After ablating N-cad$^+$ cells, no significant change was observed of cellularity in BM compared to controls (FIG. 19C). However, the numbers of HSCs were dramatically reduced: rHSCs (65.0% reduction), pHSCs (60.0% reduction), ST-HSCs (59.6% reduction), and MPPs (29.3% reduction) (FIG. 19D). This indicated that N-cad$^+$ niche cells contributed to the most primitive, including reserve, HSC maintenance.

Figure 19E:
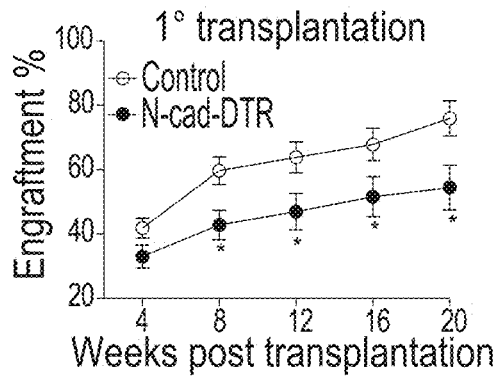
Figure 19F:
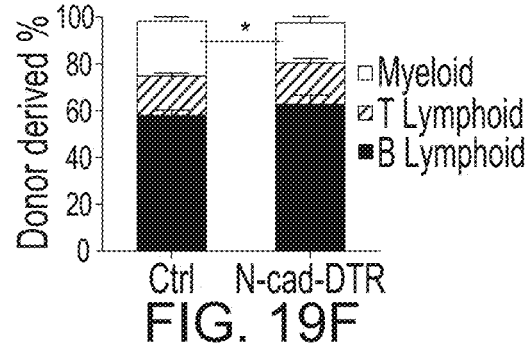
Figure 19G:
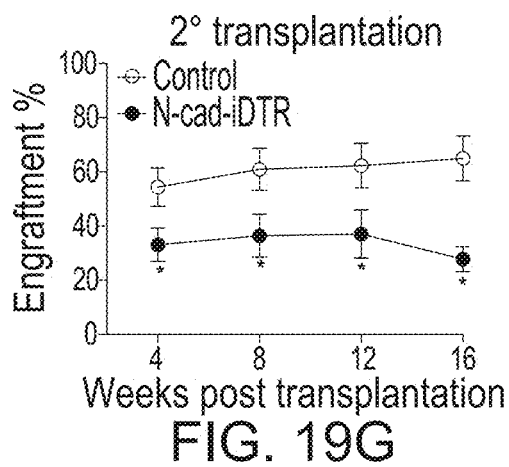
Figure 19H:
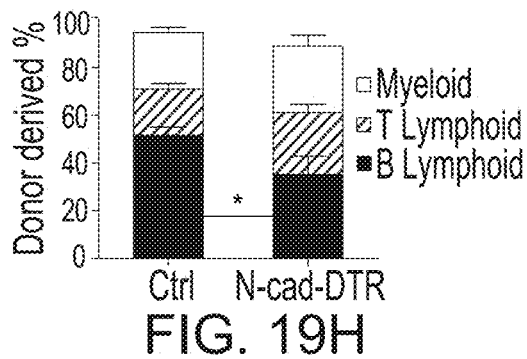

A transplantation assay was also performed to test the functional HSC numbers in N-cad$^+$ stromal cell ablated mice. It was found that bone marrow cells from N-cad$^+$ stromal cell ablated mice gave significantly lower levels of donor cell reconstitution (28.3% reduction at 20 weeks) (FIG. 19E) with reduced myeloid cell production (24.5% to 17.1%) (FIG. 19F). To further investigate whether N-cad$^+$ niche cells contributed to maintaining the long-term self-renewal of HSCs, a secondary transplantation was conducted at 20 weeks post the primary transplantation. It was observed that BM cells from the N-cad$^+$ stromal cell ablated mice had deeper reduction of donor cell reconstitution capacity in the secondary transplantation (40.5% reduction at 16 weeks) (FIG. 19G), although they were capable of multilineage reconstitution (FIG. 19H).

Figure 19I:
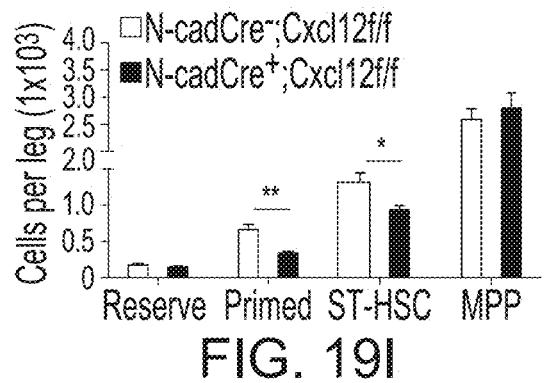
Figure 19J:
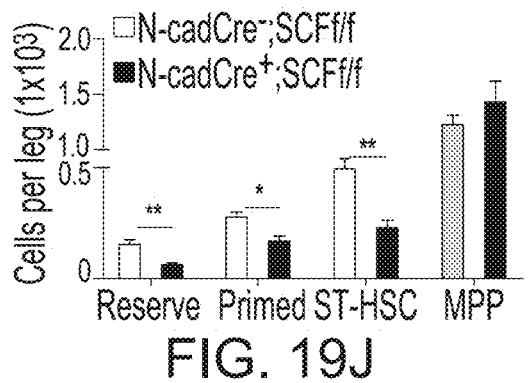

Furthermore, we found that conditional knockout of Cxcl12 from N-cad$^+$ stromal cells significantly reduced pHSCs (48% reduction) and ST-HSCs (28.8% reduction), but no significant reduction was observed in rHSCs. There was a slight albeit insignificant increase of MPPs. (FIG. 19I). Conditional deletion of SCF from N-cad$^+$ stromal cells significantly reduced rHSCs (60% reduction), pHSCs (38.6% reduction), and ST-HSCs (53.7% reduction), but with a slight increase in MPPs (FIG. 19J). Overall, we provided the first functional evidence that N-cad$^+$ niche cells contributed to HSC maintenance, including rHSCs, via producing maintenance factors.

Example B-4

Transcriptome Analysis for Hematopoietic Cells and their BM Niche Cells

Figure 20A:
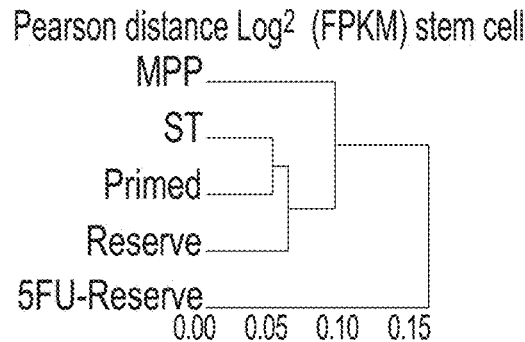
Figure 20B:
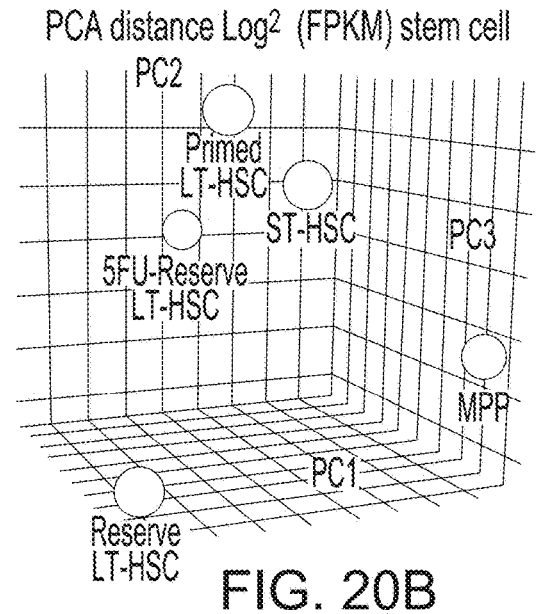
Figure 26A:
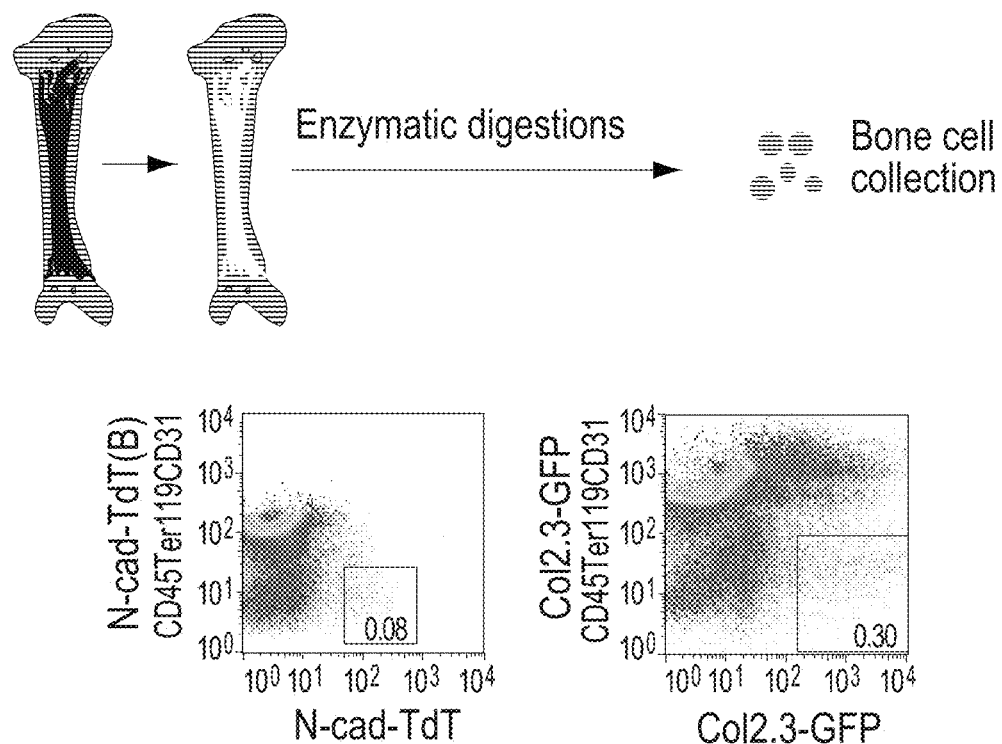
FIGS. 26A-26E: sorting strategy and signature gene expression of niche cells.
Figure 26B:
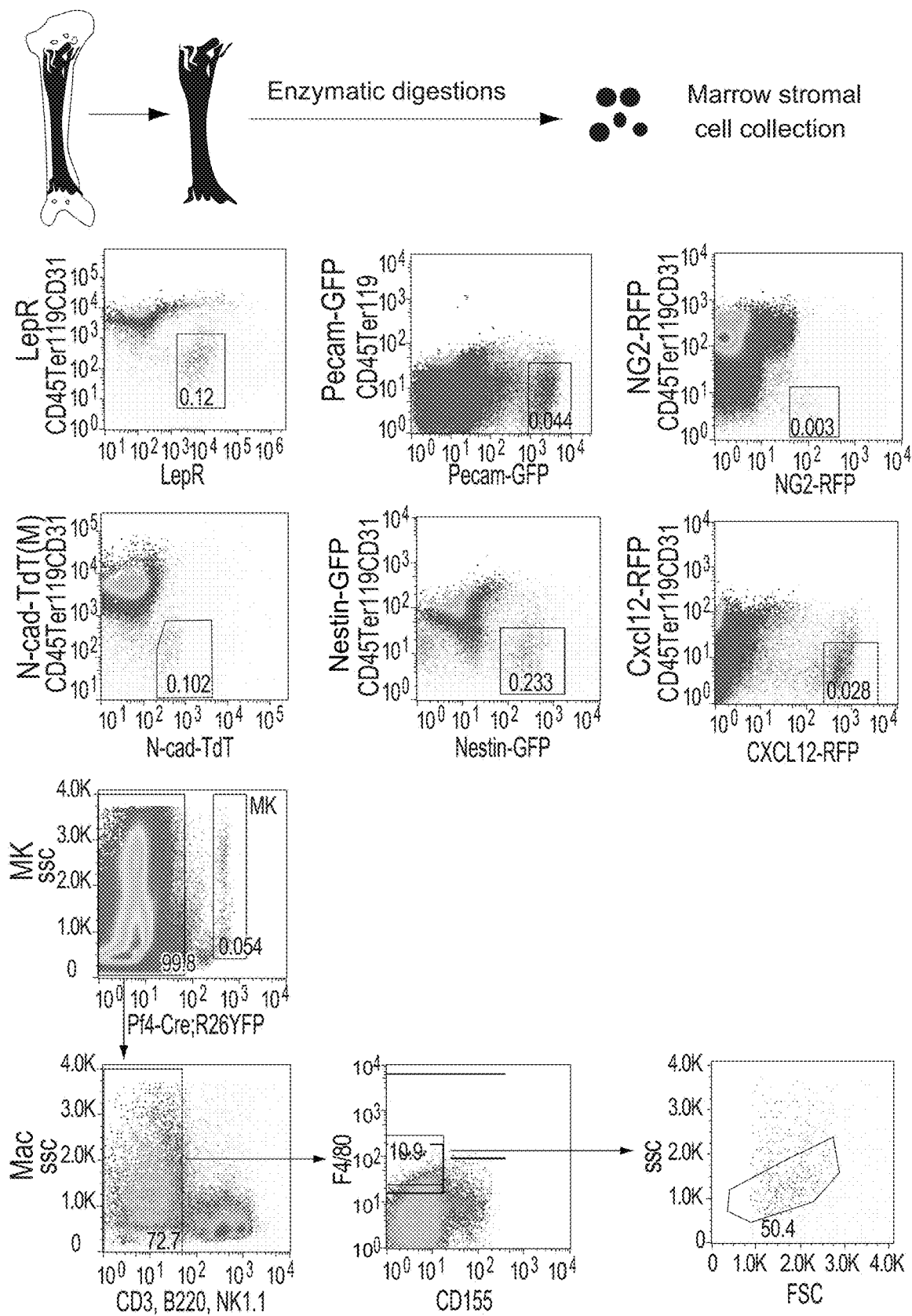

To understand the molecular mechanisms governing how different niche cells contribute to HSC subpopulation regulation, a transcriptome profiling analysis was performed on 4 types of hematopoietic stem and progenitor cells (HSPCs) during homeostasis and on rHSCs at day 3 post 5FU, as well as on 10 types of BM niche cells. The BM niche cells were harvested from different niche zones of endosteum (B) and central bone marrow (M) (FIG. 26A-B). The pearson distance tree and principal component analysis (PCA) data showed that rHSCs and pHSCs shared a unique transcriptome profiling compared to ST-HSCs and MPPs (FIG. 20A). Interestingly, rHSCs post 5FU treatment appeared to be closer to pHSCs (FIG. 20B), suggesting that surviving rHSCs were primed for activation to support subsequent hematopoietic regeneration post chemotherapy.

Figure 20C:
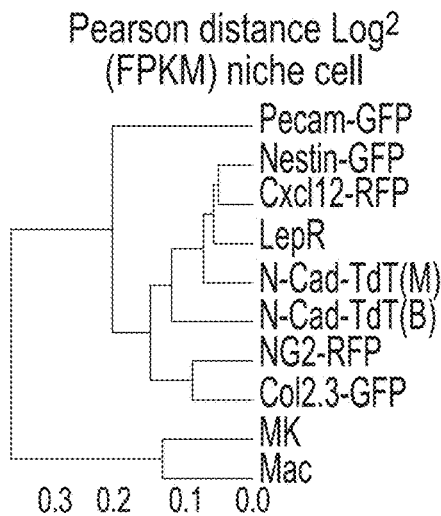
Figure 20D:
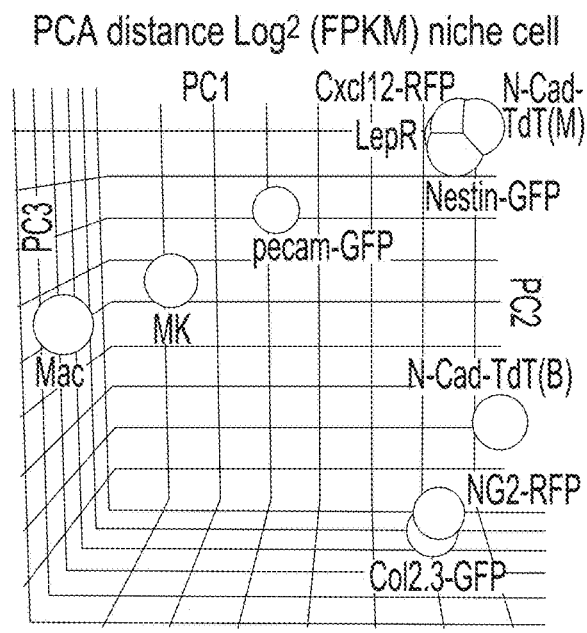
Figure 20E:
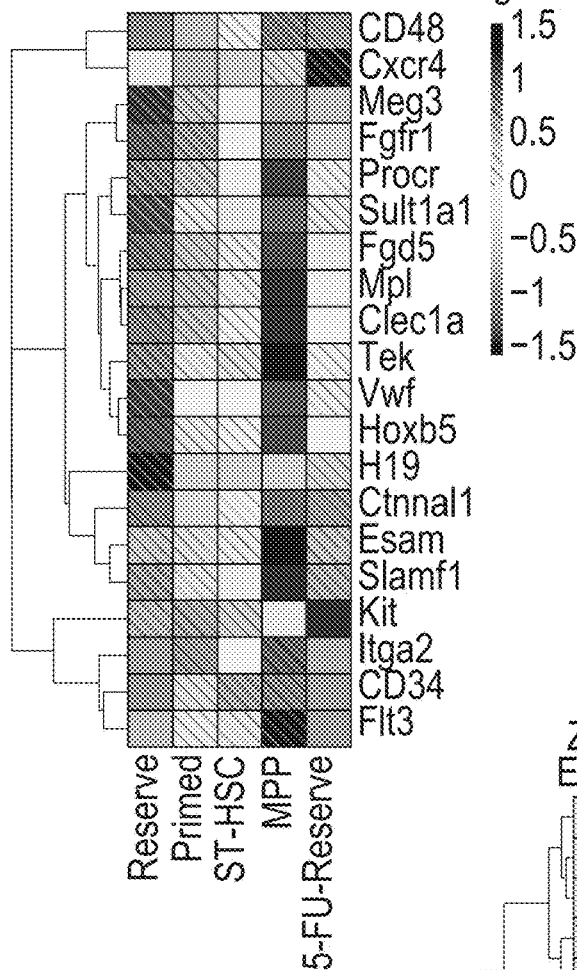

It was found that the rHSCs enriched most of the published HSC specific markers, such as Slamf1 (CD150), H19, Ctnnal1 (α-Catulin), Fgd5, vWF, Tek(Tie2), Procr(Epcr), Hoxb5 and Meg3 (or Gtl2) (Acar et al., 2015; Chen et al., 2016; Qian et al., 2015; Sanjuan-Pla et al., 2013; Venkatraman et al., 2013). Particularly, vWF in rHSCs were 6.1-fold higher than in pHSCs, suggesting that rHSCs enriched most of the vWF$^+$ HSCs which reside at the apex of the HSC hierarchy (Sanjuan-Pla et al., 2013). Consistently, progenitor signature genes such as CD34, CD48, and Flt3(Flk2) and Itga2 (CD49b) had low expression in rHSCs (Acar et al., 2015; Chen et al., 2016; Gazit et al., 2014). Interestingly, rHSCs post 5FU had high expression levels of CXCR4, Ctnnal1 (α-Catulin)(Park et al., 2002), Esam (Endothelial cell-selective adhesion molecule) and CD150 (encoding Slamf1, signaling lymphocytic activated molecule), consistent with their functions associated with the converted primed state (FIG. 20E).

Figure 26C:
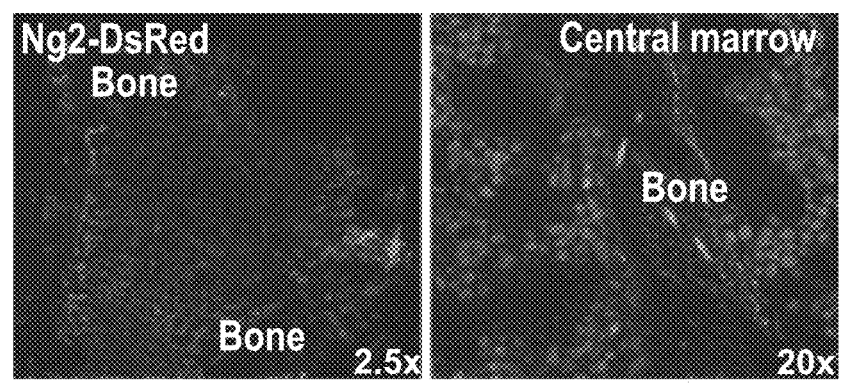

In niche cell analysis, it was found the N-cad driven tdTomato (N-cad-TdT) (M) had a very similar transcriptome profile compared to other niche cells with mesenchymal stem cell (MSC) potential such as LepR, Cxcl12-RFP, and Nestin-GFP cells in both pearson distance tree (FIG. 20C) and PCA analysis (FIG. 20D), suggesting that N-cad$^+$ cells might have MSC potential and similar function in regulating HSCs. Interestingly, NG2-RFP cells had a very similar transcriptome profile to Col2.3-GFP$^+$ osteoblasts (FIG. 20C-D). It was also found that NG2-RFP cells were predominantly restricted to endosteum in the epiphysis or diaphysis, though they were also detected in the peri-arterial region (FIG. 26C).

Figure 20F:
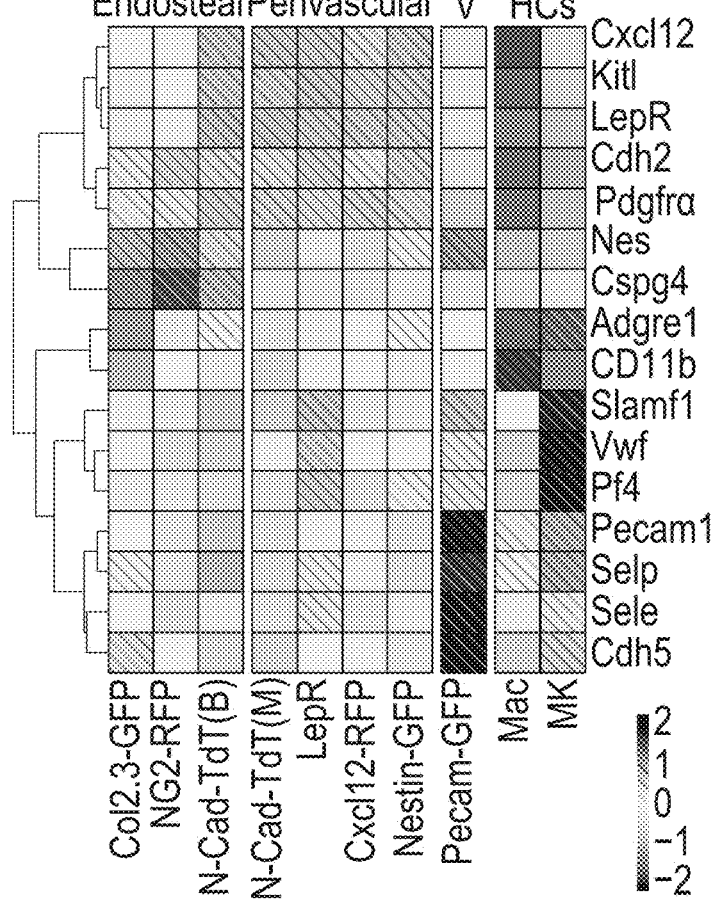
Figure 20G:
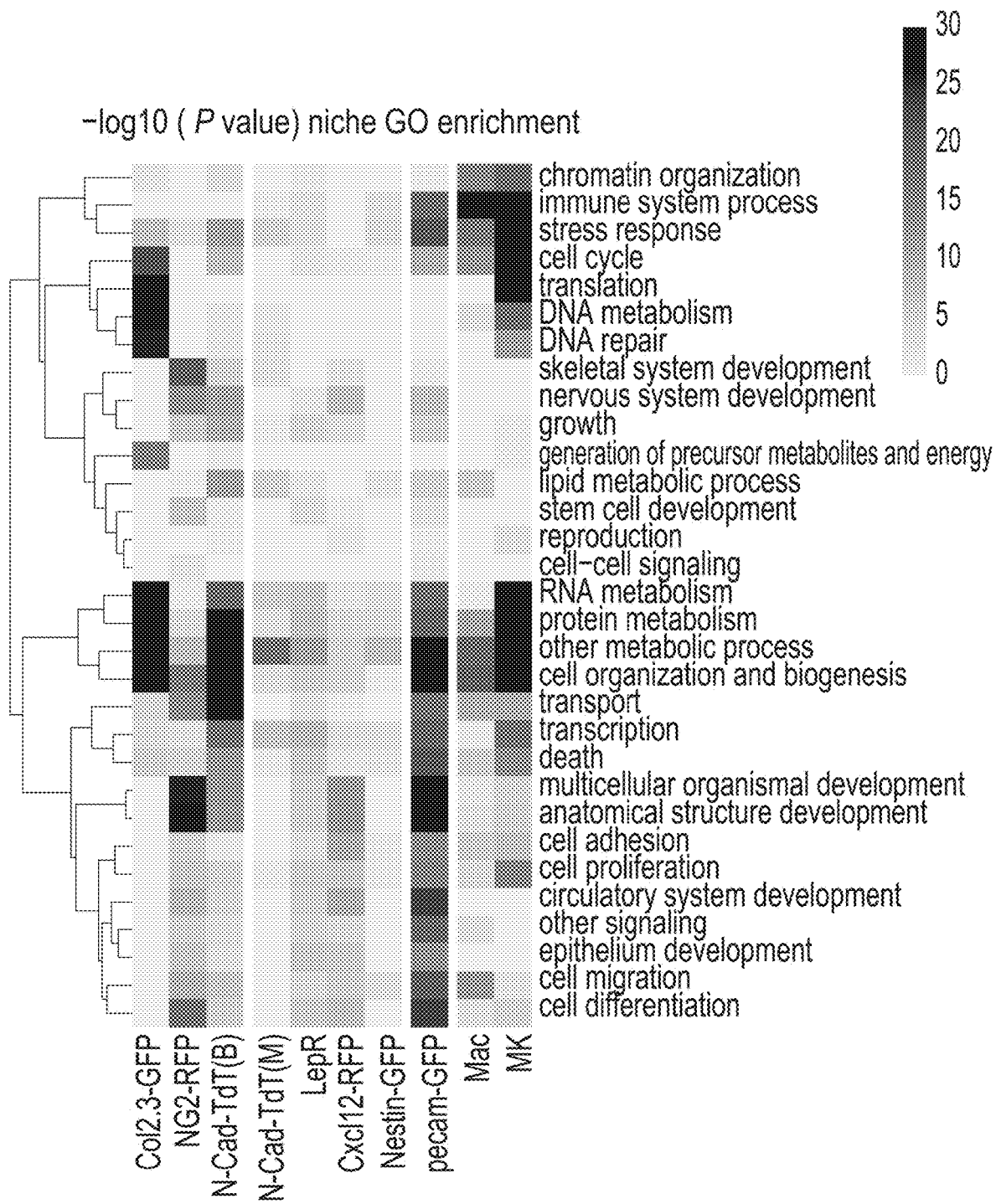
Figure 20H:
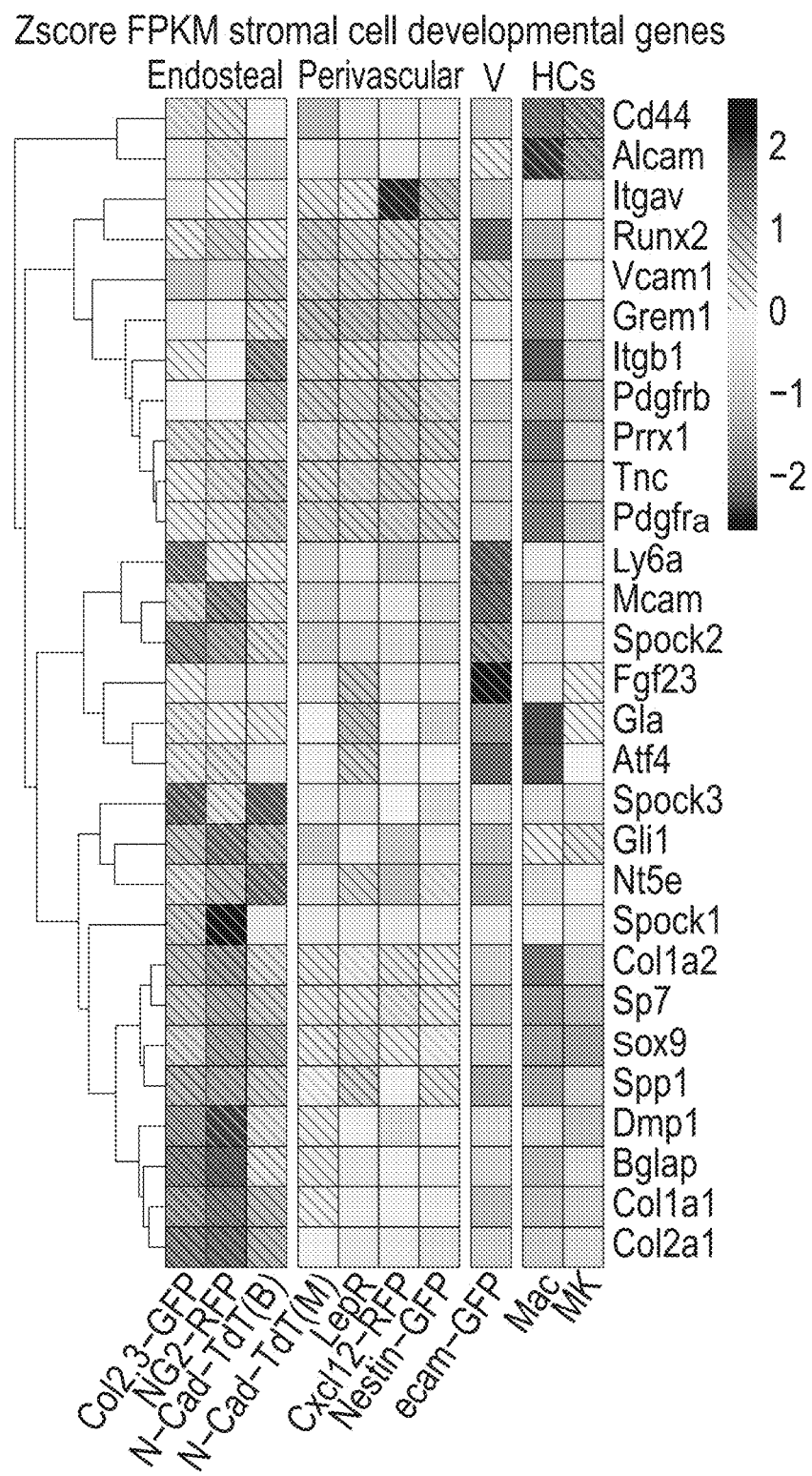

It was found that Pecam (CD31), CDH5 (VE-cadherin) were enriched in Pecam-GFP$^+$ endothelial cells. PF4 and Adgre1 were enriched in MKs and macrophages (Macs). Cspg4 (NG2) was enriched in NG2-RFP cells. Nestin-GFP cells did not have endogenous Nestin (Nes) expression, consistent with previous reports (Ding et al.,2012; Greenbaum et al., 2013). Interestingly, it was found that several marker genes such as Kitl (SCF), LepR, Cdh2 (N-cadherin, N-CAD), Cxcl12, Pdgfrα were broadly expressed in perivascular niche cells (FIG. 20F). N-cad-TdT(B) cells isolated from the endosteal zone also had high levels of SCF, Cxcl12, LepR and Pdgfrα expression compared to other cells from the endosteal zone, such as Col2.3-GFP and NG2-RFP cells (FIG. 20F). Our GO term analysis showed that Col2.3-GFP, Pecam-GFP, MK and Mac cells highly enriched RNA metabolism, protein metabolism, other metabolism pathways and translation activities, indicating that these cells were in a relatively active functional state compared to N-cad-TdT cells and other perivascular zone cells which were in a relatively lower metabolic state. Endothelial cells and perivascular cells had immune system process and stress response activities (FIG. 20G). Because N-cad$^+$ cells had transcriptome profiles similar to other MSCs such as LepR$^+$, Cxcl12-RFP, and Nestin-GFP cells, we next analyzed and compared stromal development related genes from different niche cells (FIG. 20H). It was found that Col2.3-GFP cells enriched osteoblast gene Col1a and progenitor cell gene Ly6a (SCA1) (Yang et al., 2014). N-Cad-TdT(B) cells from the endosteal region enriched chondrocyte genes Spock1, Col2a1 and Col1a2 and bone development genes such as Tnc. Interestingly both N-Cad-TdT(B) and N-Cad-TdT(M) enriched most of the mesenchymal stem and progenitor cell (MSPC) genes such as Prrx1, Pdgfr6, Pdgfrα, Sp7, Sox9 and Grem1. Marrow harvested NG2-RFP cells also had higher levels of MSPC gene expression, such as Alcam, Sp7, Mcam, Sox9 and Gli1, but with high level osteoblast and chondrocyte related genes such as Col1a1, Col2a1, and Col1a2. It was also found that among all perivascular niche cells, LepR$^+$ cells exclusively enriched Gla as well as several osteoblast and chondrocyte markers such as Atf4 and Tnc. Cxcl12-RFP cells significantly enriched MSPC gene Itgav. Furthermore, Grem1 was enriched in N-Cad-TdT(B) and in all perivascular niche cells but not in NG2-RFP cells.

Figure 26D:
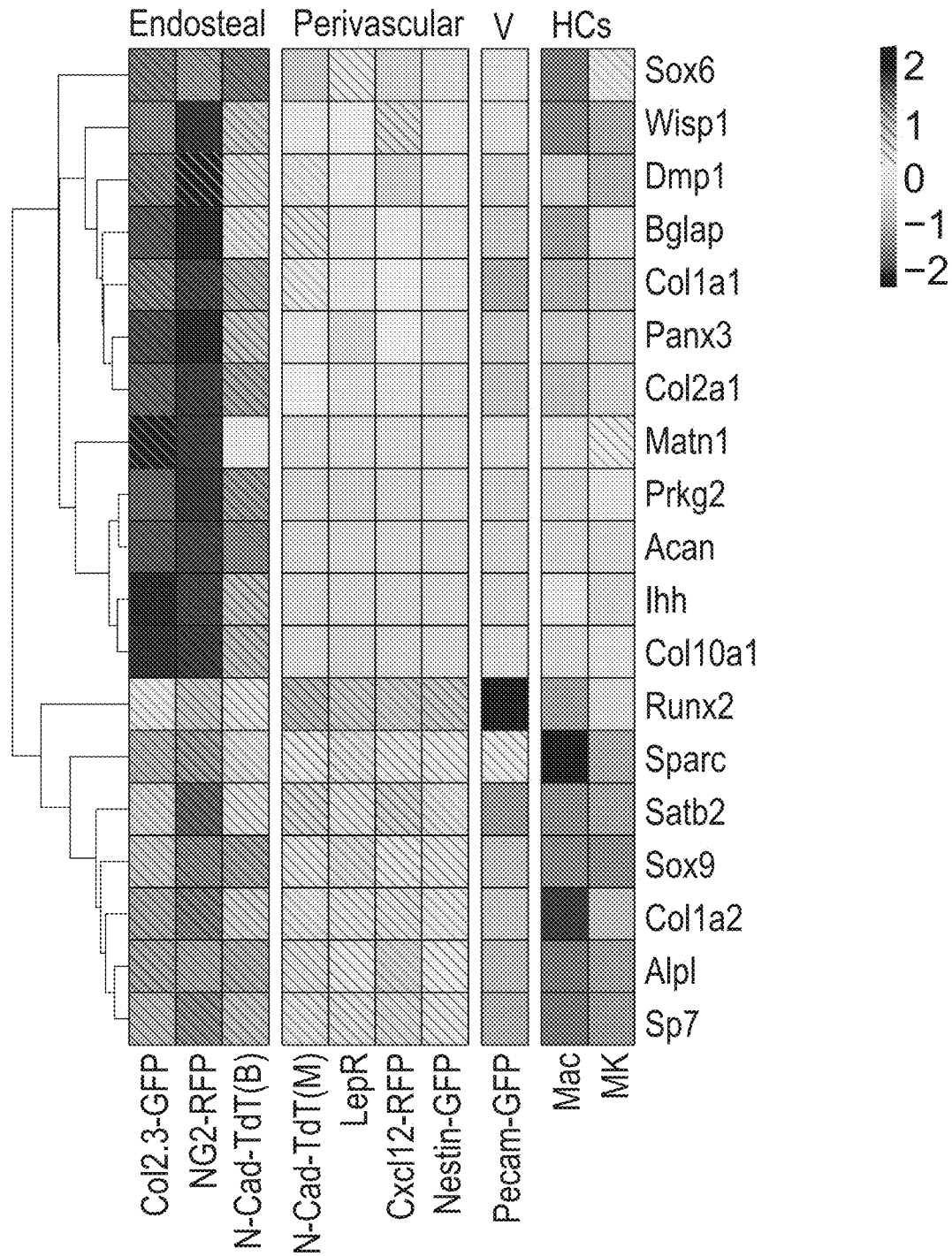
Figure 26E:
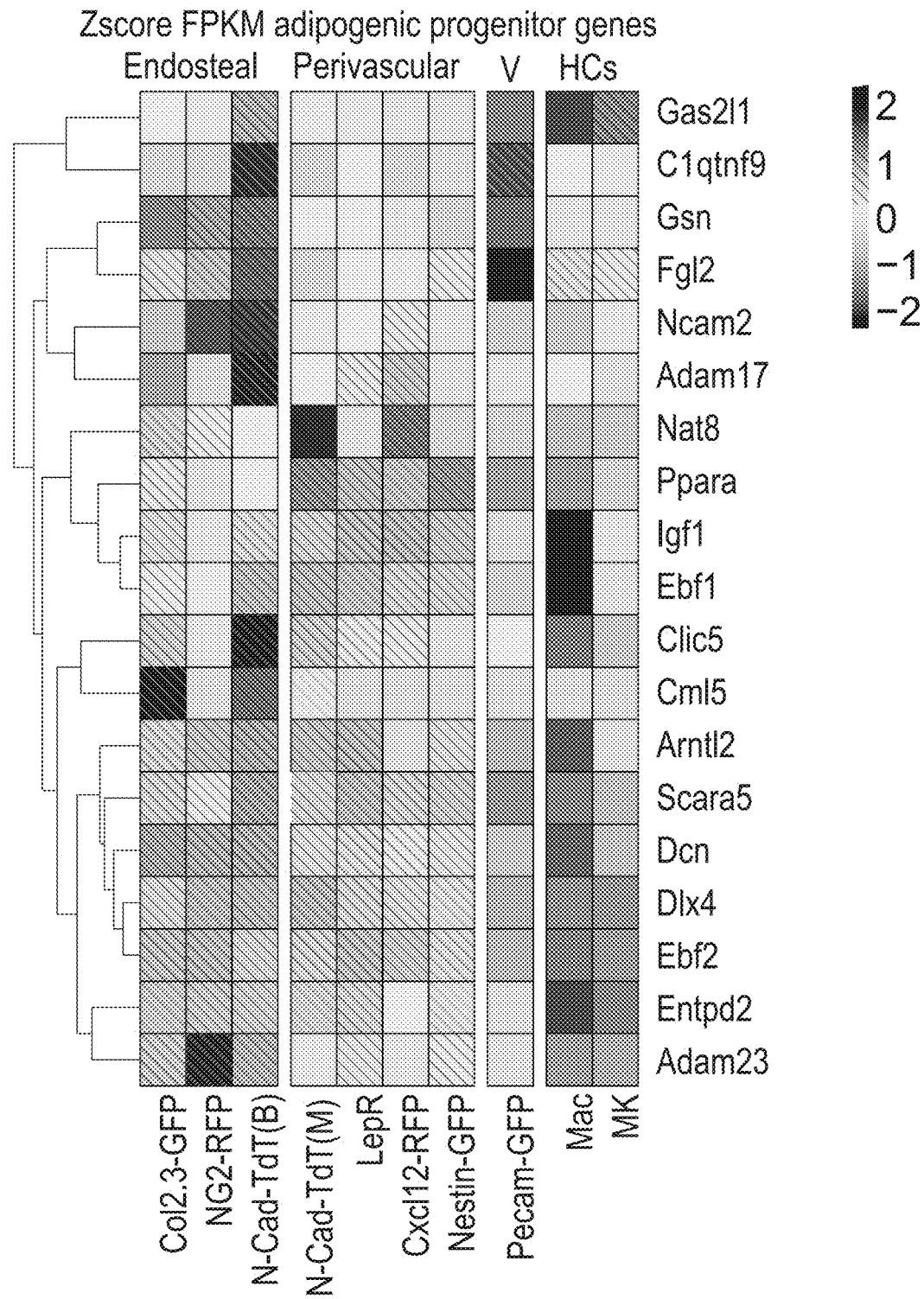

Consistent with earlier data, Col2.3-GFP cells were enriched for more mature osteo-lineage genes (Dmp1, Col1a1, Spp1, Bglap). Nestin-GFP, Cxcl12-RFP and LepR were consistent with their known role in enriching MSC genes (Prrx1, Pdgfrα, Itgb1, Grem1 (FIG. 20H). Interestingly, apart from expressing MSC genes, N-Cad-TdT(M) and N-Cad-TdT(B) were enriched for chondrogenic (Sox9, Col2a1 and Tnc), adipogenic (Cebpα, Ppary, Adipoq) and osteogenic (Col1a1, Runx2) genes, suggesting a tri-potential nature of N-Cad$^+$ stromal cells. Surprisingly, NG2-RFP was enriched for both bone development genes (Dmp1, Bglap, Sp7, Runx2, Col1a1) and chondrogenic genes (Sox9, Col2a1 and Tnc), suggesting an osteo-chondrogenic role (FIG. 26D-E). These data strongly indicated the heterogeneity of the MSPCs in BM.

Example B-5

Figure 20I:
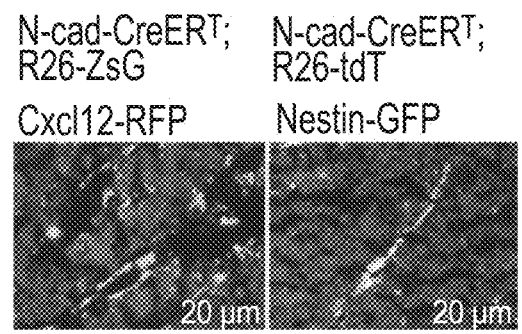
Figure 21B:
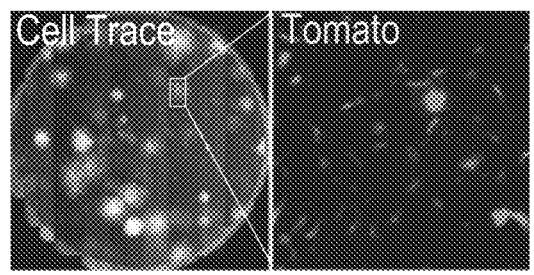
FIG. 21A-21G: in vitro differentiation potential and localization of N-cad$^+$ derived cells.

N-Cad-CreER$^T$ Induced Reporter Cells Largely Overlap with LepR$^+$ and Cxcl12$^+$ Stem/Stromal Cells To confirm the transcriptional analysis, N-cad in vivo lineage tracing was performed using the TdT or ZsG reporter, and found that, at day 3 post induction, N-cad-CreER$^T$ lineage traced cells partially overlapped with Cxcl12-RFP and Nestin-GFP cells (FIG. 20I). Moreover, 98.3% and 97.9% N-cad-CreER$^T$ derived cells were positive for LepR and Pdgfrα expression respectively (FIG. 20J). This result further supported that N-cad$^+$ stromal cells have MSC potential as suggested by the transcriptome analysis. To analyze the lineage potential of N-cad$^+$ stromal cells, colony-forming unit-fibroblasts (CFU-F) assay was performed to test their proliferating capacity. It was found that the majority of reported niche cells, whether from endosteal zone or from perivascular zone, had one out of fewer than 10 cells with CFU-F activity, apart from Nestin-GFP$^+$ cells, which had only one out of 17.6 cells with CFU-F activity. N-cad$^+$ cells from bone had one cell with CFU-F activity out of 8.79 cells. N-cad-CreER$^T$ derived bone cells had 1 in 10.7 cells with CFU-F activity, and N-cad-CreER$^T$ derived marrow cells had 1 in 7.37 cells. (FIG. 20K). Most CFU-F colonies maintained tdTomato signals (FIG. 21A-B), suggesting that N-cad$^+$ cells were the main source of MSPCs with CFU-F activity.

Example B-6

Figure 21C:
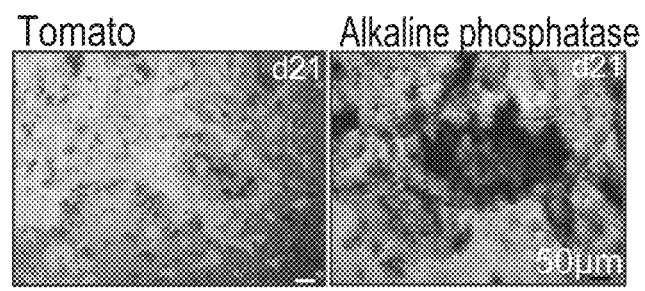
Figure 21D:
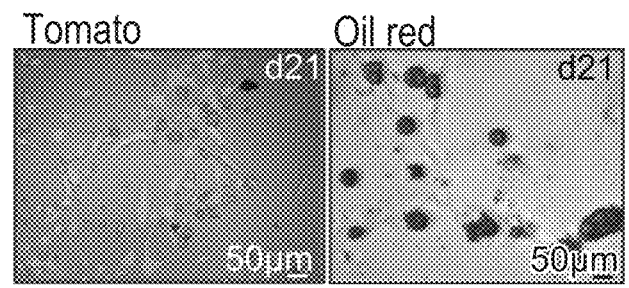
Figure 21E:
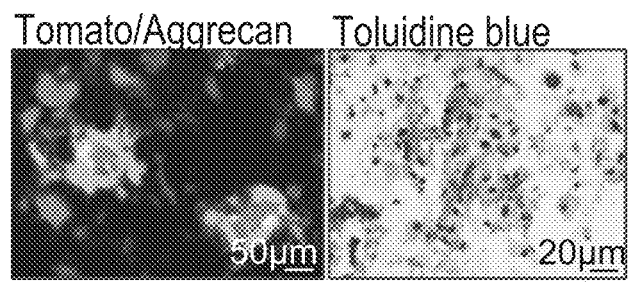

N-Cad$^+$ Stromal Cells Give Rise to Osteoblasts, Chondrocytes, and Adipocytes In Vitro and In Vivo To test the MSC potential of N-cad$^+$ cells, in vitro differentiation assay was performed by splitting cells obtained from individual CFU-F colonies formed by N-cad$^+$ cells into three aliquots and sub-cloned them into cultures permissive for bone, fat, or cartilage cell differentiation. It was found that Tomato$^+$ cells underwent multilineage differentiation, giving rising to Alkaline phosphate-positive osteoblastic cells, Oil-red-O-positive adipocytes, and Aggrecan-stained and Toluidine-blue-positive chondrocytes (FIG. 21C-E).

Figure 21F:
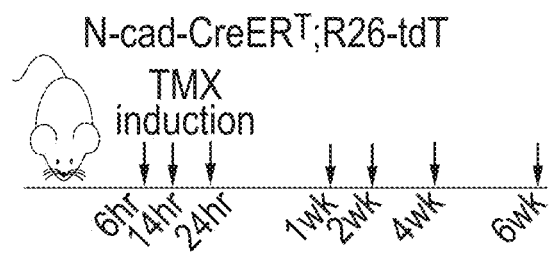
Figure 21G:
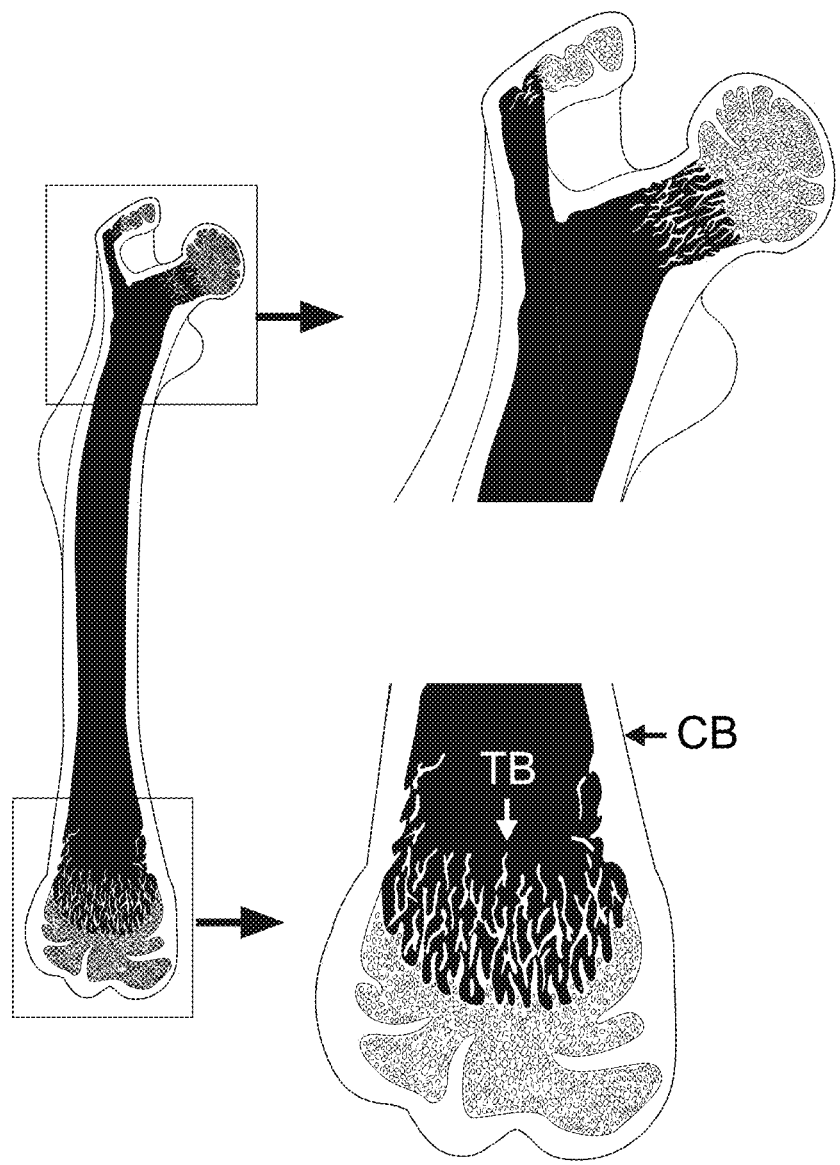
Figure 21H:
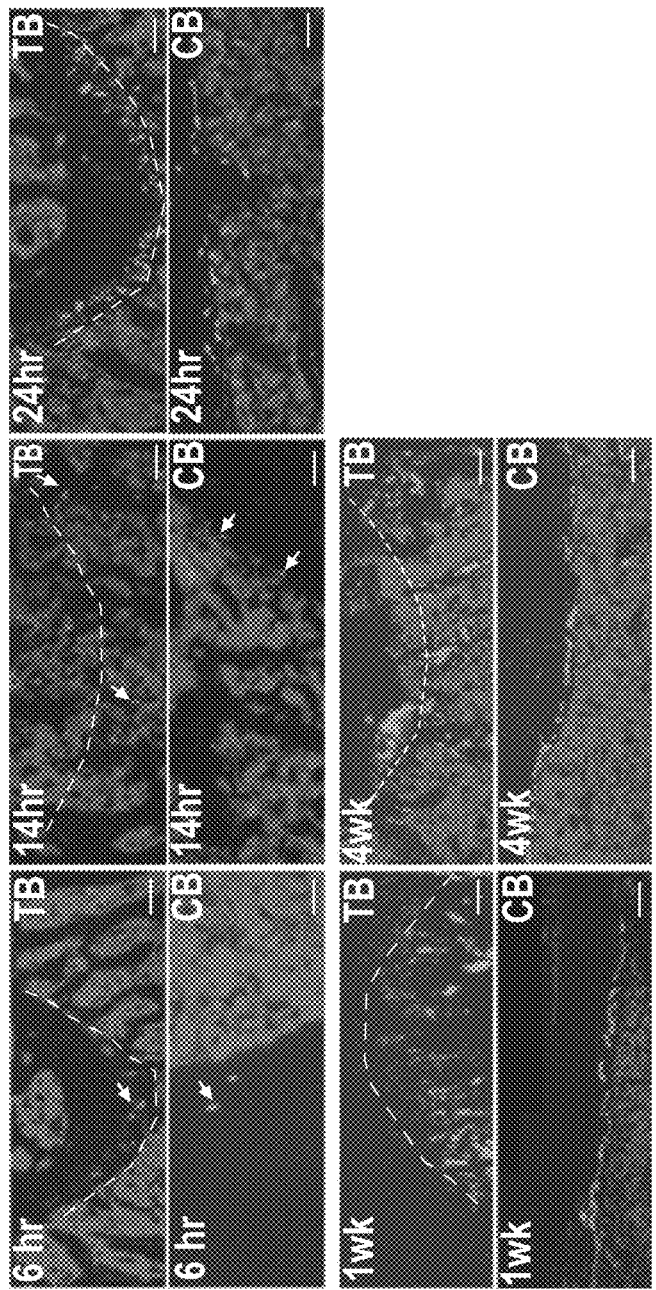
FIG. 21H shows localization of cells derived from N-cad-CreERT; R26-tdT mice post TMX injection at 6 hours, 14 hours, 24 hours, 1 week and 4 weeks.
Figure 21I:
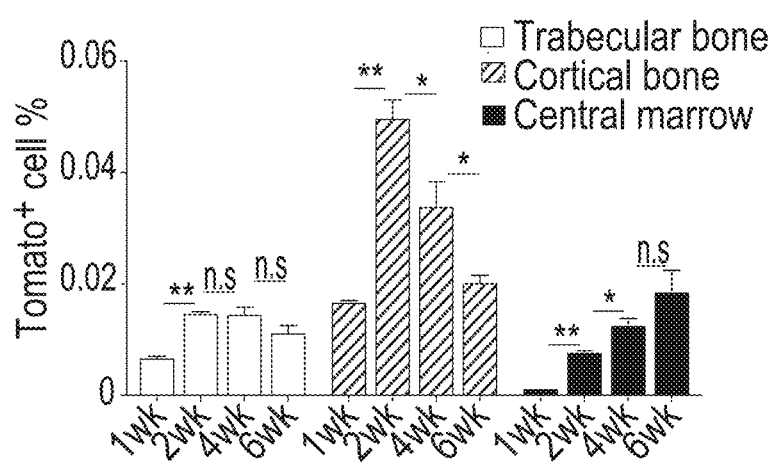
FIG. 21 I shows percentage of Tomato$^+$ cells post TMX injection at 1 week, 2 weeks, 4 weeks and 6 weeks in trabecular, cortical bone and central marrow (n=2 mice in 1 and 2 weeks group, n=3 mice in 4 and 6 weeks group. * P<0.05,  P<0.01, *P<0.001. Error bars, s.e.m.).

To characterize in vivo function of N-cad$^+$ stromal cells, the dynamic anatomical distribution of N-cad derived cells was analyzed after one dose of TMX treatment (FIG. 21F, G). Interestingly, detected N-cad derived cells were detected in metaphysis of trabecular as early as 6 hours post TMX, but only very few cells were seen in central marrow, suggesting that a large portion of N-cad$^+$ cells originated from the endosteal region (FIG. 21H). It was also observed that the number of N-cad derived cells increased by 2.2±0.2-fold in trabecular bone region from 1 to 2 weeks post TMX treatment and remained stable afterwards, in cortical bone region, the cell number increased by 2.95±0.2-fold at 2 weeks post TMX, but then declined at 6 weeks post TMX, suggesting that N-cad$^+$ cells in trabecular bone region were more quiescent compared to cortical bone region. Moreover, N-cad derived cells continuously increased in central marrow up to 6 weeks, suggesting that N-cad derived cells might be proliferating and differentiating within this area (FIG. 21I).

Figure 22A:
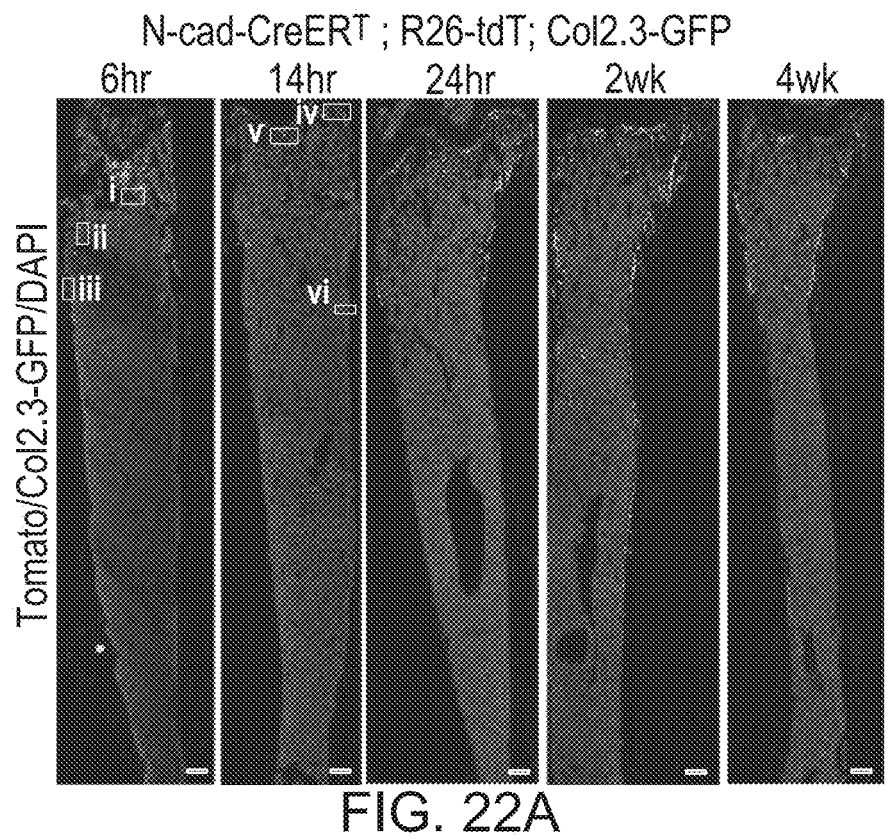
Figure 22B:
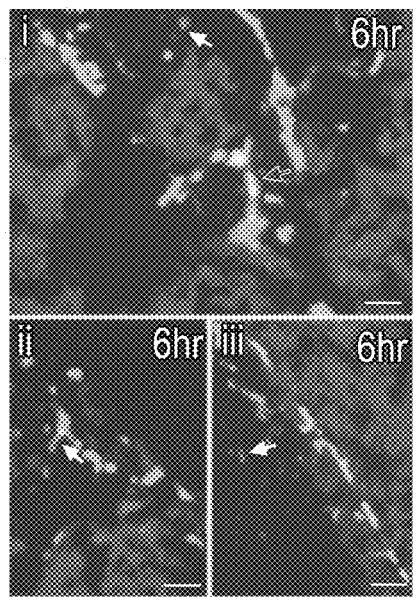
Figure 22C:
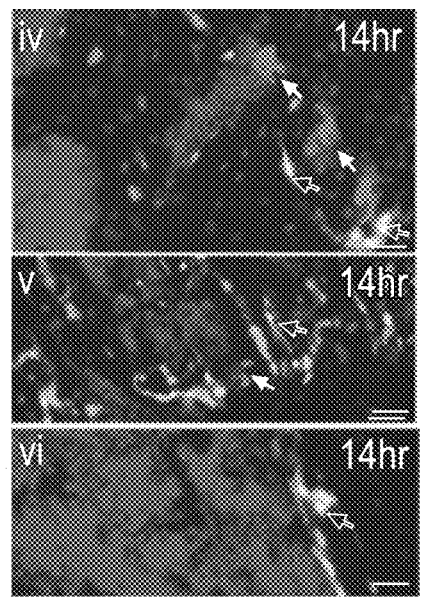
Figure 22D:
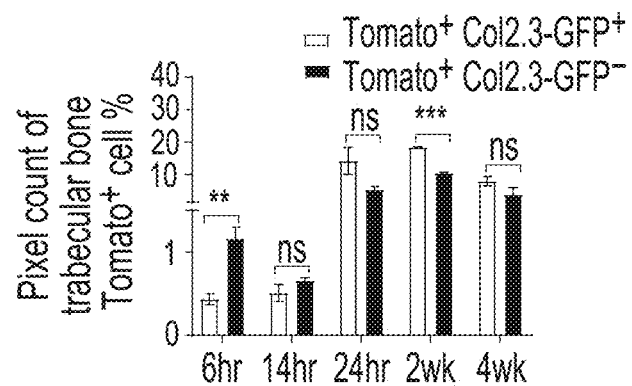
Figure 22E:
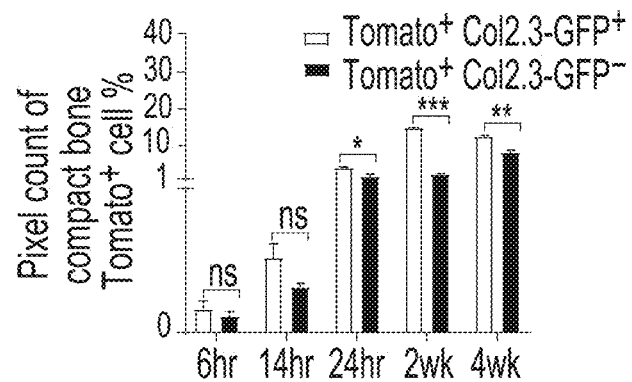
Figure 22F:
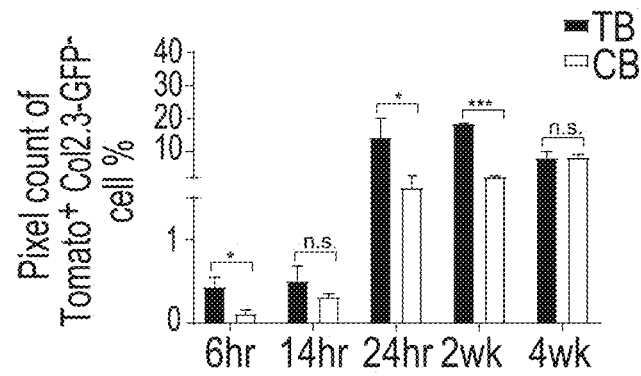
Figure 22G:
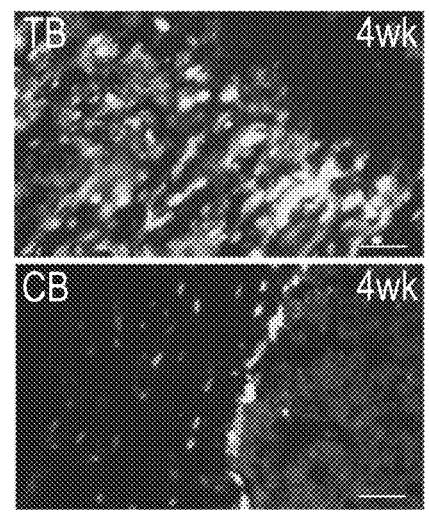
Figure 27A:
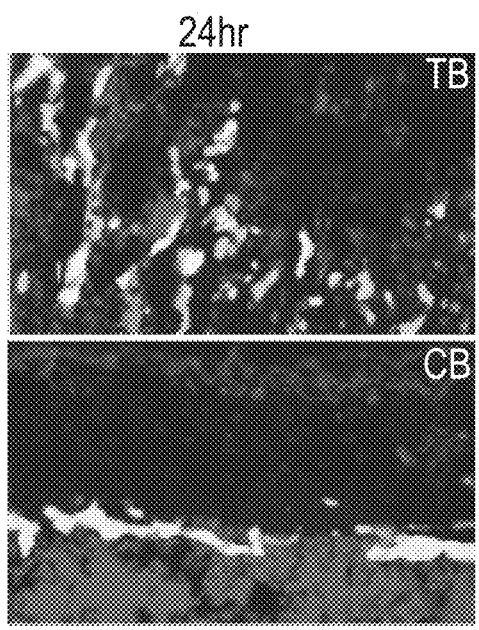
FIGS. 27A-27E: lineage tracing in N-cad-CreER$^T$; R26-tdT mice at early time point post TMX induction.
Figure 27B:
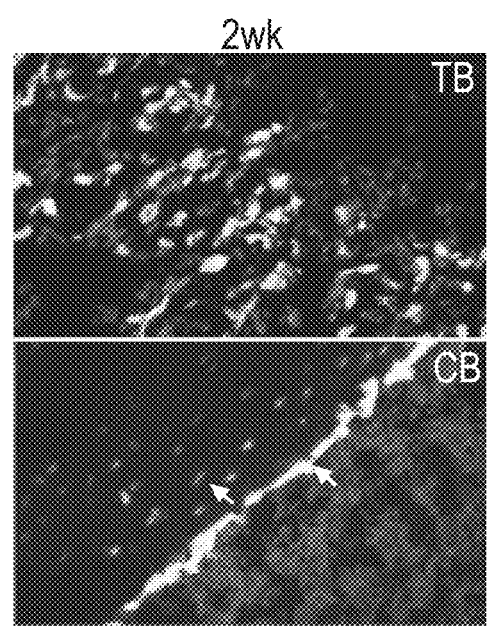
Figure 27C:
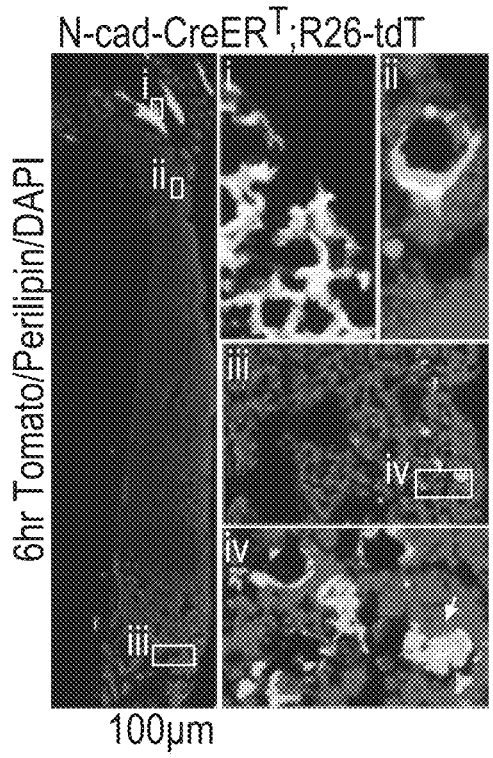
Figure 27D:
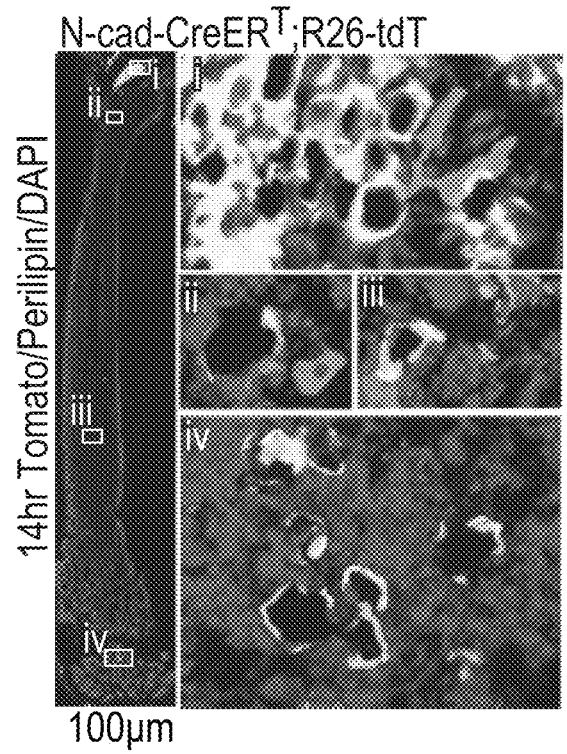
Figure 27E:
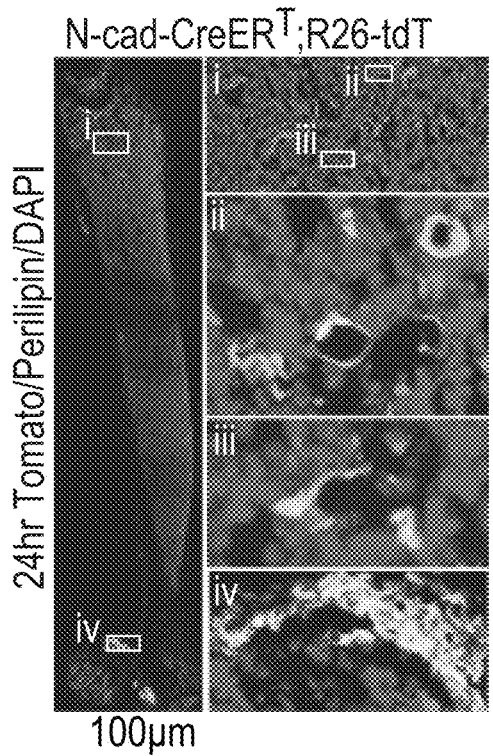

Next, an in vivo lineage tracing assay was performed and it was observed that N-cad$^+$ cells generated Col2.3-GFP$^+$ osteoblasts (Dacic et al., 2001) in a time dependent manner (FIG. 22A, FIG. 27A-B). N-cad-derived osteoblasts were detected in the peri-trabecular region as early as 6 hours post TMX induction (FIG. 22B) and in the compact bone region at 14 hours post TMX induction (FIG. 22C). Further analysis showed that at 6 hours post TMX, immature N-cad$^+$ Col2.3$^-$ cells (1.1%±0.2%) were 10-times more enriched in trabecular bone region compared to cortical bone region (0.11%±0.04%) (FIG. 22D, E). Consistently, more immature N-cad$^+$Col2.3$^-$ cells were enriched in trabecular bone region compared to compact bone region at 24 hours and 2 weeks post TMX induction (FIG. 22F). At 4 weeks post TMX induction, a large portion of Col2.3-GFP cells (72%±6%) were derived from N-cad$^+$ cells (FIG. 22G).

Figure 22H:
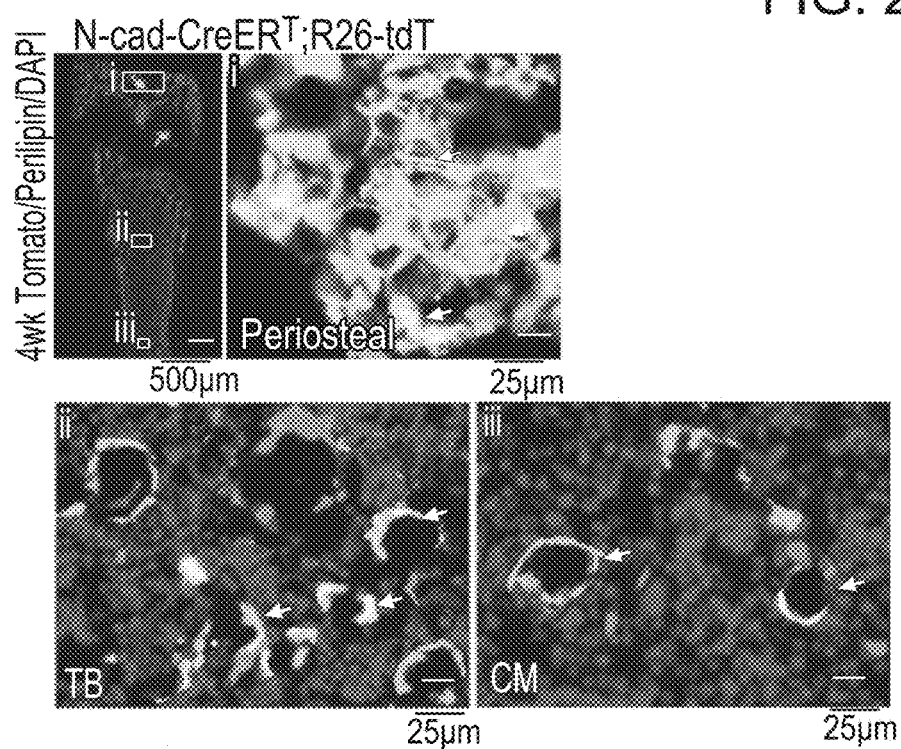
Figure 22I:
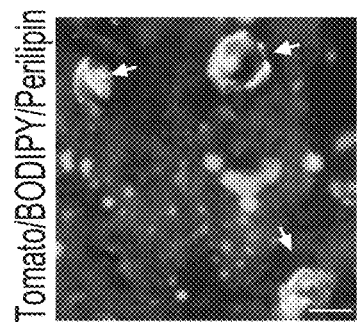

It was further observed that at 4 weeks post TMX injection, N-cad$^+$ stromal cells generated adipocytes in the trabecular bone region, particularly the endosteal cells, (FIG. 22H), and this was further confirmed by BODIPY lipid probe staining (FIG. 22I). Interestingly, the frequency of N-cad$^+$ derived adipocytes increased quickly initially and declined later on, as evidenced by the quantification that 39.3%±4.5%, 77.1%±6.7% and 17.2%±3% of N-cad$^+$ derived cells were observed at 6, 14 and 24 hours respectively after TMX induction, suggesting that adipocytes might have a frequent turnover rate (FIG. 22J-K, FIG. 27C-E). Collectively, the data demonstrated that N-cad$^+$ stromal cells generated both osteoblast and adipocyte lineages in vivo during homeostasis in adult mice.

Figure 30:
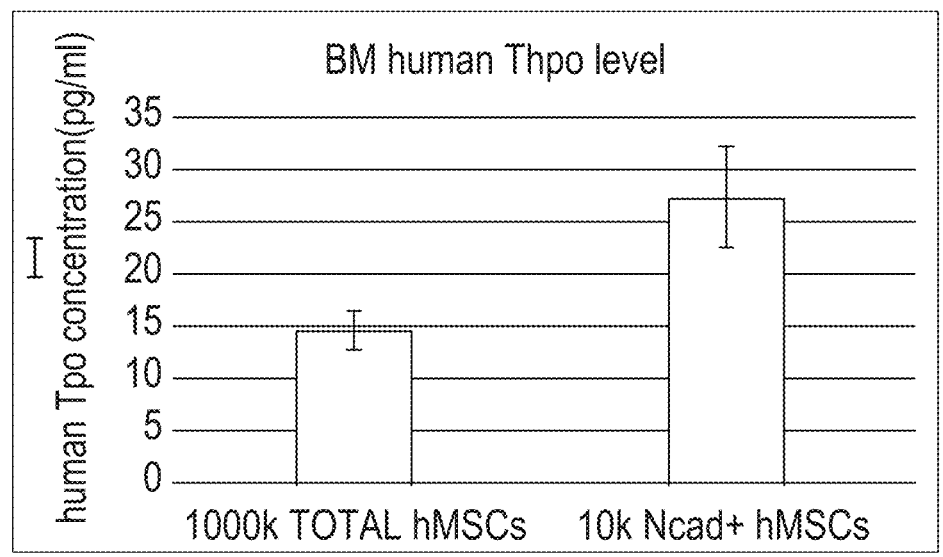
FIG. 30: Plot showing production of human Thpo by 10K ncad+ hMSCs and 1000 k total hMSCs in vivo.

Furthermore, it was found that Ncad+ MSCs were enriched >10-fold as compared to other markers. For example, as shown in FIG. 30, just 10K Ncad+ hMSCs produced even higher human thrombopoietin (THPO or TPO) than total hMSCs in vivo. Similarly, Ncad− hMSCs exhibited a function similar to the total hMSCs. Accordingly, isolating MSC with N-cadherin antibodies can provide for enrichment of the MSC population.

Example B-7

Figure 23B:
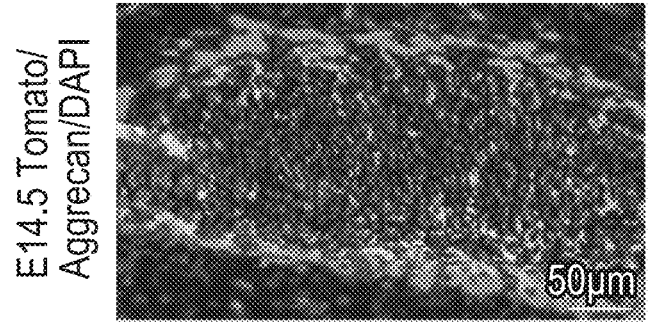
Figure 23C:
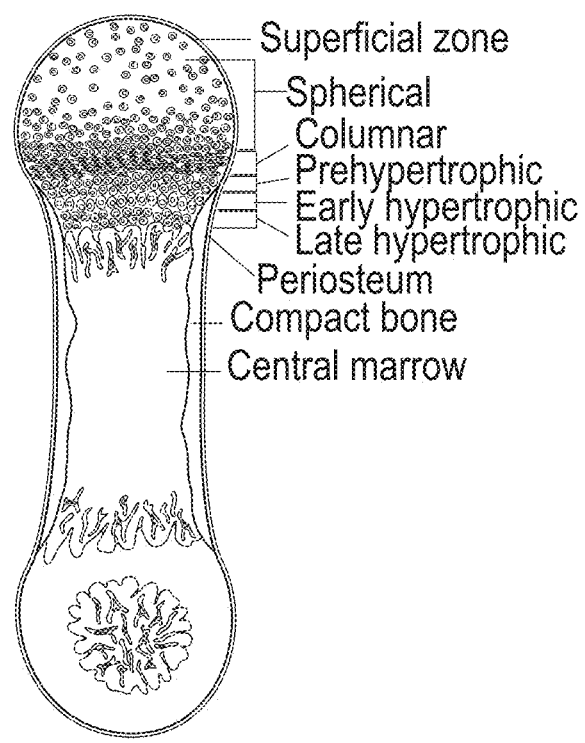
Figure 23D:
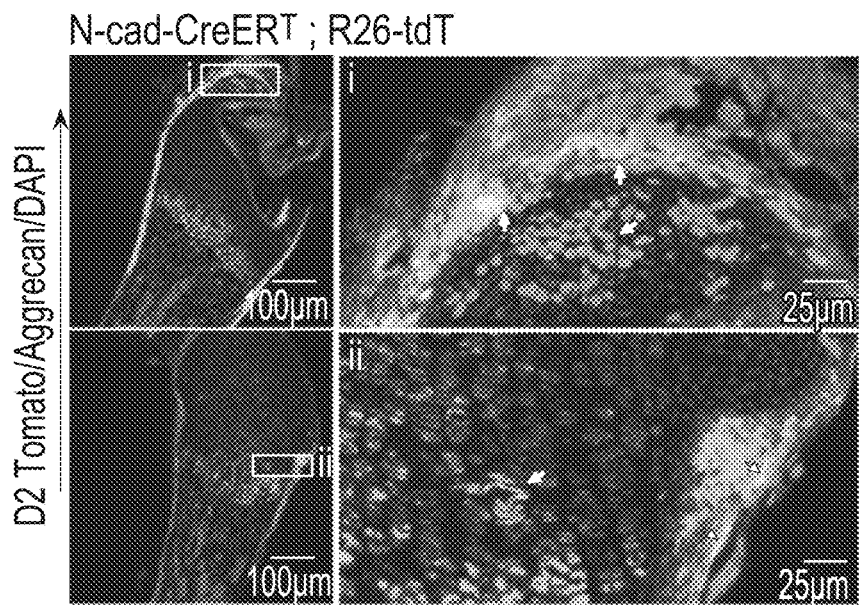
Figure 23E:
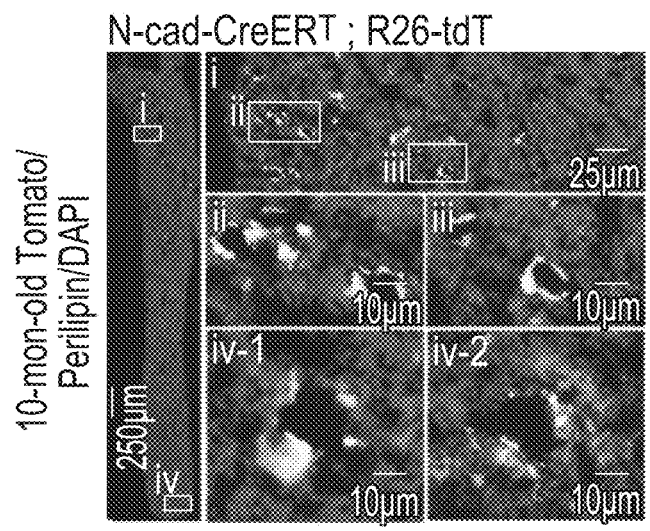
Figure 23F:
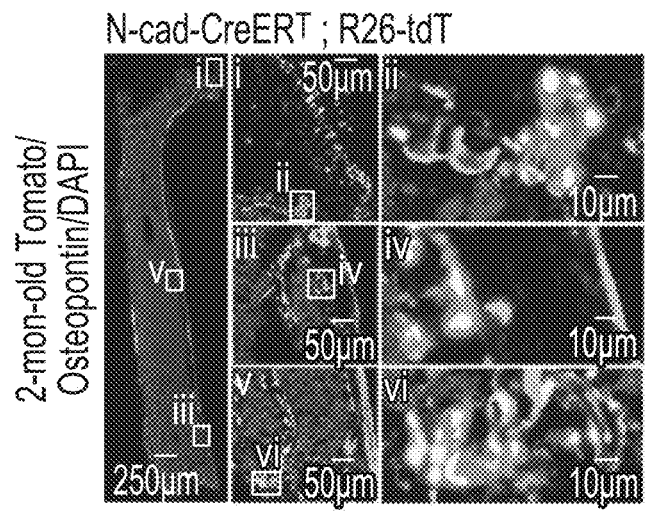
Figure 28A:
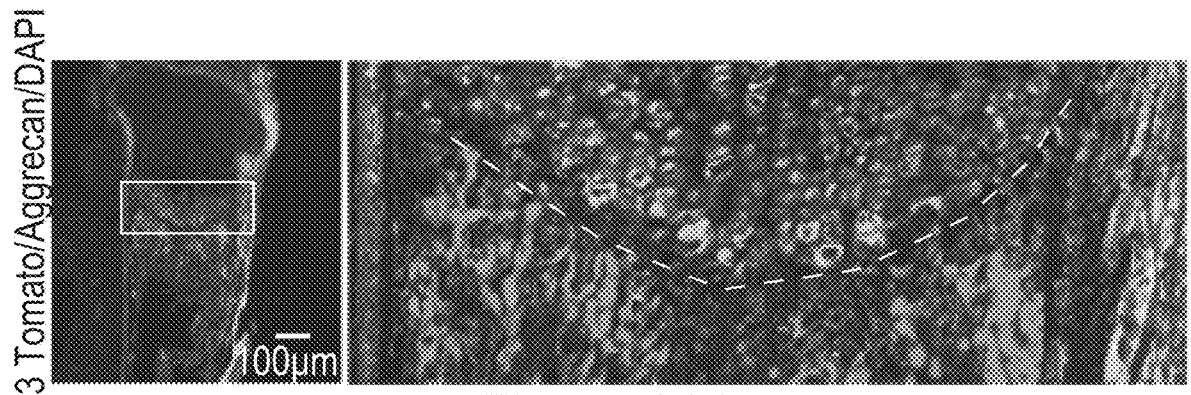
FIGS. 28A-28D: characterization of N-cad$^+$ MSCs from early development and in injury repair.
Figures 28B, 28C:
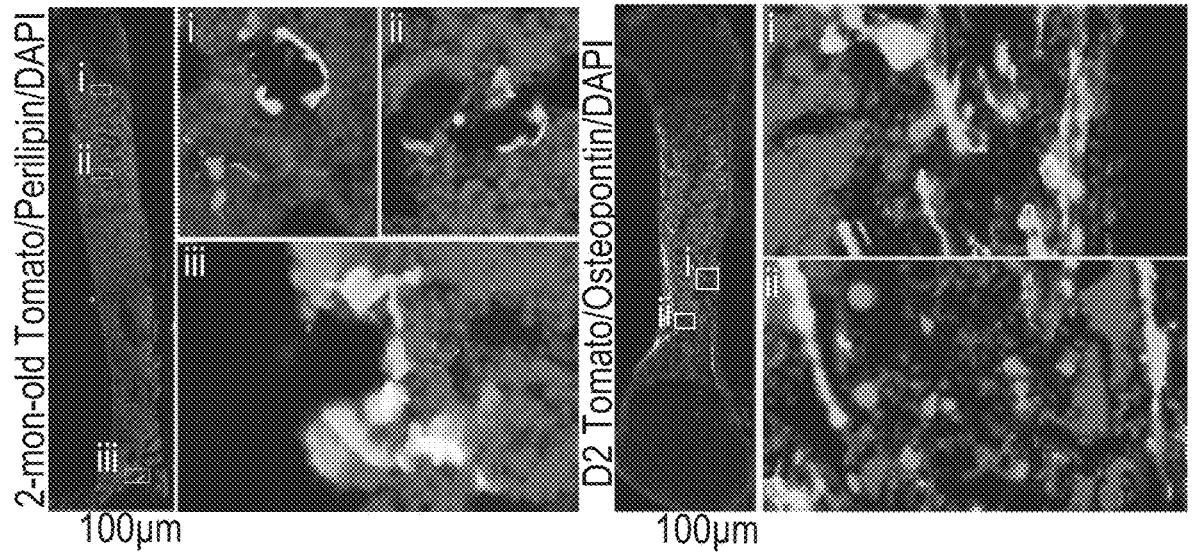

N-Cad$^+$ Stromal Cells Give Rise to Chondrocytes During Development and Post Injury Chondrogenesis is active in fetal development and rarely active in adulthood (Raghunath et al., 2005; Sophia Fox et al., 2009). In mice with TMX induction at postnatal day 2 (P2), no Tomato expression was detected among Aggrecan$^+$ chondrocytes in the femur of N-cad-CreER$^T$; R26-tdT mice (FIG. 28A) despite Tomato$^+$ osteoblasts and perichondrocytes being adjacent to the growth plate. After N-cad-CreER$^T$; R26-tdT mice were induced with TMX at 1 or 2 weeks when the growth plate develops, Tomato$^+$ chondrocytes in cartilages of femur or tibia remained undetectable (data not shown). TMX induction was started to N-cad-CreER$^T$; R26-tdT mice at embryonic stage E12.5, when MSCs were undergoing condensation and chondrocyte differentiation in the fetal bone (FIG. 23A). It was found that the majority of undifferentiated N-cad derived tdT$^+$ cells were located peripherally, with differentiated N-cad derived Tomato$^+$ chondrocytes located in the central region of the rib at E14.5 embryos (FIG. 23B). Importantly, in the trabecular region of femur at P2, N-cad derived chondrocytes were detected in both the columnar zone where the secondary ossification center forms, and in the superficial zone, which is imperative to resist the sheer force for deeper layer protection (FIG. 23C, D). Consistently, N-cad derived adipocytes were detected at 2 months and up until 10 months after birth (FIG. 23E, FIG. 28B), suggesting that N-cad$^+$ cells contributed to early and long-term adipogenesis during development. However, N-cad$^+$ cells derived Osteopontin$^+$ osteoblast and osteocyte were detected at 2 months after birth but not at early P2 (FIG. 23F, FIG. 28C). These data demonstrated that embryonic N-cad-derived cells gave rise to all three osteo-adipogenic-chondrogenic lineages, and only N-cad$^+$ at embryonic stage could efficiently form chondrocytes.

Figure 23G:
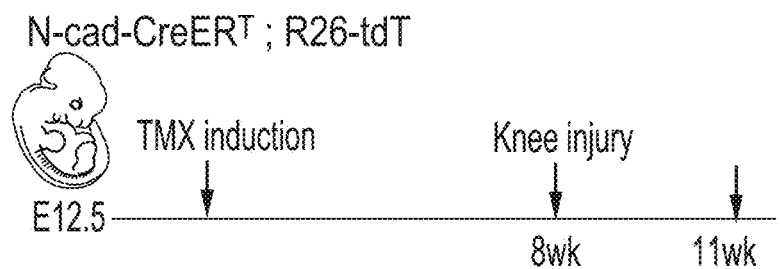
Figure 23H:
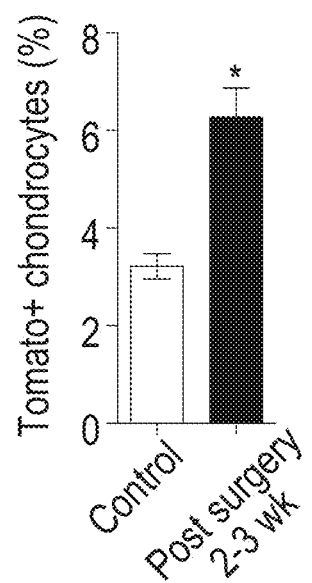
Figure 23I:
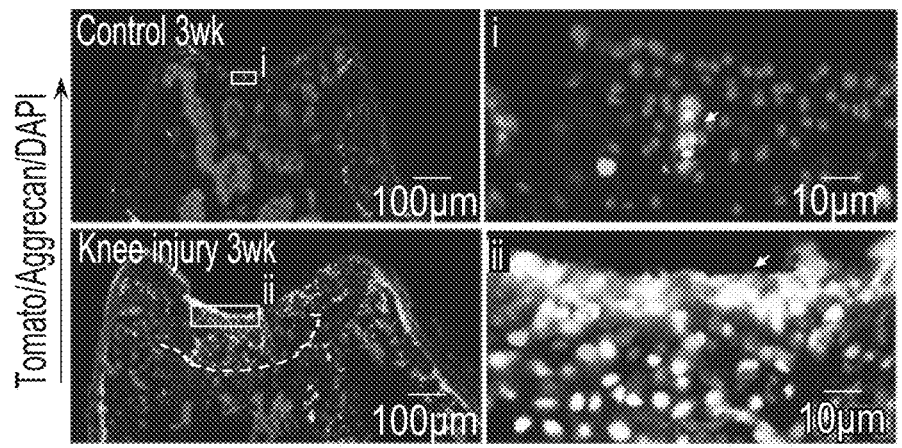
Figure 23J:
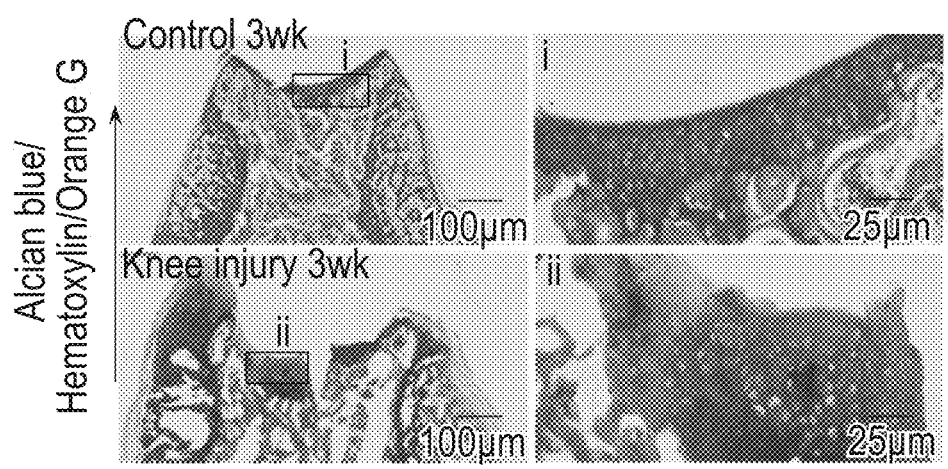
Figure 28D:
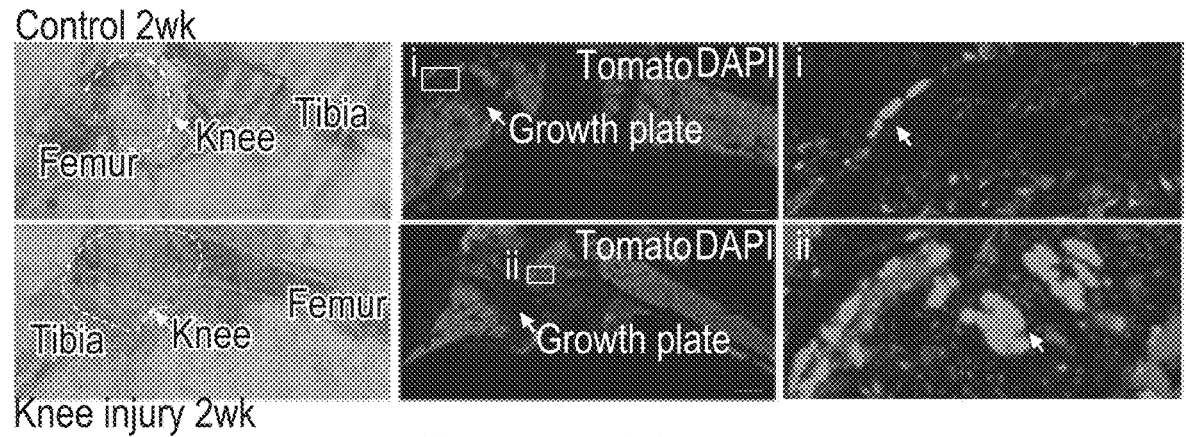

Whether N-cad$^+$ cell could generate chondrocytes in adult mice post injury was next investigated. Cartilage perforation was performed in N-cad-CreER$^T$; R26-tdT mice that received TMX induction at E12.5 (FIG. 23G). At 2 to 3 weeks post cartilage damage, we found that N-cad derived chondrocytes were clustered in the callus at the damage site with a 2-fold increase compared to undamaged control mice (FIG. 23H-I). The femorotibial joint was swollen due to articular cartilage damage in mice post-surgery (FIG. 28D). Alcian blue positive cells with a typical chondrocyte feature were dramatically increased in the post injury region (FIG. 23J), indicating that N-cad$^+$ MSCs quickly regenerated chondrocytes in response to injury.

Taken together, the data proved that N-cad-derived cells induced at the fetal stage (E12.5) could give rise to chondrocyte progenitor in adults and support chondrocyte regeneration in response to injury.

Discussion rHSCs vs. pHSCs

The heterogeneity of HSCs has been widely studied. HSCs can be maintained in either active, quiescent or deeply quiescent states. It is well known that the quiescence characterization of HSCs is functionally related to their long-term self-renewal potential (Foudi et al., 2008; Wilson et al., 2008). However, how the quiescent HSC population overcomes the consequence of myeloablation in vivo is an unanswered question. In spite of their quiescence, the majority of HSCs cannot survive chemotherapeutic stress such as 5FU (Longley et al., 2003). According to aspects herein, it was found that a small portion of the HSC subpopulation could survive 5FU treatment in primary mice and were resistant to 5FU treatment in transplantation model. Thus, this HSC subpopulation is defined as rHSCs, while other quiescent but chemotherapeutic sensitive HSC subpopulations are defined as pHSCs (Li and Clevers, 2010). Although both HSC subpopulations supported long-term hematopoiesis in transplantation experiments, pHSCs rarely gave rise to rHSCs, whereas the latter were able to give rise to pHSCs. Mechanistically, it was found that rHSCs have an attenuated DNA repair system compared to pHSCs during homeostasis, but rHSCs can quickly activate their DNA repair pathways and the stress-response program to survive chemotherapeutic stress, and support subsequent hematopoiesis to overcome the consequence of myeloablation.

Niche Matters in Term of Conferring Resistance to Chemotherapy

To explore an extrinsic mechanism underlying the chemoresistance of rHSCs, an idea was tested that they were preserved in a specific microenvironment in BM. Using whole mount HSC staining (Kunisaki et al., 2013), it was first observed that the bulk of HSCs were associated with vessels and MKs as previously reported. However, it was surprisingly found that the rHSCs were predominantly associated with the endosteal niche compared to pHSCs during homeostasis and post 5FU treatment. This indicated that the endosteal niche could form a distinct BM microenvironment to protect rHSCs from chemotherapeutic stress. Consistently, upon chemotherapeutic stress, most rHSCs were protected in the endosteal niche that enriches chemo-resistant N-cad$^+$ stromal cells, whereas the vessel and perivascular cells were sensitive to 5FU treatment, accounting for a large loss of pHSCs induced by chemotherapy. The whole mount HSC staining was done in sternum which has abundant bone branches and extensions inside the marrow. This feature makes it very similar to the trabecular bone region in the femur. The transplantation assay showing that depletion of N-cad$^+$ niche cells affected HSC maintenance, including rHSCs, supports this notion. HSC quiescence also correlated with their low metabolic state, which may be considered analogous to 'sleeping', and was termed as HSC dormancy or hibernation (Takubo et al., 2013; Wilson et al., 2008; Yamazaki et al., 2011). However, it was further showed according to aspects herein that quiescence was not the only mechanism underlying drug resistance; instead, both the intrinsic stress-response program and the extrinsic niche protection contributed to drug resistance.

Identity and Function of N-Cad Stromal Cell in HSC Maintenance in the BM Niche N-cad$^+$ stromal cells were the first identified HSC niche cells (Zhang et al., 2003) and confirmed by subsequent studies (Arai et al., 2004; Sugiyama et al., 2006). N-cad$^+$ cells were initially proposed as osteoblastic progenitor cells based on their endosteal location. According to apects herein, by using two reporter lines, it was found that N-cad$^+$ stromal cells were distributed in both endosteal region and perivascular sites. More intriguingly, it was found that the majority of N-cad$^+$ cells overlapped with LepR$^+$ cells and Pdgfra$^+$ cells. Transcriptional analysis showed that N-cad$^+$ cells, LepR$^+$ cells, Cxcl12-RFP (CAR) cells and Nestin-GFP cells had a very similar gene expression pattern. The data strongly indicated that the long-standing controversy of HSC niche concepts might very likely be due to different cell markers being used rather than to their cellular identities.

To determine the identity of N-Cad$^+$ stromal cells, their regional distribution was visualized relative to other known niche cells in the bone marrow using different niche reporter mice. N-Cad$^+$ stromal cells generated 72%±6% Col2.3-GFP$^+$ cells; however, 9.3%±4.7% N-cad$^+$Col2.3GFP$^-$ cells were also detected in the endosteal region. These immature cells accounted for the primitive MSCs, which could explain the insufficient efficiency of Col2.3-Cre genetic model in HSC niche function studies (Ding and Morrison, 2013; Ding et al., 2012; Greenbaum et al., 2013). Though both N-Cad-TdT$^+$ and Nestin-GFP$^+$ were enriched in the trabecular region, N-Cad-TdT$^+$ was concentrated in the trabecular region where engraftment of transplanted HSCs was detected as previously reported (Nilsson et al., 2001; Xie et al., 2009) and survived after stress as observed here. All these data indicated that although N-cad$^+$ cells share a similar transcriptome profile with other MSCs, their anatomic distribution may indicate their unique HSC niche function; indeed, it was shown that the N-cad$^+$ endosteal niche cell plays a critical role in preserving rHSCs.

By using an inducible DTR system, it was found that ablation of N-cad$^+$ cells eliminated both pHSCs and rHSCs in BM. This could be explained by the anatomical distribution of N-cad$^+$ niche cell in both endosteal and perivascular zones. Furthermore, it was shown that N-cad expression could be detected in a subset of HSCs; however, the N-cad-TdT reporter mouse lines did not support this observation (data not shown). This could be partially explained by the inconsistency between their protein and transcription levels, because another mouse line of N-cad-mCherry (fusion at protein level) indeed had a small subset of HSCs (CD49b$^-$CD34$^-$Flt2$^-$LSK) showing a low level of N-cad expression (primary observation). The functional transplantation data showed that ablation of N-cad$^+$ niche cells resulted in the reduced HSCs including rHSCs. By deletion of Cxcl12 and SCF from N-cad$^+$ cells, it was found N-cad$^+$ stromal cells contributed to HSC maintenance and regulation by producing these two factors. Overall, aspects herein demonstrate that N-cad$^+$ stromal cells function as MSCs and support primitive HSC maintenance, especially under stress.

Transplantation of hematopoietic stem cells (HSCs) from human umbilical cord blood (hUCB) holds great promise for treating a broad spectrum of hematological disorders including cancer, but the limited number of HSCs in a single hUCB unit can restrict its widespread use. Although extensive efforts have developed multiple methods for ex vivo expansion of human HSCs by targeting single molecules or pathways, it has been unknown whether simultaneously manipulating a large number of targets essential for stem cell self-renewal could be achievable. Recent studies have emerged that $N^6$-methyladenosine ($m^6A$) modulates expression of a group of mRNAs critical for stem cell fate determination by influencing their stability. Among several $m^6A$ readers, Ythdf2 is well recognized to promote the targeted mRNA decay. However, the physiological functions of Ythdf2 on adult stem cells are still elusive. Embodiments herein demonstrate that conditional knockout (KO) mouse Ythdf2 increased phenotypic and functional HSC numbers, but neither skewed lineage differentiation nor led to hematopoietic malignancies. Furthermore, knockdown (KD) of human YTHDF2 led to over 10-fold increase in ex vivo expansion of hUCB HSCs, 5-fold increase in colony-forming units (CFUs), and more than 8-fold increase in functional hUCB HSCs in the 2 rounds of limiting dilution transplantation assay. Mechanistically, $m^6A$ mapping of RNAs from mouse hematopoietic stem and progenitor cells (HSPCs) as well as from hUCB HSCs revealed $m^6A$ enrichment on mRNAs encoding transcription factors critical for stem cell self-renewal. These $m^6A$-marked mRNAs were recognized by Ythdf2 and underwent mRNA decay. In Ythdf2 KO HSPCs and YTHDF2 KD hUCB HSCs, these mRNAs were stabilized, leading to an increase in protein levels and facilitating HSC expansion which can be rescued by knockdown the mRNA, such as Tal1 mRNA. Therefore, embodiments show the function of Ythdf2 in adult stem cells maintenance and identify an important role of Ythdf2 in regulating HSC ex vivo expansion via the mechanism of controlling the stability of multiple mRNAs critical for HSC self-renewal, thus having a strong potential for future clinical applications.

Furthermore, regulation of hematopoietic stem cells (HSCs) by the bone marrow (BM) niches has been substantially studied, however, whether and how HSC subpopulations are distinctively regulated by different BM niches remain largely unclear. Here, reserve HSCs (rHSCs) have been functionally distinguished from primed HSCs (pHSCs) and their respective BM niches have been further examined. It has been found that both pHSCs and rHSCs could support long-term hematopoiesis under homeostasis; however, pHSCs were sensitive to chemotherapy, whereas rHSCs survived chemotherapy and supported subsequent regeneration after myeloablation. The whole-mount HSC distribution study revealed that rHSCs were preferentially maintained in the endosteal region that enriches N-cadherin$^+$ bone-lining cells during homeostasis and post-chemotherapy. pHSCs were predominantly associated with blood vessels which were vulnerable to chemotherapy compared to bone. Transcriptome profiling and in vivo lineage tracing results showed N-cadherin$^+$ stromal cells to be functional mesenchymal stem cells, which gave rise to osteoblasts, adipocytes, and chondrocytes during development and regeneration. Finally, it was demonstrated that ablation of N-cadherin$^+$ niche cells or deletion of either Scf or Cxcl12 from N-cadherin$^+$ niche cells affected HSC number and maintenance.

Example C

Expansion of CAR-T Cells Using shRNA

The effect of manipulating Ythdf2 on the expansion of CAR-T cells is being assessed using lentivirus driven human Ythdf2 shRNAs. Successful cloning of YTHDF2 shRNA in a CAR-T lentivector has occurred. The lentivirus has been used to infect human CAR-T cells, and the expansion of the human CAR-T cells is in progress. The expansion is expected to take days to weeks for results. It is believed that significantly enhanced expansion will be demonstrated in the lentivirus-infected CAR-T cell population as compared to a CAR-T control population.

All sequencing data, including the $m^6A$-seq, irCLIP-seq and RNA-seq datasets, are available through the Gene Expression Ombibus (GEO) under accession GSE107957. Original Data Repository at www.stowers.org/research/publications/LIBPB-1248.

REFERENCES

The following references, to the extent that they provide exemplary procedural or other details supplementary to those set forth herein, are specifically incorporated herein by reference.

1. Li, L. & Clevers, H. Coexistence of quiescent and active adult stem cells in mammals. *Science* 327, 542-545 (2010).
2. Weissman, I. L. Stem cells: units of development, units of regeneration, and units in evolution. *Cell* 100, 157-168 (2000).
3. Walasek, M. A., van Os, R. & de Haan, G. Hematopoietic stem cell expansion: challenges and opportunities. *Annals of the New York Academy of Sciences* 1266, 138-150 (2012).
4. Sung, A. D. & Chao, N. J. Concise review: acute graft-versus-host disease: immunobiology, prevention, and treatment. *Stem cells translational medicine* 2, 25-32 (2013).
5. Shlomchik, W. D. Graft-versus-host disease. *Nature reviews. Immunology* 7, 340-352 (2007).
6. Huang, X. et al. Activation of OCT4 enhances ex vivo expansion of human cord blood hematopoietic stem and progenitor cells by regulating HOXB4 expression. *Leukemia* 30, 144-153 (2016).
7. Boitano, A. E. et al. Aryl hydrocarbon receptor antagonists promote the expansion of human hematopoietic stem cells. *Science* 329, 1345-1348 (2010).
8. Fares, I. et al. Cord blood expansion. Pyrimidoindole derivatives are agonists of human hematopoietic stem cell self-renewal. *Science* (New York, N.Y 345, 1509-1512 (2014).
9. Amsellem, S. et al. Ex vivo expansion of human hematopoietic stem cells by direct delivery of the HOXB4 homeoprotein. *Nature medicine* 9, 1423-1427 (2003).
10. Antonchuk, J., Sauvageau, G. & Humphries, R. K. HOXB4-induced expansion of adult hematopoietic stem cells ex vivo. *Cell* 109, 39-45 (2002).
11. Rentas, S. et al. Musashi-2 attenuates AHR signalling to expand human haematopoietic stem cells. *Nature* 532, 508-511 (2016).
12. Himburg, H. A. et al. Pleiotrophin regulates the expansion and regeneration of hematopoietic stem cells. *Nature medicine* 16, 475-482 (2010).
13. North, T. E. et al. Prostaglandin E2 regulates vertebrate haematopoietic stem cell homeostasis. *Nature* 447, 1007-1011 (2007).
14. Varnum-Finney, B. et al. Pluripotent, cytokine-dependent, hematopoietic stem cells are immortalized by constitutive Notch1 signaling. *Nature medicine* 6, 1278-1281 (2000).
15. Chou, S., Flygare, J. & Lodish, H. F. Fetal hepatic progenitors support long-term expansion of hematopoietic stem cells. *Experimental hematology* 41, 479-490 e474 (2013).
16. Guo, B., Huang, X., Lee, M. R., Lee, S. A. & Broxmeyer, H. E. Antagonism of PPAR-gamma signaling expands human hematopoietic stem and progenitor cells by enhancing glycolysis. *Nature medicine* 24, 360-367 (2018).
17. Zhao, B. S., Roundtree, I. A. & He, C. Post-transcriptional gene regulation by mRNA modifications. *Nature reviews. Molecular cell biology* 18, 31-42 (2017).

18 Roundtree, I. A., Evans, M. E., Pan, T. & He, C. Dynamic RNA Modifications in Gene Expression Regulation. *Cell* 169, 1187-1200 (2017).
19 Li, S. & Mason, C. E. The pivotal regulatory landscape of RNA modifications. *Annual review of genomics and human genetics* 15, 127-150 (2014).
20 Batista, P. J. et al. m(6)A RNA modification controls cell fate transition in mammalian embryonic stem cells. *Cell stem cell* 15, 707-719 (2014).
21 Geula, S. et al. Stem cells. m6A mRNA methylation facilitates resolution of naive pluripotency toward differentiation. *Science* 347, 1002-1006 (2015).
22 Yoon, K. J. et al. Temporal Control of Mammalian Cortical Neurogenesis by m6A Methylation. *Cell* 171, 877-889 (2017).
23 Zhang, C. et al. m6A modulates haematopoietic stem and progenitor cell specification. *Nature* 549, 273-276 (2017).
24 Zhao, B. S. et al. m6A-dependent maternal mRNA clearance facilitates zebrafish maternal-to-zygotic transition. *Nature* 542, 475-478 (2017).
25 Li, Z. et al. FTO Plays an Oncogenic Role in Acute Myeloid Leukemia as a N6-Methyladenosine RNA Demethylase. *Cancer cell* 31, 127-141 (2017).
26 Vu, L. P. et al. The N6-methyladenosine (m6A)-forming enzyme METTL3 controls myeloid differentiation of normal hematopoietic and leukemia cells. *Nature medicine* 23, 1369-1376 (2017).
27 Weng, H. et al. METTL14 Inhibits Hematopoietic Stem/Progenitor Differentiation and Promotes Leukemogenesis via mRNA m(6)A Modification. *Cell stem cell* 22, 191-205 e199 (2018).
28 Barbieri, I. et al. Promoter-bound METTL3 maintains myeloid leukaemia by m(6)A-dependent translation control. *Nature* 552, 126-131 (2017).
29 Wang, X. et al. N6-methyladenosine-dependent regulation of messenger RNA stability. *Nature* 505, 117-120 (2014).
30 Meyer, K. D. et al. Comprehensive analysis of mRNA methylation reveals enrichment in 3' UTRs and near stop codons. *Cell* 149, 1635-1646 (2012).
31 Schwartz, S. et al. High-resolution mapping reveals a conserved, widespread, dynamic mRNA methylation program in yeast meiosis. *Cell* 155, 1409-1421 (2013).
32 Dominissini, D. et al. Topology of the human and mouse m6A RNA methylomes revealed by m6A-seq. *Nature* 485, 201-206 (2012).
33 Wang, Z., Li, G., Tse, W. & Bunting, K. D. Conditional deletion of STAT5 in adult mouse hematopoietic stem cells causes loss of quiescence and permits efficient nonablative stem cell replacement. *Blood* 113, 4856-4865 (2009).
34 Ebina, W. & Rossi, D. J. Transcription factor-mediated reprogramming toward hematopoietic stem cells. *The EMBO journal* 34, 694-709 (2015).
35 Orkin, S. H. & Zon, L. I. Hematopoiesis: an evolving paradigm for stem cell biology. *Cell* 132, 631-644 (2008).
36 de Pater, E. et al. Gata2 is required for HSC generation and survival. *The Journal of experimental medicine* 210, 2843-2850 (2013).
37 Hock, H. et al. Tel/Etv6 is an essential and selective regulator of adult hematopoietic stem cell survival. *Genes & development* 18, 2336-2341 (2004).
38 Lim, K. C. et al. Conditional Gata2 inactivation results in HSC loss and lymphatic mispatterning. *The Journal of clinical investigation* 122, 3705-3717 (2012).
39 Reynaud, D. et al. SCL/TAL1 expression level regulates human hematopoietic stem cell self-renewal and engraftment. *Blood* 106, 2318-2328 (2005).
40 Kato, Y. et al. Selective activation of STAT5 unveils its role in stem cell self-renewal in normal and leukemic hematopoiesis. *The Journal of experimental medicine* 202, 169-179 (2005).
41 Li, H. B. et al. m6A mRNA methylation controls T cell homeostasis by targeting the IL-7/STAT5/SOCS pathways. *Nature* 548, 338-342 (2017).
42 Pinto do, O. P., Kolterud, A. & Carlsson, L. Expression of the LIM-homeobox gene LH2 generates immortalized steel factor-dependent multipotent hematopoietic precursors. *The EMBO journal* 17, 5744-5756 (1998).
43 Zarnegar, B. J. et al. irCLIP platform for efficient characterization of protein-RNA interactions. *Nature methods* 13, 489-492 (2016).
44 Sheth, U. & Parker, R. Decapping and decay of messenger RNA occur in cytoplasmic processing bodies. *Science* 300, 805-808 (2003).
45 Kedersha, N. & Anderson, P. Mammalian stress granules and processing bodies. *Methods in enzymology* 431, 61-81 (2007).
46 Lacombe, J. et al. Scl regulates the quiescence and the long-term competence of hematopoietic stem cells. *Blood* 115, 792-803 (2010).
47 Galan-Caridad, J. M. et al. Zfx controls the self-renewal of embryonic and hematopoietic stem cells. *Cell* 129, 345-357 (2007).
48 Zheng, G. et al. ALKBH5 is a mammalian RNA demethylase that impacts RNA metabolism and mouse fertility. *Molecular cell* 49, 18-29 (2013).
49 Zhou, J. et al. Dynamic m(6)A mRNA methylation directs translational control of heat shock response. *Nature* 526, 591-594 (2015).
50 Alarcon, C. R. et al. HNRNPA2B1 Is a Mediator of m(6)A-Dependent Nuclear RNA Processing Events. *Cell* 162, 1299-1308 (2015).
51 Zhang, S. et al. m6A Demethylase ALKBH5 Maintains Tumorigenicity of Glioblastoma Stem-like Cells by Sustaining FOXM1 Expression and Cell Proliferation Program. *Cancer cell* 31, 591-606 e596 (2017).
52 Lence, T. et al. m6A modulates neuronal functions and sex determination in Drosophila. *Nature* 540, 242-247 (2016).
53 Haussmann, I. U. et al. m6A potentiates Sxl alternative pre-mRNA splicing for robust *Drosophila* sex determination. *Nature* 540, 301-304 (2016).
54 Chen, T. et al. m(6)A RNA methylation is regulated by microRNAs and promotes reprogramming to pluripotency. *Cell stem cell* 16, 289-301 (2015).
55 Alarcon, C. R., Lee, H., Goodarzi, H., Halberg, N. & Tavazoie, S. F. N6-methyladenosine marks primary microRNAs for processing. *Nature* 519, 482-485 (2015).
56 Xiao, W. et al. Nuclear m(6)A Reader YTHDC1 Regulates mRNA Splicing. *Molecular cell* 61, 507-519 (2016).
57 Wojtas, M. N. et al. Regulation of m6A Transcripts by the 3'->5' RNA Helicase YTHDC2 Is Essential for a Successful Meiotic Program in the Mammalian Germline. *Molecular cell* 68, 374-387 e312 (2017).
58 Ivanova, I. et al. The RNA m6A Reader YTHDF2 Is Essential for the Post-transcriptional Regulation of the Maternal Transcriptome and Oocyte Competence. *Molecular cell* 67, 1059-1067 e1054 (2017).
59 Fustin, J. M. et al. RNA-methylation-dependent RNA processing controls the speed of the circadian clock. *Cell* 155, 793-806 (2013).

60 Slobodin, B. et al. Transcription Impacts the Efficiency of mRNA Translation via Co-transcriptional N6-adenosine Methylation. *Cell* 169, 326-337 e312 (2017).

61 Schwartz, S. et al. Transcriptome-wide mapping reveals widespread dynamic-regulated pseudouridylation of ncRNA and mRNA. *Cell* 159, 148-162 (2014).

62 Pendleton, K. E. et al. The U6 snRNA m6A Methyltransferase METTL16 Regulates SAM Synthetase Intron Retention. *Cell* 169, 824-835 e814 (2017).

63 Shi, H. et al. YTHDF3 facilitates translation and decay of N6-methyladenosine-modified RNA. *Cell research* 27, 315-328 (2017).

64 Huang, H. et al. Recognition of RNA N(6)-methyladenosine by IGF2BP proteins enhances mRNA stability and translation. *Nature cell biology* 20, 285-295 (2018).

65 Bertero, A. et al. The SMAD2/3 interactome reveals that TGFbeta controls m(6)A mRNA methylation in pluripotency. *Nature* (2018).

66 Liu, N. et al. N(6)-methyladenosine-dependent RNA structural switches regulate RNA-protein interactions. *Nature* 518, 560-564 (2015).

67 Joseph, C. et al. Deciphering hematopoietic stem cells in their niches: a critical appraisal of genetic models, lineage tracing, and imaging strategies. *Cell stem cell* 13, 520-533 (2013).

68 Barbieri, I. et al. Promoter-bound METTL3 maintains myeloid leukaemia by m(6)A-dependent translation control. *Nature* (2017).

69 He, S., Nakada, D. & Morrison, S. J. Mechanisms of stem cell self-renewal. *Annual review of cell and developmental biology* 25, 377-406 (2009).

70 Qian, P. et al. The Dlk1-Gtl2 Locus Preserves LT-HSC Function by Inhibiting the PI3K-mTOR Pathway to Restrict Mitochondrial Metabolism. *Cell stem cell* 18, 214-228 (2016).

71 He, X. C. et al. Homing and migration assays of hematopoietic stem/progenitor cells. *Methods in molecular biology* 1185, 279-284 (2014).

72 Hu, Y. & Smyth, G. K. ELDA: extreme limiting dilution analysis for comparing depleted and enriched populations in stem cell and other assays. *Journal of immunological methods* 347, 70-78 (2009).

73 Purton, L. E. & Scadden, D. T. Limiting factors in murine hematopoietic stem cell assays. *Cell stem cell* 1, 263-270 (2007).

74 Perry, J. M. et al. Cooperation between both Wnt/{beta}-catenin and PTEN/PI3K/Akt signaling promotes primitive hematopoietic stem cell self-renewal and expansion. *Genes & development* 25, 1928-1942 (2011).

75 Simsek, D. et al. The Mammalian Ribo-interactome Reveals Ribosome Functional Diversity and Heterogeneity. *Cell* 169, 1051-1065 e1018 (2017).

76 Acar, M., Kocherlakota, K. S., Murphy, M. M., Peyer, J. G., Oguro, H., Inra, C. N., Jaiyeola, C., Zhao, Z., Luby-Phelps, K., and Morrison, S. J. (2015). Deep imaging of bone marrow shows non-dividing stem cells are mainly perisinusoidal. Nature 526, 126-130.

77 Arai, F., Hirao, A., Ohmura, M., Sato, H., Matsuoka, S., Takubo, K., Ito, K., Koh, G. Y., and Suda, T. (2004). Tie2/angiopoietin-1 signaling regulates hematopoietic stem cell quiescence in the bone marrow niche. Cell 118, 149-161.

78 Beerman, I., Seita, J., Inlay, M. A., Weissman, I. L., and Rossi, D. J. (2014). Quiescent hematopoietic stem cells accumulate DNA damage during aging that is repaired upon entry into cell cycle. Cell stem cell 15, 37-50.

79 Benveniste, P., Frelin, C., Janmohamed, S., Barbara, M., Herrington, R., Hyam, D., and Iscove, N. N. (2010). Intermediate-term hematopoietic stem cells with extended but time-limited reconstitution potential. Cell stem cell 6, 48-58.

80 Benz, C., Copley, M. R., Kent, D. G., Wohrer, S., Cortes, A., Aghaeepour, N., Ma, E., Mader, H., Rowe, K., Day, C., et a!. (2012). Hematopoietic stem cell subtypes expand differentially during development and display distinct lymphopoietic programs. Cell stem cell 10, 273-283.

81 Bowers, M., Zhang, B., Ho, Y., Agarwal, P., Chen, C. C., and Bhatia, R. (2015). Osteoblast ablation reduces normal long-term hematopoietic stem cell self-renewal but accelerates leukemia development. Blood 125, 2678-2688.

82 Bruns, I., Lucas, D., Pinho, S., Ahmed, J., Lambert, M. P., Kunisaki, Y., Scheiermann, C., Schiff, L., Poncz, M., Bergman, A., et a!. (2014). Megakaryocytes regulate hematopoietic stem cell quiescence through CXCL4 secretion. Nat Med 20, 1315-1320.

83 Calvi, L. M., Adams, G. B., Weibrecht, K. W., Weber, J. M., Olson, D. P., Knight, M. C., Martin, R. P., Schipani, E., Divieti, P., Bringhurst, F. R., et a!. (2003). Osteoblastic cells regulate the haematopoietic stem cell niche. Nature 425, 841-846.

84 Chen, J. Y., Miyanishi, M., Wang, S. K., Yamazaki, S., Sinha, R., Kao, K. S., Seita, J., Sahoo, D., Nakauchi, H., and Weissman, I. L. (2016). Hoxb5 marks long-term haematopoietic stem cells and reveals a homogenous perivascular niche. Nature 530, 223-227.

85 Dacic, S., Kalajzic, I., Visnjic, D., Lichtler, A. C., and Rowe, D. W. (2001). Col1a1-driven transgenic markers of osteoblast lineage progression. J Bone Miner Res 16, 1228-1236.

86 Ding, L., and Morrison, S. J. (2013). Haematopoietic stem cells and early lymphoid progenitors occupy distinct bone marrow niches. Nature 495, 231-235.

87 Ding, L., Saunders, T. L., Enikolopov, G., and Morrison, S. J. (2012). Endothelial and perivascular cells maintain haematopoietic stem cells. Nature 481, 457-462.

88 Dominici, M., Rasini, V., Bussolari, R., Chen, X., Hofmann, T. J., Spano, C., Bernabei, D., Veronesi, E., Bertoni, F., Paolucci, P., et a!. (2009). Restoration and reversible expansion of the osteoblastic hematopoietic stem cell niche after marrow radioablation. Blood 114, 2333-2343.

89 Fleming, W. H., Alpern, E. J., Uchida, N., Ikuta, K., Spangrude, G. J., and Weissman, I. L. (1993). Functional heterogeneity is associated with the cell cycle status of murine hematopoietic stem cells. The Journal of cell biology 122, 897-902.

90 Foudi, A., Hochedlinger, K., Van Buren, D., Schindler, J. W., Jaenisch, R., Carey, V., and Hock, H. (2008). Analysis of histone 2B-GFP retention reveals slowly cycling hematopoietic stem cells. Nature biotechnology.

91 Gazit, R., Mandal, P. K., Ebina, W., Ben-Zvi, A., Nombela-Arrieta, C., Silberstein, L. E., and Rossi, D. J. (2014). Fgd5 identifies hematopoietic stem cells in the murine bone marrow. *The Journal of experimental medicine* 211, 1315-1331.

92 Greenbaum, A., Hsu, Y. M., Day, R. B., Schuettpelz, L. G., Christopher, M. J., Borgerding, J. N., Nagasawa, T., and Link, D. C. (2013). CXCL12 in early mesenchymal progenitors is required for haematopoietic stem-cell maintenance. Nature 495, 227-230.

93 Haug, J. S., He, X. C., Grindley, J. C., Wunderlich, J. P., Gaudenz, K., Ross, J. T., Paulson, A., Wagner, K. P., Xie, Y., Zhu, R., et a!. (2008). N-cadherin expression level distinguishes reserved versus primed states of hematopoietic stem cells. Cell stem cell 2, 367-379.

94 Hooper, A. T., Butler, J. M., Nolan, D. J., Kranz, A., Iida, K., Kobayashi, M., Kopp, H. G., Shido, K., Petit, I., Yanger, K., et a!. (2009). Engraftment and reconstitution of hematopoiesis is dependent on VEGFR2-mediated regeneration of sinusoidal endothelial cells. Cell Stem Cell 4, 263-274.

95 Itkin, T., Gur-Cohen, S., Spencer, J. A., Schajnovitz, A., Ramasamy, S. K., Kusumbe, A. P., Ledergor, G., Jung, Y., Milo, I., Poulos, M. G., et a!. (2016). Corrigendum: Distinct bone marrow blood vessels differentially regulate haematopoiesis. Nature 538, 274.

96 Kiel, M. J., Yilmaz, O. H., Iwashita, T., Terhorst, C., and Morrison, S. J. (2005). SLAM family receptors distinguish hematopoietic stem and progenitor cells and reveal endothelial niches for stem cells. Cell 121, 1109-1121.

97 Kunisaki, Y., Bruns, I., Scheiermann, C., Ahmed, J., Pinho, S., Zhang, D., Mizoguchi, T., Wei, Q., Lucas, D., Ito, K., et a!. (2013). Arteriolar niches maintain haematopoietic stem cell quiescence. Nature.

98 Lerner, C., and Harrison, D. E. (1990). 5-Fluorouracil spares hemopoietic stem cells responsible for longterm repopulation. Experimental hematology 18, 114-118.

99 Li, L., and Clevers, H. (2010). Coexistence of quiescent and active adult stem cells in mammals. Science (New York, NY 327, 542-545.

100 Longley, D. B., Harkin, D. P., and Johnston, P. G. (2003). 5-fluorouracil: mechanisms of action and clinical strategies. Nature reviews Cancer 3, 330-338.

101 Mendelson, A., and Frenette, P. S. (2014). Hematopoietic stem cell niche maintenance during homeostasis and regeneration. Nat Med 20, 833-846.

102 Mendez-Ferrer, S., Michurina, T. V., Ferraro, F., Mazloom, A. R., Macarthur, B. D., Lira, S. A., Scadden, D. T., Ma'ayan, A., Enikolopov, G. N., and Frenette, P. S. (2010). Mesenchymal and haematopoietic stem cells form a unique bone marrow niche. Nature 466, 829-834.

103 Morita, Y., Ema, H., and Nakauchi, H. (2010). Heterogeneity and hierarchy within the most primitive hematopoietic stem cell compartment. The Journal of experimental medicine 207, 1173-1182. Morrison, S. J., and Scadden, D. T. (2014). The bone marrow niche for haematopoietic stem cells. Nature 505, 327-334.

104 Nilsson, S. K., Johnston, H. M., and Coverdale, J. A. (2001). Spatial localization of transplanted hemopoietic stem cells: inferences for the localization of stem cell niches. Blood 97, 2293-2299.

105 Park, B., Nguyen, N. T., Dutt, P., Merdek, K. D., Bashar, M., Sterpetti, P., Tosolini, A., Testa, J. R., and Toksoz, D. (2002). Association of Lbc Rho guanine nucleotide exchange factor with alpha-catenin-related protein, alpha-catulin/CTNNAL1, supports serum response factor activation. The Journal of biological chemistry 277, 45361-45370.

106 Qian, P., He, X. C., Paulson, A., Li, Z., Tao, F., Perry, J. M., Guo, F., Zhao, M., Zhi, L., Venkatraman, A., et a!. (2015). The Dlk1-Gt12 Locus Preserves LT-HSC Function by Inhibiting the PI3K-mTOR Pathway to Restrict Mitochondrial Metabolism. Cell stem cell.

107 Raghunath, J., Salacinski, H. J., Sales, K. M., Butler, P. E., and Seifalian, A. M. (2005). Advancing cartilage tissue engineering: the application of stem cell technology. Current opinion in biotechnology 16, 503509.

108 Rodina, A., Wang, T., Yan, P., Gomes, E. D., Dunphy, M. P., Pillarsetty, N., Koren, J., Gerecitano, J. F., Taldone, T., Zong, H., et a!. (2016). The epichaperome is an integrated chaperome network that facilitates tumour survival. Nature 538, 397-401.

109 Sanjuan-Pla, A., Macaulay, I. C., Jensen, C. T., Woll, P. S., Luis, T. C., Mead, A., Moore, S., Carella, C., Matsuoka, S., Jones, T. B., et a!. (2013). Platelet-biased stem cells reside at the apex of the haematopoietic stem-cell hierarchy. Nature.

110 Scadden, D. T. (2014). Nice Neighborhood: Emerging Concepts of the Stem Cell Niche. Cell 157, 41-50. Schofield, R. (1978). The relationship between the spleen colony-forming cell and the haemopoietic stem cell. Blood Cells 4, 7-25.

111 Sophia Fox, A. J., Bedi, A., and Rodeo, S. A. (2009). The basic science of articular cartilage: structure, composition, and function. Sports health 1, 461-468.

112 Sugimura, R., He, X. C., Venkatraman, A., Arai, F., Box, A., Semerad, C., Haug, J. S., Peng, L., Zhong, X. B., Suda, T., et a!. (2012). Noncanonical Wnt signaling maintains hematopoietic stem cells in the niche. Cell 150, 351-365.

113 Sugiyama, T., Kohara, H., Noda, M., and Nagasawa, T. (2006). Maintenance of the hematopoietic stem cell pool by CXCL12-CXCR4 chemokine signaling in bone marrow stromal cell niches. Immunity 25, 977988.

114 Takubo, K., Nagamatsu, G., Kobayashi, C. I., Nakamura-Ishizu, A., Kobayashi, H., Ikeda, E., Goda, N., Rahimi, Y., Johnson, R. S., Soga, T., et a!. (2013). Regulation of glycolysis by pdk functions as a metabolic checkpoint for cell cycle quiescence in hematopoietic stem cells. Cell stem cell 12, 49-61.

115 Venkatraman, A., He, X. C., Thorvaldsen, J. L., Sugimura, R., Perry, J. M., Tao, F., Zhao, M., Christenson, M. K., Sanchez, R., Yu, J. Y., et a!. (2013). Maternal-imprinting at H19-Igf2 locus maintains adult hematopoietic stem cell quiescence. Nature 500, 345-349.

116 Wagers, A. J., and Weissman, I. L. (2005). Differential expression of {alpha}2 integrin separates long-term and short-term reconstituting Lin−/loThy1.1loc−kit+Sca-1+ hematopoietic stem cells. Stem cells (Dayton, Ohio). Walter, D., Lier, A., Geiselhart, A., Thalheimer, F. B., Huntscha, S., Sobotta, M. C., Moehrle, B., Brocks, D., Bayindir, I., Kaschutnig, P., et a!. (2015). Exit from dormancy provokes DNA-damage-induced attrition in haematopoietic stem cells. Nature 520, 549-552.

117 Weissman, I. L. (2000). Stem cells: units of development, units of regeneration, and units in evolution. Cell 100, 157-168.

118 Wilson, A., Laurenti, E., Oser, G., van der Wath, R. C., Blanco-Bose, W., Jaworski, M., Offner, S., Dunant, C. F., Eshkind, L., Bockamp, E., et a!. (2008). Hematopoietic Stem Cells Reversibly Switch from Dormancy to Self-Renewal during Homeostasis and Repair. Cell 135, 1118-1129.

119 Xie, Y., Yin, T., Wiegraebe, W., He, X. C., Miller, D., Stark, D., Perko, K., Alexander, R., Schwartz, J., Grindley, J. C., et a!. (2009). Detection of functional haematopoietic stem cell niche using real-time imaging. Nature 457, 97-101.

120 Yamazaki, S., Ema, H., Karlsson, G., Yamaguchi, T., Miyoshi, H., Shioda, S., Taketo, M. M., Karlsson, S., Iwama, A., and Nakauchi, H. (2011). Nonmyelinating schwann cells maintain hematopoietic stem cell hibernation in the bone marrow niche. Cell 147, 1146-1158.

121 Yang, G., Zhu, L., Hou, N., Lan, Y., Wu, X. M., Zhou, B., Teng, Y., and Yang, X. (2014). Osteogenic fate of hypertrophic chondrocytes. Cell research 24, 1266-1269.

122 Yang, L., Bryder, D., Adolfsson, J., Nygren, J., Mansson, R., Sigvardsson, M., and Jacobsen, S. E. (2005). Identification of Lin(−)Sca1(+)kit(+)CD34(+)Flt3− short-term hematopoietic stem cells capable of rapidly reconstituting and rescuing myeloablated transplant recipients. Blood 105, 2717-2723.

123 Zhang, J., Niu, C., Ye, L., Huang, H., He, X., Tong, W. G., Ross, J., Haug, J., Johnson, T., Feng, J. Q., et al. (2003). Identification of the haematopoietic stem cell niche and control of the niche size. Nature 425, 836-841.

124 Zhao, M., Perry, J. M., Marshall, H., Venkatraman, A., Qian, P., He, X. C., Ahamed, J., and Li, L. (2014). Megakaryocytes maintain homeostatic quiescence and promote post-injury regeneration of hematopoietic stem cells. Nat Med 20, 1321-1326.

125 Zhou, B. O., Yu, H., Yue, R., Zhao, Z., Rios, J. J., Naveiras, O., and Morrison, S. J. (2017). Bone marrow adipocytes promote the regeneration of stem cells and haematopoiesis by secreting SCF. Nature cell biology 19, 891-903.

126 Zhou, F., Li, X., Wang, W., Zhu, P., Zhou, J., He, W., Ding, M., Xiong, F., Zheng, X., Li, Z., et al. (2016). Tracing haematopoietic stem cell formation at single-cell resolution. Nature 533, 487-492.

TABLE S1

Table S1: Key transcription factors critical for HSC self-renewal and maintenance are labeled by m6A in HSPCs.

Gata2
Gfi1
Pbx1
Lmo2
Etv6
Erg
Runx1
Tal1
Hoxa9
Meis1
Kmt2a
Kmt2b
Kmt2c
Kmt2d
Bmi1
Sox4
Evi1
Stat3
Stat5a
Hoxb4
Zfx
Foxo3
Foxp1

TABLE S2

Ythdf2 targeted mRNAs from three irCLIP-seq replicates.

| GeneID | Name | Biotype | Description |
| --- | --- | --- | --- |
| ENSMUSG00000033793 | Atp6v1h | protein_coding | ATPase, H+ transporting, lysosomal V1 subunit H [Source:MGI Symbol;Acc:MGI:1914864] |
| ENSMUSG00000067851 | Arfgef1 | protein_coding | ADP-ribosylation factor guanine nucleotide-exchange factor 1(brefeldin A-inhibited) [Source:MGI Symbol;Acc:MGI:2442988] |
| ENSMUSG00000005886 | Ncoa2 | protein_coding | nuclear receptor coactivator 2 [Source:MGI Symbol;Acc:MGI:1276533] |
| ENSMUSG00000025935 | Tram1 | protein_coding | translocating chain-associating membrane protein 1 [Source:MGI Symbol;Acc:MGI:1919515] |
| ENSMUSG00000041859 | Mcm3 | protein_coding | minichromosome maintenance deficient 3 (S. cerevisiae) [Source:MGI Symbol;Acc:MGI:101845] |
| ENSMUSG00000033569 | Bai3 | protein_coding | brain-specific angiogenesis inhibitor 3 [Source:MGI Symbol;Acc:MGI:2441837] |
| ENSMUSG00000048874 | Phf3 | protein_coding | PHD finger protein 3 [Source:MGI Symbol;Acc:MGI:2446126] |
| ENSMUSG00000042215 | Bag2 | protein_coding | BCL2-associated athanogene 2 [Source:MGI Symbol;Acc:MGI:1891254] |
| ENSMUSG00000037503 | Fam168b | protein_coding | family with sequence similarity 168, member B [Source:MGI Symbol;Acc:MGI:2448487] |
| ENSMUSG00000037470 | Uggt1 | protein_coding | UDP-glucose glycoprotein glucosyltransferase 1 [Source:MGI Symbol;Acc:MGI:2443162] |
| ENSMUSG00000026121 | Sema4c | protein_coding | sema domain, immunoglobulin domain (Ig), transmembrane domain (TM) and short cytoplasmic domain, (semaphorin) 4C [Source:MGI Symbol;Acc:MGI:109252] |
| ENSMUSG00000026113 | Inpp4a | protein_coding | inositol polyphosphate-4-phosphatase, type I [Source:MGI Symbol;Acc:MGI:1931123] |
| ENSMUSG00000037216 | Lipt1 | protein_coding | lipoyltransferase 1 [Source:MGI Symbol;Acc:MGI:3645211] |
| ENSMUSG00000026083 | Eif5b | protein_coding | eukaryotic translation initiation factor 5B [Source:MGI Symbol;Acc:MGI:2441772] |
| ENSMUSG00000037138 | Aff3 | protein_coding | AF4/FMR2 family, member 3 [Source:MGI Symbol;Acc:MGI:106927] |
| ENSMUSG00000026074 | Map4k4 | protein_coding | mitogen-activated protein kinase kinase kinase kinase 4 [Source:MGI Symbol;Acc:MGI:1349394] |
| ENSMUSG00000070939 | Tgfbrap1 | protein_coding | transforming growth factor, beta receptor associated protein 1 [Source:MGI Symbol;Acc:MGI:2447427] |
| ENSMUSG00000066877 | Nck2 | protein_coding | non-catalytic region of tyrosine kinase adaptor protein 2 [Source:MGI Symbol;Acc:MGI:1306821] |
| ENSMUSG00000043629 | 1700019D03Rik | protein_coding | RIKEN cDNA 1700019D03 gene [Source:MGI Symbol;Acc:MGI:1914330] |

TABLE S2-continued

Ythdf2 targeted mRNAs from three irCLIP-seq replicates.

| GeneID | Name | Biotype | Description |
|---|---|---|---|
| ENSMUSG00000026094 | Stk17b | protein_coding | serine/threonine kinase 17b (apoptosis-inducing) [Source:MGI Symbol;Acc:MGI:2138162] |
| ENSMUSG00000042807 | Hecw2 | protein_coding | HECT, C2 and WW domain containing E3 ubiquitin protein ligase 2 [Source:MGI Symbol;Acc:MGI:2685817] |
| ENSMUSG00000052331 | Ankrd44 | protein_coding | ankyrin repeat domain 44 [Source:MGI Symbol;Acc:MGI:3045243] |
| ENSMUSG00000025982 | Sf3b1 | protein_coding | splicing factor 3b, subunit 1 [Source:MGI Symbol;Acc:MGI:1932339] |
| ENSMUSG00000025980 | Hspd1 | protein_coding | heat shock protein 1 (chaperonin) [Source:MGI Symbol;Acc:MGI:96242] |
| ENSMUSG00000046994 | Mars2 | protein_coding | methionine-tRNA synthetase 2 (mitochondrial) [Source:MGI Symbol;Acc:MGI:2444136] |
| ENSMUSG00000038331 | Satb2 | protein_coding | special AT-rich sequence binding protein 2 [Source:MGI Symbol;Acc:MGI:2679336] |
| ENSMUSG00000051223 | Bzw1 | protein_coding | basic leucine zipper and W2 domains 1 [Source:MGI Symbol;Acc:MGI:1914132] |
| ENSMUSG00000026031 | Cflar | protein_coding | CASP8 and FADD-like apoptosis regulator [Source:MGI Symbol;Acc:MGI:1336166] |
| ENSMUSG00000026028 | Trak2 | protein_coding | trafficking protein, kinesin binding 2 [Source:MGI Symbol;Acc:MGI:1918077] |
| ENSMUSG00000026020 | Nop58 | protein_coding | NOP58 ribonucleoprotein homolog (yeast) [Source:MGI Symbol;Acc:MGI:1933184] |
| ENSMUSG00000026782 | Abi2 | protein_coding | abl-interactor 2 [Source:MGI Symbol;Acc:MGI:106913] |
| ENSMUSG00000052062 | Pard3b | protein_coding | par-3 partitioning defective 3 homolog B (*C. elegans*) [Source:MGI Symbol;Acc:MGI:1919301] |
| ENSMUSG00000025967 | Eef1b2 | protein_coding | eukaryotic translation elongation factor 1 beta 2 [Source:MGI Symbol;Acc:MGI:1929520] |
| ENSMUSG00000025959 | Klf7 | protein_coding | Kruppel-like factor 7 (ubiquitous) [Source:MGI Symbol;Acc:MGI:1935151] |
| ENSMUSG00000062209 | Erbb4 | protein_coding | v-erb-a erythroblastic leukemia viral oncogene homolog 4 (avian) [Source:MGI Symbol;Acc:MGI:104771] |
| ENSMUSG00000050296 | Abca12 | protein_coding | ATP-binding cassette, sub-family A (ABC1), member 12 [Source:MGI Symbol;Acc:MGI:2676312] |
| ENSMUSG00000026192 | Atic | protein_coding | 5-aminoimidazole-4-carboxamide ribonucleotide formyltransferase/IMP cyclohydrolase [Source:MGI Symbol;Acc:MGI:1351352] |
| ENSMUSG00000055322 | Tns1 | protein_coding | tensin 1 [Source:MGI Symbol;Acc:MGI:104552] |
| ENSMUSG00000006304 | Arpc2 | protein_coding | actin related protein 2/3 complex, subunit 2 [Source:MGI Symbol;Acc:MGI:1923959] |
| ENSMUSG00000006299 | Aamp | protein_coding | angio-associated migratory protein [Source:MGI Symbol;Acc:MGI:107809] |
| ENSMUSG00000026176 | Ctdsp1 | protein_coding | CTD (carboxy-terminal domain, RNA polymerase II, polypeptide A) small phosphatase 1 [Source:MGI Symbol;Acc:MGI:2654470] |
| ENSMUSG00000033364 | Usp37 | protein_coding | ubiquitin specific peptidase 37 [Source:MGI Symbol;Acc:MGI:2442483] |
| ENSMUSG00000026174 | Rqcd1 | protein_coding | rcd1 (required for cell differentiation) homolog 1 (*S. pombe*) [Source:MGI Symbol;Acc:MGI:1928902] |
| ENSMUSG00000026135 | Zfp142 | protein_coding | zinc finger protein 142 [Source:MGI Symbol;Acc:MGI:1924514] |
| ENSMUSG00000033257 | Ttll4 | protein_coding | tubulin tyrosine ligase-like family, member 4 [Source:MGI Symbol;Acc:MGI:1914784] |
| ENSMUSG00000049339 | Fam134a | protein_coding | family with sequence similarity 134, member A [Source:MGI Symbol;Acc:MGI:2388278] |
| ENSMUSG00000026211 | Obsl1 | protein_coding | obscurin-like 1 [Source:MGI Symbol;Acc:MGI:2138628] |
| ENSMUSG00000026245 | Farsb | protein_coding | phenylalanyl-tRNA synthetase, beta subunit [Source:MGI Symbol;Acc:MGI:1346035] |
| ENSMUSG00000004364 | Cul3 | protein_coding | cullin 3 [Source:MGI Symbol;Acc:MGI:1347360] |
| ENSMUSG00000038608 | Dock10 | protein_coding | dedicator of cytokinesis 10 [Source:MGI Symbol;Acc:MGI:2146320] |
| ENSMUSG00000026219 | Trip12 | protein_coding | thyroid hormone receptor interactor 12 [Source:MGI Symbol;Acc:MGI:1309481] |
| ENSMUSG00000036707 | Cab39 | protein_coding | calcium binding protein 39 [Source:MGI Symbol;Acc:MGI:107438] |
| ENSMUSG00000026223 | Itm2c | protein_coding | integral membrane protein 2C [Source:MGI Symbol;Acc:MGI:1927594] |
| ENSMUSG00000026229 | Psmd1 | protein_coding | proteasome (prosome, macropain) 26S subunit, non-ATPase, 1 [Source:MGI Symbol;Acc:MGI:1917497] |
| ENSMUSG00000026234 | Ncl | protein_coding | nucleolin [Source:MGI Symbol;Acc:MGI:97286] |

TABLE S2-continued

Ythdf2 targeted mRNAs from three irCLIP-seq replicates.

| GeneID | Name | Biotype | Description |
| --- | --- | --- | --- |
| ENSMUSG 00000026238 | Ptma | protein_coding | prothymosin alpha [Source:MGI Symbol;Acc:MGI:97803] |
| ENSMUSG 00000048000 | Gigyf2 | protein_coding | GRB10 interacting GYF protein 2 [Source:MGI Symbol;Acc:MGI:2138584] |
| ENSMUSG 00000026288 | Inpp5d | protein_coding | inositol polyphosphate-5-phosphatase D [Source:MGI Symbol;Acc:MGI:107357] |
| ENSMUSG 00000026289 | Atg16l1 | protein_coding | autophagy-related 16-like 1 (yeast) [Source:MGI Symbol;Acc:MGI:1924290] |
| ENSMUSG 00000055013 | Agap1 | protein_coding | ArfGAP with GTPase domain, ankyrin repeat and PH domain 1 [Source:MGI Symbol;Acc:MGI:2653690] |
| ENSMUSG 00000034486 | Gbx2 | protein_coding | gastrulation brain homeobox 2 [Source:MGI Symbol;Acc:MGI:95668] |
| ENSMUSG 00000092627 | D130058E05Rik | protein_coding | RIKEN cDNA D130058E05 gene [Source:MGI Symbol;Acc:MGI:2444614] |
| ENSMUSG 00000026301 | Iqca | protein_coding | IQ motif containing with AAA domain [Source:MGI Symbol;Acc:MGI:1922168] |
| ENSMUSG 00000034432 | Cops8 | protein_coding | COP9 (constitutive photomorphogenic) homolog, subunit 8 (*Arabidopsis thaliana*) [Source:MGI Symbol;Acc:MGI:1915363] |
| ENSMUSG 00000026305 | Lrrfip1 | protein_coding | leucine rich repeat (in FLII) interacting protein 1 [Source:MGI Symbol;Acc:MGI:1342770] |
| ENSMUSG 00000026269 | Rnpepl1 | protein_coding | arginyl aminopeptidase (aminopeptidase B)-like 1 [Source:MGI Symbol;Acc:MGI:1914170] |
| ENSMUSG 00000026275 | Ppp1r7 | protein_coding | protein phosphatase 1, regulatory (inhibitor) subunit 7 [Source:MGI Symbol;Acc:MGI:1913635] |
| ENSMUSG 00000034088 | Hdlbp | protein_coding | high density lipoprotein (HDL) binding protein [Source:MGI Symbol;Acc:MGI:99256] |
| ENSMUSG 00000026276 | 2-Sep | protein_coding | septin 2 [Source:MGI Symbol;Acc:MGI:97298] |
| ENSMUSG 00000026281 | Dtymk | protein_coding | deoxythymidylate kinase [Source:MGI Symbol;Acc:MGI:108396] |
| ENSMUSG 00000040648 | Ppip5k2 | protein_coding | diphosphoinositol pentakisphosphate kinase 2 [Source:MGI Symbol;Acc:MGI:2142810] |
| ENSMUSG 00000038866 | Zcchc2 | protein_coding | zinc finger, CCHC domain containing 2 [Source:MGI Symbol;Acc:MGI:2444114] |
| ENSMUSG 00000044340 | Phlpp1 | protein_coding | PH domain and leucine rich repeat protein phosphatase 1 [Source:MGI Symbol;Acc:MGI:2138327] |
| ENSMUSG 00000057329 | Bcl2 | protein_coding | B cell leukemia/lymphoma 2 [Source:MGI Symbol;Acc:MGI:88138] |
| ENSMUSG 00000070695 | Cntnap5a | protein_coding | contactin associated protein-like 5A [Source:MGI Symbol;Acc:MGI:3643623] |
| ENSMUSG 00000064302 | Clasp1 | protein_coding | CLIP associating protein 1 [Source:MGI Symbol;Acc:MGI:1923957] |
| ENSMUSG 00000026389 | Steap3 | protein_coding | STEAP family member 3 [Source:MGI Symbol;Acc:MGI:1915678] |
| ENSMUSG 00000036815 | Dpp10 | protein_coding | dipeptidylpeptidase 10 [Source:MGI Symbol;Acc:MGI:2442409] |
| ENSMUSG 00000026341 | Actr3 | protein_coding | ARP3 actin-related protein 3 homolog (yeast) [Source:MGI Symbol;Acc:MGI:1921367] |
| ENSMUSG 00000026343 | Gpr39 | protein_coding | G protein-coupled receptor 39 [Source:MGI Symbol;Acc:MGI:1918361] |
| ENSMUSG 00000049690 | Nckap5 | protein_coding | NCK-associated protein 5 [Source:MGI Symbol;Acc:MGI:2686394] |
| ENSMUSG 00000036155 | Mgat5 | protein_coding | mannoside acetylglucosaminyltransferase 5 [Source:MGI Symbol;Acc:MGI:894701] |
| ENSMUSG 00000056211 | R3hdm1 | protein_coding | R3H domain 1 (binds single-stranded nucleic acids) [Source:MGI Symbol;Acc:MGI:2448514] |
| ENSMUSG 00000026355 | Mcm6 | protein_coding | minichromosome maintenance deficient 6 (MIS5 homolog, *S. pombe*) (*S. cerevisiae*) [Source:MGI Symbol;Acc:MGI:1298227] |
| ENSMUSG 00000026356 | Dars | protein_coding | aspartyl-tRNA synthetase [Source:MGI Symbol;Acc:MGI:2442544] |
| ENSMUSG 00000042581 | Thsd7b | protein_coding | thrombospondin, type I, domain containing 7B [Source:MGI Symbol;Acc:MGI:2443925] |
| ENSMUSG 00000016526 | Dyrk3 | protein_coding | dual-specificity tyrosine-(Y)-phosphorylation regulated kinase 3 [Source:MGI Symbol;Acc:MGI:1330300] |
| ENSMUSG 00000026427 | Eif2d | protein_coding | eukaryotic translation initiation factor 2D [Source:MGI Symbol;Acc:MGI:109342] |
| ENSMUSG 00000026430 | Rassf5 | protein_coding | Ras association (RalGDS/AF-6) domain family member 5 [Source:MGI Symbol;Acc:MGI:1926375] |
| ENSMUSG 00000026434 | Nucks1 | protein_coding | nuclear casein kinase and cyclin-dependent kinase substrate 1 [Source:MGI Symbol;Acc:MGI:1934811] |
| ENSMUSG 00000026436 | Elk4 | protein_coding | ELK4, member of ETS oncogene family [Source:MGI Symbol;Acc:MGI:102853] |

TABLE S2-continued

Ythdf2 targeted mRNAs from three irCLIP-seq replicates.

| GeneID | Name | Biotype | Description |
|---|---|---|---|
| ENSMUSG 00000054387 | Mdm4 | protein_coding | transformed mouse 3T3 cell double minute 4 [Source:MGI Symbol;Acc:MGI:107934] |
| ENSMUSG 00000046062 | Ppp1r15b | protein_coding | protein phosphatase 1, regulatory (inhibitor) subunit 15b [Source:MGI Symbol;Acc:MGI:2444211] |
| ENSMUSG 00000026464 | Zc3h11a | protein_coding | zinc finger CCCH type containing 11A [Source:MGI Symbol;Acc:MGI:1917829] |
| ENSMUSG 00000026463 | Atp2b4 | protein_coding | ATPase, Ca++ transporting, plasma membrane 4 [Source:MGI Symbol;Acc:MGI:88111] |
| ENSMUSG 00000042207 | Kdm5b | protein_coding | lysine (K)-specific demethylase 5B [Source:MGI Symbol;Acc:MGI:1922855] |
| ENSMUSG 00000031506 | Ptpn7 | protein_coding | protein tyrosine phosphatase, non-receptor type 7 [Source:MGI Symbol;Acc:MGI:2156893] |
| ENSMUSG 00000041879 | Ipo9 | protein_coding | importin 9 [Source:MGI Symbol;Acc:MGI:1918944] |
| ENSMUSG 00000009418 | Nav1 | protein_coding | neuron navigator 1 [Source:MGI Symbol;Acc:MGI:2183683] |
| ENSMUSG 00000026421 | Csrp1 | protein_coding | cysteine and glycine-rich protein 1 [Source:MGI Symbol;Acc:MGI:88549] |
| ENSMUSG 00000041801 | Phlda3 | protein_coding | pleckstrin homology-like domain, family A, member 3 [Source:MGI Symbol;Acc:MGI:1351485] |
| ENSMUSG 00000041642 | Kif21b | protein_coding | kinesin family member 21B [Source:MGI Symbol;Acc:MGI:109234] |
| ENSMUSG 00000087230 | 2310006M14Rik | protein_coding | RIKEN cDNA 2310006M14 gene [Source:MGI Symbol;Acc:MGI:1923672] |
| ENSMUSG 00000026395 | Ptprc | protein_coding | protein tyrosine phosphatase, receptor type, C [Source:MGI Symbol;Acc:MGI:97810] |
| ENSMUSG 00000033952 | Aspm | protein_coding | asp (abnormal spindle)-like, microcephaly associated (*Drosophila*) [Source:MGI Symbol;Acc:MGI:1334448] |
| ENSMUSG 00000033898 | Cfhr2 | protein_coding | complement factor H-related 2 [Source:MGI Symbol;Acc:MGI:3611575] |
| ENSMUSG 00000026360 | Rgs2 | protein_coding | regulator of G-protein signaling 2 [Source:MGI Symbol;Acc:MGI:1098271] |
| ENSMUSG 00000026358 | Rgs1 | protein_coding | regulator of G-protein signaling 1 [Source:MGI Symbol;Acc:MGI:1354694] |
| ENSMUSG 00000026357 | Rgs18 | protein_coding | regulator of G-protein signaling 18 [Source:MGI Symbol;Acc:MGI:1927498] |
| ENSMUSG 00000035131 | Fam5c | protein_coding | family with sequence similarity 5, member C [Source:MGI Symbol;Acc:MGI:2443035] |
| ENSMUSG 00000056220 | Pla2g4a | protein_coding | phospholipase A2, group IVA (cytosolic, calcium-dependent) [Source:MGI Symbol;Acc:MGI:1195256] |
| ENSMUSG 00000006005 | Tpr | protein_coding | translocated promoter region [Source:MGI Symbol;Acc:MGI:1922066] |
| ENSMUSG 00000066842 | Hmcn1 | protein_coding | hemicentin 1 [Source:MGI Symbol;Acc:MGI:2685047] |
| ENSMUSG 00000023150 | Ivns1abp | protein_coding | influenza virus NS1A binding protein [Source:MGI Symbol;Acc:MGI:2152389] |
| ENSMUSG 00000026484 | Rnf2 | protein_coding | ring finger protein 2 [Source:MGI Symbol;Acc:MGI:1101759] |
| ENSMUSG 00000026483 | Fam129a | protein_coding | family with sequence similarity 129, member A [Source:MGI Symbol;Acc:MGI:2137237] |
| ENSMUSG 00000043019 | Edem3 | protein_coding | ER degradation enhancer, mannosidase alpha-like 3 [Source:MGI Symbol;Acc:MGI:1914217] |
| ENSMUSG 00000026482 | Rgl1 | protein_coding | ral guanine nucleotide dissociation stimulator,-like 1 [Source:MGI Symbol;Acc:MGI:107484] |
| ENSMUSG 00000042772 | Smg7 | protein_coding | Smg-7 homolog, nonsense mediated mRNA decay factor (*C. elegans*) [Source:MGI Symbol;Acc:MGI:2682334] |
| ENSMUSG 00000042699 | Dhx9 | protein_coding | DEAH (Asp-Glu-Ala-His) box polypeptide 9 [Source:MGI Symbol;Acc:MGI:108177] |
| ENSMUSG 00000042671 | Rgs8 | protein_coding | regulator of G-protein signaling 8 [Source:MGI Symbol;Acc:MGI:108408] |
| ENSMUSG 00000026475 | Rgs16 | protein_coding | regulator of G-protein signaling 16 [Source:MGI Symbol;Acc:MGI:108407] |
| ENSMUSG 00000026473 | Glul | protein_coding | glutamate-ammonia ligase (glutamine synthetase) [Source:MGI Symbol;Acc:MGI:95739] |
| ENSMUSG 00000078493 | A930039A15Rik | protein_coding | RIKEN cDNA A930039A15 gene [Source:MGI Symbol;Acc:MGI:3641728] |
| ENSMUSG 00000079255 | Gm11074 | protein_coding | predicted gene 11074 [Source:MGI Symbol;Acc:MGI:3779301] |
| ENSMUSG 00000033671 | Cep350 | protein_coding | centrosomal protein 350 [Source:MGI Symbol;Acc:MGI:1921331] |
| ENSMUSG 00000050565 | Tor1aip2 | protein_coding | torsin A interacting protein 2 [Source:MGI Symbol;Acc:MGI:3582695] |
| ENSMUSG 00000079252 | Tor1aip2 | protein_coding | torsin A interacting protein 2 [Source:MGI Symbol;Acc:MGI:3582695] |

TABLE S2-continued

Ythdf2 targeted mRNAs from three irCLIP-seq replicates.

| GeneID | Name | Biotype | Description |
|---|---|---|---|
| ENSMUSG00000026602 | Nphs2 | protein_coding | nephrosis 2 homolog, podocin (human) [Source:MGI Symbol;Acc:MGI:2157018] |
| ENSMUSG00000026600 | Soat1 | protein_coding | sterol O-acyltransferase 1 [Source:MGI Symbol;Acc:MGI:104665] |
| ENSMUSG00000026596 | Abl2 | protein_coding | v-abl Abelson murine leukemia viral oncogene homolog 2 (arg, Abelson-related gene) [Source:MGI Symbol;Acc:MGI:87860] |
| ENSMUSG00000033557 | Fam20b | protein_coding | family with sequence similarity 20, member B [Source:MGI Symbol;Acc:MGI:2443990] |
| ENSMUSG00000026594 | Ralgps2 | protein_coding | Ral GEF with PH domain and SH3 binding motif 2 [Source:MGI Symbol;Acc:MGI:1925505] |
| ENSMUSG00000040782 | Rfwd2 | protein_coding | ring finger and WD repeat domain 2 [Source:MGI Symbol;Acc:MGI:1347046] |
| ENSMUSG00000040423 | Rc3h1 | protein_coding | RING CCCH (C3H) domains 1 [Source:MGI Symbol;Acc:MGI:2685397] |
| ENSMUSG00000026701 | Prdx6 | protein_coding | peroxiredoxin 6 [Source:MGI Symbol;Acc:MGI:894320] |
| ENSMUSG00000086277 | 4930558K02Rik | protein_coding | RIKEN cDNA 4930558K02 gene [Source:MGI Symbol;Acc:MGI:1922618] |
| ENSMUSG00000026698 | Pigc | protein_coding | phosphatidylinositol glycan anchor biosynthesis, class C [Source:MGI Symbol;Acc:MGI:1914542] |
| ENSMUSG00000040225 | Prrc2c | protein_coding | proline-rich coiled-coil 2C [Source:MGI Symbol;Acc:MGI:1913754] |
| ENSMUSG00000026585 | Kifap3 | protein_coding | kinesin-associated protein 3 [Source:MGI Symbol;Acc:MGI:107566] |
| ENSMUSG00000041406 | BC055324 | protein_coding | cDNA sequence BC055324 [Source:MGI Symbol;Acc:MGI:3590554] |
| ENSMUSG00000026576 | Atp1b1 | protein_coding | ATPase, Na+/K+ transporting, beta 1 polypeptide [Source:MGI Symbol;Acc:MGI:88108] |
| ENSMUSG00000040723 | Rcsd1 | protein_coding | RCSD domain containing 1 [Source:MGI Symbol;Acc:MGI:2676394] |
| ENSMUSG00000005763 | Cd247 | protein_coding | CD247 antigen [Source:MGI Symbol;Acc:MGI:88334] |
| ENSMUSG00000026565 | Pou2f1 | protein_coding | POU domain, class 2, transcription factor 1 [Source:MGI Symbol;Acc:MGI:101898] |
| ENSMUSG00000026558 | Uck2 | protein_coding | uridine-cytidine kinase 2 [Source:MGI Symbol;Acc:MGI:1931744] |
| ENSMUSG00000026687 | Aldh9a1 | protein_coding | aldehyde dehydrogenase 9, subfamily A1 [Source:MGI Symbol;Acc:MGI:1861622] |
| ENSMUSG00000052534 | Pbx1 | protein_coding | pre B cell leukemia homeobox 1 [Source:MGI Symbol;Acc:MGI:97495] |
| ENSMUSG00000026667 | Uhmk1 | protein_coding | U2AF homology motif (UHM) kinase 1 [Source:MGI Symbol;Acc:MGI:1341908] |
| ENSMUSG00000059498 | Fcgr3 | protein_coding | Fc receptor, IgG, low affinity III [Source:MGI Symbol;Acc:MGI:95500] |
| ENSMUSG00000013593 | Ndufs2 | protein_coding | NADH dehydrogenase (ubiquinone) Fe-S protein 2 [Source:MGI Symbol;Acc:MGI:2385112] |
| ENSMUSG00000006411 | Pvrl4 | protein_coding | poliovirus receptor-related 4 [Source:MGI Symbol;Acc:MGI:1918990] |
| ENSMUSG00000048865 | Arhgap30 | protein_coding | Rho GTPase activating protein 30 [Source:MGI Symbol;Acc:MGI:2684948] |
| ENSMUSG00000026553 | Copa | protein_coding | coatomer protein complex subunit alpha [Source:MGI Symbol;Acc:MGI:1334462] |
| ENSMUSG00000026554 | Dcaf8 | protein_coding | DDB1 and CUL4 associated factor 8 [Source:MGI Symbol;Acc:MGI:91860] |
| ENSMUSG00000026547 | Tagln2 | protein_coding | transgelin 2 [Source:MGI Symbol;Acc:MGI:1312985] |
| ENSMUSG00000057335 | Cep170 | protein_coding | centrosomal protein 170 [Source:MGI Symbol;Acc:MGI:1918348] |
| ENSMUSG00000026504 | Sdccag8 | protein_coding | serologically defined colon cancer antigen 8 [Source:MGI Symbol;Acc:MGI:1924066] |
| ENSMUSG00000026502 | Pppde1 | protein_coding | PPPDE peptidase domain containing 1 [Source:MGI Symbol;Acc:MGI:1926075] |
| ENSMUSG00000039630 | Hnrnpu | protein_coding | heterogeneous nuclear ribonucleoprotein U [Source:MGI Symbol;Acc:MGI:1858195] |
| ENSMUSG00000055067 | Smyd3 | protein_coding | SET and MYND domain containing 3 [Source:MGI Symbol;Acc:MGI:1916976] |
| ENSMUSG00000038949 | Cnst | protein_coding | consortin, connexin sorting protein [Source:MGI Symbol;Acc:MGI:2445141] |
| ENSMUSG00000026491 | Ahctf1 | protein_coding | AT hook containing transcription factor 1 [Source:MGI Symbol;Acc:MGI:1915033] |
| ENSMUSG00000038855 | Itpkb | protein_coding | inositol 1,4,5-trisphosphate 3-kinase B [Source:MGI Symbol;Acc:MGI:109235] |

TABLE S2-continued

Ythdf2 targeted mRNAs from three irCLIP-seq replicates.

| GeneID | Name | Biotype | Description |
|---|---|---|---|
| ENSMUSG00000026496 | Parp1 | protein_coding | poly (ADP-ribose) polymerase family, member 1 [Source:MGI Symbol;Acc:MGI:1340806] |
| ENSMUSG00000060743 | H3f3a | protein_coding | H3 histone, family 3A [Source:MGI Symbol;Acc:MGI:1097686] |
| ENSMUSG00000038806 | BC031781 | protein_coding | cDNA sequence BC031781 [Source:MGI Symbol;Acc:MGI:2384788] |
| ENSMUSG00000026519 | Tmem63a | protein_coding | transmembrane protein 63a [Source:MGI Symbol;Acc:MGI:2384789] |
| ENSMUSG00000038733 | Wdr26 | protein_coding | WD repeat domain 26 [Source:MGI Symbol;Acc:MGI:1923825] |
| ENSMUSG00000004880 | Lbr | protein_coding | lamin B receptor [Source:MGI Symbol;Acc:MGI:2138281] |
| ENSMUSG00000026510 | Trp53bp2 | protein_coding | transformation related protein 53 binding protein 2 [Source:MGI Symbol;Acc:MGI:2138319] |
| ENSMUSG00000039318 | Rab3gap2 | protein_coding | RAB3 GTPase activating protein subunit 2 [Source:MGI Symbol;Acc:MGI:1916043] |
| ENSMUSG00000026615 | Eprs | protein_coding | glutamyl-prolyl-tRNA synthetase [Source:MGI Symbol;Acc:MGI:97838] |
| ENSMUSG00000026609 | Ush2a | protein_coding | Usher syndrome 2A (autosomal recessive, mild) homolog (human) [Source:MGI Symbol;Acc:MGI:1341292] |
| ENSMUSG00000026608 | Kctd3 | protein_coding | potassium channel tetramerisation domain containing 3 [Source:MGI Symbol;Acc:MGI:2444629] |
| ENSMUSG00000037568 | Vash2 | protein_coding | vasohibin 2 [Source:MGI Symbol;Acc:MGI:2444826] |
| ENSMUSG00000026626 | Ppp2r5a | protein_coding | protein phosphatase 2, regulatory subunit B (B56), alpha isoform [Source:MGI Symbol;Acc:MGI:2388479] |
| ENSMUSG00000058248 | Kcnh1 | protein_coding | potassium voltage-gated channel, subfamily H (eag-related), member 1 [Source:MGI Symbol;Acc:MGI:1341721] |
| ENSMUSG00000037375 | Hhat | protein_coding | hedgehog acyltransferase [Source:MGI Symbol;Acc:MGI:2444681] |
| ENSMUSG00000016494 | Cd34 | protein_coding | CD34 antigen [Source:MGI Symbol;Acc:MGI:88329] |
| ENSMUSG00000050530 | Fam171a1 | protein_coding | family with sequence similarity 171, member A1 [Source:MGI Symbol;Acc:MGI:2442917] |
| ENSMUSG00000026645 | Olah | protein_coding | oleoyl-ACP hydrolase [Source:MGI Symbol;Acc:MGI:2139018] |
| ENSMUSG00000051396 | Hspa14 | protein_coding | heat shock protein 14 [Source:MGI Symbol;Acc:MGI:1354164] |
| ENSMUSG00000026655 | Fam107b | protein_coding | family with sequence similarity 107, member B [Source:MGI Symbol;Acc:MGI:1913790] |
| ENSMUSG00000026657 | Frmd4a | protein_coding | FERM domain containing 4A [Source:MGI Symbol;Acc:MGI:1919850] |
| ENSMUSG00000026662 | Sephs1 | protein_coding | selenophosphate synthetase 1 [Source:MGI Symbol;Acc:MGI:1923580] |
| ENSMUSG00000039046 | Usp6nl | protein_coding | USP6 N-terminal like [Source:MGI Symbol;Acc:MGI:2138893] |
| ENSMUSG00000002107 | Celf2 | protein_coding | CUGBP, Elav-like family member 2 [Source:MGI Symbol;Acc:MGI:1338822] |
| ENSMUSG00000026778 | Prkcq | protein_coding | protein kinase C, theta [Source:MGI Symbol;Acc:MGI:97601] |
| ENSMUSG00000026727 | Rsu1 | protein_coding | Ras suppressor protein 1 [Source:MGI Symbol;Acc:MGI:103040] |
| ENSMUSG00000026728 | Vim | protein_coding | vimentin [Source:MGI Symbol;Acc:MGI:98932] |
| ENSMUSG00000057914 | Cacnb2 | protein_coding | calcium channel, voltage-dependent, beta 2 subunit [Source:MGI Symbol;Acc:MGI:894644] |
| ENSMUSG00000026748 | Plxdc2 | protein_coding | plexin domain containing 2 [Source:MGI Symbol;Acc:MGI:1914698] |
| ENSMUSG00000036617 | Etl4 | protein_coding | enhancer trap locus 4 [Source:MGI Symbol;Acc:MGI:95454] |
| ENSMUSG00000036591 | Arhgap21 | protein_coding | Rho GTPase activating protein 21 [Source:MGI Symbol;Acc:MGI:1918685] |
| ENSMUSG00000026786 | Apbb1ip | protein_coding | amyloid beta (A4) precursor protein-binding, family B, member 1 interacting protein [Source:MGI Symbol;Acc:MGI:1861354] |
| ENSMUSG00000026979 | Psd4 | protein_coding | pleckstrin and Sec7 domain containing 4 [Source:MGI Symbol;Acc:MGI:2674093] |
| ENSMUSG00000026974 | Zmynd19 | protein_coding | zinc finger, MYND domain containing 19 [Source:MGI Symbol;Acc:MGI:1914437] |
| ENSMUSG00000036752 | Tubb4b | protein_coding | tubulin, beta 4B class IVB [Source:MGI Symbol;Acc:MGI:1915472] |
| ENSMUSG00000048707 | Tprn | protein_coding | taperin [Source:MGI Symbol;Acc:MGI:2139535] |

TABLE S2-continued

Ythdf2 targeted mRNAs from three irCLIP-seq replicates.

| GeneID | Name | Biotype | Description |
|---|---|---|---|
| ENSMUSG 00000026965 | Anapc2 | protein_coding | anaphase promoting complex subunit 2 [Source:MGI Symbol;Acc:MGI:2139135] |
| ENSMUSG 00000026955 | 2010317E24Rik | protein_coding | RIKEN cDNA 2010317E24 gene [Source:MGI Symbol;Acc:MGI:1919330] |
| ENSMUSG 00000026941 | Mamdc4 | protein_coding | MAM domain containing 4 [Source:MGI Symbol;Acc:MGI:2685841] |
| ENSMUSG 00000036504 | Phpt1 | protein_coding | phosphohistidine phosphatase 1 [Source:MGI Symbol;Acc:MGI:1922704] |
| ENSMUSG 00000015087 | B230208H17Rik | protein_coding | RIKEN cDNA B230208H17 gene [Source:MGI Symbol;Acc:MGI:2442633] |
| ENSMUSG 00000015776 | Med22 | protein_coding | mediator complex subunit 22 [Source:MGI Symbol;Acc:MGI:98446] |
| ENSMUSG 00000062647 | Rpl7a | protein_coding | ribosomal protein L7A [Source:MGI Symbol;Acc:MGI:1353472] |
| ENSMUSG 00000014852 | Adamts13 | protein_coding | a disintegrin-like and metallopeptidase (reprolysin type) with thrombospondin type 1 motif, 13 [Source:MGI Symbol;Acc:MGI:2685556] |
| ENSMUSG 00000026918 | Brd3 | protein_coding | bromodomain containing 3 [Source:MGI Symbol;Acc:MGI:1914632] |
| ENSMUSG 00000015846 | Rxra | protein_coding | retinoid X receptor alpha [Source:MGI Symbol;Acc:MGI:98214] |
| ENSMUSG 00000035772 | Mrps2 | protein_coding | mitochondrial ribosomal protein S2 [Source:MGI Symbol;Acc:MGI:2153089] |
| ENSMUSG 00000026807 | Ak8 | protein_coding | adenylate kinase 8 [Source:MGI Symbol;Acc:MGI:1916120] |
| ENSMUSG 00000035666 | Gtf3c4 | protein_coding | general transcription factor IIIC, polypeptide 4 [Source:MGI Symbol;Acc:MGI:2138937] |
| ENSMUSG 00000043535 | Setx | protein_coding | senataxin [Source:MGI Symbol;Acc:MGI:2443480] |
| ENSMUSG 00000035513 | Ntng2 | protein_coding | netrin G2 [Source:MGI Symbol;Acc:MGI:2159341] |
| ENSMUSG 00000039844 | Rapgef1 | protein_coding | Rap guanine nucleotide exchange factor (GEF) 1 [Source:MGI Symbol;Acc:MGI:104580] |
| ENSMUSG 00000057738 | Spna2 | protein_coding | spectrin alpha 2 [Source:MGI Symbol;Acc:MGI:98386] |
| ENSMUSG 00000039715 | Wdr34 | protein_coding | WD repeat domain 34 [Source:MGI Symbol;Acc:MGI:1919070] |
| ENSMUSG 00000054766 | Set | protein_coding | SET nuclear oncogene [Source:MGI Symbol;Acc:MGI:1860267] |
| ENSMUSG 00000039515 | Ppp2r4 | protein_coding | protein phosphatase 2A, regulatory subunit B (PR 53) [Source:MGI Symbol;Acc:MGI:1346006] |
| ENSMUSG 00000026849 | Tor1a | protein_coding | torsin family 1, member A (torsin A) [Source:MGI Symbol;Acc:MGI:1353568] |
| ENSMUSG 00000075415 | Fnbp1 | protein_coding | formin binding protein 1 [Source:MGI Symbol;Acc:MGI:109606] |
| ENSMUSG 00000026842 | Abl1 | protein_coding | c-abl oncogene 1, non-receptor tyrosine kinase [Source:MGI Symbol;Acc:MGI:87859] |
| ENSMUSG 00000001855 | Nup214 | protein_coding | nucleoporin 214 [Source:MGI Symbol;Acc:MGI:1095411] |
| ENSMUSG 00000039262 | Prrc2b | protein_coding | proline-rich coiled-coil 2B [Source:MGI Symbol;Acc:MGI:1923304] |
| ENSMUSG 00000026814 | Eng | protein_coding | endoglin [Source:MGI Symbol;Acc:MGI:95392] |
| ENSMUSG 00000009555 | Cdk9 | protein_coding | cyclin-dependent kinase 9 (CDC2-related kinase) [Source:MGI Symbol;Acc:MGI:1328368] |
| ENSMUSG 00000038900 | Rpl12 | protein_coding | ribosomal protein L12 [Source:MGI Symbol;Acc:MGI:98002] |
| ENSMUSG 00000038831 | Ralgps1 | protein_coding | Ral GEF with PH domain and SH3 binding motif 1 [Source:MGI Symbol;Acc:MGI:1922008] |
| ENSMUSG 00000038765 | Lmx1b | protein_coding | LIM homeobox transcription factor 1 beta [Source:MGI Symbol;Acc:MGI:1100513] |
| ENSMUSG 00000038740 | Fam125b | protein_coding | family with sequence similarity 125, member B [Source:MGI Symbol;Acc:MGI:1919793] |
| ENSMUSG 00000038718 | Pbx3 | protein_coding | pre B cell leukemia homeobox 3 [Source:MGI Symbol;Acc:MGI:97496] |
| ENSMUSG 00000026864 | Hspa5 | protein_coding | heat shock protein 5 [Source:MGI Symbol;Acc:MGI:95835] |
| ENSMUSG 00000026869 | Psmd5 | protein_coding | proteasome (prosome, macropain) 26S subunit, non-ATPase, 5 [Source:MGI Symbol;Acc:MGI:1914248] |
| ENSMUSG 00000035778 | Ggta1 | protein_coding | glycoprotein galactosyltransferase alpha 1, 3 [Source:MGI Symbol;Acc:MGI:95704] |
| ENSMUSG 00000026883 | Dab2ip | protein_coding | disabled homolog 2 (*Drosophila*) interacting protein [Source:MGI Symbol;Acc:MGI:1916851] |

TABLE S2-continued

Ythdf2 targeted mRNAs from three irCLIP-seq replicates.

| GeneID | Name | Biotype | Description |
|---|---|---|---|
| ENSMUSG 00000035392 | Dennd1a | protein_coding | DENN/MADD domain containing 1A [Source:MGI Symbol;Acc:MGI:2442794] |
| ENSMUSG 00000000247 | Lhx2 | protein_coding | LIM homeobox protein 2 [Source:MGI Symbol;Acc:MGI:96785] |
| ENSMUSG 00000049252 | Lrp1b | protein_coding | low density lipoprotein-related protein 1B (deleted in tumors) [Source:MGI Symbol;Acc:MGI:2151136] |
| ENSMUSG 00000049744 | Arhgap15 | protein_coding | Rho GTPase activating protein 15 [Source:MGI Symbol;Acc:MGI:1923367] |
| ENSMUSG 00000026872 | Zeb2 | protein_coding | zinc finger E-box binding homeobox 2 [Source:MGI Symbol;Acc:MGI:1344407] |
| ENSMUSG 00000036792 | Mbd5 | protein_coding | methyl-CpG binding domain protein 5 [Source:MGI Symbol;Acc:MGI:2138934] |
| ENSMUSG 00000026764 | Kif5c | protein_coding | kinesin family member 5C [Source:MGI Symbol;Acc:MGI:1098269] |
| ENSMUSG 00000036202 | Rif1 | protein_coding | Rap1 interacting factor 1 homolog (yeast) [Source:MGI Symbol;Acc:MGI:1098622] |
| ENSMUSG 00000026827 | Gpd2 | protein_coding | glycerol phosphate dehydrogenase 2, mitochondrial [Source:MGI Symbol;Acc:MGI:99778] |
| ENSMUSG 00000026977 | 7-Mar | protein_coding | membrane-associated ring finger (C3HC4) 7 [Source:MGI Symbol;Acc:MGI:1931053] |
| ENSMUSG 00000026914 | Psmd14 | protein_coding | proteasome (prosome, macropain) 26S subunit, non-ATPase, 14 [Source:MGI Symbol;Acc:MGI:1913284] |
| ENSMUSG 00000035033 | Tbr1 | protein_coding | T-box brain gene 1 [Source:MGI Symbol;Acc:MGI:107404] |
| ENSMUSG 00000027068 | Dhrs9 | protein_coding | dehydrogenase/reductase (SDR family) member 9 [Source:MGI Symbol;Acc:MGI:2442798] |
| ENSMUSG 00000068882 | Ssb | protein_coding | Sjogren syndrome antigen B [Source:MGI Symbol;Acc:MGI:98423] |
| ENSMUSG 00000041997 | Tlk1 | protein_coding | tousled-like kinase 1 [Source:MGI Symbol;Acc:MGI:2441683] |
| ENSMUSG 00000027111 | Itga6 | protein_coding | integrin alpha 6 [Source:MGI Symbol;Acc:MGI:96605] |
| ENSMUSG 00000049044 | Rapgef4 | protein_coding | Rap guanine nucleotide exchange factor (GEF) 4 [Source:MGI Symbol;Acc:MGI:1917723] |
| ENSMUSG 00000027109 | Sp3 | protein_coding | trans-acting transcription factor 3 [Source:MGI Symbol;Acc:MGI:1277166] |
| ENSMUSG 00000068859 | Sp9 | protein_coding | trans-acting transcription factor 9 [Source:MGI Symbol;Acc:MGI:3574660] |
| ENSMUSG 00000075284 | Wipf1 | protein_coding | WAS/WASL interacting protein family, member 1 [Source:MGI Symbol;Acc:MGI:2178801] |
| ENSMUSG 00000027104 | Atf2 | protein_coding | activating transcription factor 2 [Source:MGI Symbol;Acc:MGI:109349] |
| ENSMUSG 00000018770 | Atp5g3 | protein_coding | ATP synthase, H+ transporting, mitochondrial F0 complex, subunit C3 (subunit 9) [Source:MGI Symbol;Acc:MGI:2442035] |
| ENSMUSG 00000043342 | Hoxd9 | protein_coding | homeobox D9 [Source:MGI Symbol;Acc:MGI:96210] |
| ENSMUSG 00000015839 | Nfe2l2 | protein_coding | nuclear factor, erythroid derived 2, like 2 [Source:MGI Symbol;Acc:MGI:108420] |
| ENSMUSG 00000051747 | Ttn | protein_coding | titin [Source:MGI Symbol;Acc:MGI:98864] |
| ENSMUSG 00000027014 | Cwc22 | protein_coding | CWC22 spliceosome-associated protein homolog (S. cerevisiae) [Source:MGI Symbol;Acc:MGI:2136773] |
| ENSMUSG 00000027007 | Ssfa2 | protein_coding | sperm specific antigen 2 [Source:MGI Symbol;Acc:MGI:1917849] |
| ENSMUSG 00000027002 | Nckap1 | protein_coding | NCK-associated protein 1 [Source:MGI Symbol;Acc:MGI:1355333] |
| ENSMUSG 00000027091 | Zc3h15 | protein_coding | zinc finger CCCH-type containing 15 [Source:MGI Symbol;Acc:MGI:1919747] |
| ENSMUSG 00000059588 | Calcrl | protein_coding | calcitonin receptor-like [Source:MGI Symbol;Acc:MGI:1926944] |
| ENSMUSG 00000034101 | Ctnnd1 | protein_coding | catenin (cadherin associated protein), delta 1 [Source:MGI Symbol;Acc:MGI:105100] |
| ENSMUSG 00000025314 | Ptprj | protein_coding | protein tyrosine phosphatase, receptor type, J [Source:MGI Symbol;Acc:MGI:104574] |
| ENSMUSG 00000002102 | Psmc3 | protein_coding | proteasome (prosome, macropain) 26S subunit, ATPase 3 [Source:MGI Symbol;Acc:MGI:1098754] |
| ENSMUSG 00000002111 | Sfpi1 | protein_coding | SFFV proviral integration 1 [Source:MGI Symbol;Acc:MGI:98282] |
| ENSMUSG 00000040549 | Ckap5 | protein_coding | cytoskeleton associated protein 5 [Source:MGI Symbol;Acc:MGI:1923036] |
| ENSMUSG 00000040506 | Ambra1 | protein_coding | autophagy/beclin 1 regulator 1 [Source:MGI Symbol;Acc:MGI:2443564] |

TABLE S2-continued

Ythdf2 targeted mRNAs from three irCLIP-seq replicates.

| GeneID | Name | Biotype | Description |
|---|---|---|---|
| ENSMUSG 00000040479 | Dgkz | protein_coding | diacylglycerol kinase zeta [Source:MGI Symbol;Acc:MGI:1278339] |
| ENSMUSG 00000058318 | Phf21a | protein_coding | PHD finger protein 21A [Source:MGI Symbol;Acc:MGI:2384756] |
| ENSMUSG 00000049922 | Slc35c1 | protein_coding | solute carrier family 35, member C1 [Source:MGI Symbol;Acc:MGI:2443301] |
| ENSMUSG 00000075028 | Prdm11 | protein_coding | PR domain containing 11 [Source:MGI Symbol;Acc:MGI:2685553] |
| ENSMUSG 00000027195 | Hsd17b12 | protein_coding | hydroxysteroid (17-beta) dehydrogenase 12 [Source:MGI Symbol;Acc:MGI:1926967] |
| ENSMUSG 00000048058 | Ldlrad3 | protein_coding | low density lipoprotein receptor class A domain containing 3 [Source:MGI Symbol;Acc:MGI:2138856] |
| ENSMUSG 00000005087 | Cd44 | protein_coding | CD44 antigen [Source:MGI Symbol;Acc:MGI:88338] |
| ENSMUSG 00000027184 | Caprin1 | protein_coding | cell cycle associated protein 1 [Source:MGI Symbol;Acc:MGI:1858234] |
| ENSMUSG 00000068373 | D430041D05Rik | protein_coding | RIKEN cDNA D430041D05 gene [Source:MGI Symbol;Acc:MGI:2181743] |
| ENSMUSG 00000027177 | Hipk3 | protein_coding | homeodomain interacting protein kinase 3 [Source:MGI Symbol;Acc:MGI:1314882] |
| ENSMUSG 00000057378 | Ryr3 | protein_coding | ryanodine receptor 3 [Source:MGI Symbol;Acc:MGI:99684] |
| ENSMUSG 00000041219 | Arhgap11a | protein_coding | Rho GTPase activating protein 11A [Source:MGI Symbol;Acc:MGI:2444300] |
| ENSMUSG 00000040383 | Aqr | protein_coding | aquarius [Source:MGI Symbol;Acc:MGI:1276102] |
| ENSMUSG 00000027351 | Spred1 | protein_coding | sprouty protein with EVH-1 domain 1, related sequence [Source:MGI Symbol;Acc:MGI:2150016] |
| ENSMUSG 00000034216 | Vps18 | protein_coding | vacuolar protein sorting 18 (yeast) [Source:MGI Symbol;Acc:MGI:2443626] |
| ENSMUSG 00000027304 | Rtf1 | protein_coding | Rtf1, Paf1/RNA polymerase II complex component, homolog (S. cerevisiae) [Source:MGI Symbol;Acc:MGI:1309480] |
| ENSMUSG 00000033943 | Mga | protein_coding | MAX gene associated [Source:MGI Symbol;Acc:MGI:1352483] |
| ENSMUSG 00000027288 | Zfp106 | protein_coding | zinc finger protein 106 [Source:MGI Symbol;Acc:MGI:1270153] |
| ENSMUSG 00000027263 | Tubgcp4 | protein_coding | tubulin, gamma complex associated protein 4 [Source:MGI Symbol;Acc:MGI:1196293] |
| ENSMUSG 00000033486 | Catsper2 | protein_coding | cation channel, sperm associated 2 [Source:MGI Symbol;Acc:MGI:2387404] |
| ENSMUSG 00000027248 | Pdia3 | protein_coding | protein disulfide isomerase associated 3 [Source:MGI Symbol;Acc:MGI:95834] |
| ENSMUSG 00000027203 | Dut | protein_coding | deoxyuridine triphosphatase [Source:MGI Symbol;Acc:MGI:1346051] |
| ENSMUSG 00000027365 | Trpm7 | protein_coding | transient receptor potential cation channel, subfamily M, member 7 [Source:MGI Symbol;Acc:MGI:1929996] |
| ENSMUSG 00000003660 | Snrnp200 | protein_coding | small nuclear ribonucleoprotein 200 (U5) [Source:MGI Symbol;Acc:MGI:2444401] |
| ENSMUSG 00000034850 | Tmem127 | protein_coding | transmembrane protein 127 [Source:MGI Symbol;Acc:MGI:1916720] |
| ENSMUSG 00000027367 | Stard7 | protein_coding | START domain containing 7 [Source:MGI Symbol;Acc:MGI:2139090] |
| ENSMUSG 00000014355 | Anapc1 | protein_coding | anaphase promoting complex subunit 1 [Source:MGI Symbol;Acc:MGI:103097] |
| ENSMUSG 00000027394 | Ttl | protein_coding | tubulin tyrosine ligase [Source:MGI Symbol;Acc:MGI:1916987] |
| ENSMUSG 00000027397 | Slc20a1 | protein_coding | solute carrier family 20, member 1 [Source:MGI Symbol;Acc:MGI:108392] |
| ENSMUSG 00000037902 | Sirpa | protein_coding | signal-regulatory protein alpha [Source:MGI Symbol;Acc:MGI:108563] |
| ENSMUSG 00000037885 | Stk35 | protein_coding | serine/threonine kinase 35 [Source:MGI Symbol;Acc:MGI:1914583] |
| ENSMUSG 00000027404 | Snrpb | protein_coding | small nuclear ribonucleoprotein B [Source:MGI Symbol;Acc:MGI:98342] |
| ENSMUSG 00000027405 | Nop56 | protein_coding | NOP56 ribonucleoprotein homolog (yeast) [Source:MGI Symbol;Acc:MGI:1914384] |
| ENSMUSG 00000027303 | Ptpra | protein_coding | protein tyrosine phosphatase, receptor type, A [Source:MGI Symbol;Acc:MGI:97808] |
| ENSMUSG 00000027329 | Spef1 | protein_coding | sperm flagellar 1 [Source:MGI Symbol;Acc:MGI:3513546] |
| ENSMUSG 00000068267 | Cenpb | protein_coding | centromere protein B [Source:MGI Symbol;Acc:MGI:88376] |
| ENSMUSG 00000039943 | Plcb4 | protein_coding | phospholipase C, beta 4 [Source:MGI Symbol;Acc:MGI:107464] |

TABLE S2-continued

Ythdf2 targeted mRNAs from three irCLIP-seq replicates.

| GeneID | Name | Biotype | Description |
|---|---|---|---|
| ENSMUSG00000068205 | Macrod2 | protein_coding | MACRO domain containing 2 [Source:MGI Symbol;Acc:MGI:1920149] |
| ENSMUSG00000027423 | Snx5 | protein_coding | sorting nexin 5 [Source:MGI Symbol;Acc:MGI:1916428] |
| ENSMUSG00000027425 | Csrp2bp | protein_coding | cysteine and glycine-rich protein 2 binding protein [Source:MGI Symbol;Acc:MGI:1917264] |
| ENSMUSG00000027429 | Sec23b | protein_coding | SEC23B (*S. cerevisiae*) [Source:MGI Symbol;Acc:MGI:1350925] |
| ENSMUSG00000063873 | Slc24a3 | protein_coding | solute carrier family 24 (sodium/potassium/calcium exchanger), member 3 [Source:MGI Symbol;Acc:MGI:2137513] |
| ENSMUSG00000037110 | Ralgapa2 | protein_coding | Ral GTPase activating protein, alpha subunit 2 (catalytic) [Source:MGI Symbol;Acc:MGI:3036245] |
| ENSMUSG00000027435 | Cd93 | protein_coding | CD93 antigen [Source:MGI Symbol;Acc:MGI:106664] |
| ENSMUSG00000074736 | Tmem90b | protein_coding | transmembrane protein 90B [Source:MGI Symbol;Acc:MGI:3702158] |
| ENSMUSG00000033059 | Pygb | protein_coding | brain glycogen phosphorylase [Source:MGI Symbol;Acc:MGI:97828] |
| ENSMUSG00000027459 | Fam110a | protein_coding | family with sequence similarity 110, member A [Source:MGI Symbol;Acc:MGI:1921097] |
| ENSMUSG00000060257 | Scrt2 | protein_coding | scratch homolog 2, zinc finger protein (*Drosophila*) [Source:MGI Symbol;Acc:MGI:2139287] |
| ENSMUSG00000074698 | Csnk2a1 | protein_coding | casein kinase 2, alpha 1 polypeptide [Source:MGI Symbol;Acc:MGI:88543] |
| ENSMUSG00000007659 | Bcl2l1 | protein_coding | BCL2-like 1 [Source:MGI Symbol;Acc:MGI:88139] |
| ENSMUSG00000027469 | Tpx2 | protein_coding | TPX2, microtubule-associated protein homolog (*Xenopus laevis*) [Source:MGI Symbol;Acc:MGI:1919369] |
| ENSMUSG00000042662 | Dusp 15 | protein_coding | dual specificity phosphatase-like 15 [Source:MGI Symbol;Acc:MGI:1934928] |
| ENSMUSG00000051413 | Plagl2 | protein_coding | pleiomorphic adenoma gene-like 2 [Source:MGI Symbol;Acc:MGI:1933165] |
| ENSMUSG00000042548 | Asxl1 | protein_coding | additional sex combs like 1 (*Drosophila*) [Source:MGI Symbol;Acc:MGI:2684063] |
| ENSMUSG00000027478 | Dnmt3b | protein_coding | DNA methyltransferase 3B [Source:MGI Symbol;Acc:MGI:1261819] |
| ENSMUSG00000027487 | Cdk5rap1 | protein_coding | CDK5 regulatory subunit associated protein 1 [Source:MGI Symbol;Acc:MGI:1914221] |
| ENSMUSG00000038467 | Chmp4b | protein_coding | charged multivesicular body protein 4B [Source:MGI Symbol;Acc:MGI:1922858] |
| ENSMUSG00000027593 | Raly | protein_coding | hnRNP-associated with lethal yellow [Source:MGI Symbol;Acc:MGI:97850] |
| ENSMUSG00000027596 | a | protein_coding | nonagouti [Source:MGI Symbol;Acc:MGI:87853] |
| ENSMUSG00000038369 | Ncoa6 | protein_coding | nuclear receptor coactivator 6 [Source:MGI Symbol;Acc:MGI:1929915] |
| ENSMUSG00000038324 | Trpc4ap | protein_coding | transient receptor potential cation channel, subfamily C, member 4 associated protein [Source:MGI Symbol;Acc:MGI:1930751] |
| ENSMUSG00000074643 | Cpne1 | protein_coding | copine I [Source:MGI Symbol;Acc:MGI:2386621] |
| ENSMUSG00000027618 | Nfs1 | protein_coding | nitrogen fixation gene 1 (*S. cerevisiae*) [Source:MGI Symbol;Acc:MGI:1316706] |
| ENSMUSG00000089824 | Rbm12 | protein_coding | RNA binding motif protein 12 [Source:MGI Symbol;Acc:MGI:1922960] |
| ENSMUSG00000062175 | Tgif2 | protein_coding | TGFB-induced factor homeobox 2 [Source:MGI Symbol;Acc:MGI:1915299] |
| ENSMUSG00000074627 | 4922505G16Rik | protein_coding | RIKEN cDNA 4922505G16 gene [Source:MGI Symbol;Acc:MGI:3603828] |
| ENSMUSG00000027642 | Rpn2 | protein_coding | ribophorin II [Source:MGI Symbol;Acc:MGI:98085] |
| ENSMUSG00000027651 | Rprd1b | protein_coding | regulation of nuclear pre-mRNA domain containing 1B [Source:MGI Symbol;Acc:MGI:1917720] |
| ENSMUSG00000037761 | Actr5 | protein_coding | ARP5 actin-related protein 5 homolog (yeast) [Source:MGI Symbol;Acc:MGI:1924748] |
| ENSMUSG00000027655 | Dhx35 | protein_coding | DEAH (Asp-Glu-Ala-His) box polypeptide 35 [Source:MGI Symbol;Acc:MGI:1918965] |
| ENSMUSG00000070544 | Top1 | protein_coding | topoisomerase (DNA) I [Source:MGI Symbol;Acc:MGI:98788] |
| ENSMUSG00000016933 | Plcg1 | protein_coding | phospholipase C, gamma 1 [Source:MGI Symbol;Acc:MGI:97615] |
| ENSMUSG00000057133 | Chd6 | protein_coding | chromodomain helicase DNA binding protein 6 [Source:MGI Symbol;Acc:MGI:1918639] |

TABLE S2-continued

Ythdf2 targeted mRNAs from three irCLIP-seq replicates.

| GeneID | Name | Biotype | Description |
|---|---|---|---|
| ENSMUSG00000016921 | Srsf6 | protein_coding | serine/arginine-rich splicing factor 6 [Source:MGI Symbol;Acc:MGI:1915246] |
| ENSMUSG00000017817 | Jph2 | protein_coding | junctophilin 2 [Source:MGI Symbol;Acc:MGI:1891496] |
| ENSMUSG00000035268 | Pkig | protein_coding | protein kinase inhibitor, gamma [Source:MGI Symbol;Acc:MGI:1343086] |
| ENSMUSG00000017697 | Ada | protein_coding | adenosine deaminase [Source:MGI Symbol;Acc:MGI:87916] |
| ENSMUSG00000018326 | Ywhab | protein_coding | tyrosine 3-monooxygenase/tryptophan 5-monooxygenase activation protein, beta polypeptide [Source:MGI Symbol;Acc:MGI:1891917] |
| ENSMUSG00000039849 | Pcif1 | protein_coding | PDX1 C-terminal inhibiting factor 1 [Source:MGI Symbol;Acc:MGI:2443858] |
| ENSMUSG00000039804 | Ncoa5 | protein_coding | nuclear receptor coactivator 5 [Source:MGI Symbol;Acc:MGI:2385165] |
| ENSMUSG00000017897 | Eya2 | protein_coding | eyes absent 2 homolog (*Drosophila*) [Source:MGI Symbol;Acc:MGI:109341] |
| ENSMUSG00000039671 | Zmynd8 | protein_coding | zinc finger, MYND-type containing 8 [Source:MGI Symbol;Acc:MGI:1918025] |
| ENSMUSG00000027678 | Ncoa3 | protein_coding | nuclear receptor coactivator 3 [Source:MGI Symbol;Acc:MGI:1276535] |
| ENSMUSG00000017999 | Ddx27 | protein_coding | DEAD (Asp-Glu-Ala-Asp) box polypeptide 27 [Source:MGI Symbol;Acc:MGI:2385884] |
| ENSMUSG00000074578 | 1500012F01Rik | protein_coding | RIKEN cDNA 1500012F01 gene [Source:MGI Symbol;Acc:MGI:1916199] |
| ENSMUSG00000047030 | Spata2 | protein_coding | spermatogenesis associated 2 [Source:MGI Symbol;Acc:MGI:2146885] |
| ENSMUSG00000027540 | Ptpn1 | protein_coding | protein tyrosine phosphatase, non-receptor type 1 [Source:MGI Symbol;Acc:MGI:97805] |
| ENSMUSG00000051149 | Adnp | protein_coding | activity-dependent neuroprotective protein [Source:MGI Symbol;Acc:MGI:1338758] |
| ENSMUSG00000047907 | Tshz2 | protein_coding | teashirt zinc finger family member 2 [Source:MGI Symbol;Acc:MGI:2153084] |
| ENSMUSG00000052056 | Zfp217 | protein_coding | zinc finger protein 217 [Source:MGI Symbol;Acc:MGI:2685408] |
| ENSMUSG00000027560 | Dok5 | protein_coding | docking protein 5 [Source:MGI Symbol;Acc:MGI:1924079] |
| ENSMUSG00000027509 | Rae1 | protein_coding | RAE1 RNA export 1 homolog (*S. pombe*) [Source:MGI Symbol;Acc:MGI:1913929] |
| ENSMUSG00000027518 | 1700021F07Rik | protein_coding | RIKEN cDNA 1700021F07 gene [Source:MGI Symbol;Acc:MGI:1919471] |
| ENSMUSG00000027523 | Gnas | protein_coding | GNAS (guanine nucleotide binding protein, alpha stimulating) complex locus [Source:MGI Symbol;Acc:MGI:95777] |
| ENSMUSG00000090625 | AL593857.1 | protein_coding | |
| ENSMUSG00000074529 | C330013J21Rik | protein_coding | RIKEN cDNA C330013J21 gene [Source:MGI Symbol;Acc:MGI:1925953] |
| ENSMUSG00000038963 | Slco4a1 | protein_coding | solute carrier organic anion transporter family, member 4a1 [Source:MGI Symbol;Acc:MGI:1351866] |
| ENSMUSG00000038914 | Dido1 | protein_coding | death inducer-obliterator 1 [Source:MGI Symbol;Acc:MGI:1344352] |
| ENSMUSG00000038848 | Ythdf1 | protein_coding | YTH domain family 1 [Source:MGI Symbol;Acc:MGI:1917431] |
| ENSMUSG00000040209 | Zfp704 | protein_coding | zinc finger protein 704 [Source:MGI Symbol;Acc:MGI:2180715] |
| ENSMUSG00000019528 | Gyg | protein_coding | glycogenin [Source:MGI Symbol;Acc:MGI:1351614] |
| ENSMUSG00000039286 | Fndc3b | protein_coding | fibronectin type III domain containing 3B [Source:MGI Symbol;Acc:MGI:1919257] |
| ENSMUSG00000027692 | Tnik | protein_coding | TRAF2 and NCK interacting kinase [Source:MGI Symbol;Acc:MGI:1916264] |
| ENSMUSG00000027684 | Mecom | protein_coding | MDS1 and EVI1 complex locus [Source:MGI Symbol;Acc:MGI:95457] |
| ENSMUSG00000027667 | Zfp639 | protein_coding | zinc finger protein 639 [Source:MGI Symbol;Acc:MGI:1915028] |
| ENSMUSG00000027669 | Gnb4 | protein_coding | guanine nucleotide binding protein (G protein), beta 4 [Source:MGI Symbol;Acc:MGI:104581] |
| ENSMUSG00000037400 | Atp11b | protein_coding | ATPase, class VI, type 11B [Source:MGI Symbol;Acc:MGI:1923545] |
| ENSMUSG00000027712 | Anxa5 | protein_coding | annexin A5 [Source:MGI Symbol;Acc:MGI:106008] |
| ENSMUSG00000027715 | Ccna2 | protein_coding | cyclin A2 [Source:MGI Symbol;Acc:MGI:108069] |
| ENSMUSG00000049940 | Pgrmc2 | protein_coding | progesterone receptor membrane component 2 [Source:MGI Symbol;Acc:MGI:1918054] |

TABLE S2-continued

Ythdf2 targeted mRNAs from three irCLIP-seq replicates.

| GeneID | Name | Biotype | Description |
|---|---|---|---|
| ENSMUSG 00000037174 | Elf2 | protein_coding | E74-like factor 2 [Source:MGI Symbol;Acc:MGI:1916507] |
| ENSMUSG 00000063273 | Naa15 | protein_coding | N(alpha)-acetyltransferase 15, NatA auxiliary subunit [Source:MGI Symbol;Acc:MGI:1922088] |
| ENSMUSG 00000074604 | Mgst2 | protein_coding | microsomal glutathione S-transferase 2 [Source:MGI Symbol;Acc:MGI:2448481] |
| ENSMUSG 00000061143 | Maml3 | protein_coding | mastermind like 3 (*Drosophila*) [Source:MGI Symbol;Acc:MGI:2389461] |
| ENSMUSG 00000027799 | Nbea | protein_coding | neurobeachin [Source:MGI Symbol;Acc:MGI:1347075] |
| ENSMUSG 00000027763 | Mbnl1 | protein_coding | muscleblind-like 1 (*Drosophila*) [Source:MGI Symbol;Acc:MGI:1928482] |
| ENSMUSG 00000036894 | Rap2b | protein_coding | RAP2B, member of RAS oncogene family [Source:MGI Symbol;Acc:MGI:1921262] |
| ENSMUSG 00000034349 | Smc4 | protein_coding | structural maintenance of chromosomes 4 [Source:MGI Symbol;Acc:MGI:1917349] |
| ENSMUSG 00000027782 | Kpna4 | protein_coding | karyopherin (importin) alpha 4 [Source:MGI Symbol;Acc:MGI:1100848] |
| ENSMUSG 00000028008 | Accn5 | protein_coding | amiloride-sensitive cation channel 5, intestinal [Source:MGI Symbol;Acc:MGI:1929259] |
| ENSMUSG 00000033910 | Gucy1a3 | protein_coding | guanylate cyclase 1, soluble, alpha 3 [Source:MGI Symbol;Acc:MGI:1926562] |
| ENSMUSG 00000033767 | D930015E06Rik | protein_coding | RIKEN cDNA D930015E06 gene [Source:MGI Symbol;Acc:MGI:2443399] |
| ENSMUSG 00000074513 | Arfip1 | protein_coding | ADP-ribosylation factor interacting protein 1 [Source:MGI Symbol;Acc:MGI:1277120] |
| ENSMUSG 00000028081 | Rps3a | protein_coding | ribosomal protein S3A [Source:MGI Symbol;Acc:MGI:1202063] |
| ENSMUSG 00000028080 | Lrba | protein_coding | LPS-responsive beige-like anchor [Source:MGI Symbol;Acc:MGI:1933162] |
| ENSMUSG 00000004895 | Prcc | protein_coding | papillary renal cell carcinoma (translocation-associated) [Source:MGI Symbol;Acc:MGI:2137738] |
| ENSMUSG 00000004897 | Hdgf | protein_coding | hepatoma-derived growth factor [Source:MGI Symbol;Acc:MGI:1194494] |
| ENSMUSG 00000028068 | Iqgap3 | protein_coding | IQ motif containing GTPase activating protein 3 [Source:MGI Symbol;Acc:MGI:3028642] |
| ENSMUSG 00000001415 | Smg5 | protein_coding | Smg-5 homolog, nonsense mediated mRNA decay factor (*C. elegans*) [Source:MGI Symbol;Acc:MGI:2447364] |
| ENSMUSG 00000008604 | Ubqln4 | protein_coding | ubiquilin 4 [Source:MGI Symbol;Acc:MGI:2150152] |
| ENSMUSG 00000054199 | Gon4l | protein_coding | gon-4-like (*C.elegans*) [Source:MGI Symbol;Acc:MGI:1917579] |
| ENSMUSG 00000059743 | Fdps | protein_coding | farnesyl diphosphate synthetase [Source:MGI Symbol;Acc:MGI:104888] |
| ENSMUSG 00000027947 | Il6ra | protein_coding | interleukin 6 receptor, alpha [Source:MGI Symbol;Acc:MGI:105304] |
| ENSMUSG 00000042520 | Ubap2l | protein_coding | ubiquitin associated protein 2-like [Source:MGI Symbol;Acc:MGI:1921633] |
| ENSMUSG 00000038902 | Pogz | protein_coding | pogo transposable element with ZNF domain [Source:MGI Symbol;Acc:MGI:2442117] |
| ENSMUSG 00000038861 | Pi4kb | protein_coding | phosphatidylinositol 4-kinase, catalytic, beta polypeptide [Source:MGI Symbol;Acc:MGI:1334433] |
| ENSMUSG 00000019338 | Zfp687 | protein_coding | zinc finger protein 687 [Source:MGI Symbol;Acc:MGI:1925516] |
| ENSMUSG 00000028126 | Pip5k1a | protein_coding | phosphatidylinositol-4-phosphate 5-kinase, type 1 alpha [Source:MGI Symbol;Acc:MGI:107929] |
| ENSMUSG 00000015714 | Lass2 | protein_coding | LAG1 homolog, ceramide synthase 2 [Source:MGI Symbol;Acc:MGI:1924143] |
| ENSMUSG 00000046519 | Golph3l | protein_coding | golgi phosphoprotein 3-like [Source:MGI Symbol;Acc:MGI:1917129] |
| ENSMUSG 00000015748 | Prpf3 | protein_coding | PRP3 pre-mRNA processing factor 3 homolog (yeast) [Source:MGI Symbol;Acc:MGI:1918017] |
| ENSMUSG 00000015749 | Anp32e | protein_coding | acidic (leucine-rich) nuclear phosphoprotein 32 family, member E [Source:MGI Symbol;Acc:MGI:1913721] |
| ENSMUSG 00000038495 | Otud7b | protein_coding | OTU domain containing 7B [Source:MGI Symbol;Acc:MGI:2654703] |
| ENSMUSG 00000068855 | Hist2h2ac | protein_coding | histone cluster 2, H2ac [Source:MGI Symbol;Acc:MGI:2448316] |
| ENSMUSG 00000038256 | Bcl9 | protein_coding | B cell CLL/lymphoma 9 [Source:MGI Symbol;Acc:MGI:1924828] |
| ENSMUSG 00000038170 | Pde4dip | protein_coding | phosphodiesterase 4D interacting protein (myomegalin) [Source:MGI Symbol;Acc:MGI:1891434] |
| ENSMUSG 00000027878 | Notch2 | protein_coding | Notch gene homolog 2 (*Drosophila*) [Source:MGI Symbol;Acc:MGI:97364] |

TABLE S2-continued

Ythdf2 targeted mRNAs from three irCLIP-seq replicates.

| GeneID | Name | Biotype | Description |
|---|---|---|---|
| ENSMUSG 00000068823 | Csde1 | protein_coding | cold shock domain containing E1, RNA binding [Source:MGI Symbol;Acc:MGI:92356] |
| ENSMUSG 00000033014 | Trim33 | protein_coding | tripartite motif-containing 33 [Source:MGI Symbol;Acc:MGI:2137357] |
| ENSMUSG 00000078620 | Gm10964 | protein_coding | predicted gene 10964 [Source:MGI Symbol;Acc:MGI:3779175] |
| ENSMUSG 00000008730 | Hipk1 | protein_coding | homeodomain interacting protein kinase 1 [Source:MGI Symbol;Acc:MGI:1314873] |
| ENSMUSG 00000052539 | Magi3 | protein_coding | membrane associated guanylate kinase, WW and PDZ domain containing 3 [Source:MGI Symbol;Acc:MGI:1923484] |
| ENSMUSG 00000032902 | Slc16a1 | protein_coding | solute carrier family 16 (monocarboxylic acid transporters), member 1 [Source:MGI Symbol;Acc:MGI:106013] |
| ENSMUSG 00000000563 | Atp5f1 | protein_coding | ATP synthase, H+ transporting, mitochondrial F0 complex, subunit B1 [Source:MGI Symbol;Acc:MGI:1100495] |
| ENSMUSG 00000055891 | Ubl4b | protein_coding | ubiquitin-like 4B [Source:MGI Symbol;Acc:MGI:1914841] |
| ENSMUSG 00000000001 | Gnai3 | protein_coding | guanine nucleotide binding protein (G protein), alpha inhibiting 3 [Source:MGI Symbol;Acc:MGI:95773] |
| ENSMUSG 00000045326 | Fndc7 | protein_coding | fibronectin type III domain containing 7 [Source:MGI Symbol;Acc:MGI:2443535] |
| ENSMUSG 00000045662 | 4921515J06Rik | protein_coding | RIKEN cDNA 4921515J06 gene [Source:MGI Symbol;Acc:MGI:1913965] |
| ENSMUSG 00000028121 | Bcar3 | protein_coding | breast cancer anti-estrogen resistance 3 [Source:MGI Symbol;Acc:MGI:1352501] |
| ENSMUSG 00000039735 | Fnbp1l | protein_coding | formin binding protein 1-like [Source:MGI Symbol;Acc:MGI:1925642] |
| ENSMUSG 00000046688 | Tifa | protein_coding | TRAF-interacting protein with forkhead-associated domain [Source:MGI Symbol;Acc:MGI:2182965] |
| ENSMUSG 00000028024 | Enpep | protein_coding | glutamyl aminopeptidase [Source:MGI Symbol;Acc:MGI:106645] |
| ENSMUSG 00000001052 | Sec24b | protein_coding | Sec24 related gene family, member B (*S. cerevisiae*) [Source:MGI Symbol;Acc:MGI:2139764] |
| ENSMUSG 00000027984 | Hadh | protein_coding | hydroxyacyl-Coenzyme A dehydrogenase [Source:MGI Symbol;Acc:MGI:96009] |
| ENSMUSG 00000028158 | Mttp | protein_coding | microsomal triglyceride transfer protein [Source:MGI Symbol;Acc:MGI:106926] |
| ENSMUSG 00000028149 | Rap1gds1 | protein_coding | RAP1, GTP-GDP dissociation stimulator 1 [Source:MGI Symbol;Acc:MGI:2385189] |
| ENSMUSG 00000047940 | B930007M17Rik | protein_coding | RIKEN cDNA B930007M17 gene [Source:MGI Symbol;Acc:MGI:2685863] |
| ENSMUSG 00000074182 | Znhit6 | protein_coding | zinc finger, HIT type 6 [Source:MGI Symbol;Acc:MGI:1916996] |
| ENSMUSG 00000036863 | Syde2 | protein_coding | synapse defective 1, Rho GTPase, homolog 2 (*C. elegans*) [Source:MGI Symbol;Acc:MGI:3036264] |
| ENSMUSG 00000028185 | Dnase2b | protein_coding | deoxyribonuclease II beta [Source:MGI Symbol;Acc:MGI:1913283] |
| ENSMUSG 00000005034 | Prkacb | protein_coding | protein kinase, cAMP dependent, catalytic, beta [Source:MGI Symbol;Acc:MGI:97594] |
| ENSMUSG 00000038975 | Rabggtb | protein_coding | RAB geranylgeranyl transferase, b subunit [Source:MGI Symbol;Acc:MGI:99537] |
| ENSMUSG 00000042228 | Lyn | protein_coding | Yamaguchi sarcoma viral (v-yes-1) oncogene homolog [Source:MGI Symbol;Acc:MGI:96892] |
| ENSMUSG 00000028234 | Rps20 | protein_coding | ribosomal protein S20 [Source:MGI Symbol;Acc:MGI:1914677] |
| ENSMUSG 00000066324 | Impad1 | protein_coding | inositol monophosphatase domain containing 1 [Source:MGI Symbol;Acc:MGI:1915720] |
| ENSMUSG 00000028249 | Sdcbp | protein_coding | syndecan binding protein [Source:MGI Symbol;Acc:MGI:1337026] |
| ENSMUSG 00000049225 | Pdp1 | protein_coding | pyruvate dehyrogenase phosphatase catalytic subunit 1 [Source:MGI Symbol;Acc:MGI:2685870] |
| ENSMUSG 00000006586 | Runx1t1 | protein_coding | runt-related transcription factor 1; translocated to, 1 (cyclin D-related) [Source:MGI Symbol;Acc:MGI:104793] |
| ENSMUSG 00000043252 | Tmem64 | protein_coding | transmembrane protein 64 [Source:MGI Symbol;Acc:MGI:2140359] |
| ENSMUSG 00000028228 | Cpne3 | protein_coding | copine III [Source:MGI Symbol;Acc:MGI:1917818] |
| ENSMUSG 00000040478 | Prdm13 | protein_coding | PR domain containing 13 [Source:MGI Symbol;Acc:MGI:2448528] |
| ENSMUSG 00000058006 | Mdn1 | protein_coding | midasin homolog (yeast) [Source:MGI Symbol;Acc:MGI:1926159] |
| ENSMUSG 00000040128 | Pnrc1 | protein_coding | proline-rich nuclear receptor coactivator 1 [Source:MGI Symbol;Acc:MGI:1917838] |

TABLE S2-continued

Ythdf2 targeted mRNAs from three irCLIP-seq replicates.

| GeneID | Name | Biotype | Description |
| --- | --- | --- | --- |
| ENSMUSG00000039967 | Zfp292 | protein_coding | zinc finger protein 292 [Source:MGI Symbol;Acc:MGI:1353423] |
| ENSMUSG00000045083 | Lingo2 | protein_coding | leucine rich repeat and Ig domain containing 2 [Source:MGI Symbol;Acc:MGI:2442298] |
| ENSMUSG00000036822 | Topors | protein_coding | topoisomerase I binding, arginine/serine-rich [Source:MGI Symbol;Acc:MGI:2146189] |
| ENSMUSG00000028413 | B4galt1 | protein_coding | UDP-Gal:betaGlcNAc beta 1,4- galactosyltransferase, polypeptide 1 [Source:MGI Symbol;Acc:MGI:95705] |
| ENSMUSG00000028416 | Bag1 | protein_coding | BCL2-associated athanogene 1 [Source:MGI Symbol;Acc:MGI:108047] |
| ENSMUSG00000028433 | Ubap2 | protein_coding | ubiquitin-associated protein 2 [Source:MGI Symbol;Acc:MGI:1916176] |
| ENSMUSG00000028436 | Dcaf12 | protein_coding | DDB1 and CUL4 associated factor 12 [Source:MGI Symbol;Acc:MGI:1916220] |
| ENSMUSG00000073889 | Il11ra1 | protein_coding | interleukin 11 receptor, alpha chain 1 [Source:MGI Symbol;Acc:MGI:107426] |
| ENSMUSG00000036078 | Sigmar1 | protein_coding | sigma non-opioid intracellular receptor 1 [Source:MGI Symbol;Acc:MGI:1195268] |
| ENSMUSG00000028451 | 1700022I11Rik | protein_coding | RIKEN cDNA 1700022I11 gene [Source:MGI Symbol;Acc:MGI:1914567] |
| ENSMUSG00000028452 | Vcp | protein_coding | valosin containing protein [Source:MGI Symbol;Acc:MGI:99919] |
| ENSMUSG00000028461 | Ccdc107 | protein_coding | coiled-coil domain containing 107 [Source:MGI Symbol;Acc:MGI:1913423] |
| ENSMUSG00000028465 | Tln1 | protein_coding | talin 1 [Source:MGI Symbol;Acc:MGI:1099832] |
| ENSMUSG00000035696 | Rnf38 | protein_coding | ring finger protein 38 [Source:MGI Symbol;Acc:MGI:1920719] |
| ENSMUSG00000035615 | Frmpd1 | protein_coding | FERM and PDZ domain containing 1 [Source:MGI Symbol;Acc:MGI:2446274] |
| ENSMUSG00000045973 | Mcart1 | protein_coding | mitochondrial carrier triple repeat 1 [Source:MGI Symbol;Acc:MGI:2684984] |
| ENSMUSG00000028333 | Anp32b | protein_coding | acidic (leucine-rich) nuclear phosphoprotein 32 family, member B [Source:MGI Symbol;Acc:MGI:1914878] |
| ENSMUSG00000028337 | Coro2a | protein_coding | coronin, actin binding protein 2A [Source:MGI Symbol;Acc:MGI:1345966] |
| ENSMUSG00000039809 | Gabbr2 | protein_coding | gamma-aminobutyric acid (GABA) B receptor, 2 [Source:MGI Symbol;Acc:MGI:2386030] |
| ENSMUSG00000053317 | Sec61b | protein_coding | Sec61 beta subunit [Source:MGI Symbol;Acc:MGI:1913462] |
| ENSMUSG00000039611 | 2810432L12Rik | protein_coding | RIKEN cDNA 2810432L12 gene [Source:MGI Symbol;Acc:MGI:1914313] |
| ENSMUSG00000028426 | Rad23b | protein_coding | RAD23b homolog (S. cerevisiae) [Source:MGI Symbol;Acc:MGI:105128] |
| ENSMUSG00000028434 | Epb4.1l4b | protein_coding | erythrocyte protein band 4.1-like 4b [Source:MGI Symbol;Acc:MGI:1859149] |
| ENSMUSG00000089945 | Gm20459 | protein_coding | predicted gene 20459 [Source:MGI Symbol;Acc:MGI:5141924] |
| ENSMUSG00000028367 | Txn1 | protein_coding | thioredoxin 1 [Source:MGI Symbol;Acc:MGI:98874] |
| ENSMUSG00000038709 | Txndc8 | protein_coding | thioredoxin domain containing 8 [Source:MGI Symbol;Acc:MGI:1914652] |
| ENSMUSG00000050812 | AI314180 | protein_coding | expressed sequence AI314180 [Source:MGI Symbol;Acc:MGI:2140220] |
| ENSMUSG00000038598 | AI481877 | protein_coding | expressed sequence AI481877 [Source:MGI Symbol;Acc:MGI:2140313] |
| ENSMUSG00000038578 | Susd1 | protein_coding | sushi domain containing 1 [Source:MGI Symbol;Acc:MGI:3651543] |
| ENSMUSG00000028382 | Rod1 | protein_coding | ROD1 regulator of differentiation 1 (S. pombe) [Source:MGI Symbol;Acc:MGI:1923334] |
| ENSMUSG00000045071 | E130308A19Rik | protein_coding | RIKEN cDNA E130308A19 gene [Source:MGI Symbol;Acc:MGI:2442164] |
| ENSMUSG00000028393 | Alad | protein_coding | aminolevulinate, delta-, dehydratase [Source:MGI Symbol;Acc:MGI:96853] |
| ENSMUSG00000028373 | Astn2 | protein_coding | astrotactin 2 [Source:MGI Symbol;Acc:MGI:1889277] |
| ENSMUSG00000028399 | Ptprd | protein_coding | protein tyrosine phosphatase, receptor type, D [Source:MGI Symbol;Acc:MGI:97812] |
| ENSMUSG00000070923 | Klhl9 | protein_coding | kelch-like 9 (Drosophila) [Source:MGI Symbol;Acc:MGI:2180122] |
| ENSMUSG00000052684 | Jun | protein_coding | Jun oncogene [Source:MGI Symbol;Acc:MGI:96646] |
| ENSMUSG00000081225 | Cyp2j12 | protein_coding | cytochrome P450, family 2, subfamily j, polypeptide 12 [Source:MGI Symbol;Acc:MGI:3717097] |

TABLE S2-continued

Ythdf2 targeted mRNAs from three irCLIP-seq replicates.

| GeneID | Name | Biotype | Description |
|---|---|---|---|
| ENSMUSG00000028565 | Nfia | protein_coding | nuclear factor I/A [Source:MGI Symbol;Acc:MGI:108056] |
| ENSMUSG00000035407 | Kank4 | protein_coding | KN motif and ankyrin repeat domains 4 [Source:MGI Symbol;Acc:MGI:3043381] |
| ENSMUSG00000028560 | Usp1 | protein_coding | ubiquitin specific peptidase 1 [Source:MGI Symbol;Acc:MGI:2385198] |
| ENSMUSG00000028530 | Jak1 | protein_coding | Janus kinase 1 [Source:MGI Symbol;Acc:MGI:96628] |
| ENSMUSG00000028525 | Pde4b | protein_coding | phosphodiesterase 4B, cAMP specific [Source:MGI Symbol;Acc:MGI:99557] |
| ENSMUSG00000078617 | Gm10963 | protein_coding | predicted gene 10963 [Source:MGI Symbol;Acc:MGI:3779174] |
| ENSMUSG00000028519 | Dab1 | protein_coding | disabled homolog 1 (Drosophila) [Source:MGI Symbol;Acc:MGI:108554] |
| ENSMUSG00000028514 | Usp24 | protein_coding | ubiquitin specific peptidase 24 [Source:MGI Symbol;Acc:MGI:1919936] |
| ENSMUSG00000034926 | Dhcr24 | protein_coding | 24-dehydrocholesterol reductase [Source:MGI Symbol;Acc:MGI:1922004] |
| ENSMUSG00000034871 | Fam151a | protein_coding | family with sequence simliarity 151, member A [Source:MGI Symbol;Acc:MGI:2657115] |
| ENSMUSG00000034853 | Acot11 | protein_coding | acyl-CoA thioesterase 11 [Source:MGI Symbol;Acc:MGI:1913736] |
| ENSMUSG00000061887 | Ssbp3 | protein_coding | single-stranded DNA binding protein 3 [Source:MGI Symbol;Acc:MGI:1919725] |
| ENSMUSG00000047143 | Dmrta2 | protein_coding | doublesex and mab-3 related transcription factor like family A2 [Source:MGI Symbol;Acc:MGI:2653629] |
| ENSMUSG00000061298 | Agbl4 | protein_coding | ATP/GTP binding protein-like 4 [Source:MGI Symbol;Acc:MGI:1918244] |
| ENSMUSG00000078598 | Skint5 | protein_coding | selection and upkeep of intraepithelial T cells 5 [Source:MGI Symbol;Acc:MGI:3650151] |
| ENSMUSG00000028718 | Stil | protein_coding | Scl/Tal1 interrupting locus [Source:MGI Symbol;Acc:MGI:107477] |
| ENSMUSG00000028717 | Tal1 | protein_coding | T cell acute lymphocytic leukemia 1 [Source:MGI Symbol;Acc:MGI:98480] |
| ENSMUSG00000028707 | Dmbx1 | protein_coding | diencephalon/mesencephalon homeobox 1 [Source:MGI Symbol;Acc:MGI:2153518] |
| ENSMUSG00000028692 | Akr1a1 | protein_coding | aldo-keto reductase family 1, member A1 (aldehyde reductase) [Source:MGI Symbol;Acc:MGI:1929955] |
| ENSMUSG00000047675 | Rps8 | protein_coding | ribosomal protein S8 [Source:MGI Symbol;Acc:MGI:98166] |
| ENSMUSG00000028677 | Rnf220 | protein_coding | ring finger protein 220 [Source:MGI Symbol;Acc:MGI:1913993] |
| ENSMUSG00000033379 | Atp6v0b | protein_coding | ATPase, H+ transporting, lysosomal V0 subunit B [Source:MGI Symbol;Acc:MGI:1890510] |
| ENSMUSG00000033326 | Kdm4a | protein_coding | lysine (K)-specific demethylase 4A [Source:MGI Symbol;Acc:MGI:2446210] |
| ENSMUSG00000006390 | Elovl1 | protein_coding | elongation of very long chain fatty acids (FEN1/Elo2, SUR4/Elo3, yeast)-like 1 [Source:MGI Symbol;Acc:MGI:1858959] |
| ENSMUSG00000006389 | Mpl | protein_coding | myeloproliferative leukemia virus oncogene [Source:MGI Symbol;Acc:MGI:97076] |
| ENSMUSG00000028645 | Slc2a1 | protein_coding | solute carrier family 2 (facilitated glucose transporter), member 1 [Source:MGI Symbol;Acc:MGI:95755] |
| ENSMUSG00000028644 | Ermap | protein_coding | erythroblast membrane-associated protein [Source:MGI Symbol;Acc:MGI:1349816] |
| ENSMUSG00000078584 | AU022252 | protein_coding | expressed sequence AU022252 [Source:MGI Symbol;Acc:MGI:2140466] |
| ENSMUSG00000028639 | Ybx1 | protein_coding | Y box protein 1 [Source:MGI Symbol;Acc:MGI:99146] |
| ENSMUSG00000032897 | Nfyc | protein_coding | nuclear transcription factor-Y gamma [Source:MGI Symbol;Acc:MGI:107901] |
| ENSMUSG00000064141 | Zfp69 | protein_coding | zinc finger protein 69 [Source:MGI Symbol;Acc:MGI:107794] |
| ENSMUSG00000032870 | Smap2 | protein_coding | stromal membrane-associated GTPase-activating protein 2 [Source:MGI Symbol;Acc:MGI:1917030] |
| ENSMUSG00000028657 | Ppt1 | protein_coding | palmitoyl-protein thioesterase 1 [Source:MGI Symbol;Acc:MGI:1298204] |
| ENSMUSG00000028656 | Cap1 | protein_coding | CAP, adenylate cyclase-associated protein 1 (yeast) [Source:MGI Symbol;Acc:MGI:88262] |
| ENSMUSG00000028649 | Macf1 | protein_coding | microtubule-actin crosslinking factor 1 [Source:MGI Symbol;Acc:MGI:108559] |
| ENSMUSG00000028646 | Rragc | protein_coding | Ras-related GTP binding C [Source:MGI Symbol;Acc:MGI:1858751] |
| ENSMUSG00000028894 | Inpp5b | protein_coding | inositol polyphosphate-5-phosphatase B [Source:MGI Symbol;Acc:MGI:103257] |

TABLE S2-continued

Ythdf2 targeted mRNAs from three irCLIP-seq replicates.

| GeneID | Name | Biotype | Description |
|---|---|---|---|
| ENSMUSG00000078570 | 1110065P20Rik | protein_coding | RIKEN cDNA 1110065P20 gene [Source:MGI Symbol;Acc:MGI:1916170] |
| ENSMUSG00000001985 | Grik3 | protein_coding | glutamate receptor, ionotropic, kainate 3 [Source:MGI Symbol;Acc:MGI:95816] |
| ENSMUSG00000043962 | Thrap3 | protein_coding | thyroid hormone receptor associated protein 3 [Source:MGI Symbol;Acc:MGI:2442637] |
| ENSMUSG00000028849 | Mtap7d1 | protein_coding | microtubule-associated protein 7 domain containing 1 [Source:MGI Symbol;Acc:MGI:2384297] |
| ENSMUSG00000042558 | Adprhl2 | protein_coding | ADP-ribosylhydrolase like 2 [Source:MGI Symbol;Acc:MGI:2140364] |
| ENSMUSG00000028837 | Psmb2 | protein_coding | proteasome (prosome, macropain) subunit, beta type 2 [Source:MGI Symbol;Acc:MGI:1347045] |
| ENSMUSG00000028820 | Sfpq | protein_coding | splicing factor proline/glutamine rich (polypyrimidine tract binding protein associated) [Source:MGI Symbol;Acc:MGI:1918764] |
| ENSMUSG00000028804 | Csmd2 | protein_coding | CUB and Sushi multiple domains 2 [Source:MGI Symbol;Acc:MGI:2386401] |
| ENSMUSG00000028796 | Phc2 | protein_coding | polyhomeotic-like 2 (*Drosophila*) [Source:MGI Symbol;Acc:MGI:1860454] |
| ENSMUSG00000028792 | Ak2 | protein_coding | adenylate kinase 2 [Source:MGI Symbol;Acc:MGI:87978] |
| ENSMUSG00000028811 | Yars | protein_coding | tyrosyl-tRNA synthetase [Source:MGI Symbol;Acc:MGI:2147627] |
| ENSMUSG00000057236 | Rbbp4 | protein_coding | retinoblastoma binding protein 4 [Source:MGI Symbol;Acc:MGI:1194912] |
| ENSMUSG00000047945 | Marcksl1 | protein_coding | MARCKS-like 1 [Source:MGI Symbol;Acc:MGI:97143] |
| ENSMUSG00000053841 | Txlna | protein_coding | taxilin alpha [Source:MGI Symbol;Acc:MGI:105968] |
| ENSMUSG00000028790 | Khdrbs1 | protein_coding | KH domain containing, RNA binding, signal transduction associated 1 [Source:MGI Symbol;Acc:MGI:893579] |
| ENSMUSG00000028788 | Ptp4a2 | protein_coding | protein tyrosine phosphatase 4a2 [Source:MGI Symbol;Acc:MGI:1277117] |
| ENSMUSG00000074088 | Snrnp40 | protein_coding | small nuclear ribonucleoprotein 40 (U5) [Source:MGI Symbol;Acc:MGI:1913835] |
| ENSMUSG00000028580 | Pum1 | protein_coding | pumilio 1 (*Drosophila*) [Source:MGI Symbol;Acc:MGI:1931749] |
| ENSMUSG00000028581 | Laptm5 | protein_coding | lysosomal-associated protein transmembrane 5 [Source:MGI Symbol;Acc:MGI:108046] |
| ENSMUSG00000028911 | Srsf4 | protein_coding | serine/arginine-rich splicing factor 4 [Source:MGI Symbol;Acc:MGI:1890577] |
| ENSMUSG00000028906 | Epb4.1 | protein_coding | erythrocyte protein band 4.1 [Source:MGI Symbol;Acc:MGI:95401] |
| ENSMUSG00000040025 | Ythdf2 | protein_coding | YTH domain family 2 [Source:MGI Symbol;Acc:MGI:2444233] |
| ENSMUSG00000028896 | Rcc1 | protein_coding | regulator of chromosome condensation 1 [Source:MGI Symbol;Acc:MGI:1913989] |
| ENSMUSG00000028886 | Eya3 | protein_coding | eyes absent 3 homolog (*Drosophila*) [Source:MGI Symbol;Acc:MGI:109339] |
| ENSMUSG00000028882 | Ppp1r8 | protein_coding | protein phosphatase 1, regulatory (inhibitor) subunit 8 [Source:MGI Symbol;Acc:MGI:2140494] |
| ENSMUSG00000037692 | Ahdc1 | protein_coding | AT hook, DNA binding motif, containing 1 [Source:MGI Symbol;Acc:MGI:2444218] |
| ENSMUSG00000028868 | Wasf2 | protein_coding | WAS protein family, member 2 [Source:MGI Symbol;Acc:MGI:1098641] |
| ENSMUSG00000028851 | Nudc | protein_coding | nuclear distribution gene C homolog (*Aspergillus*) [Source:MGI Symbol;Acc:MGI:106014] |
| ENSMUSG00000007880 | Arid1a | protein_coding | AT rich interactive domain 1A (SWI-like) [Source:MGI Symbol;Acc:MGI:1935147] |
| ENSMUSG00000003644 | Rps6ka1 | protein_coding | ribosomal protein S6 kinase polypeptide 1 [Source:MGI Symbol;Acc:MGI:104558] |
| ENSMUSG00000078521 | 2610002D18Rik | protein_coding | RIKEN cDNA 2610002D18 gene [Source:MGI Symbol;Acc:MGI:1917135] |
| ENSMUSG00000037266 | D4Wsu53e | protein_coding | DNA segment, Chr 4, Wayne State University 53, expressed [Source:MGI Symbol;Acc:MGI:106498] |
| ENSMUSG00000028809 | Srrm1 | protein_coding | serine/arginine repetitive matrix 1 [Source:MGI Symbol;Acc:MGI:1858303] |
| ENSMUSG00000066037 | Hnrnpr | protein_coding | heterogeneous nuclear ribonucleoprotein R [Source:MGI Symbol;Acc:MGI:1891692] |
| ENSMUSG00000070687 | Htr1d | protein_coding | 5-hydroxytryptamine (serotonin) receptor 1D [Source:MGI Symbol;Acc:MGI:96276] |
| ENSMUSG00000036940 | Kdm1a | protein_coding | lysine (K)-specific demethylase 1A [Source:MGI Symbol;Acc:MGI:1196256] |
| ENSMUSG00000057530 | Ece1 | protein_coding | endothelin converting enzyme 1 [Source:MGI Symbol;Acc:MGI:1101357] |

TABLE S2-continued

Ythdf2 targeted mRNAs from three irCLIP-seq replicates.

| GeneID | Name | Biotype | Description |
|---|---|---|---|
| ENSMUSG00000066036 | Ubr4 | protein_coding | ubiquitin protein ligase E3 component n-recognin 4 [Source:MGI Symbol;Acc:MGI:1916366] |
| ENSMUSG00000041025 | Iffo2 | protein_coding | intermediate filament family orphan 2 [Source:MGI Symbol;Acc:MGI:2140675] |
| ENSMUSG00000040972 | Igsf21 | protein_coding | immunoglobin superfamily, member 21 [Source:MGI Symbol;Acc:MGI:2681842] |
| ENSMUSG00000040945 | Rcc2 | protein_coding | regulator of chromosome condensation 2 [Source:MGI Symbol;Acc:MGI:1919784] |
| ENSMUSG00000036622 | Atp13a2 | protein_coding | ATPase type 13A2 [Source:MGI Symbol;Acc:MGI:1922022] |
| ENSMUSG00000040761 | Spen | protein_coding | SPEN homolog, transcriptional regulator (*Drosophila*) [Source:MGI Symbol;Acc:MGI:1891706] |
| ENSMUSG00000078515 | Ddi2 | protein_coding | DNA-damage inducible protein 2 [Source:MGI Symbol;Acc:MGI:1917244] |
| ENSMUSG00000044496 | 2510039O18Rik | protein_coding | RIKEN cDNA 2510039O18 gene [Source:MGI Symbol;Acc:MGI:1924284] |
| ENSMUSG00000028991 | Mtor | protein_coding | mechanistic target of rapamycin (serine/threonine kinase) [Source:MGI Symbol;Acc:MGI:1928394] |
| ENSMUSG00000041459 | Tardbp | protein_coding | TAR DNA binding protein [Source:MGI Symbol;Acc:MGI:2387629] |
| ENSMUSG00000028977 | Casz1 | protein_coding | castor homolog 1, zinc finger (*Drosophila*) [Source:MGI Symbol;Acc:MGI:1196251] |
| ENSMUSG00000028961 | Pgd | protein_coding | phosphogluconate dehydrogenase [Source:MGI Symbol;Acc:MGI:97553] |
| ENSMUSG00000063524 | Eno1 | protein_coding | enolase 1, alpha non-neuron [Source:MGI Symbol;Acc:MGI:95393] |
| ENSMUSG00000039852 | Rere | protein_coding | arginine glutamic acid dipeptide (RE) repeats [Source:MGI Symbol;Acc:MGI:2683486] |
| ENSMUSG00000028964 | Park7 | protein_coding | Parkinson disease (autosomal recessive, early onset) 7 [Source:MGI Symbol;Acc:MGI:2135637] |
| ENSMUSG00000014592 | Camta1 | protein_coding | calmodulin binding transcription activator 1 [Source:MGI Symbol;Acc:MGI:2140230] |
| ENSMUSG00000028948 | Nol9 | protein_coding | nucleolar protein 9 [Source:MGI Symbol;Acc:MGI:1921285] |
| ENSMUSG00000028937 | Acot7 | protein_coding | acyl-CoA thioesterase 7 [Source:MGI Symbol;Acc:MGI:1917275] |
| ENSMUSG00000028936 | Rpl22 | protein_coding | ribosomal protein L22 [Source:MGI Symbol;Acc:MGI:99262] |
| ENSMUSG00000028931 | Kcnab2 | protein_coding | potassium voltage-gated channel, shaker-related subfamily, beta member 2 [Source:MGI Symbol;Acc:MGI:109239] |
| ENSMUSG00000039577 | Nphp4 | protein_coding | nephronophthisis 4 (juvenile) homolog (human) [Source:MGI Symbol;Acc:MGI:2384210] |
| ENSMUSG00000057751 | Megf6 | protein_coding | multiple EGF-like-domains 6 [Source:MGI Symbol;Acc:MGI:1919351] |
| ENSMUSG00000039410 | Prdm16 | protein_coding | PR domain containing 16 [Source:MGI Symbol;Acc:MGI:1917923] |
| ENSMUSG00000029050 | Ski | protein_coding | ski sarcoma viral oncogene homolog (avian) [Source:MGI Symbol;Acc:MGI:98310] |
| ENSMUSG00000042202 | Slc35e2 | protein_coding | solute carrier family 35, member E2 [Source:MGI Symbol;Acc:MGI:2444240] |
| ENSMUSG00000040274 | Cdk6 | protein_coding | cyclin-dependent kinase 6 [Source:MGI Symbol;Acc:MGI:1277162] |
| ENSMUSG00000040351 | Ankib1 | protein_coding | ankyrin repeat and IBR domain containing 1 [Source:MGI Symbol;Acc:MGI:1918047] |
| ENSMUSG00000001467 | Cyp51 | protein_coding | cytochrome P450, family 51 [Source:MGI Symbol;Acc:MGI:106040] |
| ENSMUSG00000028926 | Cdk14 | protein_coding | cyclin-dependent kinase 14 [Source:MGI Symbol;Acc:MGI:894318] |
| ENSMUSG00000002297 | Dbf4 | protein_coding | DBF4 homolog (*S. cerevisiae*) [Source:MGI Symbol;Acc:MGI:1351328] |
| ENSMUSG00000040118 | Cacna2d1 | protein_coding | calcium channel, voltage-dependent, alpha2/delta subunit 1 [Source:MGI Symbol;Acc:MGI:88295] |
| ENSMUSG00000028780 | Sema3c | protein_coding | sema domain, immunoglobulin domain (Ig), short basic domain, secreted, (semaphorin) 3C [Source:MGI Symbol;Acc:MGI:107557] |
| ENSMUSG00000040003 | Magi2 | protein_coding | membrane associated guanylate kinase, WW and PDZ domain containing 2 [Source:MGI Symbol;Acc:MGI:1354953] |
| ENSMUSG00000039968 | Rsbn1l | protein_coding | round spermatid basic protein 1-like [Source:MGI Symbol;Acc:MGI:3036237] |
| ENSMUSG00000028771 | Ptpn12 | protein_coding | protein tyrosine phosphatase, non-receptor type 12 [Source:MGI Symbol;Acc:MGI:104673] |
| ENSMUSG00000028932 | Psmc2 | protein_coding | proteasome (prosome, macropain) 26S subunit, ATPase 2 [Source:MGI Symbol;Acc:MGI:109555] |

TABLE S2-continued

Ythdf2 targeted mRNAs from three irCLIP-seq replicates.

| GeneID | Name | Biotype | Description |
|---|---|---|---|
| ENSMUSG 00000029004 | Mll5 | protein_coding | myeloid/lymphoid or mixed-lineage leukemia 5 [Source:MGI Symbol;Acc:MGI:1924825] |
| ENSMUSG 00000028973 | Abcb8 | protein_coding | ATP-binding cassette, sub-family B (MDR/TAP), member 8 [Source:MGI Symbol;Acc:MGI:1351667] |
| ENSMUSG 00000028969 | Cdk5 | protein_coding | cyclin-dependent kinase 5 [Source:MGI Symbol;Acc:MGI:101765] |
| ENSMUSG 00000038181 | Chpf2 | protein_coding | chondroitin polymerizing factor 2 [Source:MGI Symbol;Acc:MGI:1917522] |
| ENSMUSG 00000028949 | Smarcd3 | protein_coding | SWI/SNF related, matrix associated, actin dependent regulator of chromatin, subfamily d, member 3 [Source:MGI Symbol;Acc:MGI:1914243] |
| ENSMUSG 00000025747 | Tyms | protein_coding | thymidylate synthase [Source:MGI Symbol;Acc:MGI:98878] |
| ENSMUSG 00000029163 | Emilin1 | protein_coding | elastin microfibril interfacer 1 [Source:MGI Symbol;Acc:MGI:1926189] |
| ENSMUSG 00000045302 | Preb | protein_coding | prolactin regulatory element binding [Source:MGI Symbol;Acc:MGI:1355326] |
| ENSMUSG 00000013629 | Cad | protein_coding | carbamoyl-phosphate synthetase 2, aspartate transcarbamylase, and dihydroorotase [Source:MGI Symbol;Acc:MGI:1916969] |
| ENSMUSG 00000029147 | Ppm1g | protein_coding | protein phosphatase 1G (formerly 2C), magnesium-dependent, gamma isoform [Source:MGI Symbol;Acc:MGI:106065] |
| ENSMUSG 00000059434 | Gckr | protein_coding | glucokinase regulatory protein [Source:MGI Symbol;Acc:MGI:1096345] |
| ENSMUSG 00000093574 | RP23-118L1.1 | protein_coding | MCG2531, isoform CRA_h; Uncharacterized protein [Source:UniProtKB/TrEMBL;Acc:Q3TJ76] |
| ENSMUSG 00000054280 | C330019G07Rik | protein_coding | RIKEN cDNA C330019G07 gene [Source:MGI Symbol;Acc:MGI:2443658] |
| ENSMUSG 00000037373 | Ctbp1 | protein_coding | C-terminal binding protein 1 [Source:MGI Symbol;Acc:MGI:1201685] |
| ENSMUSG 00000079562 | Maea | protein_coding | macrophage erythroblast attacher [Source:MGI Symbol;Acc:MGI:1891748] |
| ENSMUSG 00000029110 | Rnf4 | protein_coding | ring finger protein 4 [Source:MGI Symbol;Acc:MGI:1201691] |
| ENSMUSG 00000037210 | Fam193a | protein_coding | family with sequence similarity 193, member A [Source:MGI Symbol;Acc:MGI:2447768] |
| ENSMUSG 00000029104 | Htt | protein_coding | huntingtin [Source:MGI Symbol;Acc:MGI:96067] |
| ENSMUSG 00000045318 | Adra2c | protein_coding | adrenergic receptor, alpha 2c [Source:MGI Symbol;Acc:MGI:87936] |
| ENSMUSG 00000029094 | Afap1 | protein_coding | actin filament associated protein 1 [Source:MGI Symbol;Acc:MGI:1917542] |
| ENSMUSG 00000029093 | Sorcs2 | protein_coding | sortilin-related VPS10 domain containing receptor 2 [Source:MGI Symbol;Acc:MGI:1932289] |
| ENSMUSG 00000043430 | Psapl1 | protein_coding | prosaposin-like 1 [Source:MGI Symbol;Acc:MGI:1924193] |
| ENSMUSG 00000029190 | D5Ertd579e | protein_coding | DNA segment, Chr 5, ERATO Doi 579, expressed [Source:MGI Symbol;Acc:MGI:1261849] |
| ENSMUSG 00000029122 | Evc | protein_coding | Ellis van Creveld gene homolog (human) [Source:MGI Symbol;Acc:MGI:1890596] |
| ENSMUSG 00000005103 | Wdr1 | protein_coding | WD repeat domain 1 [Source:MGI Symbol;Acc:MGI:1337100] |
| ENSMUSG 00000029088 | Kcnip4 | protein_coding | Kv channel interacting protein 4 [Source:MGI Symbol;Acc:MGI:1933131] |
| ENSMUSG 00000029108 | Pcdh7 | protein_coding | protocadherin 7 [Source:MGI Symbol;Acc:MGI:1860487] |
| ENSMUSG 00000037795 | N4bp2 | protein_coding | NEDD4 binding protein 2 [Source:MGI Symbol;Acc:MGI:2684414] |
| ENSMUSG 00000029206 | Nsun7 | protein_coding | NOL1/NOP2/Sun domain family, member 7 [Source:MGI Symbol;Acc:MGI:1918168] |
| ENSMUSG 00000092060 | Bend4 | protein_coding | BEN domain containing 4 [Source:MGI Symbol;Acc:MGI:3648414] |
| ENSMUSG 00000029212 | Gabrb1 | protein_coding | gamma-aminobutyric acid (GABA) A receptor, subunit beta 1 [Source:MGI Symbol;Acc:MGI:95619] |
| ENSMUSG 00000070733 | Fryl | protein_coding | furry homolog-like (*Drosophila*) [Source:MGI Symbol;Acc:MGI:1919563] |
| ENSMUSG 00000029227 | Fip1l1 | protein_coding | FIP1 like 1 (*S. cerevisiae*) [Source:MGI Symbol;Acc:MGI:1914149] |
| ENSMUSG 00000005672 | Kit | protein_coding | kit oncogene [Source:MGI Symbol;Acc:MGI:96677] |
| ENSMUSG 00000036377 | C530008M17Rik | protein_coding | RIKEN cDNA C530008M17 gene [Source:MGI Symbol;Acc:MGI:2444817] |
| ENSMUSG 00000029249 | Rest | protein_coding | RE1-silencing transcription factor [Source:MGI Symbol;Acc:MGI:104897] |

TABLE S2-continued

Ythdf2 targeted mRNAs from three irCLIP-seq replicates.

| GeneID | Name | Biotype | Description |
| --- | --- | --- | --- |
| ENSMUSG00000029250 | Polr2b | protein_coding | polymerase (RNA) II (DNA directed) polypeptide B [Source:MGI Symbol;Acc:MGI:2388280] |
| ENSMUSG00000055204 | Ankrd17 | protein_coding | ankyrin repeat domain 17 [Source:MGI Symbol;Acc:MGI:1932101] |
| ENSMUSG00000029373 | Pf4 | protein_coding | platelet factor 4 [Source:MGI Symbol;Acc:MGI:1888711] |
| ENSMUSG00000029405 | G3bp2 | protein_coding | GTPase activating protein (SH3 domain) binding protein 2 [Source:MGI Symbol;Acc:MGI:2442040] |
| ENSMUSG00000034663 | Bmp2k | protein_coding | BMP2 inducible kinase [Source:MGI Symbol;Acc:MGI:2155456] |
| ENSMUSG00000055725 | Paqr3 | protein_coding | progestin and adipoQ receptor family member III [Source:MGI Symbol;Acc:MGI:2679683] |
| ENSMUSG00000057816 | 1700007G11Rik | protein_coding | RIKEN cDNA 1700007G11 gene [Source:MGI Symbol;Acc:MGI:1916571] |
| ENSMUSG00000029333 | Rasgef1b | protein_coding | RasGEF domain family, member 1B [Source:MGI Symbol;Acc:MGI:2443755] |
| ENSMUSG00000000568 | Hnrnpd | protein_coding | heterogeneous nuclear ribonucleoprotein D [Source:MGI Symbol;Acc:MGI:101947] |
| ENSMUSG00000029328 | Hnrpdl | protein_coding | heterogeneous nuclear ribonucleoprotein D-like [Source:MGI Symbol;Acc:MGI:1355299] |
| ENSMUSG00000035325 | Sec31a | protein_coding | Sec31 homolog A (S. cerevisiae) [Source:MGI Symbol;Acc:MGI:1916412] |
| ENSMUSG00000035273 | Hpse | protein_coding | heparanase [Source:MGI Symbol;Acc:MGI:1343124] |
| ENSMUSG00000043940 | Wdfy3 | protein_coding | WD repeat and FYVE domain containing 3 [Source:MGI Symbol;Acc:MGI:1096875] |
| ENSMUSG00000029313 | Aff1 | protein_coding | AF4/FMR2 family, member 1 [Source:MGI Symbol;Acc:MGI:1100819] |
| ENSMUSG00000070639 | Lrrc8b | protein_coding | leucine rich repeat containing 8 family, member B [Source:MGI Symbol;Acc:MGI:2141353] |
| ENSMUSG00000046079 | Lrrc8d | protein_coding | leucine rich repeat containing 8D [Source:MGI Symbol;Acc:MGI:1922368] |
| ENSMUSG00000049606 | Zfp644 | protein_coding | zinc finger protein 644 [Source:MGI Symbol;Acc:MGI:1277212] |
| ENSMUSG00000011831 | Evi5 | protein_coding | ecotropic viral integration site 5 [Source:MGI Symbol;Acc:MGI:104736] |
| ENSMUSG00000058558 | Rpl5 | protein_coding | ribosomal protein L5 [Source:MGI Symbol;Acc:MGI:102854] |
| ENSMUSG00000029267 | Mtf2 | protein_coding | metal response element binding transcription factor 2 [Source:MGI Symbol;Acc:MGI:105050] |
| ENSMUSG00000062234 | Gak | protein_coding | cyclin G associated kinase [Source:MGI Symbol;Acc:MGI:2442153] |
| ENSMUSG00000043323 | Fbrsl1 | protein_coding | fibrosin-like 1 [Source:MGI Symbol;Acc:MGI:1920907] |
| ENSMUSG00000029507 | Pus1 | protein_coding | pseudouridine synthase 1 [Source:MGI Symbol;Acc:MGI:1929237] |
| ENSMUSG00000029345 | Tfip11 | protein_coding | tuftelin interacting protein 11 [Source:MGI Symbol;Acc:MGI:1930075] |
| ENSMUSG00000058153 | Sez6l | protein_coding | seizure related 6 homolog like [Source:MGI Symbol;Acc:MGI:1935121] |
| ENSMUSG00000048163 | Selplg | protein_coding | selectin, platelet (p-selectin) ligand [Source:MGI Symbol;Acc:MGI:106689] |
| ENSMUSG00000004530 | Coro1c | protein_coding | coronin, actin binding protein 1C [Source:MGI Symbol;Acc:MGI:1345964] |
| ENSMUSG00000042010 | Acacb | protein_coding | acetyl-Coenzyme A carboxylase beta [Source:MGI Symbol;Acc:MGI:2140940] |
| ENSMUSG00000066952 | Myo1h | protein_coding | myosin 1H [Source:MGI Symbol;Acc:MGI:1914674] |
| ENSMUSG00000001098 | Kctd10 | protein_coding | potassium channel tetramerisation domain containing 10 [Source:MGI Symbol;Acc:MGI:2141207] |
| ENSMUSG00000029577 | Ube3b | protein_coding | ubiquitin protein ligase E3B [Source:MGI Symbol;Acc:MGI:1891295] |
| ENSMUSG00000041890 | Git2 | protein_coding | G protein-coupled receptor kinase-interactor 2 [Source:MGI Symbol;Acc:MGI:1347053] |
| ENSMUSG00000041870 | Ankrd13a | protein_coding | ankyrin repeat domain 13a [Source:MGI Symbol;Acc:MGI:1915670] |
| ENSMUSG00000029550 | Sppl3 | protein_coding | signal peptide peptidase 3 [Source:MGI Symbol;Acc:MGI:1891433] |
| ENSMUSG00000072693 | Gm10401 | protein_coding | predicted gene 10401 [Source:MGI Symbol;Acc:MGI:3704254] |
| ENSMUSG00000048578 | Mlec | protein_coding | malectin [Source:MGI Symbol;Acc:MGI:1924015] |
| ENSMUSG00000041740 | Rnf10 | protein_coding | ring finger protein 10 [Source:MGI Symbol;Acc:MGI:1859162] |
| ENSMUSG00000029535 | Triap1 | protein_coding | TP53 regulated inhibitor of apoptosis 1 [Source:MGI Symbol;Acc:MGI:1916326] |

TABLE S2-continued

Ythdf2 targeted mRNAs from three irCLIP-seq replicates.

| GeneID | Name | Biotype | Description |
|---|---|---|---|
| ENSMUSG00000041697 | Cox6a1 | protein_coding | cytochrome c oxidase, subunit VI a, polypeptide 1 [Source:MGI Symbol;Acc:MGI:103099] |
| ENSMUSG00000029528 | Pxn | protein_coding | paxillin [Source:MGI Symbol;Acc:MGI:108295] |
| ENSMUSG00000029518 | Rab35 | protein_coding | RAB35, member RAS oncogene family [Source:MGI Symbol;Acc:MGI:1924657] |
| ENSMUSG00000029516 | Cit | protein_coding | citron [Source:MGI Symbol;Acc:MGI:105313] |
| ENSMUSG00000029363 | Rfc5 | protein_coding | replication factor C (activator 1) 5 [Source:MGI Symbol;Acc:MGI:1919401] |
| ENSMUSG00000029361 | Nos1 | protein_coding | nitric oxide synthase 1, neuronal [Source:MGI Symbol;Acc:MGI:97360] |
| ENSMUSG00000018076 | Med13l | protein_coding | mediator complex subunit 13-like [Source:MGI Symbol;Acc:MGI:2670178] |
| ENSMUSG00000043733 | Ptpn11 | protein_coding | protein tyrosine phosphatase, non-receptor type 11 [Source:MGI Symbol;Acc:MGI:99511] |
| ENSMUSG00000029614 | Rpl6 | protein_coding | ribosomal protein L6 [Source:MGI Symbol;Acc:MGI:108057] |
| ENSMUSG00000042744 | Gm15800 | protein_coding | predicted gene 15800 [Source:MGI Symbol;Acc:MGI:3647820] |
| ENSMUSG00000029616 | Erp29 | protein_coding | endoplasmic reticulum protein 29 [Source:MGI Symbol;Acc:MGI:1914647] |
| ENSMUSG00000029455 | Aldh2 | protein_coding | aldehyde dehydrogenase 2, mitochondrial [Source:MGI Symbol;Acc:MGI:99600] |
| ENSMUSG00000042594 | Sh2b3 | protein_coding | SH2B adaptor protein 3 [Source:MGI Symbol;Acc:MGI:893598] |
| ENSMUSG00000042589 | Cux2 | protein_coding | cut-like homeobox 2 [Source:MGI Symbol;Acc:MGI:107321] |
| ENSMUSG00000064267 | Hvcn1 | protein_coding | hydrogen voltage-gated channel 1 [Source:MGI Symbol;Acc:MGI:1921346] |
| ENSMUSG00000038582 | Pptc7 | protein_coding | PTC7 protein phosphatase homolog (S. cerevisiae) [Source:MGI Symbol;Acc:MGI:2444593] |
| ENSMUSG00000029465 | Arpc3 | protein_coding | actin related protein 2/3 complex, subunit 3 [Source:MGI Symbol;Acc:MGI:1928375] |
| ENSMUSG00000029467 | Atp2a2 | protein_coding | ATPase, Ca++ transporting, cardiac muscle, slow twitch 2 [Source:MGI Symbol;Acc:MGI:88110] |
| ENSMUSG00000029475 | Kdm2b | protein_coding | lysine (K)-specific demethylase 2B [Source:MGI Symbol;Acc:MGI:1354737] |
| ENSMUSG00000049686 | Orai1 | protein_coding | ORAI calcium release-activated calcium modulator 1 [Source:MGI Symbol;Acc:MGI:1925542] |
| ENSMUSG00000038384 | Setd1b | protein_coding | SET domain containing 1B [Source:MGI Symbol;Acc:MGI:2652820] |
| ENSMUSG00000029438 | Bcl7a | protein_coding | B cell CLL/lymphoma 7A [Source:MGI Symbol;Acc:MGI:1924295] |
| ENSMUSG00000038342 | Mlxip | protein_coding | MLX interacting protein [Source:MGI Symbol;Acc:MGI:2141183] |
| ENSMUSG00000023106 | Denr | protein_coding | density-regulated protein [Source:MGI Symbol;Acc:MGI:1915434] |
| ENSMUSG00000029394 | Cdk2ap1 | protein_coding | CDK2 (cyclin-dependent kinase 2)-associated protein 1 [Source:MGI Symbol;Acc:MGI:1202069] |
| ENSMUSG00000038095 | Sbno1 | protein_coding | sno, strawberry notch homolog 1 (Drosophila) [Source:MGI Symbol;Acc:MGI:2384298] |
| ENSMUSG00000038023 | Atp6v0a2 | protein_coding | ATPase, H+ transporting, lysosomal V0 subunit A2 [Source:MGI Symbol;Acc:MGI:104855] |
| ENSMUSG00000079215 | Zfp664 | protein_coding | zinc finger protein 664 [Source:MGI Symbol;Acc:MGI:2442505] |
| ENSMUSG00000051911 | Zfp664 | protein_coding | zinc finger protein 664 [Source:MGI Symbol;Acc:MGI:2442505] |
| ENSMUSG00000029478 | Ncor2 | protein_coding | nuclear receptor co-repressor 2 [Source:MGI Symbol;Acc:MGI:1337080] |
| ENSMUSG00000037905 | Bri3bp | protein_coding | Bri3 binding protein [Source:MGI Symbol;Acc:MGI:1924059] |
| ENSMUSG00000029482 | Aacs | protein_coding | acetoacetyl-CoA synthetase [Source:MGI Symbol;Acc:MGI:1926144] |
| ENSMUSG00000034324 | Tmem132c | protein_coding | transmembrane protein 132C [Source:MGI Symbol;Acc:MGI:2443061] |
| ENSMUSG00000034310 | Tmem132d | protein_coding | transmembrane protein 132D [Source:MGI Symbol;Acc:MGI:3044963] |
| ENSMUSG00000029420 | Rimbp2 | protein_coding | RIMS binding protein 2 [Source:MGI Symbol;Acc:MGI:2443235] |
| ENSMUSG00000029439 | Sfswap | protein_coding | splicing factor, suppressor of white-apricot homolog (Drosophila) [Source:MGI Symbol;Acc:MGI:101760] |
| ENSMUSG00000029447 | Cct6a | protein_coding | chaperonin containing Tcp1, subunit 6a (zeta) [Source:MGI Symbol;Acc:MGI:107943] |
| ENSMUSG00000025537 | Phkg1 | protein_coding | phosphorylase kinase gamma 1 [Source:MGI Symbol;Acc:MGI:97579] |

TABLE S2-continued

Ythdf2 targeted mRNAs from three irCLIP-seq replicates.

| GeneID | Name | Biotype | Description |
| --- | --- | --- | --- |
| ENSMUSG00000025340 | Rabgef1 | protein_coding | RAB guanine nucleotide exchange factor (GEF) 1 [Source:MGI Symbol;Acc:MGI:1929459] |
| ENSMUSG00000034040 | Wbscr17 | protein_coding | Williams-Beuren syndrome chromosome region 17 homolog (human) [Source:MGI Symbol;Acc:MGI:2137594] |
| ENSMUSG00000029673 | Auts2 | protein_coding | autism susceptibility candidate 2 [Source:MGI Symbol;Acc:MGI:1919847] |
| ENSMUSG00000060261 | Gtf2i | protein_coding | general transcription factor II I [Source:MGI Symbol;Acc:MGI:1202722] |
| ENSMUSG00000063146 | Clip2 | protein_coding | CAP-GLY domain containing linker protein 2 [Source:MGI Symbol;Acc:MGI:1313136] |
| ENSMUSG00000040731 | Eif4h | protein_coding | eukaryotic translation initiation factor 4H [Source:MGI Symbol;Acc:MGI:1341822] |
| ENSMUSG00000002748 | Baz1b | protein_coding | bromodomain adjacent to zinc finger domain, 1B [Source:MGI Symbol;Acc:MGI:1353499] |
| ENSMUSG00000053293 | Pom121 | protein_coding | nuclear pore membrane protein 121 [Source:MGI Symbol;Acc:MGI:2137624] |
| ENSMUSG00000019179 | Mdh2 | protein_coding | malate dehydrogenase 2, NAD (mitochondrial) [Source:MGI Symbol;Acc:MGI:97050] |
| ENSMUSG00000051391 | Ywhag | protein_coding | tyrosine 3-monooxygenase/tryptophan 5-monooxygenase activation protein, gamma polypeptide [Source:MGI Symbol;Acc:MGI:108109] |
| ENSMUSG00000029705 | Cux1 | protein_coding | cut-like homeobox 1 [Source:MGI Symbol;Acc:MGI:88568] |
| ENSMUSG00000037411 | Serpine1 | protein_coding | serine (or cysteine) peptidase inhibitor, clade E, member 1 [Source:MGI Symbol;Acc:MGI:97608] |
| ENSMUSG00000043279 | Trim56 | protein_coding | tripartite motif-containing 56 [Source:MGI Symbol;Acc:MGI:2685298] |
| ENSMUSG00000037364 | Srrt | protein_coding | serrate RNA effector molecule homolog (*Arabidopsis*) [Source:MGI Symbol;Acc:MGI:1933527] |
| ENSMUSG00000029711 | Epo | protein_coding | erythropoietin [Source:MGI Symbol;Acc:MGI:95407] |
| ENSMUSG00000029723 | Tsc22d4 | protein_coding | TSC22 domain family, member 4 [Source:MGI Symbol;Acc:MGI:1926079] |
| ENSMUSG00000029726 | Mepce | protein_coding | methylphosphate capping enzyme [Source:MGI Symbol;Acc:MGI:106477] |
| ENSMUSG00000029730 | Mcm7 | protein_coding | minichromosome maintenance deficient 7 (*S. cerevisiae*) [Source:MGI Symbol;Acc:MGI:1298398] |
| ENSMUSG00000025858 | Get4 | protein_coding | golgi to ER traffic protein 4 homolog (*S. cerevisiae*) [Source:MGI Symbol;Acc:MGI:1914854] |
| ENSMUSG00000029547 | Ints1 | protein_coding | integrator complex subunit 1 [Source:MGI Symbol;Acc:MGI:1915760] |
| ENSMUSG00000029554 | Mad1l1 | protein_coding | MAD1 mitotic arrest deficient 1-like 1 [Source:MGI Symbol;Acc:MGI:1341857] |
| ENSMUSG00000056076 | Eif3b | protein_coding | eukaryotic translation initiation factor 3, subunit B [Source:MGI Symbol;Acc:MGI:106478] |
| ENSMUSG00000036565 | Ttyh3 | protein_coding | tweety homolog 3 (*Drosophila*) [Source:MGI Symbol;Acc:MGI:1925589] |
| ENSMUSG00000050022 | Amz1 | protein_coding | archaelysin family metallopeptidase 1 [Source:MGI Symbol;Acc:MGI:2442258] |
| ENSMUSG00000000149 | Gna12 | protein_coding | guanine nucleotide binding protein, alpha 12 [Source:MGI Symbol;Acc:MGI:95767] |
| ENSMUSG00000039683 | Sdk1 | protein_coding | sidekick homolog 1 (chicken) [Source:MGI Symbol;Acc:MGI:2444413] |
| ENSMUSG00000056493 | Foxk1 | protein_coding | forkhead box K1 [Source:MGI Symbol;Acc:MGI:1347488] |
| ENSMUSG00000029580 | Actb | protein_coding | actin, beta [Source:MGI Symbol;Acc:MGI:87904] |
| ENSMUSG00000039244 | E130309D02Rik | protein_coding | RIKEN cDNA E130309D02 gene [Source:MGI Symbol;Acc:MGI:2442621] |
| ENSMUSG00000001847 | Rac1 | protein_coding | RAS-related C3 botulinum substrate 1 [Source:MGI Symbol;Acc:MGI:97845] |
| ENSMUSG00000051306 | Usp42 | protein_coding | ubiquitin specific peptidase 42 [Source:MGI Symbol;Acc:MGI:1924050] |
| ENSMUSG00000045482 | Trrap | protein_coding | transformation/transcription domain-associated protein [Source:MGI Symbol;Acc:MGI:2153272] |
| ENSMUSG00000029622 | Arpc1b | protein_coding | actin related protein 2/3 complex, subunit 1B [Source:MGI Symbol;Acc:MGI:1343142] |
| ENSMUSG00000029623 | Pdap1 | protein_coding | PDGFA associated protein 1 [Source:MGI Symbol;Acc:MGI:2448536] |
| ENSMUSG00000016510 | Mtif3 | protein_coding | mitochondrial translational initiation factor 3 [Source:MGI Symbol;Acc:MGI:1923616] |
| ENSMUSG00000029647 | Pan3 | protein_coding | PAN3 polyA specific ribonuclease subunit homolog (*S. cerevisiae*) [Source:MGI Symbol;Acc:MGI:1919837] |
| ENSMUSG00000029651 | Mtus2 | protein_coding | microtubule associated tumor suppressor candidate 2 [Source:MGI Symbol;Acc:MGI:1915388] |

TABLE S2-continued

Ythdf2 targeted mRNAs from three irCLIP-seq replicates.

| GeneID | Name | Biotype | Description |
|---|---|---|---|
| ENSMUSG00000041313 | Slc7a1 | protein_coding | solute carrier family 7 (cationic amino acid transporter, y+ system), member 1 [Source:MGI Symbol;Acc:MGI:88117] |
| ENSMUSG00000029658 | Wdr95 | protein_coding | WD40 repeat domain 95 [Source:MGI Symbol;Acc:MGI:1923042] |
| ENSMUSG00000029657 | Hsph1 | protein_coding | heat shock 105 kDa/110k Da protein 1 [Source:MGI Symbol;Acc:MGI:105053] |
| ENSMUSG00000034021 | Pds5b | protein_coding | PDS5, regulator of cohesion maintenance, homolog B (S. cerevisiae) [Source:MGI Symbol;Acc:MGI:2140945] |
| ENSMUSG00000001376 | Ccdc132 | protein_coding | coiled-coil domain containing 132 [Source:MGI Symbol;Acc:MGI:1920538] |
| ENSMUSG00000032827 | Ppp1r9a | protein_coding | protein phosphatase 1, regulatory (inhibitor) subunit 9A [Source:MGI Symbol;Acc:MGI:2442401] |
| ENSMUSG00000060882 | Kcnd2 | protein_coding | potassium voltage-gated channel, Shal-related family, member 2 [Source:MGI Symbol;Acc:MGI:102663] |
| ENSMUSG00000062980 | A430107O13Rik | protein_coding | RIKEN cDNA A430107O13 gene [Source:MGI Symbol;Acc:MGI:2444814] |
| ENSMUSG00000017978 | Cadps2 | protein_coding | Ca2+-dependent activator protein for secretion 2 [Source:MGI Symbol;Acc:MGI:2443963] |
| ENSMUSG00000029708 | Gcc1 | protein_coding | golgi coiled coil 1 [Source:MGI Symbol;Acc:MGI:1921625] |
| ENSMUSG00000001424 | Snd1 | protein_coding | staphylococcal nuclease and tudor domain containing 1 [Source:MGI Symbol;Acc:MGI:1929266] |
| ENSMUSG00000049939 | Lrrc4 | protein_coding | leucine rich repeat containing 4 [Source:MGI Symbol;Acc:MGI:2182081] |
| ENSMUSG00000058831 | Opn1sw | protein_coding | opsin 1 (cone pigments), short-wave-sensitive (color blindness, tritan) [Source:MGI Symbol;Acc:MGI:99438] |
| ENSMUSG00000073209 | Klf14 | protein_coding | Kruppel-like factor 14 [Source:MGI Symbol;Acc:MGI:3577024] |
| ENSMUSG00000029765 | Plxna4 | protein_coding | plexin A4 [Source:MGI Symbol;Acc:MGI:2179061] |
| ENSMUSG00000018999 | Slc35b4 | protein_coding | solute carrier family 35, member B4 [Source:MGI Symbol;Acc:MGI:1931249] |
| ENSMUSG00000038759 | Nup205 | protein_coding | nucleoporin 205 [Source:MGI Symbol;Acc:MGI:2141625] |
| ENSMUSG00000029840 | Mtpn | protein_coding | myotrophin [Source:MGI Symbol;Acc:MGI:99445] |
| ENSMUSG00000029833 | Trim24 | protein_coding | tripartite motif-containing 24 [Source:MGI Symbol;Acc:MGI:109275] |
| ENSMUSG00000047749 | Zc3hav1l | protein_coding | zinc finger CCCH-type, antiviral 1-like [Source:MGI Symbol;Acc:MGI:2443387] |
| ENSMUSG00000029826 | Zc3hav1 | protein_coding | zinc finger CCCH type, antiviral 1 [Source:MGI Symbol;Acc:MGI:1926031] |
| ENSMUSG00000061436 | Hipk2 | protein_coding | homeodomain interacting protein kinase 2 [Source:MGI Symbol;Acc:MGI:1314872] |
| ENSMUSG00000042599 | Jhdm1d | protein_coding | jumonji C domain-containing histone demethylase 1 homolog D (S. cerevisiae) [Source:MGI Symbol;Acc:MGI:2443388] |
| ENSMUSG00000029863 | Casp2 | protein_coding | caspase 2 [Source:MGI Symbol;Acc:MGI:97295] |
| ENSMUSG00000029860 | Zyx | protein_coding | zyxin [Source:MGI Symbol;Acc:MGI:103072] |
| ENSMUSG00000039419 | Cntnap2 | protein_coding | contactin associated protein-like 2 [Source:MGI Symbol;Acc:MGI:1914047] |
| ENSMUSG00000025821 | Zfp282 | protein_coding | zinc finger protein 282 [Source:MGI Symbol;Acc:MGI:2141413] |
| ENSMUSG00000071477 | Zfp777 | protein_coding | zinc finger protein 777 [Source:MGI Symbol;Acc:MGI:1919556] |
| ENSMUSG00000057691 | Zfp746 | protein_coding | zinc finger protein 746 [Source:MGI Symbol;Acc:MGI:1916478] |
| ENSMUSG00000029810 | Tmem176b | protein_coding | transmembrane protein 176B [Source:MGI Symbol;Acc:MGI:1916348] |
| ENSMUSG00000004980 | Hnrnpa2b1 | protein_coding | heterogeneous nuclear ribonucleoprotein A2/B1 [Source:MGI Symbol;Acc:MGI:104819] |
| ENSMUSG00000059182 | Skap2 | protein_coding | src family associated phosphoprotein 2 [Source:MGI Symbol;Acc:MGI:1889206] |
| ENSMUSG00000029844 | Hoxa1 | protein_coding | homeobox A1 [Source:MGI Symbol;Acc:MGI:96170] |
| ENSMUSG00000093412 | RP23-103L13.8 | protein_coding | |
| ENSMUSG00000079560 | Hoxa3 | protein_coding | homeobox A3 [Source:MGI Symbol;Acc:MGI:96175] |
| ENSMUSG00000059723 | Hoxa3 | protein_coding | homeobox A3 [Source:MGI Symbol;Acc:MGI:96175] |

TABLE S2-continued

Ythdf2 targeted mRNAs from three irCLIP-seq replicates.

| GeneID | Name | Biotype | Description |
|---|---|---|---|
| ENSMUSG00000004535 | Tax1bp1 | protein_coding | Tax1 (human T cell leukemia virus type I) binding protein 1 [Source:MGI Symbol;Acc:MGI:1289308] |
| ENSMUSG00000063568 | Jazf1 | protein_coding | JAZF zinc finger 1 [Source:MGI Symbol;Acc:MGI:2141450] |
| ENSMUSG00000002930 | Ppp1r17 | protein_coding | protein phosphatase 1, regulatory subunit 17 [Source:MGI Symbol;Acc:MGI:1333876] |
| ENSMUSG00000039578 | Fam190a | protein_coding | family with sequence similarity 190, member A [Source:MGI Symbol;Acc:MGI:3045354] |
| ENSMUSG00000071424 | Grid2 | protein_coding | glutamate receptor, ionotropic, delta 2 [Source:MGI Symbol;Acc:MGI:95813] |
| ENSMUSG00000049001 | A930038C07Rik | protein_coding | RIKEN cDNA A930038C07 gene [Source:MGI Symbol;Acc:MGI:1915419] |
| ENSMUSG00000036371 | Serbp1 | protein_coding | serpine1 mRNA binding protein 1 [Source:MGI Symbol;Acc:MGI:1914120] |
| ENSMUSG00000002222 | Rmnd5a | protein_coding | required for meiotic nuclear division 5 homolog A (S. cerevisiae) [Source:MGI Symbol;Acc:MGI:1915727] |
| ENSMUSG00000063884 | Ptcd3 | protein_coding | pentatricopeptide repeat domain 3 [Source:MGI Symbol;Acc:MGI:1917206] |
| ENSMUSG00000037621 | Atoh8 | protein_coding | atonal homolog 8 (Drosophila) [Source:MGI Symbol;Acc:MGI:1918343] |
| ENSMUSG00000056305 | Usp39 | protein_coding | ubiquitin specific peptidase 39 [Source:MGI Symbol;Acc:MGI:107622] |
| ENSMUSG00000053907 | Mat2a | protein_coding | methionine adenosyltransferase II, alpha [Source:MGI Symbol;Acc:MGI:2443731] |
| ENSMUSG00000055799 | Tcf7l1 | protein_coding | transcription factor 7 like 1 (T cell specific, HMG box) [Source:MGI Symbol;Acc:MGI:1202876] |
| ENSMUSG00000052581 | Lrrtm4 | protein_coding | leucine rich repeat transmembrane neuronal 4 [Source:MGI Symbol;Acc:MGI:2389180] |
| ENSMUSG00000030036 | Mogs | protein_coding | mannosyl-oligosaccharide glucosidase [Source:MGI Symbol;Acc:MGI:1929872] |
| ENSMUSG00000034832 | Tet3 | protein_coding | tet methylcytosine dioxygenase 3 [Source:MGI Symbol;Acc:MGI:2446229] |
| ENSMUSG00000063415 | Cyp26b1 | protein_coding | cytochrome P450, family 26, subfamily b, polypeptide 1 [Source:MGI Symbol;Acc:MGI:2176159] |
| ENSMUSG00000033769 | Exoc6b | protein_coding | exocyst complex component 6B [Source:MGI Symbol;Acc:MGI:1923164] |
| ENSMUSG00000030007 | Cct7 | protein_coding | chaperonin containing Tcp1, subunit 7 (eta) [Source:MGI Symbol;Acc:MGI:107184] |
| ENSMUSG00000051695 | Pcbp1 | protein_coding | poly(rC) binding protein 1 [Source:MGI Symbol;Acc:MGI:1345635] |
| ENSMUSG00000029992 | Gfpt1 | protein_coding | glutamine fructose-6-phosphate transaminase 1 [Source:MGI Symbol;Acc:MGI:95698] |
| ENSMUSG00000030047 | Arhgap25 | protein_coding | Rho GTPase activating protein 25 [Source:MGI Symbol;Acc:MGI:2443687] |
| ENSMUSG00000030055 | Rab43 | protein_coding | RAB43, member RAS oncogene family [Source:MGI Symbol;Acc:MGI:1917084] |
| ENSMUSG00000030057 | Cnbp | protein_coding | cellular nucleic acid binding protein [Source:MGI Symbol;Acc:MGI:88431] |
| ENSMUSG00000084950 | Gm5577 | protein_coding | predicted gene 5577 [Source:MGI Symbol;Acc:MGI:3648213] |
| ENSMUSG00000079477 | Rab7 | protein_coding | RAB7, member RAS oncogene family [Source:MGI Symbol;Acc:MGI:105068] |
| ENSMUSG00000015053 | Gata2 | protein_coding | GATA binding protein 2 [Source:MGI Symbol;Acc:MGI:95662] |
| ENSMUSG00000033216 | Eefsec | protein_coding | eukaryotic elongation factor, selenocysteine-tRNA-specific [Source:MGI Symbol;Acc:MGI:2137092] |
| ENSMUSG00000030082 | Sec61a1 | protein_coding | Sec61 alpha 1 subunit (S. cerevisiae) [Source:MGI Symbol;Acc:MGI:1858417] |
| ENSMUSG00000002870 | Mcm2 | protein_coding | minichromosome maintenance deficient 2 mitotin (S. cerevisiae) [Source:MGI Symbol;Acc:MGI:105380] |
| ENSMUSG00000030086 | Chchd6 | protein_coding | coiled-coil-helix-coiled-coil-helix domain containing 6 [Source:MGI Symbol;Acc:MGI:1913348] |
| ENSMUSG00000034430 | Zxdc | protein_coding | ZXD family zinc finger C [Source:MGI Symbol;Acc:MGI:1933108] |
| ENSMUSG00000030091 | Nup210 | protein_coding | nucleoporin 210 [Source:MGI Symbol;Acc:MGI:1859555] |
| ENSMUSG00000030096 | Slc6a6 | protein_coding | solute carrier family 6 (neurotransmitter transporter, taurine), member 6 [Source:MGI Symbol;Acc:MGI:98488] |
| ENSMUSG00000045095 | Magi1 | protein_coding | membrane associated guanylate kinase, WW and PDZ domain containing 1 [Source:MGI Symbol;Acc:MGI:1203522] |
| ENSMUSG00000090667 | Gm765 | protein_coding | predicted gene 765 [Source:MGI Symbol;Acc:MGI:2685611] |
| ENSMUSG00000030067 | Foxp1 | protein_coding | forkhead box P1 [Source:MGI Symbol;Acc:MGI:1914004] |

TABLE S2-continued

Ythdf2 targeted mRNAs from three irCLIP-seq replicates.

| GeneID | Name | Biotype | Description |
|---|---|---|---|
| ENSMUSG 00000030257 | Srgap3 | protein_coding | SLIT-ROBO Rho GTPase activating protein 3 [Source:MGI Symbol;Acc:MGI:2152938] |
| ENSMUSG 00000034269 | Setd5 | protein_coding | SET domain containing 5 [Source:MGI Symbol;Acc:MGI:1920145] |
| ENSMUSG 00000079426 | Arpc4 | protein_coding | actin related protein 2/3 complex, subunit 4 [Source:MGI Symbol;Acc:MGI:1915339] |
| ENSMUSG 00000030276 | Ttll3 | protein_coding | tubulin tyrosine ligase-like family, member 3 [Source:MGI Symbol;Acc:MGI:2141418] |
| ENSMUSG 00000051256 | Jagn1 | protein_coding | jagunal homolog 1 (*Drosophila*) [Source:MGI Symbol;Acc:MGI:1915017] |
| ENSMUSG 00000030314 | Atg7 | protein_coding | autophagy-related 7 (yeast) [Source:MGI Symbol;Acc:MGI:1921494] |
| ENSMUSG 00000000441 | Raf1 | protein_coding | v-raf-leukemia viral oncogene 1 [Source:MGI Symbol;Acc:MGI:97847] |
| ENSMUSG 00000057841 | Rpl32 | protein_coding | ribosomal protein L32 [Source:MGI Symbol;Acc:MGI:98038] |
| ENSMUSG 00000030123 | Plxnd1 | protein_coding | plexin D1 [Source:MGI Symbol;Acc:MGI:2154244] |
| ENSMUSG 00000030126 | Tmcc1 | protein_coding | transmembrane and coiled coil domains 1 [Source:MGI Symbol;Acc:MGI:2442368] |
| ENSMUSG 00000042079 | Hnrnpf | protein_coding | heterogeneous nuclear ribonucleoprotein F [Source:MGI Symbol;Acc:MGI:2138741] |
| ENSMUSG 00000030110 | Ret | protein_coding | ret proto-oncogene [Source:MGI Symbol;Acc:MGI:97902] |
| ENSMUSG 00000030168 | Adipor2 | protein_coding | adiponectin receptor 2 [Source:MGI Symbol;Acc:MGI:93830] |
| ENSMUSG 00000030170 | Wnt5b | protein_coding | wingless-related MMTV integration site 5B [Source:MGI Symbol;Acc:MGI:98959] |
| ENSMUSG 00000030019 | Fbxl14 | protein_coding | F-box and leucine-rich repeat protein 14 [Source:MGI Symbol;Acc:MGI:2141676] |
| ENSMUSG 00000045962 | Wnk1 | protein_coding | WNK lysine deficient protein kinase 1 [Source:MGI Symbol;Acc:MGI:2442092] |
| ENSMUSG 00000030180 | Kdm5a | protein_coding | lysine (K)-specific demethylase 5A [Source:MGI Symbol;Acc:MGI:2136980] |
| ENSMUSG 00000002897 | Il17ra | protein_coding | interleukin 17 receptor A [Source:MGI Symbol;Acc:MGI:107399] |
| ENSMUSG 00000051586 | Mical3 | protein_coding | microtubule associated monoxygenase, calponin and LIM domain containing 3 [Source:MGI Symbol;Acc:MGI:2442733] |
| ENSMUSG 00000040669 | Phc1 | protein_coding | polyhomeotic-like 1 (Drosophila) [Source:MGI Symbol;Acc:MGI:103248] |
| ENSMUSG 00000004264 | Phb2 | protein_coding | prohibitin 2 [Source:MGI Symbol;Acc:MGI:102520] |
| ENSMUSG 00000004266 | Ptpn6 | protein_coding | protein tyrosine phosphatase, non-receptor type 6 [Source:MGI Symbol;Acc:MGI:96055] |
| ENSMUSG 00000004263 | Atn1 | protein_coding | atrophin 1 [Source:MGI Symbol;Acc:MGI:104725] |
| ENSMUSG 00000063870 | Chd4 | protein_coding | chromodomain helicase DNA binding protein 4 [Source:MGI Symbol;Acc:MGI:1344380] |
| ENSMUSG 00000038252 | Ncapd2 | protein_coding | non-SMC condensin I complex, subunit D2 [Source:MGI Symbol;Acc:MGI:1915548] |
| ENSMUSG 00000030339 | Ltbr | protein_coding | lymphotoxin B receptor [Source:MGI Symbol;Acc:MGI:104875] |
| ENSMUSG 00000030342 | Cd9 | protein_coding | CD9 antigen [Source:MGI Symbol;Acc:MGI:88348] |
| ENSMUSG 00000038115 | Ano2 | protein_coding | anoctamin 2 [Source:MGI Symbol;Acc:MGI:2387214] |
| ENSMUSG 00000000184 | Ccnd2 | protein_coding | cyclin D2 [Source:MGI Symbol;Acc:MGI:88314] |
| ENSMUSG 00000001517 | Foxm1 | protein_coding | forkhead box M1 [Source:MGI Symbol;Acc:MGI:1347487] |
| ENSMUSG 00000030357 | Fkbp4 | protein_coding | FK506 binding protein 4 [Source:MGI Symbol;Acc:MGI:95543] |
| ENSMUSG 00000030161 | Gabarapl1 | protein_coding | gamma-aminobutyric acid (GABA) A receptor-associated protein-like 1 [Source:MGI Symbol;Acc:MGI:1914980] |
| ENSMUSG 00000030189 | Csda | protein_coding | cold shock domain protein A [Source:MGI Symbol;Acc:MGI:2137670] |
| ENSMUSG 00000030199 | Etv6 | protein_coding | ets variant gene 6 (TEL oncogene) [Source:MGI Symbol;Acc:MGI:109336] |
| ENSMUSG 00000030201 | Lrp6 | protein_coding | low density lipoprotein receptor-related protein 6 [Source:MGI Symbol;Acc:MGI:1298218] |
| ENSMUSG 00000030203 | Dusp 16 | protein_coding | dual specificity phosphatase 16 [Source:MGI Symbol;Acc:MGI:1917936] |
| ENSMUSG 00000030204 | Ddx47 | protein_coding | DEAD (Asp-Glu-Ala-Asp) box polypeptide 47 [Source:MGI Symbol;Acc:MGI:1915005] |

TABLE S2-continued

Ythdf2 targeted mRNAs from three irCLIP-seq replicates.

| GeneID | Name | Biotype | Description |
|---|---|---|---|
| ENSMUSG00000030209 | Grin2b | protein_coding | glutamate receptor, ionotropic, NMDA2B (epsilon 2) [Source:MGI Symbol;Acc:MGI:95821] |
| ENSMUSG00000030220 | Arhgdib | protein_coding | Rho, GDP dissociation inhibitor (GDI) beta [Source:MGI Symbol;Acc:MGI:101940] |
| ENSMUSG00000030224 | Strap | protein_coding | serine/threonine kinase receptor associated protein [Source:MGI Symbol;Acc:MGI:1329037] |
| ENSMUSG00000041741 | Pde3a | protein_coding | phosphodiesterase 3A, cGMP inhibited [Source:MGI Symbol;Acc:MGI:1860764] |
| ENSMUSG00000030279 | 5730419I09Rik | protein_coding | RIKEN cDNA 5730419I09 gene [Source:MGI Symbol;Acc:MGI:1921991] |
| ENSMUSG00000030275 | Etnk1 | protein_coding | ethanolamine kinase 1 [Source:MGI Symbol;Acc:MGI:1922570] |
| ENSMUSG00000041540 | Sox5 | protein_coding | SRY-box containing gene 5 [Source:MGI Symbol;Acc:MGI:98367] |
| ENSMUSG00000030306 | Tmtc1 | protein_coding | transmembrane and tetratricopeptide repeat containing 1 [Source:MGI Symbol;Acc:MGI:3039590] |
| ENSMUSG00000040029 | Ipo8 | protein_coding | importin 8 [Source:MGI Symbol;Acc:MGI:2444611] |
| ENSMUSG00000006333 | Rps9 | protein_coding | ribosomal protein S9 [Source:MGI Symbol;Acc:MGI:1924096] |
| ENSMUSG00000019254 | Ppp1r12c | protein_coding | protein phosphatase 1, regulatory (inhibitor) subunit 12C [Source:MGI Symbol;Acc:MGI:1924258] |
| ENSMUSG00000063802 | Hspbp1 | protein_coding | HSPA (heat shock 70 kDa) binding protein, cytoplasmic cochaperone 1 [Source:MGI Symbol;Acc:MGI:1913495] |
| ENSMUSG00000030435 | U2af2 | protein_coding | U2 small nuclear ribonucleoprotein auxiliary factor (U2AF) 2 [Source:MGI Symbol;Acc:MGI:98886] |
| ENSMUSG00000035203 | Epn1 | protein_coding | epsin 1 [Source:MGI Symbol;Acc:MGI:1333763] |
| ENSMUSG00000012848 | Rps5 | protein_coding | ribosomal protein S5 [Source:MGI Symbol;Acc:MGI:1097682] |
| ENSMUSG00000049600 | Zbtb45 | protein_coding | zinc finger and BTB domain containing 45 [Source:MGI Symbol;Acc:MGI:2685003] |
| ENSMUSG00000005566 | Trim28 | protein_coding | tripartite motif-containing 28 [Source:MGI Symbol;Acc:MGI:109274] |
| ENSMUSG00000041560 | Gltscr2 | protein_coding | glioma tumor suppressor candidate region gene 2 [Source:MGI Symbol;Acc:MGI:2154441] |
| ENSMUSG00000006024 | Napa | protein_coding | N-ethylmaleimide sensitive fusion protein attachment protein alpha [Source:MGI Symbol;Acc:MGI:104563] |
| ENSMUSG00000052833 | Sae1 | protein_coding | SUMO1 activating enzyme subunit 1 [Source:MGI Symbol;Acc:MGI:1929264] |
| ENSMUSG00000059273 | Zc3h4 | protein_coding | zinc finger CCCH-type containing 4 [Source:MGI Symbol;Acc:MGI:2682314] |
| ENSMUSG00000019158 | Tmem160 | protein_coding | transmembrane protein 160 [Source:MGI Symbol;Acc:MGI:1916344] |
| ENSMUSG00000058230 | Grlf1 | protein_coding | glucocorticoid receptor DNA binding factor 1 [Source:MGI Symbol;Acc:MGI:1929494] |
| ENSMUSG00000048920 | Fkrp | protein_coding | fukutin related protein [Source:MGI Symbol;Acc:MGI:2447586] |
| ENSMUSG00000019370 | Calm3 | protein_coding | calmodulin 3 [Source:MGI Symbol;Acc:MGI:103249] |
| ENSMUSG00000044030 | Irf2bp1 | protein_coding | interferon regulatory factor 2 binding protein 1 [Source:MGI Symbol;Acc:MGI:2442159] |
| ENSMUSG00000023118 | Sympk | protein_coding | symplekin [Source:MGI Symbol;Acc:MGI:1915438] |
| ENSMUSG00000040811 | Eml2 | protein_coding | echinoderm microtubule associated protein like 2 [Source:MGI Symbol;Acc:MGI:1919455] |
| ENSMUSG00000030403 | Vasp | protein_coding | vasodilator-stimulated phosphoprotein [Source:MGI Symbol;Acc:MGI:109268] |
| ENSMUSG00000040734 | Ppp1r13l | protein_coding | protein phosphatase 1, regulatory (inhibitor) subunit 13 like [Source:MGI Symbol;Acc:MGI:3525053] |
| ENSMUSG00000044709 | Gemin7 | protein_coding | gem (nuclear organelle) associated protein 7 [Source:MGI Symbol;Acc:MGI:1916981] |
| ENSMUSG00000002984 | Tomm40 | protein_coding | translocase of outer mitochondrial membrane 40 homolog (yeast) [Source:MGI Symbol;Acc:MGI:1858259] |
| ENSMUSG00000040940 | Arhgef1 | protein_coding | Rho guanine nucleotide exchange factor (GEF) 1 [Source:MGI Symbol;Acc:MGI:1353510] |
| ENSMUSG00000003378 | Grik5 | protein_coding | glutamate receptor, ionotropic, kainate 5 (gamma 2) [Source:MGI Symbol;Acc:MGI:95818] |
| ENSMUSG00000045252 | Zfp574 | protein_coding | zinc finger protein 574 [Source:MGI Symbol;Acc:MGI:2442951] |
| ENSMUSG00000057177 | Gsk3a | protein_coding | glycogen synthase kinase 3 alpha [Source:MGI Symbol;Acc:MGI:2152453] |
| ENSMUSG00000040857 | Erf | protein_coding | Ets2 repressor factor [Source:MGI Symbol;Acc:MGI:109637] |

TABLE S2-continued

Ythdf2 targeted mRNAs from three irCLIP-seq replicates.

| GeneID | Name | Biotype | Description |
|---|---|---|---|
| ENSMUSG 00000005442 | Cic | protein_coding | capicua homolog (*Drosophila*) [Source:MGI Symbol;Acc:MGI:1918972] |
| ENSMUSG 00000061286 | Exosc5 | protein_coding | exosome component 5 [Source:MGI Symbol;Acc:MGI:107889] |
| ENSMUSG 00000002603 | Tgfb1 | protein_coding | transforming growth factor, beta 1 [Source:MGI Symbol;Acc:MGI:98725] |
| ENSMUSG 00000002608 | Ccdc97 | protein_coding | coiled-coil domain containing 97 [Source:MGI Symbol;Acc:MGI:1196455] |
| ENSMUSG 00000040725 | Hnrnpul1 | protein_coding | heterogeneous nuclear ribonucleoprotein U-like 1 [Source:MGI Symbol;Acc:MGI:2443517] |
| ENSMUSG 00000058709 | Egln2 | protein_coding | EGL nine homolog 2 (*C. elegans*) [Source:MGI Symbol;Acc:MGI:1932287] |
| ENSMUSG 00000011751 | Spnb4 | protein_coding | spectrin beta 4 [Source:MGI Symbol;Acc:MGI:1890574] |
| ENSMUSG 00000070709 | 1700049G17Rik | protein_coding | RIKEN cDNA 1700049G17 gene [Source:MGI Symbol;Acc:MGI:1920680] |
| ENSMUSG 00000003435 | Supt5h | protein_coding | suppressor of Ty 5 homolog (*S. cerevisiae*) [Source:MGI Symbol;Acc:MGI:1202400] |
| ENSMUSG 00000037563 | Rps16 | protein_coding | ribosomal protein S16 [Source:MGI Symbol;Acc:MGI:98118] |
| ENSMUSG 00000030600 | Lrfn1 | protein_coding | leucine rich repeat and fibronectin type III domain containing 1 [Source:MGI Symbol;Acc:MGI:2136810] |
| ENSMUSG 00000015165 | Hnrnpl | protein_coding | heterogeneous nuclear ribonucleoprotein L [Source:MGI Symbol;Acc:MGI:104816] |
| ENSMUSG 00000054083 | Capn12 | protein_coding | calpain 12 [Source:MGI Symbol;Acc:MGI:1891369] |
| ENSMUSG 00000030591 | Psmd8 | protein_coding | proteasome (prosome, macropain) 26S subunit, non-ATPase, 8 [Source:MGI Symbol;Acc:MGI:1888669] |
| ENSMUSG 00000037166 | Ppp1r14a | protein_coding | protein phosphatase 1, regulatory (inhibitor) subunit 14A [Source:MGI Symbol;Acc:MGI:1931139] |
| ENSMUSG 00000030583 | Sipa1l3 | protein_coding | signal-induced proliferation-associated 1 like 3 [Source:MGI Symbol;Acc:MGI:1921456] |
| ENSMUSG 00000001794 | Capns1 | protein_coding | calpain, small subunit 1 [Source:MGI Symbol;Acc:MGI:88266] |
| ENSMUSG 00000074211 | Sdhaf1 | protein_coding | succinate dehydrogenase complex assembly factor 1 [Source:MGI Symbol;Acc:MGI:1915582] |
| ENSMUSG 00000074210 | E130208F15Rik | protein_coding | RIKEN cDNA E130208F15 gene [Source:MGI Symbol;Acc:MGI:3767226] |
| ENSMUSG 00000036733 | Rbm42 | protein_coding | RNA binding motif protein 42 [Source:MGI Symbol;Acc:MGI:1915285] |
| ENSMUSG 00000078762 | Haus5 | protein_coding | HAUS augmin-like complex, subunit 5 [Source:MGI Symbol;Acc:MGI:1919159] |
| ENSMUSG 00000058239 | Usf2 | protein_coding | upstream transcription factor 2 [Source:MGI Symbol;Acc:MGI:99961] |
| ENSMUSG 00000052997 | Uba2 | protein_coding | ubiquitin-like modifier activating enzyme 2 [Source:MGI Symbol;Acc:MGI:1858313] |
| ENSMUSG 00000036427 | Gpi1 | protein_coding | glucose phosphate isomerase 1 [Source:MGI Symbol;Acc:MGI:95797] |
| ENSMUSG 00000066568 | Lsm14a | protein_coding | LSM14 homolog A (SCD6, *S. cerevisiae*) [Source:MGI Symbol;Acc:MGI:1914320] |
| ENSMUSG 00000060402 | Chst8 | protein_coding | carbohydrate (N-acetylgalactosamine 4-0) sulfotransferase 8 [Source:MGI Symbol;Acc:MGI:1916197] |
| ENSMUSG 00000034957 | Cebpa | protein_coding | CCAAT/enhancer binding protein (C/EBP), alpha [Source:MGI Symbol;Acc:MGI:99480] |
| ENSMUSG 00000034867 | Ankrd27 | protein_coding | ankyrin repeat domain 27 (VPS9 domain) [Source:MGI Symbol;Acc:MGI:2444103] |
| ENSMUSG 00000044452 | Zfp507 | protein_coding | zinc finger protein 507 [Source:MGI Symbol;Acc:MGI:1916378] |
| ENSMUSG 00000045411 | 2410002F23Rik | protein_coding | RIKEN cDNA 2410002F23 gene [Source:MGI Symbol;Acc:MGI:1914226] |
| ENSMUSG 00000047085 | Lrrc4b | protein_coding | leucine rich repeat containing 4B [Source:MGI Symbol;Acc:MGI:3027390] |
| ENSMUSG 00000008140 | 2310044H10Rik | protein_coding | RIKEN cDNA 2310044H10 gene [Source:MGI Symbol;Acc:MGI:1916933] |
| ENSMUSG 00000062785 | Kcnc3 | protein_coding | potassium voltage gated channel, Shaw-related subfamily, member 3 [Source:MGI Symbol;Acc:MGI:96669] |
| ENSMUSG 00000030739 | Myh14 | protein_coding | myosin, heavy polypeptide 14 [Source:MGI Symbol;Acc:MGI:1919210] |
| ENSMUSG 00000048012 | Zfp473 | protein_coding | zinc finger protein 473 [Source:MGI Symbol;Acc:MGI:2442697] |
| ENSMUSG 00000002205 | Vrk3 | protein_coding | vaccinia related kinase 3 [Source:MGI Symbol;Acc:MGI:2182465] |
| ENSMUSG 00000043858 | Nup62 | protein_coding | nucleoporin 62 [Source:MGI Symbol;Acc:MGI:1351500] |

TABLE S2-continued

Ythdf2 targeted mRNAs from three irCLIP-seq replicates.

| GeneID | Name | Biotype | Description |
| --- | --- | --- | --- |
| ENSMUSG 00000074141 | Il4i1 | protein_coding | interleukin 4 induced 1 [Source:MGI Symbol;Acc:MGI:109552] |
| ENSMUSG 00000038502 | Ptov1 | protein_coding | prostate tumor over expressed gene 1 [Source:MGI Symbol;Acc:MGI:1933946] |
| ENSMUSG 00000038406 | Scaf1 | protein_coding | SR-related CTD-associated factor 1 [Source:MGI Symbol;Acc:MGI:2141980] |
| ENSMUSG 00000046574 | Prr12 | protein_coding | proline rich 12 [Source:MGI Symbol;Acc:MGI:2679002] |
| ENSMUSG 00000003429 | Rps11 | protein_coding | ribosomal protein S11 [Source:MGI Symbol;Acc:MGI:1351329] |
| ENSMUSG 00000038260 | Trpm4 | protein_coding | transient receptor potential cation channel, subfamily M, member 4 [Source:MGI Symbol;Acc:MGI:1915917] |
| ENSMUSG 00000063511 | Snrnp70 | protein_coding | small nuclear ribonucleoprotein 70 (U1) [Source:MGI Symbol;Acc:MGI:98341] |
| ENSMUSG 00000003873 | Bax | protein_coding | BCL2-associated X protein [Source:MGI Symbol;Acc:MGI:99702] |
| ENSMUSG 00000030826 | Bcat2 | protein_coding | branched chain aminotransferase 2, mitochondrial [Source:MGI Symbol;Acc:MGI:1276534] |
| ENSMUSG 00000057342 | Sphk2 | protein_coding | sphingosine kinase 2 [Source:MGI Symbol;Acc:MGI:1861380] |
| ENSMUSG 00000053801 | Grwd1 | protein_coding | glutamate-rich WD repeat containing 1 [Source:MGI Symbol;Acc:MGI:2141989] |
| ENSMUSG 00000002771 | Grin2d | protein_coding | glutamate receptor, ionotropic, NMDA2D (epsilon 4) [Source:MGI Symbol;Acc:MGI:95823] |
| ENSMUSG 00000002778 | Kdelr1 | protein_coding | KDEL (Lys-Asp-Glu-Leu) endoplasmic reticulum protein retention receptor 1 [Source:MGI Symbol;Acc:MGI:1915387] |
| ENSMUSG 00000030835 | Nomo1 | protein_coding | nodal modulator 1 [Source:MGI Symbol;Acc:MGI:2385850] |
| ENSMUSG 00000040136 | Abcc8 | protein_coding | ATP-binding cassette, sub-family C (CFTR/MRP), member 8 [Source:MGI Symbol;Acc:MGI:1352629] |
| ENSMUSG 00000030839 | Sergef | protein_coding | secretion regulating guanine nucleotide exchange factor [Source:MGI Symbol;Acc:MGI:1351630] |
| ENSMUSG 00000063229 | Ldha | protein_coding | lactate dehydrogenase A [Source:MGI Symbol;Acc:MGI:96759] |
| ENSMUSG 00000052512 | Nav2 | protein_coding | neuron navigator 2 [Source:MGI Symbol;Acc:MGI:2183691] |
| ENSMUSG 00000055409 | Nell1 | protein_coding | NEL-like 1 (chicken) [Source:MGI Symbol;Acc:MGI:2443902] |
| ENSMUSG 00000030451 | Herc2 | protein_coding | hect (homologous to the E6-AP (UBE3A) carboxyl terminus) domain and RCC1 (CHC1)-like domain (RLD) 2 [Source:MGI Symbol;Acc:MGI:103234] |
| ENSMUSG 00000000948 | Snrpn | protein_coding | small nuclear ribonucleoprotein N [Source:MGI Symbol;Acc:MGI:98347] |
| ENSMUSG 00000052040 | Klf13 | protein_coding | Kruppel-like factor 13 [Source:MGI Symbol;Acc:MGI:1354948] |
| ENSMUSG 00000030518 | Fam189a1 | protein_coding | family with sequence similarity 189, member A1 [Source:MGI Symbol;Acc:MGI:1917888] |
| ENSMUSG 00000015133 | Lrrk1 | protein_coding | leucine-rich repeat kinase 1 [Source:MGI Symbol;Acc:MGI:2142227] |
| ENSMUSG 00000005533 | Igf1r | protein_coding | insulin-like growth factor I receptor [Source:MGI Symbol;Acc:MGI:96433] |
| ENSMUSG 00000078671 | Chd2 | protein_coding | chromodomain helicase DNA binding protein 2 [Source:MGI Symbol;Acc:MGI:2448567] |
| ENSMUSG 00000025790 | Slco3a1 | protein_coding | solute carrier organic anion transporter family, member 3a1 [Source:MGI Symbol;Acc:MGI:1351867] |
| ENSMUSG 00000066406 | Akap13 | protein_coding | A kinase (PRKA) anchor protein 13 [Source:MGI Symbol;Acc:MGI:2676556] |
| ENSMUSG 00000030605 | Mfge8 | protein_coding | milk fat globule-EGF factor 8 protein [Source:MGI Symbol;Acc:MGI:102768] |
| ENSMUSG 00000030534 | Vps33b | protein_coding | vacuolar protein sorting 33B (yeast) [Source:MGI Symbol;Acc:MGI:2446237] |
| ENSMUSG 00000038886 | Man2a2 | protein_coding | mannosidase 2, alpha 2 [Source:MGI Symbol;Acc:MGI:2150656] |
| ENSMUSG 00000030530 | Furin | protein_coding | furin (paired basic amino acid cleaving enzyme) [Source:MGI Symbol;Acc:MGI:97513] |
| ENSMUSG 00000030536 | Iqgap1 | protein_coding | IQ motif containing GTPase activating protein 1 [Source:MGI Symbol;Acc:MGI:1352757] |
| ENSMUSG 00000005621 | Zfp592 | protein_coding | zinc finger protein 592 [Source:MGI Symbol;Acc:MGI:2443541] |
| ENSMUSG 00000057706 | Mex3b | protein_coding | mex3 homolog B (C. elegans) [Source:MGI Symbol;Acc:MGI:1918252] |
| ENSMUSG 00000063902 | Gm7964 | protein_coding | predicted gene 7964 [Source:MGI Symbol;Acc:MGI:3646150] |
| ENSMUSG 00000070462 | Mesdc1 | protein_coding | mesoderm development candidate 1 [Source:MGI Symbol;Acc:MGI:1891420] |

TABLE S2-continued

Ythdf2 targeted mRNAs from three irCLIP-seq replicates.

| GeneID | Name | Biotype | Description |
|---|---|---|---|
| ENSMUSG 00000038459 | Fam108c | protein_coding | family with sequence similarity 108, member C [Source:MGI Symbol;Acc:MGI:1917428] |
| ENSMUSG 00000039361 | Picalm | protein_coding | phosphatidylinositol binding clathrin assembly protein [Source:MGI Symbol;Acc:MGI:2385902] |
| ENSMUSG 00000052572 | Dlg2 | protein_coding | discs, large homolog 2 (*Drosophila*) [Source:MGI Symbol;Acc:MGI:1344351] |
| ENSMUSG 00000041328 | Pcf11 | protein_coding | cleavage and polyadenylation factor subunit homolog (*S. cerevisiae*) [Source:MGI Symbol;Acc:MGI:1919579] |
| ENSMUSG 00000054061 | Gm9934 | protein_coding | predicted gene 9934 [Source:MGI Symbol;Acc:MGI:3641747] |
| ENSMUSG 00000048078 | Odz4 | protein_coding | odd Oz/ten-m homolog 4 (*Drosophila*) [Source:MGI Symbol;Acc:MGI:2447063] |
| ENSMUSG 00000035623 | Rsf1 | protein_coding | remodeling and spacing factor 1 [Source:MGI Symbol;Acc:MGI:2682305] |
| ENSMUSG 00000030753 | Prkrir | protein_coding | protein-kinase, interferon-inducible double stranded RNA dependent inhibitor, repressor of (P58 repressor) [Source:MGI Symbol;Acc:MGI:1920231] |
| ENSMUSG 00000030744 | Rps3 | protein_coding | ribosomal protein S3 [Source:MGI Symbol;Acc:MGI:1350917] |
| ENSMUSG 00000018909 | Arrb1 | protein_coding | arrestin, beta 1 [Source:MGI Symbol;Acc:MGI:99473] |
| ENSMUSG 00000058761 | Rnf169 | protein_coding | ring finger protein 169 [Source:MGI Symbol;Acc:MGI:1920257] |
| ENSMUSG 00000047248 | C2cd3 | protein_coding | C2 calcium-dependent domain containing 3 [Source:MGI Symbol;Acc:MGI:2142166] |
| ENSMUSG 00000029461 | Fam168a | protein_coding | family with sequence similarity 168, member A [Source:MGI Symbol;Acc:MGI:2442372] |
| ENSMUSG 00000032875 | Arhgef17 | protein_coding | Rho guanine nucleotide exchange factor (GEF) 17 [Source:MGI Symbol;Acc:MGI:2673002] |
| ENSMUSG 00000066306 | Numa1 | protein_coding | nuclear mitotic apparatus protein 1 [Source:MGI Symbol;Acc:MGI:2443665] |
| ENSMUSG 00000073982 | Rhog | protein_coding | ras homolog gene family, member G [Source:MGI Symbol;Acc:MGI:1928370] |
| ENSMUSG 00000030978 | Rrm1 | protein_coding | ribonucleotide reductase M1 [Source:MGI Symbol;Acc:MGI:98180] |
| ENSMUSG 00000036862 | Dchs1 | protein_coding | dachsous 1 (*Drosophila*) [Source:MGI Symbol;Acc:MGI:2685011] |
| ENSMUSG 00000031029 | Eif3f | protein_coding | eukaryotic translation initiation factor 3, subunit F [Source:MGI Symbol;Acc:MGI:1913335] |
| ENSMUSG 00000046364 | Rpl27a | protein_coding | ribosomal protein L27A [Source:MGI Symbol;Acc:MGI:1347076] |
| ENSMUSG 00000035901 | Dennd5a | protein_coding | DENN/MADD domain containing 5A [Source:MGI Symbol;Acc:MGI:1201681] |
| ENSMUSG 00000066232 | Ipo7 | protein_coding | importin 7 [Source:MGI Symbol;Acc:MGI:2152414] |
| ENSMUSG 00000031015 | Swap 70 | protein_coding | SWA-70 protein [Source:MGI Symbol;Acc:MGI:1298390] |
| ENSMUSG 00000005610 | Eif4g2 | protein_coding | eukaryotic translation initiation factor 4, gamma 2 [Source:MGI Symbol;Acc:MGI:109207] |
| ENSMUSG 00000059263 | Usp47 | protein_coding | ubiquitin specific peptidase 47 [Source:MGI Symbol;Acc:MGI:1922246] |
| ENSMUSG 00000038187 | Btbd10 | protein_coding | BTB (POZ) domain containing 10 [Source:MGI Symbol;Acc:MGI:1916065] |
| ENSMUSG 00000051910 | Sox6 | protein_coding | SRY-box containing gene 6 [Source:MGI Symbol;Acc:MGI:98368] |
| ENSMUSG 00000045659 | Plekha7 | protein_coding | pleckstrin homology domain containing, family A member 7 [Source:MGI Symbol;Acc:MGI:2445094] |
| ENSMUSG 00000030872 | Gga2 | protein_coding | golgi associated, gamma adaptin ear containing, ARF binding protein 2 [Source:MGI Symbol;Acc:MGI:1921355] |
| ENSMUSG 00000030870 | Ubfd1 | protein_coding | ubiquitin family domain containing 1 [Source:MGI Symbol;Acc:MGI:107301] |
| ENSMUSG 00000052889 | Prkcb | protein_coding | protein kinase C, beta [Source:MGI Symbol;Acc:MGI:97596] |
| ENSMUSG 00000030779 | Rbbp6 | protein_coding | retinoblastoma binding protein 6 [Source:MGI Symbol;Acc:MGI:894835] |
| ENSMUSG 00000030748 | Il4ra | protein_coding | interleukin 4 receptor, alpha [Source:MGI Symbol;Acc:MGI:105367] |
| ENSMUSG 00000046182 | Gsg1l | protein_coding | GSG1-like [Source:MGI Symbol;Acc:MGI:2685483] |
| ENSMUSG 00000000131 | Xpo6 | protein_coding | exportin 6 [Source:MGI Symbol;Acc:MGI:2429950] |
| ENSMUSG 00000032637 | Atxn2l | protein_coding | ataxin 2-like [Source:MGI Symbol;Acc:MGI:2446242] |
| ENSMUSG 00000030738 | Eif3c | protein_coding | eukaryotic translation initiation factor 3, subunit C [Source:MGI Symbol;Acc:MGI:1926966] |

TABLE S2-continued

Ythdf2 targeted mRNAs from three irCLIP-seq replicates.

| GeneID | Name | Biotype | Description |
|---|---|---|---|
| ENSMUSG00000030707 | Coro1a | protein_coding | coronin, actin binding protein 1A [Source:MGI Symbol;Acc:MGI:1345961] |
| ENSMUSG00000030695 | Aldoa | protein_coding | aldolase A, fructose-bisphosphate [Source:MGI Symbol;Acc:MGI:87994] |
| ENSMUSG00000030689 | Ino80e | protein_coding | INO80 complex subunit E [Source:MGI Symbol;Acc:MGI:2141881] |
| ENSMUSG00000030680 | 2900092E17Rik | protein_coding | RIKEN cDNA 2900092E17 gene [Source:MGI Symbol;Acc:MGI:1914528] |
| ENSMUSG00000030678 | Maz | protein_coding | MYC-associated zinc finger protein (purine-binding transcription factor) [Source:MGI Symbol;Acc:MGI:1338823] |
| ENSMUSG00000045165 | AI467606 | protein_coding | expressed sequence AI467606 [Source:MGI Symbol;Acc:MGI:2141979] |
| ENSMUSG00000051457 | Spn | protein_coding | sialophorin [Source:MGI Symbol;Acc:MGI:98384] |
| ENSMUSG00000042502 | Cd2bp2 | protein_coding | CD2 antigen (cytoplasmic tail) binding protein 2 [Source:MGI Symbol;Acc:MGI:1917483] |
| ENSMUSG00000049091 | Sephs2 | protein_coding | selenophosphate synthetase 2 [Source:MGI Symbol;Acc:MGI:108388] |
| ENSMUSG00000053877 | Srcap | protein_coding | Snf2-related CREBBP activator protein [Source:MGI Symbol;Acc:MGI:2444036] |
| ENSMUSG00000090663 | Srcap | protein_coding | Snf2-related CREBBP activator protein [Source:MGI Symbol;Acc:MGI:2444036] |
| ENSMUSG00000030811 | Fbxl19 | protein_coding | F-box and leucine-rich repeat protein 19 [Source:MGI Symbol;Acc:MGI:3039600] |
| ENSMUSG00000042308 | Setd1a | protein_coding | SET domain containing 1A [Source:MGI Symbol;Acc:MGI:2446244] |
| ENSMUSG00000042289 | Hsd3b7 | protein_coding | hydroxy-delta-5-steroid dehydrogenase, 3 beta- and steroid delta-isomerase 7 [Source:MGI Symbol;Acc:MGI:2141879] |
| ENSMUSG00000049739 | Zfp646 | protein_coding | zinc finger protein 646 [Source:MGI Symbol;Acc:MGI:3665412] |
| ENSMUSG00000030795 | Fus | protein_coding | fusion, derived from t(12;16) malignant liposarcoma (human) [Source:MGI Symbol;Acc:MGI:1353633] |
| ENSMUSG00000030786 | Itgam | protein_coding | integrin alpha M [Source:MGI Symbol;Acc:MGI:96607] |
| ENSMUSG00000030846 | Tial1 | protein_coding | Tia1 cytotoxic granule-associated RNA binding protein-like 1 [Source:MGI Symbol;Acc:MGI:107913] |
| ENSMUSG00000030849 | Fgfr2 | protein_coding | fibroblast growth factor receptor 2 [Source:MGI Symbol;Acc:MGI:95523] |
| ENSMUSG00000066979 | Bub3 | protein_coding | budding uninhibited by benzimidazoles 3 homolog (*S. cerevisiae*) [Source:MGI Symbol;Acc:MGI:1343463] |
| ENSMUSG00000040125 | Gpr26 | protein_coding | G protein-coupled receptor 26 [Source:MGI Symbol;Acc:MGI:2441758] |
| ENSMUSG00000030930 | Chst15 | protein_coding | carbohydrate (N-acetylgalactosamine 4-sulfate 6-0) sulfotransferase 15 [Source:MGI Symbol;Acc:MGI:1924840] |
| ENSMUSG00000030946 | Lhpp | protein_coding | phospholysine phosphohistidine inorganic pyrophosphate phosphatase [Source:MGI Symbol;Acc:MGI:1923679] |
| ENSMUSG00000030956 | Fam53b | protein_coding | family with sequence similarity 53, member B [Source:MGI Symbol;Acc:MGI:1925188] |
| ENSMUSG00000030970 | Ctbp2 | protein_coding | C-terminal binding protein 2 [Source:MGI Symbol;Acc:MGI:1201686] |
| ENSMUSG00000030979 | Uros | protein_coding | uroporphyrinogen III synthase [Source:MGI Symbol;Acc:MGI:98917] |
| ENSMUSG00000041836 | Ptpre | protein_coding | protein tyrosine phosphatase, receptor type, E [Source:MGI Symbol;Acc:MGI:97813] |
| ENSMUSG00000031004 | Mki67 | protein_coding | antigen identified by monoclonal antibody Ki 67 [Source:MGI Symbol;Acc:MGI:106035] |
| ENSMUSG00000025491 | Ifitm1 | protein_coding | interferon induced transmembrane protein 1 [Source:MGI Symbol;Acc:MGI:1915963] |
| ENSMUSG00000038580 | Sct | protein_coding | secretin [Source:MGI Symbol;Acc:MGI:99466] |
| ENSMUSG00000025508 | Rplp2 | protein_coding | ribosomal protein, large P2 [Source:MGI Symbol;Acc:MGI:1914436] |
| ENSMUSG00000025515 | Muc2 | protein_coding | mucin 2 [Source:MGI Symbol;Acc:MGI:1339364] |
| ENSMUSG00000007891 | Ctsd | protein_coding | cathepsin D [Source:MGI Symbol;Acc:MGI:88562] |
| ENSMUSG00000009545 | Kcnq1 | protein_coding | potassium voltage-gated channel, subfamily Q, member 1 [Source:MGI Symbol;Acc:MGI:108083] |
| ENSMUSG00000059119 | Nap1l4 | protein_coding | nucleosome assembly protein 1-like 4 [Source:MGI Symbol;Acc:MGI:1316687] |
| ENSMUSG00000004565 | Pnpla6 | protein_coding | patatin-like phospholipase domain containing 6 [Source:MGI Symbol;Acc:MGI:1354723] |

TABLE S2-continued

Ythdf2 targeted mRNAs from three irCLIP-seq replicates.

| GeneID | Name | Biotype | Description |
|---|---|---|---|
| ENSMUSG00000004626 | Stxbp2 | protein_coding | syntaxin binding protein 2 [Source:MGI Symbol;Acc:MGI:107370] |
| ENSMUSG00000040028 | Elavl1 | protein_coding | ELAV (embryonic lethal, abnormal vision, *Drosophila*)-like 1 (Hu antigen R) [Source:MGI Symbol;Acc:MGI:1100851] |
| ENSMUSG00000008206 | Lass4 | protein_coding | LAG1 homolog, ceramide synthase 4 [Source:MGI Symbol;Acc:MGI:1914510] |
| ENSMUSG00000043192 | Gm1840 | protein_coding | predicted gene 1840 [Source:MGI Symbol;Acc:MGI:3037698] |
| ENSMUSG00000040459 | Arglu1 | protein_coding | arginine and glutamate rich 1 [Source:MGI Symbol;Acc:MGI:2442985] |
| ENSMUSG00000045969 | Ing1 | protein_coding | inhibitor of growth family, member 1 [Source:MGI Symbol;Acc:MGI:1349481] |
| ENSMUSG00000031511 | Arhgef7 | protein_coding | Rho guanine nucleotide exchange factor (GEF7) [Source:MGI Symbol;Acc:MGI:1860493] |
| ENSMUSG00000074473 | A230072I06Rik | protein_coding | RIKEN cDNA A230072I06 gene [Source:MGI Symbol;Acc:MGI:3588221] |
| ENSMUSG00000031441 | Atp11a | protein_coding | ATPase, class VI, type 11A [Source:MGI Symbol;Acc:MGI:1354735] |
| ENSMUSG00000031446 | Cul4a | protein_coding | cullin 4A [Source:MGI Symbol;Acc:MGI:1914487] |
| ENSMUSG00000031447 | Lamp1 | protein_coding | lysosomal-associated membrane protein 1 [Source:MGI Symbol;Acc:MGI:96745] |
| ENSMUSG00000038506 | Dcun1d2 | protein_coding | DCN1, defective in cullin neddylation 1, domain containing 2 (*S. cerevisiae*) [Source:MGI Symbol;Acc:MGI:2142792] |
| ENSMUSG00000047495 | Dlgap2 | protein_coding | discs, large (*Drosophila*) homolog-associated protein 2 [Source:MGI Symbol;Acc:MGI:2443181] |
| ENSMUSG00000031480 | Thsd1 | protein_coding | thrombospondin, type I, domain 1 [Source:MGI Symbol;Acc:MGI:1929096] |
| ENSMUSG00000031540 | Myst3 | protein_coding | MYST histone acetyltransferase (monocytic leukemia) 3 [Source:MGI Symbol;Acc:MGI:2442415] |
| ENSMUSG00000031543 | Ank1 | protein_coding | ankyrin 1, erythroid [Source:MGI Symbol;Acc:MGI:88024] |
| ENSMUSG00000037492 | Zmat4 | protein_coding | zinc finger, matrin type 4 [Source:MGI Symbol;Acc:MGI:2443497] |
| ENSMUSG00000031557 | Plekha2 | protein_coding | pleckstrin homology domain-containing, family A (phosphoinositide binding specific) member 2 [Source:MGI Symbol;Acc:MGI:1928144] |
| ENSMUSG00000065954 | Tacc1 | protein_coding | transforming, acidic coiled-coil containing protein 1 [Source:MGI Symbol;Acc:MGI:2443510] |
| ENSMUSG00000054823 | Whsc1l1 | protein_coding | Wolf-Hirschhorn syndrome candidate 1-like 1 (human) [Source:MGI Symbol;Acc:MGI:2142581] |
| ENSMUSG00000031490 | Eif4ebp1 | protein_coding | eukaryotic translation initiation factor 4E binding protein 1 [Source:MGI Symbol;Acc:MGI:103267] |
| ENSMUSG00000031577 | Tti2 | protein_coding | TELO2 interacting protein 2 [Source:MGI Symbol;Acc:MGI:2384576] |
| ENSMUSG00000031586 | Rbpms | protein_coding | RNA binding protein gene with multiple splicing [Source:MGI Symbol;Acc:MGI:1334446] |
| ENSMUSG00000031516 | Dctn6 | protein_coding | dynactin 6 [Source:MGI Symbol;Acc:MGI:1343154] |
| ENSMUSG00000031530 | Dusp4 | protein_coding | dual specificity phosphatase 4 [Source:MGI Symbol;Acc:MGI:2442191] |
| ENSMUSG00000031529 | Tnks | protein_coding | tankyrase, TRF1-interacting ankyrin-related ADP-ribose polymerase [Source:MGI Symbol;Acc:MGI:1341087] |
| ENSMUSG00000031523 | Dlc1 | protein_coding | deleted in liver cancer 1 [Source:MGI Symbol;Acc:MGI:1354949] |
| ENSMUSG00000039431 | Mtmr7 | protein_coding | myotubularin related protein 7 [Source:MGI Symbol;Acc:MGI:1891693] |
| ENSMUSG00000053038 | Gm6180 | protein_coding | predicted pseudogene 6180 [Source:MGI Symbol;Acc:MGI:3643972] |
| ENSMUSG00000038291 | Snx25 | protein_coding | sorting nexin 25 [Source:MGI Symbol;Acc:MGI:2142610] |
| ENSMUSG00000031633 | Slc25a4 | protein_coding | solute carrier family 25 (mitochondrial carrier, adenine nucleotide translocator), member 4 [Source:MGI Symbol;Acc:MGI:1353495] |
| ENSMUSG00000031608 | Galnt7 | protein_coding | UDP-N-acetyl-alpha-D-galactosamine: polypeptide N-acetylgalactosaminyltransferase 7 [Source:MGI Symbol;Acc:MGI:1349449] |
| ENSMUSG00000031642 | Sh3rf1 | protein_coding | SH3 domain containing ring finger 1 [Source:MGI Symbol;Acc:MGI:1913066] |
| ENSMUSG00000031604 | Sc4mol | protein_coding | sterol-C4-methyl oxidase-like [Source:MGI Symbol;Acc:MGI:1913484] |
| ENSMUSG00000036356 | Csgalnact1 | protein_coding | chondroitin sulfate N-acetylgalactosaminyltransferase 1 [Source:MGI Symbol;Acc:MGI:2442354] |

TABLE S2-continued

Ythdf2 targeted mRNAs from three irCLIP-seq replicates.

| GeneID | Name | Biotype | Description |
|---|---|---|---|
| ENSMUSG00000006273 | Atp6v1b2 | protein_coding | ATPase, H+ transporting, lysosomal V1 subunit B2 [Source:MGI Symbol;Acc:MGI:109618] |
| ENSMUSG00000036180 | Gatad2a | protein_coding | GATA zinc finger domain containing 2A [Source:MGI Symbol;Acc:MGI:2384585] |
| ENSMUSG00000003573 | Homer3 | protein_coding | homer homolog 3 (Drosophila) [Source:MGI Symbol;Acc:MGI:1347359] |
| ENSMUSG00000057788 | Ddx49 | protein_coding | DEAD (Asp-Glu-Ala-Asp) box polypeptide 49 [Source:MGI Symbol;Acc:MGI:2136689] |
| ENSMUSG00000058301 | Upf1 | protein_coding | UPF1 regulator of nonsense transcripts homolog (yeast) [Source:MGI Symbol;Acc:MGI:107995] |
| ENSMUSG00000070002 | Ell | protein_coding | elongation factor RNA polymerase II [Source:MGI Symbol;Acc:MGI:109377] |
| ENSMUSG00000019139 | Isyna1 | protein_coding | myo-inositol 1-phosphate synthase A1 [Source:MGI Symbol;Acc:MGI:1919030] |
| ENSMUSG00000071076 | Jund | protein_coding | Jun proto-oncogene related gene d [Source:MGI Symbol;Acc:MGI:96648] |
| ENSMUSG00000080058 | Gm11175 | protein_coding | predicted gene 11175 [Source:MGI Symbol;Acc:MGI:3809055] |
| ENSMUSG00000031833 | Mast3 | protein_coding | microtubule associated serine/threonine kinase 3 [Source:MGI Symbol;Acc:MGI:2683541] |
| ENSMUSG00000019261 | Mtap1s | protein_coding | microtubule-associated protein 1S [Source:MGI Symbol;Acc:MGI:2443304] |
| ENSMUSG00000004677 | Myo9b | protein_coding | myosin IXb [Source:MGI Symbol;Acc:MGI:106624] |
| ENSMUSG00000031805 | Jak3 | protein_coding | Janus kinase 3 [Source:MGI Symbol;Acc:MGI:99928] |
| ENSMUSG00000003037 | Rab8a | protein_coding | RAB8A, member RAS oncogene family [Source:MGI Symbol;Acc:MGI:96960] |
| ENSMUSG00000003039 | Fam32a | protein_coding | family with sequence similarity 32, member A [Source:MGI Symbol;Acc:MGI:1915172] |
| ENSMUSG00000019731 | Slc35e1 | protein_coding | solute carrier family 35, member E1 [Source:MGI Symbol;Acc:MGI:2142403] |
| ENSMUSG00000031622 | Sin3b | protein_coding | transcriptional regulator, SIN3B (yeast) [Source:MGI Symbol;Acc:MGI:107158] |
| ENSMUSG00000004383 | Large | protein_coding | like-glycosyltransferase [Source:MGI Symbol;Acc:MGI:1342270] |
| ENSMUSG00000005410 | Mcm5 | protein_coding | minichromosome maintenance deficient 5, cell division cycle 46 (S. cerevisiae) [Source:MGI Symbol;Acc:MGI:103197] |
| ENSMUSG00000031684 | Slc10a7 | protein_coding | solute carrier family 10 (sodium/bile acid cotransporter family), member 7 [Source:MGI Symbol;Acc:MGI:1924025] |
| ENSMUSG00000031681 | Smad1 | protein_coding | MAD homolog 1 (Drosophila) [Source:MGI Symbol;Acc:MGI:109452] |
| ENSMUSG00000058355 | Abce1 | protein_coding | ATP-binding cassette, sub-family E (OABP), member 1 [Source:MGI Symbol;Acc:MGI:1195458] |
| ENSMUSG00000031715 | Smarca5 | protein_coding | SWI/SNF related, matrix associated, actin dependent regulator of chromatin, subfamily a, member 5 [Source:MGI Symbol;Acc:MGI:1935129] |
| ENSMUSG00000038250 | Usp38 | protein_coding | ubiquitin specific peptidase 38 [Source:MGI Symbol;Acc:MGI:1922091] |
| ENSMUSG00000037940 | Inpp4b | protein_coding | inositol polyphosphate-4-phosphatase, type II [Source:MGI Symbol;Acc:MGI:2158925] |
| ENSMUSG00000031708 | Tecr | protein_coding | trans-2,3-enoyl-CoA reductase [Source:MGI Symbol;Acc:MGI:1915408] |
| ENSMUSG00000019433 | Gipc1 | protein_coding | GIPC PDZ domain containing family, member 1 [Source:MGI Symbol;Acc:MGI:1926252] |
| ENSMUSG00000019464 | Ptger1 | protein_coding | prostaglandin E receptor 1 (subtype EP1) [Source:MGI Symbol;Acc:MGI:97793] |
| ENSMUSG00000004815 | Ddx39 | protein_coding | DEAD (Asp-Glu-Ala-Asp) box polypeptide 39 [Source:MGI Symbol;Acc:MGI:1915528] |
| ENSMUSG00000013033 | Lphn1 | protein_coding | latrophilin 1 [Source:MGI Symbol;Acc:MGI:1929461] |
| ENSMUSG00000074219 | Gm10644 | protein_coding | predicted gene 10644 [Source:MGI Symbol;Acc:MGI:3704314] |
| ENSMUSG00000079003 | Samd1 | protein_coding | sterile alpha motif domain containing 1 [Source:MGI Symbol;Acc:MGI:2142433] |
| ENSMUSG00000031706 | Rfx1 | protein_coding | regulatory factor X, 1 (influences HLA class II expression) [Source:MGI Symbol;Acc:MGI:105982] |
| ENSMUSG00000037103 | Dcaf15 | protein_coding | DDB1 and CUL4 associated factor 15 [Source:MGI Symbol;Acc:MGI:2684420] |
| ENSMUSG00000004996 | Mri1 | protein_coding | methylthioribose-1-phosphate isomerase homolog (S. cerevisiae) [Source:MGI Symbol;Acc:MGI:1915123] |
| ENSMUSG00000053560 | Ier2 | protein_coding | immediate early response 2 [Source:MGI Symbol;Acc:MGI:104815] |

TABLE S2-continued

Ythdf2 targeted mRNAs from three irCLIP-seq replicates.

| GeneID | Name | Biotype | Description |
|---|---|---|---|
| ENSMUSG00000001910 | Nacc1 | protein_coding | nucleus accumbens associated 1, BEN and BTB (POZ) domain containing [Source:MGI Symbol;Acc:MGI:1914080] |
| ENSMUSG00000001911 | Nfix | protein_coding | nuclear factor I/X [Source:MGI Symbol;Acc:MGI:97311] |
| ENSMUSG00000034041 | Lyl1 | protein_coding | lymphoblastomic leukemia 1 [Source:MGI Symbol;Acc:MGI:96891] |
| ENSMUSG00000003814 | Calr | protein_coding | calreticulin [Source:MGI Symbol;Acc:MGI:88252] |
| ENSMUSG00000003808 | Farsa | protein_coding | phenylalanyl-tRNA synthetase, alpha subunit [Source:MGI Symbol;Acc:MGI:1913840] |
| ENSMUSG00000005161 | Prdx2 | protein_coding | peroxiredoxin 2 [Source:MGI Symbol;Acc:MGI:109486] |
| ENSMUSG00000041203 | 2310036O22Rik | protein_coding | RIKEN cDNA 2310036O22 gene [Source:MGI Symbol;Acc:MGI:1922833] |
| ENSMUSG00000031691 | Tnpo2 | protein_coding | transportin 2 (importin 3, karyopherin beta 2b) [Source:MGI Symbol;Acc:MGI:2384849] |
| ENSMUSG00000005142 | Man2b1 | protein_coding | mannosidase 2, alpha B1 [Source:MGI Symbol;Acc:MGI:107286] |
| ENSMUSG00000074194 | Zfp791 | protein_coding | zinc finger protein 791 [Source:MGI Symbol;Acc:MGI:3648473] |
| ENSMUSG00000031701 | Dnaja2 | protein_coding | DnaJ (Hsp40) homolog, subfamily A, member 2 [Source:MGI Symbol;Acc:MGI:1931882] |
| ENSMUSG00000031652 | N4bp1 | protein_coding | NEDD4 binding protein 1 [Source:MGI Symbol;Acc:MGI:2136825] |
| ENSMUSG00000031659 | Adcy7 | protein_coding | adenylate cyclase 7 [Source:MGI Symbol;Acc:MGI:102891] |
| ENSMUSG00000055932 | Fto | protein_coding | fat mass and obesity associated [Source:MGI Symbol;Acc:MGI:1347093] |
| ENSMUSG00000031751 | Amfr | protein_coding | autocrine motility factor receptor [Source:MGI Symbol;Acc:MGI:1345634] |
| ENSMUSG00000031774 | Fam192a | protein_coding | family with sequence similarity 192, member A [Source:MGI Symbol;Acc:MGI:1919637] |
| ENSMUSG00000031776 | Arl2bp | protein_coding | ADP-ribosylation factor-like 2 binding protein [Source:MGI Symbol;Acc:MGI:1349429] |
| ENSMUSG00000031785 | Gpr56 | protein_coding | G protein-coupled receptor 56 [Source:MGI Symbol;Acc:MGI:1340051] |
| ENSMUSG00000046556 | Zfp319 | protein_coding | zinc finger protein 319 [Source:MGI Symbol;Acc:MGI:1890618] |
| ENSMUSG00000036550 | Cnot1 | protein_coding | CCR4-NOT transcription complex, subunit 1 [Source:MGI Symbol;Acc:MGI:2442402] |
| ENSMUSG00000031672 | Got2 | protein_coding | glutamate oxaloacetate transaminase 2, mitochondrial [Source:MGI Symbol;Acc:MGI:95792] |
| ENSMUSG00000014859 | E2f4 | protein_coding | E2F transcription factor 4 [Source:MGI Symbol;Acc:MGI:103012] |
| ENSMUSG00000038604 | Fam65a | protein_coding | family with sequence similarity 65, member A [Source:MGI Symbol;Acc:MGI:1922937] |
| ENSMUSG00000005698 | Ctcf | protein_coding | CCCTC-binding factor [Source:MGI Symbol;Acc:MGI:109447] |
| ENSMUSG00000037415 | Ranbp10 | protein_coding | RAN binding protein 10 [Source:MGI Symbol;Acc:MGI:1921584] |
| ENSMUSG00000036442 | Thap11 | protein_coding | THAP domain containing 11 [Source:MGI Symbol;Acc:MGI:1930964] |
| ENSMUSG00000008450 | Nutf2 | protein_coding | nuclear transport factor 2 [Source:MGI Symbol;Acc:MGI:1915301] |
| ENSMUSG00000048310 | Pskh1 | protein_coding | protein serine kinase H1 [Source:MGI Symbol;Acc:MGI:3528383] |
| ENSMUSG00000017765 | Slc12a4 | protein_coding | solute carrier family 12, member 4 [Source:MGI Symbol;Acc:MGI:1309465] |
| ENSMUSG00000031904 | Slc7a6 | protein_coding | solute carrier family 7 (cationic amino acid transporter, y+ system), member 6 [Source:MGI Symbol;Acc:MGI:2142598] |
| ENSMUSG00000046691 | Chtf8 | protein_coding | CTF8, chromosome transmission fidelity factor 8 homolog (S. cerevisiae) [Source:MG Symbol;Acc:MGI:2443370] |
| ENSMUSG00000031913 | Vps4a | protein_coding | vacuolar protein sorting 4a (yeast) [Source:MGI Symbol;Acc:MGI:1890520] |
| ENSMUSG00000031916 | Cog8 | protein_coding | component of oligomeric golgi complex 8 [Source:MGI Symbol;Acc:MGI:2142885] |
| ENSMUSG00000031921 | Terf2 | protein_coding | telomeric repeat binding factor 2 [Source:MGI Symbol;Acc:MGI:1195972] |
| ENSMUSG00000031924 | Cyb5b | protein_coding | cytochrome b5 type B [Source:MGI Symbol;Acc:MGI:1913677] |
| ENSMUSG00000003848 | Nob1 | protein_coding | NIN1/RPN12 binding protein 1 homolog (S. cerevisiae) [Source:MGI Symbol;Acc:MGI:1914869] |

TABLE S2-continued

Ythdf2 targeted mRNAs from three irCLIP-seq replicates.

| GeneID | Name | Biotype | Description |
|---|---|---|---|
| ENSMUSG00000039067 | Psmd7 | protein_coding | proteasome (prosome, macropain) 26S subunit, non-ATPase, 7 [Source:MGI Symbol;Acc:MGI:1351511] |
| ENSMUSG00000037993 | Dhx38 | protein_coding | DEAH (Asp-Glu-Ala-His) box polypeptide 38 [Source:MGI Symbol;Acc:MGI:1927617] |
| ENSMUSG00000048827 | Pkd1l3 | protein_coding | polycystic kidney disease 1 like 3 [Source:MGI Symbol;Acc:MGI:2664670] |
| ENSMUSG00000031729 | 2400003C14Rik | protein_coding | RIKEN cDNA 2400003C14 gene [Source:MGI Symbol;Acc:MGI:1919205] |
| ENSMUSG00000069895 | Atxn1l | protein_coding | ataxin 1-like [Source:MGI Symbol;Acc:MGI:3694797] |
| ENSMUSG00000031731 | Ap1g1 | protein_coding | adaptor protein complex AP-1, gamma 1 subunit [Source:MGI Symbol;Acc:MGI:101919] |
| ENSMUSG00000059854 | Hydin | protein_coding | HYDIN, axonemal central pair apparatus protein [Source:MGI Symbol;Acc:MGI:2389007] |
| ENSMUSG00000033732 | Sf3b3 | protein_coding | splicing factor 3b, subunit 3 [Source:MGI Symbol;Acc:MGI:1289341] |
| ENSMUSG00000031749 | St3gal2 | protein_coding | ST3 beta-galactoside alpha-2,3-sialyltransferase 2 [Source:MGI Symbol;Acc:MGI:99427] |
| ENSMUSG00000015023 | Ddx19a | protein_coding | DEAD (Asp-Glu-Ala-Asp) box polypeptide 19a [Source:MGI Symbol;Acc:MGI:99526] |
| ENSMUSG00000031960 | Aars | protein_coding | alanyl-tRNA synthetase [Source:MGI Symbol;Acc:MGI:2384560] |
| ENSMUSG00000033624 | Pdpr | protein_coding | pyruvate dehydrogenase phosphatase regulatory subunit [Source:MGI Symbol;Acc:MGI:2442188] |
| ENSMUSG00000033545 | Znrf1 | protein_coding | zinc and ring finger 1 [Source:MGI Symbol;Acc:MGI:2177308] |
| ENSMUSG00000031948 | Kars | protein_coding | lysyl-tRNA synthetase [Source:MGI Symbol;Acc:MGI:1934754] |
| ENSMUSG00000078908 | Mon1b | protein_coding | MON1 homolog b (yeast) [Source:MGI Symbol;Acc:MGI:1923231] |
| ENSMUSG00000004637 | Wwox | protein_coding | WW domain-containing oxidoreductase [Source:MGI Symbol;Acc:MGI:1931237] |
| ENSMUSG00000034390 | 4933407C03Rik | protein_coding | RIKEN cDNA 4933407C03 gene [Source:MGI Symbol;Acc:MGI:1921690] |
| ENSMUSG00000034330 | Plcg2 | protein_coding | phospholipase C, gamma 2 [Source:MGI Symbol;Acc:MGI:97616] |
| ENSMUSG00000031841 | Cdh13 | protein_coding | cadherin 13 [Source:MGI Symbol;Acc:MGI:99551] |
| ENSMUSG00000031837 | Necab2 | protein_coding | N-terminal EF-hand calcium binding protein 2 [Source:MGI Symbol;Acc:MGI:2152211] |
| ENSMUSG00000031835 | Mbtps1 | protein_coding | membrane-bound transcription factor peptidase, site 1 [Source:MGI Symbol;Acc:MGI:1927235] |
| ENSMUSG00000031832 | Taf1c | protein_coding | TATA box binding protein (Tbp)-associated factor, RNA polymerase I, C [Source:MGI Symbol;Acc:MGI:109576] |
| ENSMUSG00000034105 | 4632415K11Rik | protein_coding | RIKEN cDNA 4632415K11 gene [Source:MGI Symbol;Acc:MGI:1921597] |
| ENSMUSG00000031827 | Cotl1 | protein_coding | coactosin-like 1 (*Dictyostelium*) [Source:MGI Symbol;Acc:MGI:1919292] |
| ENSMUSG00000031826 | Usp10 | protein_coding | ubiquitin specific peptidase 10 [Source:MGI Symbol;Acc:MGI:894652] |
| ENSMUSG00000092329 | Gm20388 | protein_coding | predicted gene 20388 [Source:MGI Symbol;Acc:MGI:5141853] |
| ENSMUSG00000031823 | Zdhhc7 | protein_coding | zinc finger, DHHC domain containing 7 [Source:MGI Symbol;Acc:MGI:2142662] |
| ENSMUSG00000031822 | Gse1 | protein_coding | genetic suppressor element 1 [Source:MGI Symbol;Acc:MGI:1098275] |
| ENSMUSG00000031821 | Gins2 | protein_coding | GINS complex subunit 2 (Psf2 homolog) [Source:MGI Symbol;Acc:MGI:1921019] |
| ENSMUSG00000031818 | Cox4i1 | protein_coding | cytochrome c oxidase subunit IV isoform 1 [Source:MGI Symbol;Acc:MGI:88473] |
| ENSMUSG00000031812 | Map1lc3b | protein_coding | microtubule-associated protein 1 light chain 3 beta [Source:MGI Symbol;Acc:MGI:1914693] |
| ENSMUSG00000040010 | Slc7a5 | protein_coding | solute carrier family 7 (cationic amino acid transporter, y+ system), member 5 [Source:MGI Symbol;Acc:MGI:1298205] |
| ENSMUSG00000025316 | Banp | protein_coding | BTG3 associated nuclear protein [Source:MGI Symbol;Acc:MGI:1889023] |
| ENSMUSG00000049577 | Zfpm1 | protein_coding | zinc finger protein, multitype 1 [Source:MGI Symbol;Acc:MGI:1095400] |
| ENSMUSG00000017478 | Zc3h18 | protein_coding | zinc finger CCCH-type containing 18 [Source:MGI Symbol;Acc:MGI:1923264] |
| ENSMUSG00000014444 | Fam38a | protein_coding | family with sequence similarity 38, member A [Source:MGI Symbol;Acc:MGI:3603204] |
| ENSMUSG00000006585 | Cdt1 | protein_coding | chromatin licensing and DNA replication factor 1 [Source:MGI Symbol;Acc:MGI:1914427] |

TABLE S2-continued

Ythdf2 targeted mRNAs from three irCLIP-seq replicates.

| GeneID | Name | Biotype | Description |
| --- | --- | --- | --- |
| ENSMUSG00000006589 | Aprt | protein_coding | adenine phosphoribosyl transferase [Source:MGI Symbol;Acc:MGI:88061] |
| ENSMUSG00000006362 | Cbfa2t3 | protein_coding | core-binding factor, runt domain, alpha subunit 2, translocated to, 3 (human) [Source:MGI Symbol;Acc:MGI:1338013] |
| ENSMUSG00000035569 | Ankrd11 | protein_coding | ankyrin repeat domain 11 [Source:MGI Symbol;Acc:MGI:1924337] |
| ENSMUSG00000000740 | Rpl13 | protein_coding | ribosomal protein L13 [Source:MGI Symbol;Acc:MGI:105922] |
| ENSMUSG00000032815 | Fanca | protein_coding | Fanconi anemia, complementation group A [Source:MGI Symbol;Acc:MGI:1341823] |
| ENSMUSG00000001472 | Tcf25 | protein_coding | transcription factor 25 (basic helix-loop-helix) [Source:MGI Symbol;Acc:MGI:1914105] |
| ENSMUSG00000019478 | Rab4a | protein_coding | RAB4A, member RAS oncogene family [Source:MGI Symbol;Acc:MGI:105069] |
| ENSMUSG00000031974 | Abcb10 | protein_coding | ATP-binding cassette, sub-family B (MDR/TAP), member 10 [Source:MGI Symbol;Acc:MGI:1860508] |
| ENSMUSG00000038697 | Taf5l | protein_coding | TAF5-like RNA polymerase II, p300/CBP-associated factor (PCAF)-associated factor [Source:MGI Symbol;Acc:MGI:1919039] |
| ENSMUSG00000031976 | Urb2 | protein_coding | URB2 ribosome biogenesis 2 homolog (S. cerevisiae) [Source:MGI Symbol;Acc:MGI:2681124] |
| ENSMUSG00000089704 | Galnt2 | protein_coding | UDP-N-acetyl-alpha-D-galactosamine:polypeptide N-acetylgalactosaminyltransferase 2 [Source:MGI Symbol;Acc:MGI:894694] |
| ENSMUSG00000074030 | Exoc8 | protein_coding | exocyst complex component 8 [Source:MGI Symbol;Acc:MGI:2142527] |
| ENSMUSG00000031987 | Egln1 | protein_coding | EGL nine homolog 1 (C. elegans) [Source:MGI Symbol;Acc:MGI:1932286] |
| ENSMUSG00000031853 | BC021891 | protein_coding | cDNA sequence BC021891 [Source:MGI Symbol;Acc:MGI:2385307] |
| ENSMUSG00000051495 | Irf2bp2 | protein_coding | interferon regulatory factor 2 binding protein 2 [Source:MGI Symbol;Acc:MGI:2443921] |
| ENSMUSG00000058779 | Tomm20 | protein_coding | translocase of outer mitochondrial membrane 20 homolog (yeast) [Source:MGI Symbol;Acc:MGI:1915202] |
| ENSMUSG00000042360 | 4930433N12Rik | protein_coding | RIKEN cDNA 4930433N12 gene [Source:MGI Symbol;Acc:MGI:2149746] |
| ENSMUSG00000025898 | Cwf19l2 | protein_coding | CWF19-like 2, cell cycle control (S. pombe) [Source:MGI Symbol;Acc:MGI:1918023] |
| ENSMUSG00000025893 | Kbtbd3 | protein_coding | kelch repeat and BTB (POZ) domain containing 3 [Source:MGI Symbol;Acc:MGI:1916399] |
| ENSMUSG00000013076 | Amotl1 | protein_coding | angiomotin-like 1 [Source:MGI Symbol;Acc:MGI:1922973] |
| ENSMUSG00000031939 | Taf1d | protein_coding | TATA box binding protein (Tbp)-associated factor, RNA polymerase I, D [Source:MGI Symbol;Acc:MGI:1922566] |
| ENSMUSG00000046111 | 5830418K08Rik | protein_coding | RIKEN cDNA 5830418K08 gene [Source:MGI Symbol;Acc:MGI:2442521] |
| ENSMUSG00000060510 | Zfp266 | protein_coding | zinc finger protein 266 [Source:MGI Symbol;Acc:MGI:1924769] |
| ENSMUSG00000004099 | Dnmt1 | protein_coding | DNA methyltransferase (cytosine-5) 1 [Source:MGI Symbol;Acc:MGI:94912] |
| ENSMUSG00000010205 | Raver1 | protein_coding | ribonucleoprotein, PTB-binding 1 [Source:MGI Symbol;Acc:MGI:1919016] |
| ENSMUSG00000019471 | Cdc37 | protein_coding | cell division cycle 37 homolog (S. cerevisiae) [Source:MGI Symbol;Acc:MGI:109531] |
| ENSMUSG00000003308 | Keap1 | protein_coding | kelch-like ECH-associated protein 1 [Source:MGI Symbol;Acc:MGI:1858732] |
| ENSMUSG00000002820 | Atg4d | protein_coding | autophagy-related 4D (yeast) [Source:MGI Symbol;Acc:MGI:2444308] |
| ENSMUSG00000035047 | Kri1 | protein_coding | KRI1 homolog (S. cerevisiae) [Source:MGI Symbol;Acc:MGI:2384899] |
| ENSMUSG00000032178 | Ilf3 | protein_coding | interleukin enhancer binding factor 3 [Source:MGI Symbol;Acc:MGI:1339973] |
| ENSMUSG00000032185 | Carm1 | protein_coding | coactivator-associated arginine methyltransferase 1 [Source:MGI Symbol;Acc:MGI:1913208] |
| ENSMUSG00000032187 | Smarca4 | protein_coding | SWI/SNF related, matrix associated, actin dependent regulator of chromatin, subfamily a, member 4 [Source:MGI Symbol;Acc:MGI:88192] |
| ENSMUSG00000032193 | Ldlr | protein_coding | low density lipoprotein receptor [Source:MGI Symbol;Acc:MGI:96765] |
| ENSMUSG00000003402 | Prkcsh | protein_coding | protein kinase C substrate 80K-H [Source:MGI Symbol;Acc:MGI:107877] |

TABLE S2-continued

Ythdf2 targeted mRNAs from three irCLIP-seq replicates.

| GeneID | Name | Biotype | Description |
|---|---|---|---|
| ENSMUSG 00000031963 | Bmper | protein_coding | BMP-binding endothelial regulator [Source:MGI Symbol;Acc:MGI:1920480] |
| ENSMUSG 00000062257 | Opcml | protein_coding | opioid binding protein/cell adhesion molecule-like [Source:MGI Symbol;Acc:MGI:97397] |
| ENSMUSG 00000031996 | Aplp2 | protein_coding | amyloid beta (A4) precursor-like protein 2 [Source:MGI Symbol;Acc:MGI:88047] |
| ENSMUSG 00000016087 | Fli1 | protein_coding | Friend leukemia integration 1 [Source:MGI Symbol;Acc:MGI:95554] |
| ENSMUSG 00000032036 | Kirrel3 | protein_coding | kin of IRRE like 3 (*Drosophila*) [Source:MGI Symbol;Acc:MGI:1914953] |
| ENSMUSG 00000032118 | Fez1 | protein_coding | fasciculation and elongation protein zeta 1 (zygin I) [Source:MGI Symbol;Acc:MGI:2670976] |
| ENSMUSG 00000035934 | Pknox2 | protein_coding | Pbx/knotted 1 homeobox 2 [Source:MGI Symbol;Acc:MGI:2445415] |
| ENSMUSG 00000053310 | Nrgn | protein_coding | neurogranin [Source:MGI Symbol;Acc:MGI:1927184] |
| ENSMUSG 00000040111 | Gramd1b | protein_coding | GRAM domain containing 1B [Source:MGI Symbol;Acc:MGI:1925037] |
| ENSMUSG 00000032020 | Ubash3b | protein_coding | ubiquitin associated and SH3 domain containing, B [Source:MGI Symbol;Acc:MGI:1920078] |
| ENSMUSG 00000032017 | Grik4 | protein_coding | glutamate receptor, ionotropic, kainate 4 [Source:MGI Symbol;Acc:MGI:95817] |
| ENSMUSG 00000034342 | Cbl | protein_coding | Casitas B-lineage lymphoma [Source:MGI Symbol;Acc:MGI:88279] |
| ENSMUSG 00000049932 | H2afx | protein_coding | H2A histone family, member X [Source:MGI Symbol;Acc:MGI:102688] |
| ENSMUSG 00000063382 | Bcl9l | protein_coding | B cell CLL/lymphoma 9-like [Source:MGI Symbol;Acc:MGI:1933114] |
| ENSMUSG 00000032097 | Ddx6 | protein_coding | DEAD (Asp-Glu-Ala-Asp) box polypeptide 6 [Source:MGI Symbol;Acc:MGI:104976] |
| ENSMUSG 00000034908 | Sidt2 | protein_coding | SID1 transmembrane family, member 2 [Source:MGI Symbol;Acc:MGI:2446134] |
| ENSMUSG 00000003131 | Pafah1b2 | protein_coding | platelet-activating factor acetylhydrolase, isoform 1b, subunit 2 [Source:MGI Symbol;Acc:MGI:108415] |
| ENSMUSG 00000034135 | Sik3 | protein_coding | SIK family kinase 3 [Source:MGI Symbol;Acc:MGI:2446296] |
| ENSMUSG 00000032076 | Cadm1 | protein_coding | cell adhesion molecule 1 [Source:MGI Symbol;Acc:MGI:1889272] |
| ENSMUSG 00000066687 | Zbtb16 | protein_coding | zinc finger and BTB domain containing 16 [Source:MGI Symbol;Acc:MGI:103222] |
| ENSMUSG 00000032058 | Ppp2r1b | protein_coding | protein phosphatase 2 (formerly 2A), regulatory subunit A (PR 65), beta isoform [Source:MGI Symbol;Acc:MGI:1920949] |
| ENSMUSG 00000032050 | Rdx | protein_coding | radixin [Source:MGI Symbol;Acc:MGI:97887] |
| ENSMUSG 00000034218 | Atm | protein_coding | ataxia telangiectasia mutated homolog (human) [Source:MGI Symbol;Acc:MGI:107202] |
| ENSMUSG 00000074305 | C230081A13Rik | protein_coding | RIKEN cDNA C230081A13 gene [Source:MGI Symbol;Acc:MGI:2442366] |
| ENSMUSG 00000032329 | Hmg20a | protein_coding | high mobility group 20A [Source:MGI Symbol;Acc:MGI:1914117] |
| ENSMUSG 00000032288 | Imp3 | protein_coding | IMP3, U3 small nucleolar ribonucleoprotein, homolog (yeast) [Source:MGI Symbol;Acc:MGI:1916119] |
| ENSMUSG 00000032300 | 1700017B05Rik | protein_coding | RIKEN cDNA 1700017B05 gene [Source:MGI Symbol;Acc:MGI:1921461] |
| ENSMUSG 00000032312 | Csk | protein_coding | c-src tyrosine kinase [Source:MGI Symbol;Acc:MGI:88537] |
| ENSMUSG 00000032340 | Neo1 | protein_coding | neogenin [Source:MGI Symbol;Acc:MGI:1097159] |
| ENSMUSG 00000025234 | Arih1 | protein_coding | ariadne ubiquitin-conjugating enzyme E2 binding protein homolog 1 (*Drosophila*) [Source:MGI Symbol;Acc:MGI:1344363] |
| ENSMUSG 00000032294 | Pkm2 | protein_coding | pyruvate kinase, muscle [Source:MGI Symbol;Acc:MGI:97591] |
| ENSMUSG 00000032280 | Tle3 | protein_coding | transducin-like enhancer of split 3, homolog of *Drosophila* E(spl) [Source:MGI Symbol;Acc:MGI:104634] |
| ENSMUSG 00000007892 | Rplp1 | protein_coding | ribosomal protein, large, P1 [Source:MGI Symbol;Acc:MGI:1927099] |
| ENSMUSG 00000032244 | Fem1b | protein_coding | feminization 1 homolog b (*C. elegans*) [Source:MGI Symbol;Acc:MGI:1335087] |
| ENSMUSG 00000032399 | Rpl4 | protein_coding | ribosomal protein L4 [Source:MGI Symbol;Acc:MGI:1915141] |
| ENSMUSG 00000032397 | Tipin | protein_coding | timeless interacting protein [Source:MGI Symbol;Acc:MGI:1921571] |

TABLE S2-continued

Ythdf2 targeted mRNAs from three irCLIP-seq replicates.

| GeneID | Name | Biotype | Description |
|---|---|---|---|
| ENSMUSG00000004771 | Rab11a | protein_coding | RAB11a, member RAS oncogene family [Source:MGI Symbol;Acc:MGI:1858202] |
| ENSMUSG00000034263 | 2010321M09Rik | protein_coding | RIKEN cDNA 2010321M09 gene [Source:MGI Symbol;Acc:MGI:1917132] |
| ENSMUSG00000032392 | Parp16 | protein_coding | poly (ADP-ribose) polymerase family, member 16 [Source:MGI Symbol;Acc:MGI:2446133] |
| ENSMUSG00000050721 | Plekho2 | protein_coding | pleckstrin homology domain containing, family O member 2 [Source:MGI Symbol;Acc:MGI:2143132] |
| ENSMUSG00000040524 | Zfp609 | protein_coding | zinc finger protein 609 [Source:MGI Symbol;Acc:MGI:2674092] |
| ENSMUSG00000032384 | Csnk1g1 | protein_coding | casein kinase 1, gamma 1 [Source:MGI Symbol;Acc:MGI:2660884] |
| ENSMUSG00000038664 | Herc1 | protein_coding | hect (homologous to the E6-AP (UBE3A) carboxyl terminus) domain and RCC1 (CHC1)-like domain (RLD) 1 [Source:MGI Symbol;Acc:MGI:2384589] |
| ENSMUSG00000032366 | Tpm1 | protein_coding | tropomyosin 1, alpha [Source:MGI Symbol;Acc:MGI:98809] |
| ENSMUSG00000052698 | Tln2 | protein_coding | talin 2 [Source:MGI Symbol;Acc:MGI:1917799] |
| ENSMUSG00000032238 | Rora | protein_coding | RAR-related orphan receptor alpha [Source:MGI Symbol;Acc:MGI:104661] |
| ENSMUSG00000032220 | Myo1e | protein_coding | myosin IE [Source:MGI Symbol;Acc:MGI:106621] |
| ENSMUSG00000054693 | Adam10 | protein_coding | a disintegrin and metallopeptidase domain 10 [Source:MGI Symbol;Acc:MGI:109548] |
| ENSMUSG00000032199 | Polr2m | protein_coding | polymerase (RNA) II (DNA directed) polypeptide M [Source:MGI Symbol;Acc:MGI:107282] |
| ENSMUSG00000092137 | Gcom1 | protein_coding | GRINL1A complex locus [Source:MGI Symbol;Acc:MGI:5141967] |
| ENSMUSG00000041361 | Myzap | protein_coding | myocardial zonula adherens protein [Source:MGI Symbol;Acc:MGI:2142908] |
| ENSMUSG00000032228 | Tcf12 | protein_coding | transcription factor 12 [Source:MGI Symbol;Acc:MGI:101877] |
| ENSMUSG00000037674 | Rfx7 | protein_coding | regulatory factor X, 7 [Source:MGI Symbol;Acc:MGI:2442675] |
| ENSMUSG00000032216 | Nedd4 | protein_coding | neural precursor cell expressed, developmentally down-regulated 4 [Source:MGI Symbol;Acc:MGI:97297] |
| ENSMUSG00000062151 | Unc13c | protein_coding | unc-13 homolog C (C. elegans) [Source:MGI Symbol;Acc:MGI:2149021] |
| ENSMUSG00000007656 | Arpp19 | protein_coding | cAMP-regulated phosphoprotein 19 [Source:MGI Symbol;Acc:MGI:1891691] |
| ENSMUSG00000034593 | Myo5a | protein_coding | myosin VA [Source:MGI Symbol;Acc:MGI:105976] |
| ENSMUSG00000042688 | Mapk6 | protein_coding | mitogen-activated protein kinase 6 [Source:MGI Symbol;Acc:MGI:1354946] |
| ENSMUSG00000032355 | 2310046A06Rik | protein_coding | RIKEN cDNA 2310046A06 gene [Source:MGI Symbol;Acc:MGI:1916892] |
| ENSMUSG00000037742 | Eef1a1 | protein_coding | eukaryotic translation elongation factor 1 alpha 1 [Source:MGI Symbol;Acc:MGI:1096881] |
| ENSMUSG00000034252 | Senp6 | protein_coding | SUMO/sentrin specific peptidase 6 [Source:MGI Symbol;Acc:MGI:1922075] |
| ENSMUSG00000043289 | Mei4 | protein_coding | meiosis-specific, MEI4 homolog (S. cerevisiae) [Source:MGI Symbol;Acc:MGI:1922283] |
| ENSMUSG00000032253 | Phip | protein_coding | pleckstrin homology domain interacting protein [Source:MGI Symbol;Acc:MGI:1932404] |
| ENSMUSG00000032265 | Fam46a | protein_coding | family with sequence similarity 46, member A [Source:MGI Symbol;Acc:MGI:2670964] |
| ENSMUSG00000035941 | Ibtk | protein_coding | inhibitor of Bruton agammaglobulinemia tyrosine kinase [Source:MGI Symbol;Acc:MGI:1918677] |
| ENSMUSG00000092541 | Gm20537 | protein_coding | predicted gene 20537 [Source:MGI Symbol;Acc:MGI:5142002] |
| ENSMUSG00000032423 | Syncrip | protein_coding | synaptotagmin binding, cytoplasmic RNA interacting protein [Source:MGI Symbol;Acc:MGI:1891690] |
| ENSMUSG00000032407 | 2610101N10Rik | protein_coding | RIKEN cDNA 2610101N10 gene [Source:MGI Symbol;Acc:MGI:1915208] |
| ENSMUSG00000032411 | Tfdp2 | protein_coding | transcription factor Dp 2 [Source:MGI Symbol;Acc:MGI:107167] |
| ENSMUSG00000032412 | Atp1b3 | protein_coding | ATPase, Na+/K+ transporting, beta 3 polypeptide [Source:MGI Symbol;Acc:MGI:107788] |
| ENSMUSG00000032413 | Rasa2 | protein_coding | RAS p21 protein activator 2 [Source:MGI Symbol;Acc:MGI:2149960] |
| ENSMUSG00000066415 | Msl2 | protein_coding | male-specific lethal 2 homolog (Drosophila) [Source:MGI Symbol;Acc:MGI:1925103] |
| ENSMUSG00000032803 | Cdv3 | protein_coding | carnitine deficiency-associated gene expressed in ventricle 3 [Source:MGI Symbol;Acc:MGI:2448759] |

TABLE S2-continued

Ythdf2 targeted mRNAs from three irCLIP-seq replicates.

| GeneID | Name | Biotype | Description |
|---|---|---|---|
| ENSMUSG00000032564 | Cpne4 | protein_coding | copine IV [Source:MGI Symbol;Acc:MGI:1921270] |
| ENSMUSG00000032571 | Pik3r4 | protein_coding | phosphatidylinositol 3 kinase, regulatory subunit, polypeptide 4, p150 [Source:MGI Symbol;Acc:MGI:1922919] |
| ENSMUSG00000020257 | Wdr82 | protein_coding | WD repeat domain containing 82 [Source:MGI Symbol;Acc:MGI:1924555] |
| ENSMUSG00000023277 | Twf2 | protein_coding | twinfilin, actin-binding protein, homolog 2 (Drosophila) [Source:MGI Symbol;Acc:MGI:1346078] |
| ENSMUSG00000040661 | Rad54l2 | protein_coding | RAD54 like 2 (S. cerevisiae) [Source:MGI Symbol;Acc:MGI:1933196] |
| ENSMUSG00000032575 | Manf | protein_coding | mesencephalic astrocyte-derived neurotrophic factor [Source:MGI Symbol;Acc:MGI:1922090] |
| ENSMUSG00000045365 | Rbm15b | protein_coding | RNA binding motif protein 15B [Source:MGI Symbol;Acc:MGI:1923598] |
| ENSMUSG00000010066 | Cacna2d2 | protein_coding | calcium channel, voltage-dependent, alpha 2/delta subunit 2 [Source:MGI Symbol;Acc:MGI:1929813] |
| ENSMUSG00000032562 | Gnai2 | protein_coding | guanine nucleotide binding protein (G protein), alpha inhibiting 2 [Source:MGI Symbol;Acc:MGI:95772] |
| ENSMUSG00000032580 | Rbm5 | protein_coding | RNA binding motif protein 5 [Source:MGI Symbol;Acc:MGI:1933204] |
| ENSMUSG00000032586 | Traip | protein_coding | TRAF-interacting protein [Source:MGI Symbol;Acc:MGI:1096377] |
| ENSMUSG00000079323 | Cdhr4 | protein_coding | cadherin-related family member 4 [Source:MGI Symbol;Acc:MGI:1916648] |
| ENSMUSG00000042106 | 6230427J02Rik | protein_coding | RIKEN cDNA 6230427J02 gene [Source:MGI Symbol;Acc:MGI:1915426] |
| ENSMUSG00000039952 | Dag1 | protein_coding | dystroglycan 1 [Source:MGI Symbol;Acc:MGI:101864] |
| ENSMUSG00000007815 | Rhoa | protein_coding | ras homolog gene family, member A [Source:MGI Symbol;Acc:MGI:1096342] |
| ENSMUSG00000063856 | Gpx1 | protein_coding | glutathione peroxidase 1 [Source:MGI Symbol;Acc:MGI:104887] |
| ENSMUSG00000049305 | Ccdc71 | protein_coding | coiled-coil domain containing 71 [Source:MGI Symbol;Acc:MGI:1919704] |
| ENSMUSG00000006673 | Qrich1 | protein_coding | glutamine-rich 1 [Source:MGI Symbol;Acc:MGI:1916482] |
| ENSMUSG00000066357 | Wdr6 | protein_coding | WD repeat domain 6 [Source:MGI Symbol;Acc:MGI:1930140] |
| ENSMUSG00000032479 | Mtap4 | protein_coding | microtubule-associated protein 4 [Source:MGI Symbol;Acc:MGI:97178] |
| ENSMUSG00000032480 | Dhx30 | protein_coding | DEAH (Asp-Glu-Ala-His) box polypeptide 30 [Source:MGI Symbol;Acc:MGI:1920081] |
| ENSMUSG00000032481 | Smarcc1 | protein_coding | SWI/SNF related, matrix associated, actin dependent regulator of chromatin, subfamily c, member 1 [Source:MGI Symbol;Acc:MGI:1203524] |
| ENSMUSG00000056724 | Nbeal2 | protein_coding | neurobeachin-like 2 [Source:MGI Symbol;Acc:MGI:2448554] |
| ENSMUSG00000032504 | Pdcd6ip | protein_coding | programmed cell death 6 interacting protein [Source:MGI Symbol;Acc:MGI:1333753] |
| ENSMUSG00000032507 | Fbxl2 | protein_coding | F-box and leucine-rich repeat protein 2 [Source:MGI Symbol;Acc:MGI:1919429] |
| ENSMUSG00000032436 | Cmtm7 | protein_coding | CKLF-like MARVEL transmembrane domain containing 7 [Source:MGI Symbol;Acc:MGI:2447166] |
| ENSMUSG00000032437 | Stt3b | protein_coding | STT3, subunit of the oligosaccharyltransferase complex, homolog B (S. cerevisiae) [Source:MGI Symbol;Acc:MGI:1915542] |
| ENSMUSG00000039607 | Rbms3 | protein_coding | RNA binding motif, single stranded interacting protein [Source:MGI Symbol;Acc:MGI:2444477] |
| ENSMUSG00000047409 | Ctdspl | protein_coding | CTD (carboxy-terminal domain, RNA polymerase II, polypeptide A) small phosphatase-like [Source:MGI Symbol;Acc:MGI:1916524] |
| ENSMUSG00000052336 | Cx3cr1 | protein_coding | chemokine (C-X3-C) receptor 1 [Source:MGI Symbol;Acc:MGI:1333815] |
| ENSMUSG00000032518 | Rpsa | protein_coding | ribosomal protein SA [Source:MGI Symbol;Acc:MGI:105381] |
| ENSMUSG00000006941 | Eif1b | protein_coding | eukaryotic translation initiation factor 1B [Source:MGI Symbol;Acc:MGI:1916219] |
| ENSMUSG00000006932 | Ctnnb1 | protein_coding | catenin (cadherin associated protein), beta 1 [Source:MGI Symbol;Acc:MGI:88276] |
| ENSMUSG00000032525 | Nktr | protein_coding | natural killer tumor recognition sequence [Source:MGI Symbol;Acc:MGI:97346] |
| ENSMUSG00000025786 | Zdhhc3 | protein_coding | zinc finger, DHHC domain containing 3 [Source:MGI Symbol;Acc:MGI:1926134] |

TABLE S4

Table S4. Percentages of human donor derived chimerism used to calculate CRU

| | Percentage of hCD45 + GFP + cells in TNC |
|---|---|
| Primary LDA | |
| Control 50K | 1.20% |
| | 1.11% |
| | 0.85% |
| | 4.29% |
| Control 20K | 1.66% |
| | 1.51% |
| | 1.47% |
| | 2.10% |
| YTHDF2 KD 50K | 7.37% |
| | 67.90% |
| | 22.80% |
| | 21.00% |
| YTHDF2 KD 20K | 12.30% |
| | 8.23% |
| | 4.57% |
| | 1.53% |
| Control 10K * | 0.17% |
| | 0.46% |
| | 1.00% |
| | 0.65% |
| | 1.23% |
| YTHDF2 KD 20K | 2.51% |
| | 1.60% |
| | 1.28% |
| | 1.40% |
| | 1.66% |
| | 3.07% |
| | 0.95% |
| Secondary LDA | |
| Control 12E+6 | 0.27% |
| | 0.26% |
| | 0.35% |
| Control 8E+6 | 0.02% |
| | 0.01% |
| | 7.57E−05 |
| Control 4E+6 | 0.03% |
| | 0.02% |
| | 0.01% |
| | 0.02% |
| YTHDF2 KD 12E+6 | 0.92% |
| | 1.13% |
| | 1.45% |
| YTHDF2 KD 8E+6 | 0.38% |
| | 0.37% |
| | 0.72% |
| YTHDF2 KD 4E+6 | 0.27% |
| | 0.29% |
| | 0.19% |
| | 0.44% |

* Control 10K group also transplanted 7 mice. However, 2 mice were dead before the time point of analysis partially due to the deficiency in hematopoietic recovery.

TABLE S5 qPCR primers used to verify the expressional levels of transcription factors in wt and Ythdf2 KO HSPCs.

| | |
|---|---|
| mouse Tal1 qPCR primer F | CGCTGCTCTATAGCCTTAGCC (SEQ ID NO: 10) |
| mouse Tal1 qPCR primer R | CTCTTCACCCGGTTGTTGTT (SEQ ID NO: 11) |
| mouse Gata2 qPCR primer F | CAACCCTTACTACGCCAACC (SEQ ID NO: 12) |
| mouse Gata2 qPCR primer R | GCTGTGCAACAAGTGTGGTC (SEQ ID NO: 13) |
| mouse Runx1 qPCR primer F | CCAGCCTCTCTGCAGAACTT (SEQ ID NO: 14) |
| mouse Runx1 qPCR primer R | GGAGATGGACGGCAGAGTAG (SEQ ID NO: 15) |
| mouse Stat5a qPCR primer F | AGAAGCAAGTGTCCCTGGAG (SEQ ID NO: 16) |
| mouse Stat5a qPCR primer R | GTCGTCCAGGATGATGGTCT (SEQ ID NO: 17) |
| mouse Actb qPCR primer F | TGTCACCAACTGGGACGATA (SEQ ID NO: 18) |
| mouse Actb qPCR primer R | ACCCTCATAGATGGGCACAG (SEQ ID NO: 19) |

What is claimed is:

1. A method for expanding a population of hematopoietic stem cells (HSCs) obtained from a tissue selected from the group consisting of peripheral blood, cord blood, and bone marrow, the method comprising modulating an $N^6$-Methyladenosine ($m^6A$) mRNA modification pathway in the population of stem cells, to expand the number of stem cells, wherein modulating the $m^6A$ mRNA modification pathway comprises knocking out or knocking down expression of the Ythdf2 gene.

2. The method according to claim 1, wherein knocking out expression of the Ythdf2 gene comprises exposing the stem cells to an Mx1-Cre targeting system that inactivates or deletes the Ythdf2 gene.

3. The method according to claim 1, wherein the expansion of the stem cells is by a factor of at least 2-fold.

4. The method according to claim 3, wherein the expansion of the stem cells is by a factor of at least 4-fold.

5. The method according to claim 4, wherein the expansion of the stem cells is by a factor of at least 5-fold.

6. The method according to claim 5, wherein the expansion of the stem cells is by a factor of at least 8-fold.

7. The method according to claim 6, wherein the expansion of the stem cells is by a factor of at least 10-fold.

8. The method according to claim 1, wherein the expanded cells have at least a 5-fold increase in total colony-forming units (CFU).

9. The method according to claim 1, wherein the expanded cells have at least a 3.8-fold increase in CFU-granulocyte erythrocyte monocyte megakaryocyte (GEMM) colonies.

10. The method according to claim 1, wherein knocking down expression of the Ythdf2 gene comprises introducing an shRNA into the stem cells to reduce expression of the Ythdf2 gene.

11. The method according to claim 10, wherein the shRNA is introduced by contacting the stem cells with a lentivirus to deliver the shRNA.

12. The method according to claim 10, wherein the shRNA has the sequence: 5'-AAGGACGTTCCCAATAGC-CAA-3' (SEQ ID NO 8).

* * * * *